US012037398B2

(12) United States Patent
Ferrant-Orgettas et al.

(10) Patent No.: US 12,037,398 B2
(45) Date of Patent: Jul. 16, 2024

(54) ANTI-VLA-4 ANTIBODIES HAVING REDUCED EFFECTOR FUNCTION

(71) Applicant: BIOGEN MA INC., Cambridge, MA (US)

(72) Inventors: Janine Lisa Ferrant-Orgettas, Gloucester, MA (US); Robert Blake Pepinsky, Arlington, MA (US); Ellen Duggan Cahir-McFarland, Newtonville, MA (US); Nadia Giselle D'Lima, Cambridge, MA (US); Joseph Walter Arndt, Swampscott, MA (US); Karl John Mortley Hanf, Billerica, MA (US); Thomas Owen Cameron, Cambridge, MA (US); Ellen Garber Stark, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 498 days.

(21) Appl. No.: 15/734,915

(22) PCT Filed: May 31, 2019

(86) PCT No.: PCT/US2019/034962
§ 371 (c)(1),
(2) Date: Dec. 3, 2020

(87) PCT Pub. No.: WO2019/236417
PCT Pub. Date: Dec. 12, 2019

(65) Prior Publication Data
US 2021/0238289 A1 Aug. 5, 2021

Related U.S. Application Data

(60) Provisional application No. 62/833,319, filed on Apr. 12, 2019, provisional application No. 62/782,876, filed on Dec. 20, 2018, provisional application No. 62/680,466, filed on Jun. 4, 2018.

(51) Int. Cl.
*A61P 35/00* (2006.01)
*C07K 16/00* (2006.01)
*C07K 16/28* (2006.01)
*A61K 39/00* (2006.01)

(52) U.S. Cl.
CPC .... *C07K 16/2842* (2013.01); *A61K 2039/505* (2013.01); *A61K 2039/545* (2013.01); *C07K 2317/24* (2013.01); *C07K 2317/524* (2013.01); *C07K 2317/526* (2013.01); *C07K 2317/92* (2013.01); *C07K 2317/94* (2013.01)

(58) Field of Classification Search
CPC ............ A61K 2039/505; C07K 2317/52
USPC ................................................ 424/133.1
See application file for complete search history.

(56) References Cited

U.S. PATENT DOCUMENTS

| | | |
|---|---|---|
| 4,399,216 A | 8/1983 | Axel et al. |
| 4,439,196 A | 3/1984 | Higuchi |
| 4,447,224 A | 5/1984 | Decant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,494,880 A | 1/1985 | Su |
| 4,596,556 A | 6/1986 | Morrow et al. |
| 4,634,665 A | 1/1987 | Axel et al. |
| 4,790,824 A | 12/1988 | Morrow et al. |
| 4,816,397 A | 3/1989 | Boss et al. |
| 4,816,567 A | 3/1989 | Cabilly et al. |
| 4,816,587 A | 3/1989 | Megyeri et al. |
| 4,833,092 A | 5/1989 | Geysen |
| 4,941,880 A | 7/1990 | Burns |
| 5,064,413 A | 11/1991 | McKinnon et al. |
| 5,179,017 A | 1/1993 | Axel et al. |
| 5,217,870 A | 6/1993 | Hession et al. |
| 5,260,210 A | 11/1993 | Rubin et al. |
| 5,272,263 A | 12/1993 | Hession et al. |
| 5,312,335 A | 5/1994 | McKinnon et al. |
| 5,367,056 A | 11/1994 | Hession et al. |
| 5,383,851 A | 1/1995 | McKinnon, Jr. et al. |
| 5,399,163 A | 3/1995 | Peterson et al. |
| 5,530,101 A | 6/1996 | Queen et al. |
| 5,585,089 A | 12/1996 | Queen et al. |

(Continued)

FOREIGN PATENT DOCUMENTS

| | | |
|---|---|---|
| EP | 239400 A2 | 9/1987 |
| EP | 2050462 A1 | 4/2009 |

(Continued)

OTHER PUBLICATIONS

Herbener et al.(PLOS One (2018), 13(4), e0195823/1-e0195823/22).*
Second Examination Report issued in Saudi Arabian Application No. 520420679, dated Dec. 26, 2022 9 pages.
Communication pursuant to Rule 164(1) EPC, Partial Supplemental Search Report issued in European Application No. 19815783.6 dated Jan. 28, 2022, 19 pages.
Gazitt, "Mobilization of myeloma cells involves SDF-1/CXCR4 signaling and downregulation of VLA-4." (2004) Stem Cells 22:65-73.

(Continued)

*Primary Examiner* — Lynn A Bristol
(74) *Attorney, Agent, or Firm* — McCarter & English, LLP; Jill Mello

(57) ABSTRACT

The invention relates to anti-VLA-4 antibodies and binding fragments thereof. The invention further includes polynucleotides encoding said antibodies and binding fragments thereof and methods of manufacturing said antibodies and binding fragments thereof. The invention further includes methods of treating patients suffering from multiple sclerosis and/or epilepsy by administration of said antibodies and binding fragments thereof. The invention further includes methods of reducing the susceptibility to scrambling of a recombinant anti-alpha 4 antibody or a binding fragment thereof.

42 Claims, 50 Drawing Sheets

Specification includes a Sequence Listing.

(56) References Cited

U.S. PATENT DOCUMENTS

| | | | |
|---|---|---|---|
| 5,648,260 A | 7/1997 | Winter et al. |
| 5,672,622 A | 9/1997 | Hedgepeth et al. |
| 5,693,761 A | 12/1997 | Queen et al. |
| 5,693,762 A | 12/1997 | Queen et al. |
| 5,695,755 A | 12/1997 | Papayannopoulou |
| 5,789,650 A | 8/1998 | Lonberg et al. |
| 5,798,230 A | 8/1998 | Bomkamrn et al. |
| 5,824,304 A | 10/1998 | Papayannopoulou |
| 5,840,299 A | 11/1998 | Bendig et al. |
| 5,843,438 A | 12/1998 | Papayannopoulou |
| 5,849,992 A | 12/1998 | Meade et al. |
| 5,859,205 A | 1/1999 | Adair et al. |
| 5,871,734 A | 2/1999 | Lobb et al. |
| 5,888,507 A | 3/1999 | Burkly |
| 5,932,214 A | 8/1999 | Lobb et al. |
| 6,033,665 A | 3/2000 | Yednock |
| 6,153,653 A | 11/2000 | Shashoua |
| 6,252,043 B1 | 6/2001 | Hession et al. |
| 6,277,393 B1 | 8/2001 | Yrjanheikki et al. |
| 6,307,025 B1 | 10/2001 | Hession et al. |
| 6,407,213 B1 | 6/2002 | Carter et al. |
| 6,432,404 B1 | 8/2002 | Gallatin et al. |
| 6,482,409 B1 | 11/2002 | Lobb et al. |
| 6,509,376 B1 | 1/2003 | Joshi et al. |
| 6,602,503 B1 | 8/2003 | Lobb et al. |
| 6,616,926 B1 | 9/2003 | Burkly et al. |
| 6,680,302 B2 | 1/2004 | Seidman et al. |
| 6,894,033 B2 | 5/2005 | Cruz et al. |
| 7,094,397 B2 | 8/2006 | Stratton et al. |
| 7,157,086 B2 | 1/2007 | Lobb et al. |
| 7,232,830 B2 | 6/2007 | Delack |
| 7,482,003 B2 | 1/2009 | Lobb et al. |
| 7,557,190 B2 | 7/2009 | Barbosa et al. |
| 7,576,101 B2 | 8/2009 | Kartik et al. |
| 7,678,371 B2 | 3/2010 | Lugovskoy et al. |
| 7,829,092 B2 | 11/2010 | Lobb et al. |
| 10,335,485 B2 | 7/2019 | Lugovskoy et al. |
| 11,083,791 B2 | 8/2021 | Lugovskoy et al. |
| 11,571,477 B2 | 2/2023 | Lugovskoy et al. |
| 2002/0025348 A1 | 2/2002 | Basu et al. |
| 2003/0070185 A1 | 4/2003 | Jakobovits et al. |
| 2003/0135887 A1 | 7/2003 | Brandle et al. |
| 2003/0223972 A1 | 12/2003 | Goldman et al. |
| 2003/0232333 A1 | 12/2003 | Ladner et al. |
| 2004/0009163 A1 | 1/2004 | Schimmel et al. |
| 2004/0009169 A1 | 1/2004 | Taylor et al. |
| 2004/0043931 A1 | 3/2004 | Hersberg et al. |
| 2004/0110226 A1 | 6/2004 | Lazar et al. |
| 2004/0203031 A1 | 10/2004 | Whitehead et al. |
| 2005/0053598 A1 | 3/2005 | Burke et al. |
| 2005/0074443 A1 | 4/2005 | Treadwell |
| 2005/0215565 A1 | 9/2005 | Karlik et al. |
| 2006/0235207 A1 | 10/2006 | Tsuchiya |
| 2006/0258852 A1 | 11/2006 | Lugovskoy |
| 2007/0004775 A1 | 1/2007 | Perry |
| 2007/0048255 A1 | 3/2007 | Hunter |
| 2008/0025971 A1 | 1/2008 | Fong et al. |
| 2008/0075719 A1 | 3/2008 | Chan et al. |
| 2009/0004189 A1 | 1/2009 | Behrens et al. |
| 2009/0169477 A1 | 7/2009 | Panzara et al. |
| 2009/0202527 A1 | 8/2009 | Panzara et al. |
| 2011/0318346 A1 | 12/2011 | Steinman et al. |
| 2014/0161794 A1 | 6/2014 | Lugovskoy et al. |

FOREIGN PATENT DOCUMENTS

| | | |
|---|---|---|
| JP | 8-507680 | 8/1996 |
| JP | 9-508272 | 8/1997 |
| JP | 2007-531761 A | 11/2007 |
| WO | 86/01533 A1 | 3/1986 |
| WO | 86/05807 A1 | 10/1986 |
| WO | 87/04462 A1 | 7/1987 |
| WO | 89/01036 A1 | 2/1989 |
| WO | 89/07454 A1 | 8/1989 |
| WO | 89/10404 A1 | 11/1989 |
| WO | 9007861 A1 | 7/1990 |
| WO | 9013300 A1 | 11/1990 |
| WO | 9109967 A1 | 7/1991 |
| WO | 92000995 A1 | 1/1992 |
| WO | 92/04381 A1 | 3/1992 |
| WO | 9313798 A1 | 7/1993 |
| WO | 9315764 A1 | 8/1993 |
| WO | 9411027 A1 | 5/1994 |
| WO | 94/16094 A2 | 7/1994 |
| WO | 9417818 A1 | 8/1994 |
| WO | 9519790 A1 | 7/1995 |
| WO | 1995019790 A1 | 7/1995 |
| WO | 9607861 A1 | 3/1996 |
| WO | 9634096 A1 | 10/1996 |
| WO | 9718838 A1 | 5/1997 |
| WO | 1997018838 A1 | 5/1997 |
| WO | 98004247 A1 | 2/1998 |
| WO | 9906436 A1 | 2/1999 |
| WO | 9961421 A1 | 12/1999 |
| WO | 0155112 A1 | 8/2001 |
| WO | 0230488 A2 | 4/2002 |
| WO | 03072040 A2 | 9/2003 |
| WO | 05047327 A2 | 5/2005 |
| WO | 2005099776 A2 | 10/2005 |
| WO | 0623649 A2 | 3/2006 |
| WO | 2006023629 A2 | 3/2006 |
| WO | 2006055871 A2 | 5/2006 |
| WO | 2006060787 A2 | 6/2006 |
| WO | 2006096653 A2 | 9/2006 |
| WO | 06131200 A1 | 12/2006 |
| WO | 07/140249 A1 | 12/2007 |
| WO | 2008021954 A2 | 2/2008 |
| WO | 2008143954 A2 | 11/2008 |
| WO | 2008157356 A2 | 12/2008 |
| WO | 2010085682 A2 | 7/2010 |
| WO | 2011/130603 A2 | 10/2011 |
| WO | 2013057092 A1 | 4/2013 |
| WO | 2014150973 A1 | 9/2014 |

OTHER PUBLICATIONS

Gonzalez et al., "Complex interactions between the laminin alpha 4 subunit and integrins regulate endothelial cell behavior in vitro and angiogenesis in vivo." (2002) Proc. Natl. Acad. Sci. USA 99:16075-16080.

Gracia et al., "Influx of Leukocytes and Platelets in an Evolving Brain Infarct (Wistar Rat)", Am. J. Pathol., vol. 144, No. 1, p. 188-199 (1994).

Grayson et al., "Alphadbeta2 Integrin is Expressed on Human Eosinophils and Functions as an Alternative Ligand for Vascular Cell Adhesion Molecule 1 (VCAM-1)", J. Exp. Med., vol. 188, No. 11, p. 2187-2191 (1998).

Green et al., "Antigen-specific human monoclonal antibodies from mice engineered with human Ig heavy and light chain YACs". Nature Genetics. 1994, vol. 7, pp. 13-21.

Hall & Gibson, "Regulation of lymphoid and myeloid leukemic cell survival: role of stromal cell adhesion molecules," (2004) Leuk. Lymphoma 45:35-48.

Kaufman et al., "Amplification and expression of sequence cotransfected with a modular dihydrofolate reductase complementary DNA gene", Mol. Biol., 1982, vol. 159, pp. 601-621.

Campanero et al., "An Alternative Leukocyte Homotypic Adhesion Mechanism, LFA-1/ICAM-1-Independent, Triggered Through the Human VLA-4 Integrin", The Journal of Cell Biology, vol. 110, No. 6, pp. 2157-2165, (1990).

Kurtzke, "Clinical definition for multiple sclerosis treatment trials", Ann. Neurol., 1994, vol. 36, pp. S73-S79.

Kussie et al., "A Single Engineered Amino Acid Substitution Changes Antibody Fine Specificity", Journal of Immunology, 152, pp. 146-152 (1994).

Liesz et al., "Inhibition of Lymphocyte Trafficking Shields the Brain Against Deleterious Neuroinflammation Alter Stroke", Brain A Journal of Neurology, 134; pp. 704-720, (2011).

Masellis-Smith et al., "Adhesion of multiple myeloma peripheral blood B cells to bone marrow fibroblasts: a requirement for CD44 and alpha-beta?" Cancer Research 1997, 57, 930-936, XP002132841.

(56) References Cited

OTHER PUBLICATIONS

McDonald et al., "Are magnetic resonance findings predictive of clinical outcome in therapeutic trials in multiple sclerosis: The dilemma of interferon-b", Ann. Neurol., 1994, vol. 36, pp. 14-18.
Möhle et al., "Differential Expression of L-Selectin, VLA-4, and LFA-1 on CD34 Progenitor Cells from Bone Marrow and Peripheral Blood DuringG-CSF-Enhariced Recovery", Experimental Hematology, vol. 23, No. 14, pp. 1535-1542, (1995).
Patti et al., "A Double Blind, Placebo-Controlled, Phase II, add-on Study of Cyclophosphamide (CTX) for 24 months in Patients Affected by Multiple Sclerosis on a Background Therapy with Interferon-Beta Study Denomination: CYCLIN", Journal of the Neurological Sciences, vol. 223, No. 1, pp. 69-71, (2004).
Paty et al., "Interferon beta-1b is effective in relapsing-remitting multiple sclerosis. II. MRI analysis results of a multicenter, randomized, double-blind, placebo-controlled trial," UBC MS/MRI Study Group and the IFNB Multiple Sclerosis Study Group. Neurology 43:665, 1993.
Persson et al., "Generation of diverse high-affinity human monoclonal antibodies by repertoire cloning", PNAS USA, 1991, vol. 88, pp. 2432-2436.
Polman et al., "A randomized, placebo-controlled trial of natalizumab for relapsing multiple sclerosis", The New England Journal of Medicine, Mar. 2, 2006, vol. 354, No. 9, pp. 899-910, Massachusetts Medical Society, Waltham, MA.US.
Polman et al., Clinical results from AFFIRM: a randomized, double-blind, placebo-controlled, multicenter natalizumab in patients with relapsing multiple sclerosis (MSt, Neurology, Mar. 2005, vol. 64, No. 6, Suppl. 1, pp. A146, Abstract $16.003.
Polman, et al., "New and Emerging Treatment Options for Multiple Sclerosis", The Lancet Neurology, vol. 2, pp. 563-566, (2003).
Poon et al., "Emigrated Neutrophils Regulate Ventricular Contractility via Alpha4 Integrin", Gire. Res., vol. 84, No. 11, p. 1245-51 (1999).
Poser et al., "New diagnostic criteria for multiple sclerosis: guidelines for research protocols", Ann. Neural., 1983, vol. 13, pp. 227-231.
Powers el al., "Expression of single-chain Fv-Fc fusions in Pichia pastoris", J. Immunol. Methods, 2001, vol. 251, pp. 123-135.
Pozzilli el al., "Corticosteroids Treatment", Journal of the Neurological Sciences, vol. 223, No. 1, pp. 47-51, (2004).
Press et al., "Ricin A-Chain Containing Immunotoxins Directed Against Different Epitopes on the CO2 Molecule Differ in Their Ability to Kill Normal and Malignant T Cells", The Journal of Immunology, vol. 141, No. 12, pp. 4410-4417, (1988).
Pugliatti et al., "Multiple sclerosis distribution in northern Sardinia: spatial cluster analysis of prevalence", Neurology, 2002, vol. 58, No. 2, pp. 277-282.
European Search Report for Application No. 14165153 dated Nov. 6, 2014.
European Search Report for Application No. 14174865 dated Oct. 24, 2014.
Extended European Search Report issued in EP Application No. 14820267, mailed May 4, 2017.
Extended European Search Report for 0582495.4 dated Aptil 29, 2010.
Fillipini et al., "Interferons in Relapsing Remitting Multiple Sclerosis: A Systematic Review", The Lancet, vol. 361, pp. 545-552, (2003).
Hoogenboom et al., "Antibody phage display technology and its applications", Immunotechnology, 1998, vol. 4, pp. 1-20.
Hoogenboom et al., "Natural and designer binding sites made by phage display technology", Immunol. Today, 2000, vol. 2, pp. 371-378.
International Preliminary Report on Patentability for PCT/US2011/032641 dated Oct. 16, 2012.
International Search Report for International Application No. PCTU2014045457 dated Nov. 3, 2014.
International Search Report for PCT/US2011/032641 dated Jan. 24, 2012.

Japanese Office Action for Application 2007-543322 dated Feb. 23, 2012.
Jefferis et al., "IgG-Fc-mediated effector functions: molecular definition of interaction sites for effector ligands and the role of glycosylation", Immunol. Rev., 1998, vol. 163, pp. 59-76.
Jiang et al., "A Novel Peptide Isolated from a Phage Display Peptide Library with Transtuzumab Can Mimic Antigen Epitope of HER-2", The Journal of Biological Chemistry, vol. 280, No. 6, pp. 4656-4662, (2005).
Chen et al., "Enhancement and destruction of antibody function by somatic mutation: unequal occurrence is controlled by V gene combinatorial associates", The EMBO Journal, vol. 14, No. 12, pp. 2784-2794 (1995).
Written Opinion for International Application No. PCT/US2014/045457 dated Nov. 3, 2014.
Written Opinion for PCT/US2005/029407 dated Jun. 20, 2006.
Csanaky et al., "Adhesion receptors on peripheral blood leukemic B cells. A comparative study, on B cells. A comparative study on B cell chronic lymphocytic leukemia and related lymphoma/leukemias", (1997), Leukemia 11:408-415.
Berge et al., "Pharmaceutical salts", J. Pharm. Sci., 1977, vol. 66, pp. 1-19.
Berger et al., "Progressive Multifocal Leukoencephalopathy Lessons from AIDS and Natalizumab", Neurological Research, vol. 28, No. 3, pp. 299-305, (2006).
Bilińska et al., "Progression of multiple sclerosis is associated with exon 1 CTLA-4 gene polymorphism", Acta Neurol. Scand., 2004 vol. 110, No. 1, pp. 67-71.
Bird et al., Single-chain antigen-binding proteins., Science, 1988, vol. 242, pp. 423-426.
Burton et al., "Human antibody effector function", Adv. Immunol., 1992, vol. 51, pp. 1-84.
International Search Report and the Written Opinion of the International Searching Authority, issued in corresponding International Application No. PCT/US2019/034962, dated Nov. 13, 2019, 29 pages.
Sotgiu et al. "Treatment of refractory epilepsy with natalizumab in a patient with multiple sclerosis. Case report" BMC Neurology, 2010, http://www.biomedcentral.com/1471-2377/10/84, 10:84, 8 pages.
Peters et al. "Engineering an Improved IgG4 Molecule with Reduced Disulfide Bond Heterogeneity and Increased Fab Domain Thermal Stability" Journal of Biological Chemistry, Jul. 13, 2012 American Society for Biochemistry and Molecular Biology, vol. 287, No. 29, pp. 24525-24533.
Scott et al., "Searching for peptide ligands with an epitope library." (1990) Science 249:386-390.
Skolnick et al., "From Genes to Protein Structure and Function", Trends in Biotech, (2000), vol. 18, pp. 34-39.
Söderstrom et al., "Optic neuritis: prognosis for multiple sclerosis from MRI, CSF, and HLA findings", Neurology, (1998), vol. 50, pp. 708-714.
Soilu-Hänninen et al., "Therapy with Antibody Against Leukocyte Integrin VLA-4 (CD49d) is Effective and Safe in Virus-Facilitated Experimental Allergic Encephalomyelitis", J. Neuroimmunol, vol. 72, No. 1, p. 95-105 (1997).
Supplemental European Search Report for EP 05 80 4218.5 dated Dec. 15, 2008.
Hart et al., "Modelling of multiple sclerosis: lessons learned in a non-human primate," Oct. 2004, The Lancet Neurology 3(10):588-597.
Papadopoulos et al., "Pattern of Expression of integrins in alveolar epithelia of fetal and adult lungs and interstitial lung diseases," Verhandfungen Der Deutschen Gesellschaft For Pathologie, vol. 77, (1993), pp. 292-295.
Taylor et al., "Survival signals within the tumour microenvironment suppress drug-induced apoptosis: lessons learned from B lymphomas." (1999) Endocr. Related Cancer 6:21-23.
The Merck Manual of Diagnosis and Therapy, (1999), pp. 302-312, Seventeenth Edition, edited by Beers et al., published by Merck Research Laboratories, Whitehouse Station, NJ.
The Written Opinion of International Application No. PCT/US10/31407, dated Jun. 29, 2010.

(56) References Cited

OTHER PUBLICATIONS

Tintore et al., "Isolated demyeliniating syndromes: comparison of different MR imaging criteria to predict conversion to clinically definite multiple sclerosis", AJNR Am. J. Neuroradiol., (2000), vol. 21, pp. 702-706.
Tubridy, "The effect of anti-[alpha]4 integrin antibody on brain lesion activity in MS. The UK Antegren Study Group." Neurology, (1999), vol. 53, No. 3, pp. 466-472.
Uchiyama et al., "Characterization of adhesion molecules on human myeloma cell lines." (1992) Blood 80:2306-2314.
Vaughan et al., "Human antibodies with sub-nanomolar affinities isolated from a large non-immunized phage display library", Nat. Biotechnol., (1996), vol. 14, No. 3, pp. 309-314.
Vollmer et al., "An open-label safety and drug interaction study of natalizumab (AntegrenTM) in combination with interferon-beta (Avonex®) in patients with multiple sclerosis", Multiple Sclerosis, (2004), vol. 10, No. 5, pp. 511-520, Abstract only.
Wahl et al., "Synthetic fibronectin peptides suppress arthritis in rats by interrupting leukocyte adhesion and recruitment." (1994) J. Clin. Invest. 94:655-662.
Weekes et al., "VLA-4 mediated adhesion to bone marrow stromal cells confers chemoresistance to adherent lymphoma cells." (2001) Leuk. Lymphoma 40:631-45.
Witzig "The role of adhesion receptors in the pathogenesis of multiple myeloma." (1999) Hematol. Oncol. Clin. North D Am. 13:1127-1143.
Wolinsky, J.S., et al., "Rational therapy for relapsing multiple sclerosis", Lancet Neural., 2:5(271-272) 2003.
Written Opinion for PCT/US2005/029407 dated Feb. 20, 2007.
Written Opinion PCT/US2005/029403 dated Apr. 13, 2006.
Written Opinion PCT/US2005/043980 dated Feb. 1, 2007.
Rudikoff et al., "Single amino acid substitution altering antigen-binding specificity", Proc Natl Acad Sci USA 79: 1979-1983 (1982).
Elkins J, et al., "Primary Results of the ACTION trial of Natalizumab in Acute Ischemic Stroke (AIS)'," International Stroke Conference, (2016), 1-16.
Spelman et al., "Comparative efficacy of switching to natalizumab in active multiple sclerosis", Annals of Clinical and Translational Neurology, 2015; 2(4), pp. 373-387.
Purse, Maria, "Therapeutic Level, Therapeutic Drug Leve0—Definition", downloaded from internet About.com, About Health, Bipolar Dictionary of Bipolar Terms on Oct. 1, 2015, http://bipolar.about.com/od/glossaryt/g/gltherapeutic_level.htm.
Sotgiu et al. "Treatment of Refractory Epilepsy with Natalizumab in a Patient with Multiple Sclerosis" Case Report BMC Neurology 2010, 10:84, pp. 1-8.
Peters et al. "Engineering an Improved igG4 Molecule with Reduced Disulfide Bond Heterogeneity and Increased Fab Domain Thermal Stability" The Journal Of Biological Chemistry, vol. 287, Jul. 13, 2012, No. 29, pp. 24525-24533; DOI 10.1074/jbc.M112.369744.
Rapalino et. al., "Implantation of Stimulated homologous Macrophages Results in Partial Recovery of Paraplegic Rats", Nat. Med., vol. 4., p. 814-821 (1998).
Reindl et al., "Antibodies against the myelin oligodendrocyte glycoprotein and the myelin basic protein in multiple sclerosis and other neurological diseases: a comparative study", Brain, (1999), vol. 122, pp. 2047-2056.
Relton et. at., "Inhibition of Alpha4 Integrin Protects Against Transient Focal Cerebral Ischemia in Normotensive and Hypertensive Rats", Stroke, vol. 31, No. 1, p. 199-205 (2001).
Rizzo et al., "Risk of developing multiple sclerosis after uncomplicated optic neuritis: a long-term prospective study", Neurology, 1988, vol. 38, pp. 185-190.
Michigami et al., "Cell-cell contact between marrow stromal cells and myeloma cells via VCAM-1 and alpha(4)beta (1)-integrin enhances production of osteoclast-stimulating activity." (2000) Blood 96:1953-1960.
Miller et al., "A controlled trial of natalizumab for relapsing multiple sclerosis", New England Journal of Medicine, Jan. 2, 2003, vol. 384, No. 1, pp. 15-23, Massachusetts Medical Society, Boston MA, US.
Miller et al., "Colloquim C15: natalizumab (anti-VLA4 antibody) in multiple sclerosis", Journal of NeuroChemistry, Jan. 1, 2003, vol. 85, No. Suppl. 1, pp. 96, New York, NY, US.
Miller et al., "Gadolineum enhances (Gd+) lesions and baseline relapse rate as potential predictiors of disease activity and responsiveness to natalizemab (Antegren) treatment in subjects with relapsing multiple sclerosis (MS)" Multiple Sclerosis, 2003, vol. 9, Suppl 1, pp. S140-S141, Abstract p. 562.
Miller et al., "Natalizumab (anti-VLA4 antibody) in multiple sclerosis", Journal of Neurochemistry, 2003, vol. 85, No. Suppl. 1, pp. 96, (C15-04).
Möller et al., "Adhesion molecules VLA-1 to VLA-6 define discrete stages of peripheral B lymphocyte development and characterize different types of B cell neoplasia." (1992) Leukemia 6:256-264.
Mori et al., "Anti-alpha4 integrin antibody suppresses the development of multiple myeloma and associated osteoclastic osteolysis." (2004) Blood 104:2149-2154, epub May 11, 2004.
Mulligan et. al., "Cytokine and Adhesion Molecule Requirements for Lung Injury Induced by Anti-Glomerular Basaement Membrane Antibody", Inflammation, vol. 22, No. 4, p. 403-17 (1998).
Nakao et al., "Synergistic effect of TNF-alpha in soluble VCAM-1-induced angiogenesis through alpha 4 integrins." (2003) Immunol. 170:5704-5711.
Nowlin et al., "A novel cyclic pentapeptide inhibits alpha 4 beta 1 and alpha 5 beta 1 integrin-mediated cell adhesion." (1993) J. Biol. Chem. 268(27):20352-20359.
O'Connor et al., "Safety, tolerability and immunogenicity of natalizumab: results from the AFFIRM trial", Neurology, Mar. 1, 2005, vol. 64, No. 6, Suppl. 1, pp. A146, Abstract S16.004. Lippincott Williams & Wilkins. Philadelphia, US.
O'Riordan et al., "The prognostic value of brain MRI in clinically isolated syndromes of the CNS. A 10-year follow-up", Brain, 1998, vol. 121, PI. 3, pp. 495-503.
Olerup et al., HLA class II-associated genetic susceptibility in multiple sclerosis: a critical evaluation, Tissue Antigens, 1991, vol. 38, pp. 1-15.
Paavonen et al. "In vivo evidence of the role of alpha 4 beta 1-VCAM-1 interaction in sarcoma, but not in carcinoma extravasation," (1994) Int. J. Cancer 58:298-302.
Paty et al., "MRI in the diagnosis of MS: a prospective study with comparison of clinical evaluation, evoked potentials oligoclonal banding, and CT", Neurology, 1988, vol. 38, pp. 180-185.
Pericak-Vance et al., "Linkage and association analysis of chromosome 19q13 in multiple sclerosis", Neurogenetics, 2001, vol. 3, pp. 195-201.
Perkin et al., "IgG ratios and oligoclonal IgG in multiple sclerosis and other neurological disorders", J. Neural. Sci., 1983, vol. 60, No. 2, pp. 325-336.
Biogen Idec and Elan Corp., "Antegren one-year data from phase III AFFIRM study showed compelling results in meeting primary endpoint in multiple sclerosis", [Online] (2004).
Doctor's Guide to the Internet, Antegren one-year data show compelling results in meeting primary endpoint in multiple sclerosis [Online] (2004), http://docguide.com/dg.nsf/PrintPrint149282311DB732C5985256F470074BAC1 >.
Arnason, "Interferon beta in multiple sclerosis", Neurology, 1993, vol. 43, pp. 641-643.
Apatoff, Brian R., "Multiple Sclerosis (MS)". Merck, pp. 1-6, 2008.
Arai, M., "The usefulness of oligoclonal bands in cerebrospinal fluids for diagnosis in multiple sclerosis", Biophysical Chemistry, 44:4(295-300), 2000.
Arthritis & Rheumatism, "Abstract Supplement", 1996, vol. 39, No. 9, pp. 8284.
Atwood, "The Babel of Bioinformatics", Science, 2000, vol. 290, pp. 471-473.
Barcellos et al., "Chromosome 19 single-locus and multilocus haplotype associations with multiple sclerosis. Evidence of a new susceptibility locus in Caucasian and Chinese patients". JAMA, 1997, vol. 278, pp. 1256-1271.

(56) References Cited

OTHER PUBLICATIONS

Barkhof et al., "Comparison of MRI criteria at first presentation to predict conversion to clinically definite multiple sclerosis", Brain, 1997, vol. 120, pp. 2059-2069.
Bavbek et al., "Monoclonal Antibodies Against ICAM-1 and CD18 Attenuate Cerebral Vasospasm After Experimental Subarachnoid Hemorrhage in Rabbits", Stroke, vol. 29, No. 9, p. 1930-1935 (1998).
Beck et al., "The effect of corticosteroids for acute optic neuritis on the subsequent development of multiple sclerosis. The Optic Neuritis Study Group", N. Engl. J. Med., 1993, vol. 329, pp. 1764-1769.
Becker et. al., "Antibody to the Alpha4 Integrin Decreases Infarct Size in Transient Focal Cerebral Ischemia in Rats", Stroke, vol. 32, No. 1, p. 206-211 (2001).
Becker et. al., "Immunologic Tolerance to Myelin Basic Protein Decreases Stroke Sixe After Tansient Focal Cerebral schemia", Proc. Natl. Acad. Seo USA, vol. 94, No. 20, p. 10873-10878 (1997).
Bilinska et al., "Progression of multiple sclerosis is associated with exon 1 CTLA-4 gene polymorphism", Acta Neural. Scand., 2004 vol. 110, No. 1, pp. 67-71.
Boerner et al., "Production of antigen-specific human monoclonal antibodies from in vitro-primed human splenocytes", J. Immunol., 1991, vol. 147, pp. 86-95.
Bot et al., "Differentiation of multiple sclerosis from other inflammatory disorders and cerebrovascular disease: value of spinal MR imaging", Radiology, 2002, vol. 112. pp. 46-56.
Brex et al., "Assessing the risk of early multiple sclerosis in patients with clinically isolated syndromes: the role of a follow up MRI," Mar. 2001, J Neural Neurosurg Psychiatry 70(3):390-393.
Brugge et al., "A mouse model for chronic lymphocytic leukemia based on expression of the SV40 large T antigen" Blood, online Mar. 30, 2009, 001 10.1182/blood-2009-01-198937.
Calabresi et al., "VLA-4 expression on peripheral blood lymphocytes is downregulated after treatment of multiple sclerosis with interferon b", Neurology, 1997, vol. 49, pp. 1111-1116.
Choudry et al., "Single-patient study for the emergency use of natalizumab (Antegren) in the treatment of pediatric multiple sclerosis", Neurology, 2004, vol. 62, Suppl., 5, pp. A488-A489, Abstract P06.082.
Clark et al., "Antibodies against Mac-1 Attenuate Neutrophil Accumulation After Tramatic Brain Injury in Rats", Journal of Neurotrauma, vol. 13, No. 6, p. 333-341 (1996).
Clark et al., "Reduction of Central Nervous System Ischemic Injury in Rabbits Using Leukosyte Adhesion Antibody Treatment," Stroke, vol. 22, No. 7, p. 877-883 (1991).
emice.nci.nih.gov/emice/mouse_models/organ_models/hema_models/hema_mouse_tools dated Oct. 30, 2004.
Endo K, "Review/Advances in Neurological Therapeutics (2003). Multiple Sclerosis", Neurological Therapeutics, 21:4 (387-392), 2004.
European Search Report for EP05 00 7878.1 dated Oct. 15, 2013.
Extended European Search Report for EP 05853017.1 dated Nov. 5, 2008.
Extended European Search Report for 05824954.1 dated Apr. 29, 2010.
Fazekas et al., "Criteria for an increased specificity of MRI interpretation in elderly subjects with suspected multiple sclerosis", Neurology, 1988, vol. 38, pp. 1822-1825.
Ferguson et al., "Two integrin-binding peptides abrogate T cell-mediated immune responses in vivo," (1991) Proc. Natl. Acad. Sci. USA, 88:8072-8076.
Fleming, J., et al., "alpa4beta1 Integrin Blockade After Spinal Cord Injury Decrease Damage and Improves Neurological Function", Experimental Neurology, vol. 214, p. 147-159 (2008).
Fox et al., "Multiple Sclerosis: The importance of early recognition and treatment", Clevaland Clin. J. Med., 2001, vol. 68, pp. 157-171.
Frohman et al., "The utility of MRI in suspected MS: report of the Therapeutic and Technology Assessment Subcommittee of the American Academy of Neurology", Neurology, 2003, vol. 61, No. 5, pp. 602-611.

Galetta et al., "The effects of natalizumab on disaility progression as measured by the Multiple Sclerosis Functionaly Composite (MSFC) and visual function in patients with relapsing MS," Journal of Neurological Sciences, Jan. 1, 2005, vol. 238, Abstract OPL 100, Elsevier Scientific Publishing CO, Amsterdam, NL.
Extended European Search Report issued in European Application No. 19815783.6 dated Apr. 29, 2022, 14 pages.
Chothia et al., "Canonical structures for the hypervariable regions of immunoglobulins", J. Mol. Biol., 1987, vol. 196, pp. 901-917.
Clinica, 1996, vol. 23, No. 5, p. 389-393. (English Abstract).
Colman, "Effects of amino acid sequence changes on antibody-antigen interactions", Research in Immunology, 145, pp. 33-36 (1994).
Cuypers et al., "Discriminative power of visual evoked potential characteristics in multiple sclerosis", Doc. Ophthalmol., 1995, vol. 90, No. 3, pp. 247-257.
Dalton et al., "Early development of multiple sclerosis is associated with progressive grey matter atrophy in patients presenting with clinically isolated syndromes", Brain, 2004, vol. 127, Pt. 5, pp. 1101-1107.
Dalton et al., "Effect of natalizumab on conversion of gadolinium enhancing lesions to T1 hypointense lesion in relapsing multiple sclerosis", Journal of Neurolinguistics, 2004, vol. 251, pp. 407-413.
Damiano et al., "Cell adhesion mediated drug resistance (CAM-DR): role of integrins and resistance to apoptosis in human myeloma cell lines." (1999) Blood 93:1658:1667.
Damiano et al., "Cell adhesion-mediated drug resistance (CAM-DR) protects the K562 chronic myelogenous leukemia cell line from apoptosis induced by BCR/ABL inhibition, cytotoxic drugs, and gamma-irradiation." (2001) Leukemia 15:1232-1239.
De La Fuente et al., "Engagement of alpha4beta1 integrin by fibronectin induces in vitro resistance of B chronic lymphocytic leukemia cells to fludarabine." (2002) J. Leukocyt. Biol. 71 :495-502.
De La Fuente et al., "Fibronectin interaction with alpha4beta1 integrin prevents apoptosis in B cell chronic lymphocytic leukemia: correlation with Bcl-2 and Bax." (1999} Leukemia 13:266-274.
De Waele et al., "Different Expression of Adhesion Molecules on CD34 Cells in AML and B-Lineage ALL and Their Normal Bone Marrow Counterparts", Eur. J. Haematol, vol. 63, No. 3, pp. 192-201, (1999).
Devlin et al., "Random peptide libraries: a source of specific protein binding molecules." (1990) Science 249:404-406.
Dillman, "The History and Rationale for Monoclonal Antibodies in the Treatment of Hematologic Malignancy", Current Pharmaceutical Biotechnology, vol. 2, No. 4, pp. 293-300, (2001).
Drillenburg et al., "Preferential expression of the mucosal homing receptor integrin alpha 4 beta 7 in gastrointestinal non-Hodgkin's lymphomas" (1997) Am. J. Pathol. 150:919-927.
Edan, "Rationale for the Use of Mitoxantrone in Multiple Sclerosis", Journal of Neurological Sciences, vol. 223, No. 1, pp. 35-39, (2004).
Kurtzke, "Rating neurologic impairment in multiple sclerosis: an expanded disability status scale (EDSS)." Neurology 33:1444, (1983).
Powers et al. "Expression of single-chain Fv-Fc fusions in Pichia pastoris." (2001) J. Immunol. Methods 251:123-35.
Pulido et al., "Functional evidence for three distinct and independenl1y inhibitable adhesion activities mediated by the human integrin VLA-4. Correlation with distinct alpha 4 epitopes" J. Biol. Chem. 266:10241-10245, (1991).
Riechmann et al., "Reshaping human antibodies for therapy." (1988), Nature 332, 323-327.
Sanchez-Madrid et al., VLA-3: a novel polypeptide association within the VLA molecular complex: cell distribution and biochemical characterization. Eur. J. Immunol. 16:1343-1349, (1996).
Sipe et al., "A neurologic rating scale (NRS) for use in multiple sclerosis" Neurology 34:1368, (1984).
Sobel et al., "The immunopathology of experimental allergic encephalomyelitis. I. Quantitative analysis of Inflammatory cells in situ" J. Immunol. (1984) 132: 2393-2401.

(56) References Cited

OTHER PUBLICATIONS

Traugott, Detailed analysis of early immunopathologic events during lesion formation in acute experimental autoimmune encephalomyeliitis (Cell Immunol. (1989) 119: 114-129).
Tuohy et al., "A synthetic peptide from myelin proteolipid protein induces experimental allergic encephalomyelitis" J. Immunol. (1988) 141: 1126-1130.
Urlaub and Chasin, "Isolation of Chinese hamster cell mutants deficient in dihydrofolate reductase activity." (1980) Proc. Natl. Acad. Sci. USA 77:4216-4220.
Verhoeyen et al., Reshaping human antibodies: grafting an antilysozyme activity. (1988), Science 239, 1534-1536.
Ward et al., "Binding activities of a repertoire of single immunoglobulin variable domains secreted from *Escherichia coli*" (1989) Nature 341:544-546.
Williams, et al., "The immunoglobulin superfamily-domains for cell surface recognition" (1988) Ann. Rev. Immunol. 6:381-405.
Written Opinion for PCT/US2011/032641 dated Oct. 16, 2012.
Riemer et al., "Matching of Transtuzumab (Herceptin®) Epitope Mimics onto the Surface of Her-2/neu—A New Method of Epitope Definition", Molecular Immunology, vol. 42, pp. 1121-1124, (2005).
Sandborn et al., "Efficacy assessment of natalizumab in patients with Crohn's disease and prior history of anti-TNF therapy: Results from ENACT-1.", Gastroenterology, 126(suppl 2), pp. 571-580, Jul. 2004 (Jul. 2004).
Stancovski et al., "Mechanistic Aspects of the Opposing Effects of Monoclonal Antibodies to the ERBB2 receptor on Tumor Growth", Proceedings of the National Academy of Science USA, vol. 88, pp. 8691-8695, (1991).
Sweet, "Natalizumab Update", American Journal of Health-System Pharmacy, vol. 64, No. 7, pp. 705-716.
Tagliaferri et al., "Pharmacological Modulation of Peptide Growth Factor Receptor Expression on Tumor Cells as a Basis for Cancer Therapy", Anti-Cancer Drugs, vol. 5, No. 4, pp. 379-393, (1994).
Velders et al., "Immunotherapy with Low and High Affinity Monoclonal Antibodies 17-17A and 323/A3 in a Nude Mouse Xenograft Carcinoma Model", Cancer Research, vol. 55, No. 19, (1995).
Roy-Chaudhury et al., "Adhesion molecule interactions in human glomerulonephritis: importance of the tubulointerstitium." Kidney International, vol. 49, No. 1, Jan. 1996 (Jan. 1996), pp. 127-134.
Rudick et al., "Baseline patient characteristics of the SENTINEL study: a study designed to determine the efficacy and safety of natalizumab (Antegren) in combination with interferon b-1a (Avonex) for the treatment of relapsing-remitting multiple sclerosis (RRMS)" Multiple Sclerosis, (2003), vol. 9, Suppl., 1, pp. S141-S142, Abstract p. 565.
Rudick et al., "Natalizumab: a4-integrin antagonist selective adhesion molecule inhibitors for MS", Expert Review of Neurotherapeutics, (2004), vol. 4-, No. 1, pp. 571-580.
Rudick et al., "Study designs of two phase III trials to determine the safety and efficacy of natalizumab (Antegren) alone and when added to interferon b-1a (Aveonex) in patients with relapsing-remitting multiple sclerosis", Neurology, (2003), vol. 60, No. 5, Supplement 1, pp. A479.
Sadovnick, Clinical Neurology and Neurosurgery, (2002), vol. 104, pp. 199-202.
Sandborn et al., "Efficacy assessment of natalizumab in patients with Crohn's disease and prior history of anit-TNF therapy: results from ENACT-1", Database Biosis, (2004), Biosciences Information Service, Philadelphia, PA.
Sandborn, et al., "AGA Abstracts", Gastroenterology, 4; vol. 126, No. 4, p. A76 (2004).
Schiffer et al., "A multiple sclerosis cluster associated with a small, north-central Illinois community", Arch. Environ. Health, (2001), vol. 56, No. 5, pp. 389-395.
Schmidt et al., "Association of polymorphisms in the apolipoprotein E region with susceptibility to and progression of multiple sclerosis", Am. J. Hum. Genet., (2002), vol. 70, pp. 708-717.

Schnell, L. et al., "Acute Inflammatory Response to Mechanical Lesions in 1he CNS: Differences Between Brain and Spinal Cord," Eur J Neurosci, vol. 11, p. 3648-3658 (1999).
Schnell. L. et al., "Cytokine-induced Acute Inflammation in the Brain and Spinal Cord," J Neuropathol Exp Neurol, vol. 55, p. 245-254 (1999).
Schwartz et al., "Potential Repair of Rat Spinal Cord Injuries Using Stimulated Homologous Macrophages," Neurosurgery, vol. 44, p. 1041-1045 (1999).
Schwartz et al., "Protection Autoimmunity in Acute and Chronic CNS Disorders: Therapeutic Vaccines, Immunolog, and Hematopoiesis", pp. 234-235 (2002).
Schwartz et. al., "Autoimmunity for Central Nervous System Maintenance, Regeneration, and Renewal: Development of a T Cell-Based Vaccination Against Neurodegeneration," Stem cell and Gene-Based Therapy, pp. 251-257 (2006).
Schwartz et. al., "Innate and Adaptive immune Response Can be Beneficial for CNS Repair", Trends in Neurscienses, vol. 22, p. 295-299 (1999).
Yanaka et al., "Neuronal Protection from Cerebral Ischemia by Synthetic Fibronectic Peptides to Keukoycyte Adhesion Molecules", Journal of Cerebral Blood Flow & Metabolism, p. 1120-1125, 16 (1996).
Yednock et al., "Prevention of experimental autoimmune encephalomyelitis by antibodies against alpha 4 beta 1 integrin," Nature, 1992, vol. 3356, pp. 63-66.
Yin et al., Drug Discovery Today: Disease Models 3(2):137-142 (2006).
International Preliminary Report on Patentability issued in PCT/US2011/032641 dated Oct. 16, 2012, 19 pages.
Written Opinion of the International Searching Authority issued in PCT/US2011/032641 dated Oct. 16, 2012, 18 pages.
Communication pursuant to Article 94(3) EPC issued in European Application No. 11 730 120.0-1403 dated Aug. 28, 2013, 21 pages.
Response filed in European Application No. 11730120.0 dated Mar. 7, 2014, 10 pages.
Communication pursuant to Article 94(3) EPC issued in European Application No. 11 730 120.0-1403 dated Oct. 21, 2014, 8 pages.
Response filed in European Application No. 11730120.0 dated Apr. 30, 2015, 8 pages.
Communication pursuant to Article 94(3) EPC issued in European Application No. 11 730 120.0-1403 dated Jan. 26, 2016, 7 pages.
Response filed in European Application No. 11730120.0 dated Aug. 5, 2016, 11 pages.
Office Action cited in U.S. Appl. No. 13/641,199 dated Feb. 8, 2016, 12 pages.
Extended European Search Report dated Apr. 21, 2017, cited in application No. 17163411.6-1403, 8 pages.
Response to Search Opinion in European application No. 17163411.6, dated Jun. 4, 2018, 8 pages.
Communication pursuant to Article 94(3) EPC issued in European Application No. 17 163 411.6 dated Aug. 6, 2018, 5 pages.
Response filed in European Application No. 17163411.6 dated Oct. 8, 2018, 15 pages.
Office Action cited in Indian Application No. 8968/DELNP/2012 dated May 3, 2018, 7 pages.
Hall el al., "Heterophilic interactions between cell adhesion molecule L 1 and alpha-v beta3-integrin induce HUVEC process extension in vitro and angiogenesis in vivo." (2004) Angiogenesis 7:213-23.
Hamada et al., "Involvement of an Intercellular Adhesion Molecule 1-Dependant Pathway in the Pathogenesis of Secondary Changes After Spinal Cord Injury in Rats," J Neurochem, vol. 66, No. 4, p. 1525-1531 (Apr. 1996).
Hemler et al., "Characterization of the cell surface heterodimer VLA-4 and related peptides", J. Biol. Chem., 1987, vol. 2, pp. 11478-11485.
Hernan et al., "Recombinant hepatitis B vaccine and the risk of multiple sclerosis: a prospective study", Neurology, 2004, vol. 63, pp. 838-842.
Hokibara et al.: "Effects of monoclonal antibodies to adhesion molecules on eosinophilic myocarditis in Toxocara canis-infected

(56) References Cited

OTHER PUBLICATIONS

CBA/J mice." Clinical and Experimental Immunology, vol. 114, No. 2, Nov. 1998 (Nov. 1998), pp. 236-244.
Holzmann et al. "alpha 4 integrins and tumor metastasis." (1998) Current Topics on Micbiological Immunology 231 :125-141.
http://emice.nci.nih.gov/emice/mouse_models/organ _ models/ hema _ models/hema_mouse_tools/selected_references; dated Oct. 31, 2004 dowloaded from http://replay.waybackmachineorg/20041 031161411 /http:1/emice.nci.D nih.gov/emice/ D mouse_models/ organ _ models/hema _ models/hema _mouse_tools/selected _references on Oct. 14, 2010.
Huang et al., "Construction of representative immunoglobulin variable region cDNA libraries from human peripheral blood lymphocytes without in vitro stimulation", J. Immunol. Methods, 1991, vol. 141, No. 2. pp. 227-236.
Huston et al., "Protein engineering of antibody binding sites: recovery of specific activity in an anti-digoxin single-chain Fv analogue produced in *Escherichia coli*", PNAS USA, 1988, vol. 85, pp. 5879-5883.
International Preliminary Report on Patentability & Written Opinion for PCT/US05/29569 dated Feb. 20, 2007.
International Search Report for PCT/US05/29407 mailed Jun. 20, 2006.
International Search Report for PCT/US05/29569 dated Oct. 19, 2006.
International Search Report for PCT/US05/43980 mailed Feb. 1, 2007.
International Search Report for PCT/US2005/029403 dated Apr. 13, 2006.
International Search Report of International Application No. PCT/US10/31407, dated Jun. 29, 2010.
Issekutz et al., "Effect of a new monoclonal antibody, TA-2, that inhibits lymphocyte adherence to cytokine stimulated endothelium in the rat", J. Immunol., 1991. vol. 147, pp. 109-116.
Jacobs et al., "Intramuscular interferon b-1a for disease progression in relapsing multiple sclerosis." The Multiple Sclerosis Collaborative Research Group (MSCRG), Ann. Neurol., 1996, vol. 39, pp. 285-294.
Jander et al., "Vascular Cell Adhesion Molecule-1 mRNA is Express in Immune-Mediated and Ischemic Injury of the Rat Nervous System", J Neuroimmunol, vol. 70, No. 1, p. 75-80 (1996).
Jin et al., "A homing mechanism for bone marrow-derived progenitor cell recruitment to the neovasculature." (2006) J. Clin. Invest. 116(3):652-62.
Jin et al., "Integrin alpha4beta1 promotes monocyte trafficking and angiogenesis in tumors." (2006) Cancer Res. 66(4):2146-2152.
Kapadia et al., Soluble TNF binding proteins modulate the negative inotropic properties of TNF-alpha in vitro, Amer. J. Physiol.—Heart and Circulatory Physiology, 1995, vol. 268, pp. H517-H525.
Kaplan et al., "VEGFR1-positive haematopoietic bone marrow progenitors initiate the pre-metastatic niche." (2005) Nature 438:820-827.
Knoblach et al., "Early Neuronal Expression of Tumor Necrosis Factor-Alpha After Experimantal Brain Injury Contributes to Neurological Impairment," Journal of Neuroimmunology, vol. 95, No. 1-2, p. 115-125 (1999).
Kohlschütter et al., "Drug delivery in acute myeloid leukemia." (Expert Opin. Drug Deliv. Jun. 2008; 5 (6): 653-63).
Komoriya et al., "The minimal essential sequence for a major cell type-specific adhesion site (CS1) within the alternatively spliced type III connecting segment domain of fibronectin is leucine-aspartic acid-valine." (1991) J. Biol. Chem. 266(23):15075-15079.
Labinez et al., "Infusion of an Antialpha4 Integrin Antibody is Associated with Less Neoadventitial Formation After Ballon Injury of Porcine Coroanry Arteries", Can. J. Cardiol., vol. 16, No. 2, p. 187-196 (2000).
Lin et al., "Very late antigen 4 (VLA4) antagonists as anti-inflammatory agents" Current Opinion in Chemical Biology, vol. 2, No. 4, Aug. 1998, p. 453-457.
Lobb et al., "The role of alpha-4 integrins in lung pathophysiology." European Respiratory Journal, Supplement, vol. 9. No. suppl. 22, Aug. 1996 (Aug. 1996) pp. 104S-108S.
Lobb et al., "The Pathophysiologic Role of Alpha4 Integrins in Vivo," J. Clin. Invest., vol. 94, No. 5, p. 1722-1728 (1994).
Mabon, J., "Strategies to Reduce Inflammation in the Central Nervous System", Master of Science Thesis, The University of Western Ontario, London, Ontario, Canada (Jan. 1999).
Matsunaga et al., "Combination therapy of an anticancer drug with the FNIII14 peptide of fibronectin effectively overcomes cell adhesion-mediated drug resistance of acute myelogenous leukemia." (2008) Leukemia 22:353-360.
Matsunaga et al., "Interaction between leukemic-cell VLA-4 and stromal fibronectin is a decisive factor for minimal residual disease of acute myelogenous leukemia." (2003) Nat. Med. 9: 1158-1165.
McDonald et al., "Recommended diagnostic criteria for multiple sclerosis: guidelines from the International Panel on the Diagnosis of Multiple Sclerosis", Ann. Neural., 2001, vol. 50, pp. 121-127.
Ausubel et al., Hybridization with Radioactive Probes. Current Protocols in Molecular Biology. pp. 6.3.1-6.3.6, (1993).
European Office Action for Application No. 0582495.4, dated Jun. 16, 2010, 13 pages.

\* cited by examiner

ESKYGPPCPS̄CPAPEFLGGPSVFLFPPKPKD
TLMISRTPEVTCVVVDVSQEDPEVQFNWYV
DGVEVHNAKTKPREEQFN̄STYRVVSVLTVLH
QDWLNGKEYCKVSNKGLPSSIEKTISKAK<u>G</u>
<u>QPREPQVYTLPPSQEEMTKNQVSLTCLVKG</u>
<u>FYPSDIAVEWESNGQPENNYKTTPPVLDSD</u>
<u>GSFFLYSRLTVDKSRWQEGNVFSCSVMHEA</u>
<u>LHNHYTQKSLSLSLG</u>

FIG. 5

```
huIgG1_CH1  PSVFPLAPSSKSTSGGTAALGCLVKDYF-P-EP-VTVSWN----SGAL-T---SGVHTFPAVLQSS----GLYSLSSVVTV-
huIgG1_CH3  PQVYTLPPSRDELTKNQVSLTCLVKGFY-P-SD-IAVEWESNGQPEN-N----YKTTPPVLDSD----GSFFLYSKLTV-
hukappa_CL  PSVFIFPPSDEQLKSGTASVVCLLNFY-P-RE-AKVQWKVDN-ALQ-S---GNSQESVTEQDSKD----STYSLSSTLTL-
huIgG1_CH2  PSVFLFPPKPKDTLMISRTPEVTCVVVDVS-HEDPEVKFNWYVDG-VEV-H---NAKTKPREEQYS----STYRVVSVLTVL
            1234569012345678 90 123456789012 56 901 2    34567890 1234       789012345678
Kabat#      5555556777777778 88 888888888999 9 900 0    00000000 1111       111222222222
            2222222222222222 22 222222222222 2 233 3    33333333 3333       333333333333

89012367890123 45 67 89012345678901 234 5    67890 1234567       89012345 6789
EU index    334445555555 66 66 66777777777778 888 8    88889 9999999       99000000 0000
            222222222222 22 22 22222222222222 222 2    22222 2222222       22333333 3333 huIgG1_CH1  PS-SSLGT----QTYICNVNHK-PS------NTKVDKR-V-ES-----
huIgG1_CH3  DK-SRWQQG----NVFSCSVMH-EA-LHN-HYTQKS-L-SS-----
hukappa_CL  SK-ADYEK----HKVYACEVTH---QG-L---SSPVTKS-F-NC-----
huIgG1_CH2  -H-QDWLNG----KEYKCKVSN---KA-LPA--PIEKT-I-SK-----
             9 012345    678901234   56 789   01234 5 78
Kabat#      2 333333    333344444   44 444   55555 5 55
            3 333333    333333333   33 333   33333 3 33

0 123456    789012345   67 890   12345 6 78
EU index    1 111111    111222222   22 223   33333 3 33
            3 333333    333333333   33 333   33333 3 33
```

FIG. 11B

```
                              2 2 22   2
                              6 6 66   7
                              2 4 67   2
Wild-type IgG sequence:     _VTCVVVDVSHEDPEVKFNWY_
Fully modified IgG sequence: _VTCLVIDISP-DP-VKFNWY_
```

FIG. 22A

```
      ATG GAT ATG CGC GTG CCT GCC CAA CTT CTC GGA CTT CTC CTC CTT TGG CTG CCT GGA GCC
  1    M   D   M   R   V   P   A   Q   L   L   G   L   L   L   L   W   L   P   G   A
      CGA TGT gag gtg cag ctg gtg cag agc ggc gcc gag gtg aag aag ccc ggc gcc acc gtg
 21    R   C   E   V   Q   L   V   Q   S   G   A   E   V   K   K   P   G   A   T   V
      aag atc agc tgc aag gcc agc ggc ttc aac atc aag gac acc tac atg cac tgg gtg cag
 41    K   I   S   C   K   A   S   G   F   N   I   K   D   T   Y   M   H   W   V   Q
      cag gcc ccc ggc aag ggc ctg gag tgg atg ggc cgc atc gac ccc gcc agc ggc gac acc
 61    Q   A   P   G   K   G   L   E   W   M   G   R   I   D   P   A   S   G   D   T
      aaA Tac gac ccc aag ttc caa GTC cgg gtg acc atc acc gcc gac acc agc acc gac acc
 81    K   Y   D   P   K   F   Q   V   R   V   T   I   T   A   D   T   S   T   D   T
      gcc tac atg gag ctg agc agc ctg cgc agc gag gac acc gcc gtg tac tac tgc gcc gac
101    A   Y   M   E   L   S   S   L   R   S   E   D   T   A   V   Y   Y   C   A   D
      ggc atg tgg GTC agc acc ggc tac gcc ctg gac ttc tgg cag cag ggc acc ctg gtg acc
121    G   M   W   V   S   T   G   Y   A   L   D   F   W   Q   Q   G   T   L   V   T
      gtC TCG AGC GCT AGT ACC AAG GGC CCA TCG GTC TTC CCC CTG GCG CCC TGC TCC CGG AGC
141    V   S   S   A   S   T   K   G   P   S   V   F   P   L   A   P   C   S   R   S
      ACC TCC GAG AGC ACA GCC GCC CTG GGC TGC CTG GTC AAG GAC TAC TTC CCC GAA CCT GTG
161    T   S   E   S   T   A   A   L   G   C   L   V   K   D   Y   F   P   E   P   V
      ACG GTG TCG TGG AAC TCA GGC GCC CTG ACC AGC GGC GTG CAC ACC TTC CCG GCT GTC CTA
181    T   V   S   W   N   S   G   A   L   T   S   G   V   H   T   F   P   A   V   L
      CAA TCC TCA GGA CTC TAC TCC CTC TCT TCC GTG GTG ACC GTG CCC TCC AGC AGC TTG GGC
201    Q   S   S   G   L   Y   S   L   S   S   V   V   T   V   P   S   S   S   L   G
      ACG AAG ACC TAC ACC TGT AAC GTA GAT CAC AAG CCC AGC AAC ACC AAG GTG GAC AAG AGA
221    T   K   T   Y   T   C   N   V   D   H   K   P   S   N   T   K   V   D   K   R
      GTT GAG TCC AAA TAT GGT CCC CCA TGC CCA CCT TGC CCA GCA CCT GAG TTC CTG GGG GGA
241    V   E   S   K   Y   G   P   P   C   P   P   C   P   A   P   E   F   L   G   G
      CCA TCA GTC TTC CTG TTC CCC CCA AAA CCC AAG GAC ACT CTC ATG ATC TCC CGG ACC CCT
261    P   S   V   F   L   F   P   P   K   P   K   D   T   L   M   I   S   R   T   P
      GAG GTC ACT TGC GTG GTG GTG GAT GTG AGC CAG GAA GAC CCC GAG GTC CAG TTT AAC TGG
281    E   V   T   C   V   V   V   D   V   S   Q   E   D   P   E   V   Q   F   N   W
      TAC GTG GAT GGC GTG GAA GTC CAC AAT GCC AAG ACA AAG CCG CGG GAG GAG CAG TTC CAA
301    Y   V   D   G   V   E   V   H   N   A   K   T   K   P   R   E   E   Q   F   Q
      AGC ACG TAC CGT GTG GTC AGC GTC CTC ACC GTC CTG CAC CAA GAC TGG CTG AAC GGC AAG
321    S   T   Y   R   V   V   S   V   L   T   V   L   H   Q   D   W   L   N   G   K
      GAG TAC AAG TGC AAG GTG TCC AAC AAA GGC CTC CCG TCC TCC ATC GAG AAA ACC ATC TCC
341    E   Y   K   C   K   V   S   N   K   G   L   P   S   S   I   E   K   T   I   S
      AAA GCC AAA GGG CAG CCC CGA GAA CCA CAG GTG TAC ACC CTG CCC CCA TCG CGG GAT GAG
361    K   A   K   G   Q   P   R   E   P   Q   V   Y   T   L   P   P   S   R   D   E
      CTG ACC AAG AAC CAG GTC TCG CTG ACC TGC CTG GTC AAA GGC TTC TAT CCC TCC GAC ATT
381    L   T   K   N   Q   V   S   L   T   C   L   V   K   G   F   Y   P   S   D   I
      GCC GTG GAG TGG GAG AGC AAT GGG CAG CCG GAG AAC AAC TAC AAG ACC ACG CCT CCC GTG
401    A   V   E   W   E   S   N   G   Q   P   E   N   N   Y   K   T   T   P   P   V
      TTG GAC TCC GAC GGC TCC TTC TTT CTC TAC TCC AAA CTC ACC GTG GAC AAG AGC AGG TGG
421    L   D   S   D   G   S   F   F   L   Y   S   K   L   T   V   D   K   S   R   W
      CAG CAG GGG AAC GTC TTC TCA TGC TCC GTG ATG CAT GAG GCT CTG CAC AAC CAC TAC ACG
441    Q   Q   G   N   V   F   S   C   S   V   M   H   E   A   L   H   N   H   Y   T
      CAA AAA AGC CTC TCC CTC AGC CCG GGC TGA
461    Q   K   S   L   S   L   S   P   G   *
```

FIG. 22B

Light Chain (HP1/2 L3 kappa ND001)

MDMRVPAQLL GLLLLWFPGS RCSIVMTQSP DSLAVSLGER ATINCKASQS VTNDVAWYQQ
KPGQPPKLLI YYASNRYTGV PDRFSGSGYG TDFTFTISSL QAEDVATYFC QQDYSSPYTI
GQGTKVEIKR TVAAPSVFIF PPSDEQLKSG TASVVCLLNN FYPREAKVQW KVDNALQSGI
SQESVTEQDS KDSTYSLSST LTLSKADYEK HKVYACEVTH QGLSSPVTKS FNRGEC

Heavy Chain (HP1/2 huIgG4/IgG1 agly N297Q H1 ND004/ND006)

MGWSLILLFL VAVATRVLSE VQLVQSGAEV KKPGATVKIS CKASGFNIKD TYMHWVQQAI
GKGLEWMGRI DPASGDTKYD PKFQVRVTIT ADTSTDTAYM ELSSLRSEDT AVYYCADGML
VSTGYALDFW GQGTLVTVSS ASTKGPSVFP LAPCSRSTSE STAALGCLVK DYFPEPVTVS
WNSGALTSGV HTFPAVLQSS GLYSLSSVVT VPSSSLGTKT YTCNVDHKPS NTKVDKRVES
KYGPPCPPCP APEFLGGPSV FLFPPKPKDT LMISRTPEVT CVVVDVSQED PEVQFNWYVD
GVEVHNAKTK PREEQFQSTY RVVSVLTVLH QDWLNGKEYK CKVSNKGLPS SIEKTISKAK
GQPREPQVYT LPPSRDELTK NQVSLTCLVK GFYPSDIAVE WESNGQPENN YKTTPPVLDS
DGSFFLYSKL TVDKSRWQQG NVFSCSVMHE ALHNHYTQKS LSLSPG

FIG. 23A

Mature light chain of HP1/2 hG4P agly(N297Q) G1 H1L3 ND0001 (SEQ ID NO: 81)

SIVMTQSPDS LAVSLGERAT INCKASQSVT NDVAWYQQKP GQPPKLLIYY
ASNRYTGVPD RFSGSGYGTD FTFTISSLQA EDVATYFCQQ DYSSPYTFGQ
GTKVEIKRTV AAPSVFIFPP SDEQLKSGTA SVVCLLNNFY PREAKVQWKV
DNALQSGNSQ ESVTEQDSKD STYSLSSTLT LSKADYEKHK VYACEVTHQG
LSSPVTKSFN RGEC

Mature heavy chain of HP1/2 hG4P agly(N297Q) G1 H1L3 ND0004/ND006 (SEQ ID NO: 80)

EVQLVQSGAE VKKPGATVKI SCKASGFNIK DTYMHWVQQA PGKGLEWMGR
IDPASGDTKY DPKFQVRVTI TADTSTDTAY MELSSLRSED TAVYYCADGM
WVSTGYALDF WGQGTLVTVS SASTKGPSVF PLAPCSRSTS ESTAALGCLV
KDYFPEPVTV SWNSGALTSG VHTFPAVLQS SGLYSLSSVV TVPSSSLGTK
TYTCNVDHKP SNTKVDKRVE SKYGPPCPPC PAPEFLGGPS VFLFPPKPKD
TLMISRTPEV TCVVVDVSQE DPEVQFNWYV DGVEVHNAKT KPREEQFQST
YRVVSVLTVL HQDWLNGKEY KCKVSNKGLP SSIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPG

FIG. 23B

1, HP 1/2 huIgG4P ag G1 HIL3 K15DKO, pI 6.22
2, HP 1/2 huIgG4P ag G1 HIL3 DG44i, pI 6.22
3, HP 1/2 huIgG4P H1L3, pI 6.01
4, HP 1/2 huIgG4PE H1L3, pI 5.91
5, Tysabri hG4P ag/G1, pI 8.09
6, IEF Marker 3-10

SEQUENCE LISTING

<160> NUMBER OF SEQ ID NOS: 103

<210> SEQ ID NO 1
<211> LENGTH: 121
<212> TYPE: PRT
<213> ORGANISM: Mus spretus

<400> SEQUENCE: 1

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Ser Gly Asp Thr Lys Tyr Asp Pro Lys Phe
    50                  55                  60

Gln Val Lys Ala Thr Ile Thr Ala Asp Thr Ser Ser Asn Thr Ala Trp
65                  70                  75                  80

Leu Gln Leu Ser Ser Leu Thr Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser
        115                 120
```

<210> SEQ ID NO 2
<211> LENGTH: 98
<212> TYPE: PRT
<213> ORGANISM: Homo sapiens

<400> SEQUENCE: 2

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr
```

<210> SEQ ID NO 3
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 3

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Met His Trp Val Gln Gln Ala Pro Gly Lys Gly Leu Glu Trp Met
```

```
                35                  40                  45
Gly Arg Ile Asp Pro Ala Ser Gly Asp Thr Lys Tyr Asp Pro Lys Phe
     50                  55                  60

Gln Val Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Met Trp Val Ser Gly Tyr Ala Leu Asp Phe Trp Gly
             100                 105                 110

Gln Gly Thr Leu Val Thr Val Ser Ser
         115                 120

<210> SEQ ID NO 4
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 4

Glu Val Gln Leu Val Gln Ser Gly Ala Glu Val Lys Lys Pro Gly Ala
  1               5                  10                  15

Thr Val Lys Ile Ser Cys Lys Ala Ser Gly Phe Asn Ile Lys Asp Thr
                 20                  25                  30

Tyr Met His Trp Val Gln Gln Ala Pro Gly Lys Gly Leu Glu Trp Met
             35                  40                  45

Gly Arg Ile Asp Pro Ala Ser Gly Asp Thr Lys Tyr Asp Pro Lys Phe
     50                  55                  60

Gln Val Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Asp Gly Met Trp Val Ser Gly Tyr Ala Leu Asp Phe Trp Gly
             100                 105                 110

Gln Gly Thr Leu Val Thr Val Ser Ser
         115                 120

<210> SEQ ID NO 5
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 5

Glu Val Gln Leu Val Gln Ser Gly Ala Glu Val Lys Lys Pro Gly Ala
  1               5                  10                  15

Thr Val Lys Ile Ser Cys Lys Ala Ser Gly Phe Asn Ile Lys Asp Thr
                 20                  25                  30

Tyr Met His Trp Val Gln Gln Ala Pro Gly Lys Gly Leu Glu Trp Ile
             35                  40                  45

Gly Arg Ile Asp Pro Ala Ser Gly Asp Thr Lys Tyr Asp Pro Lys Phe
     50                  55                  60

Gln Val Arg Ala Thr Ile Thr Ala Asp Thr Ser Thr Asn Thr Ala Tyr
 65                  70                  75                  80

Leu Glu Leu Ser Ser Leu Arg Ser Glu Asp Thr Ala Val Tyr Tyr Cys
                 85                  90                  95
```

Ala Asp Gly Met Trp Val Ser Thr Gly Tyr Ala Leu Asp Phe Trp Gly
            100                 105                 110

Gln Gly Thr Leu Val Thr Val Ser Ser
        115                 120

<210> SEQ ID NO 6
<211> LENGTH: 107
<212> TYPE: PRT
<213> ORGANISM: Mus spretus

<400> SEQUENCE: 6

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Thr Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 7
<211> LENGTH: 101
<212> TYPE: PRT
<213> ORGANISM: Homo sapiens

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 8
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Thr Asn Asp
                20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Pro Tyr
                85                  90                  95

Thr Phe Gly Gln Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 9

Ser Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Thr Asn Asp
            20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Pro Tyr
                85                  90                  95

Thr Phe Gly Gln Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 10

Ser Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Thr Asn Asp
            20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
        50                  55                  60

Ser Gly Tyr Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Pro Tyr
                85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 11

```
Ser Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Thr Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Ala
65                  70                  75                  80

Glu Asp Val Ala Thr Tyr Phe Cys Gln Gln Asp Tyr Ser Ser Pro Tyr
                85                  90                  95

Thr Phe Gly Gln Gly Thr Lys Val Glu Ile Lys
            100                 105
```

<210> SEQ ID NO 12
<211> LENGTH: 107
<212> TYPE: PRT
<213> ORGANISM: Homo sapiens

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Lys Thr Tyr
            20                  25                  30

Leu Ser Trp Phe Gln Gln Lys Pro Gly Lys Pro Pro Lys Leu Leu Ile
        35                  40                  45

Ser Asp Ala Ser Gly Phe Gln Pro Gly Val Pro Ser Arg Phe Ser Gly
    50                  55                  60

Ser Gly Tyr Gly Thr Asp Phe Ser Phe Thr Ile Thr Ser Leu Arg Pro
65                  70                  75                  80

Asp Asp Thr Ala Thr Tyr Tyr Cys Gln Gln Tyr Glu Lys Val Pro Phe
                85                  90                  95

Thr Phe Gly Pro Gly Lys Val Gly Phe Asn Arg
            100                 105
```

<210> SEQ ID NO 13
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 13

```
Asp Ile Val Met Thr Gln Ser Pro Asp Ser Leu Ala Val Ser Leu Gly
1               5                   10                  15

Glu Arg Ala Thr Ile Asn Cys Gln Ala Ser Gln Asp Ile Lys Thr Tyr
            20                  25                  30

Leu Ser Trp Tyr Gln Gln Lys Pro Gly Gln Pro Pro Lys Leu Leu Ile
        35                  40                  45

Tyr Asp Ala Ser Gly Phe Gln Pro Gly Val Pro Asp Arg Phe Ser Gly
```

```
            50                  55                  60
Ser Gly Tyr Gly Thr Asp Phe Thr Phe Thr Ile Ser Ser Leu Gln Ala
 65                  70                  75                  80

Glu Asp Val Ala Thr Tyr Tyr Cys Gln Gln Tyr Lys Val Pro Tyr
                 85                  90                  95

Thr Phe Gly Gln Gly Thr Lys Val Glu Ile Lys
            100                 105

<210> SEQ ID NO 14
<211> LENGTH: 228
<212> TYPE: PRT
<213> ORGANISM: Artificial Sequence
<220> FEATURE:
<223> OTHER INFORMATION: Synthetic Polypeptide

<400> SEQUENCE: 14

Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 15
<211> LENGTH: 235
<212> TYPE: PRT
<213> ORGANISM: Homo sapiens

<400> SEQUENCE: 15

Met Asp Met Arg Val Pro Ala Gln Leu Leu Gly Leu Leu Leu Leu Trp
 1               5                  10                  15

Leu Ser Gly Ala Arg Cys Asp Ile Gln Met Thr Gln Ser Pro Ser Ser
             20                  25                  30
```

-continued

```
Leu Ser Ala Ser Val Gly Asp Arg Val Thr Ile Thr Cys Gln Ala Ser
             35                  40                  45

Gln Asp Ile Lys Thr Tyr Leu Ser Trp Phe Gln Gln Lys Pro Gly Lys
 50                  55                  60

Pro Pro Lys Leu Leu Ile Ser Asp Ala Ser Gly Phe Gln Pro Gly Val
 65                  70                  75                  80

Pro Ser Arg Phe Ser Gly Ser Gly Tyr Gly Thr Asp Phe Ser Phe Thr
                 85                  90                  95

Ile Thr Ser Leu Arg Pro Asp Asp Thr Ala Thr Tyr Tyr Cys Gln Gln
            100                 105                 110

Tyr Glu Lys Val Pro Phe Thr Phe Gly Pro Gly Lys Val Gly Phe Asn
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 16
<211> LENGTH: 228
<212> TYPE: PRT
<213> ORGANISM: Homo sapiens

<400> SEQUENCE: 16

Glu Ser Lys Tyr Gly Pro Pro Cys Pro Pro Cys Pro Ala Pro Glu Phe
 1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Lys Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
```

```
                        165                 170                 175
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly
225
```

<210> SEQ ID NO 17
<211> LENGTH: 228
<212> TYPE: PRT
<213> ORGANISM: Homo sapiens

<400> SEQUENCE: 17

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Lys Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Phe Met His Glu Ala Leu His Asn His Tyr Thr Gln Lys Ser Leu Ser
            210                 215                 220

Leu Ser Leu Gly
225
```

<210> SEQ ID NO 18
<211> LENGTH: 227
<212> TYPE: PRT
<213> ORGANISM: Homo sapiens

<400> SEQUENCE: 18

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
```

```
                    20                  25                  30
Leu Met Ile Ser Arg Thr Pro Glu Val Thr Cys Val Val Asp Val
            35                  40                  45
Ser Gln Glu Asp Pro Glu Val Gln Phe Asn Trp Tyr Val Asp Gly Val
50                  55                  60
Glu Val His Asn Ala Lys Thr Lys Pro Arg Glu Glu Gln Phe Asn Ser
65                  70                  75                  80
Lys Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
                115                 120                 125
Gln Val Tyr Thr Leu Pro Pro Ser Gln Glu Glu Met Thr Lys Asn Gln
        130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Ser Asp Gly Ser Phe Phe Leu Tyr Ser Arg Leu Thr
                180                 185                 190
Val Asp Lys Ser Arg Trp Gln Glu Gly Asn Val Phe Ser Cys Ser Val
                195                 200                 205
Met His Glu Ala Leu His Asn His Tyr Thr Gln Lys Ser Leu Ser Leu
        210                 215                 220
Ser Leu Gly
225

<210> SEQ ID NO 19
<211> LENGTH: 306
<212> TYPE: PRT
<213> ORGANISM: Homo sapiens

<400> SEQUENCE: 19

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
            35                  40                  45
Ser Gln Glu Asp Pro Glu Val Gln Phe Asn Trp Tyr Val Asp Gly Val
50                  55                  60
Glu Val His Asn Ala Lys Thr Lys Pro Arg Glu Glu Gln Phe Asn Ser
65                  70                  75                  80
Thr Tyr Arg Val Val Ser Val Leu Pro Val Leu His Gln Asp Trp Leu
                85                  90                  95
Asn Gly Lys Glu Tyr Lys Cys Lys Val Ser Asn Lys Gly Leu Pro Ser
                100                 105                 110
Ile Glu Lys Thr Ile Ser Lys Ala Lys Gly Gln Pro Arg Glu Pro Gln
                115                 120                 125
Val Tyr Thr Leu Pro Pro Ser Gln Glu Glu Met Thr Lys Asn Gln Val
        130                 135                 140
Ser Leu Thr Cys Leu Val Lys Gly Phe Tyr Pro Ser Asp Ile Ala Val
145                 150                 155                 160
```

```
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Arg Leu Thr
            180                 185                 190
Val Asp Lys Ser Arg Trp Gln Glu Gly Asn Val Phe Ser Cys Ser Phe
            195                 200                 205
Met His Glu Ala Leu His Asn His Tyr Thr Gln Lys Ser Leu Ser Leu
            210                 215                 220
Ser Leu Gly Pro Pro Val Leu Asp Ser Asp Gly Ser Phe Phe Leu Tyr
225                 230                 235                 240
Ser Arg Leu Thr Val Asp Lys Ser Arg Trp Gln Glu Gly Asn Val Phe
                245                 250                 255
Ser Cys Ser Phe Met His Glu Ala Leu His Asn His Tyr Thr Gln Lys
                260                 265                 270
Ser Leu Ser Leu Ser Leu Gly Gly Asn Val Phe Ser Cys Ser Phe Met
            275                 280                 285
His Glu Ala Leu His Asn His Tyr Thr Gln Lys Ser Leu Ser Leu Ser
            290                 295                 300
Leu Gly
305

<210> SEQ ID NO 20
<211> LENGTH: 227
<212> TYPE: PRT
<213> ORGANISM: Homo sapiens

<400> SEQUENCE: 20

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
50                  55                  60
Glu Val His Asn Ala Lys Thr Lys Pro Arg Glu Glu Gln Phe Asn Ser
65                  70                  75                  80
Thr Tyr Arg Val Val Ser Val Leu Pro Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu Thr
            180                 185                 190
Val Asp Lys Ser Arg Trp Gln Glu Gly Asn Val Phe Ser Cys Ser Val
            195                 200                 205
Met His Glu Ala Leu His Asn His Tyr Thr Gln Lys Ser Leu Ser Leu
            210                 215                 220
```

Ser Leu Gly
225

<210> SEQ ID NO 21
<211> LENGTH: 227
<212> TYPE: PRT
<213> ORGANISM: Homo sapiens

<400> SEQUENCE: 21

| | | | | | | | | | | | |
|---|---|---|---|---|---|---|---|---|---|---|---|
| Glu | Ser | Lys | Tyr | Gly | Pro | Pro | Cys | Pro | Pro | Cys | Pro | Ala | Pro | Glu | Phe |
| 1 | | | | 5 | | | | | 10 | | | | | 15 | |

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Lys Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Phe
        195                 200                 205

Met His Glu Ala Leu His Asn His Tyr Thr Gln Lys Ser Leu Ser Leu
    210                 215                 220

Ser Leu Gly
225

<210> SEQ ID NO 22
<211> LENGTH: 227
<212> TYPE: PRT
<213> ORGANISM: Homo sapiens

<400> SEQUENCE: 22

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

```
Thr Tyr Arg Val Val Ser Val Leu Pro Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Phe
        195                 200                 205

Met His Glu Ala Leu His Asn His Tyr Thr Gln Lys Ser Leu Ser Leu
    210                 215                 220

Ser Leu Gly
225

<210> SEQ ID NO 23
<211> LENGTH: 228
<212> TYPE: PRT
<213> ORGANISM: Homo sapiens

<400> SEQUENCE: 23

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Lys Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Phe Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Phe Met His Glu Ala Leu His Asn His Tyr Thr Gln Lys Ser Leu Ser
```

```
            210                 215                 220

Leu Ser Leu Gly
225

<210> SEQ ID NO 24
<211> LENGTH: 228
<212> TYPE: PRT
<213> ORGANISM: Homo sapiens

<400> SEQUENCE: 24

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Pro Val Leu His Gln Asp Trp Leu
                85                  90                  95

Asn Gly Lys Glu Tyr Lys Cys Lys Phe Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 25
<211> LENGTH: 228
<212> TYPE: PRT
<213> ORGANISM: Homo sapiens

<400> SEQUENCE: 25

Glu Ser Lys Tyr Gly Pro Pro Cys Pro Pro Cys Pro Ala Pro Glu Phe
1               5                   10                  15

Leu Gly Gly Pro Ser Phe Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
```

```
                65                  70                  75                  80
Thr Tyr Arg Val Val Ser Val Leu Thr Val Leu His Gln Asp Trp Leu
                    85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
    210                 215                 220

Leu Ser Leu Gly
225

<210> SEQ ID NO 26
<211> LENGTH: 228
<212> TYPE: PRT
<213> ORGANISM: Homo sapiens

<400> SEQUENCE: 26

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Pro Val Leu His Gln Asp Trp Leu
                    85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205
```

```
Val Met His Glu Ala Leu His Asn His Tyr Thr Gln Lys Ser Leu Ser
    210                 215                 220

Leu Ser Leu Gly
225

<210> SEQ ID NO 27
<211> LENGTH: 227
<212> TYPE: PRT
<213> ORGANISM: Homo sapiens

<400> SEQUENCE: 27

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Pro His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 28
<211> LENGTH: 227
<212> TYPE: PRT
<213> ORGANISM: Homo sapiens

<400> SEQUENCE: 28

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Asn Ser
 65                  70                  75                  80

Thr Tyr Arg Val Val Ser Val Leu Thr Val Met His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 29
<211> LENGTH: 227
<212> TYPE: PRT
<213> ORGANISM: Homo sapiens

<400> SEQUENCE: 29

Glu Ser Lys Tyr Gly Pro Pro Cys Pro Pro Cys Pro Ala Pro Glu Phe
  1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Lys His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205
```

```
Met His Glu Ala Leu His Asn His Tyr Thr Gln Lys Ser Leu Ser Leu
    210                 215                 220

Ser Leu Gly
225

<210> SEQ ID NO 30
<211> LENGTH: 227
<212> TYPE: PRT
<213> ORGANISM: Homo sapiens

<400> SEQUENCE: 30

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Pro Val Lys His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 31
<211> LENGTH: 227
<212> TYPE: PRT
<213> ORGANISM: Homo sapiens

<400> SEQUENCE: 31

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Gln Phe Asn Ser
 65                  70                  75                  80

Thr Tyr Arg Val Val Ser Val Leu Pro Val Met His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
                180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
210                 215                 220

Ser Leu Gly
225

<210> SEQ ID NO 32
<211> LENGTH: 227
<212> TYPE: PRT
<213> ORGANISM: Homo sapiens

<400> SEQUENCE: 32

Glu Ser Lys Tyr Gly Pro Pro Cys Pro Pro Cys Pro Ala Pro Glu Phe
 1               5                  10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
 65                  70                  75                  80

Thr Tyr Arg Val Val Ser Val Leu Pro Val Lys His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
                180                 185                 190

Val Asp Lys Ser Arg Trp Gln Glu Gly Asn Val Phe Ser Cys Ser Val
```

```
                    195                 200                 205
Met His Glu Ala Leu His Asn His Tyr Thr Gln Lys Ser Leu Ser Leu
    210                 215                 220

Ser Leu Gly
225

<210> SEQ ID NO 33
<211> LENGTH: 227
<212> TYPE: PRT
<213> ORGANISM: Homo sapiens

<400> SEQUENCE: 33

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Ala Tyr Arg Val Val Ser Val Leu Pro Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 34
<211> LENGTH: 227
<212> TYPE: PRT
<213> ORGANISM: Homo sapiens

<400> SEQUENCE: 34

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

50                  55                  60
Glu Val His Asn Ala Lys Thr Lys Pro Arg Glu Glu Gln Phe Asn Ser
 65                  70                  75                  80

Ala Tyr Arg Val Val Ser Val Leu Thr Val Lys His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 35
<211> LENGTH: 227
<212> TYPE: PRT
<213> ORGANISM: Homo sapiens

<400> SEQUENCE: 35

Glu Ser Lys Tyr Gly Pro Pro Cys Pro Pro Cys Pro Ala Pro Glu Phe
 1               5                  10                  15

Leu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
 65                  70                  75                  80

Ala Tyr Arg Val Val Ser Val Leu Pro Val Lys His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

```
Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 36
<211> LENGTH: 227
<212> TYPE: PRT
<213> ORGANISM: Homo sapiens

<400> SEQUENCE: 36

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Lys Tyr Arg Val Val Ser Val Leu Pro Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 37
<211> LENGTH: 227
<212> TYPE: PRT
<213> ORGANISM: Homo sapiens

<400> SEQUENCE: 37

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

```
Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Lys Tyr Arg Val Val Ser Val Leu Thr Val Lys His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 38
<211> LENGTH: 227
<212> TYPE: PRT
<213> ORGANISM: Homo sapiens

<400> SEQUENCE: 38

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Lys Tyr Arg Val Val Ser Val Leu Pro Val Lys His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Asp Gly Ser Phe Phe Leu Tyr Ser Arg Leu Thr
            180                 185                 190
```

```
Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly
225

<210> SEQ ID NO 39
<211> LENGTH: 228
<212> TYPE: PRT
<213> ORGANISM: Homo sapiens

<400> SEQUENCE: 39

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Ala Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly
225

<210> SEQ ID NO 40
<211> LENGTH: 228
<212> TYPE: PRT
<213> ORGANISM: Homo sapiens

<400> SEQUENCE: 40

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

```
Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Lys Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
                180                 185                 190

Thr Val Asp Lys Ser Arg Trp Gln Gln Gly Asn Val Phe Ser Cys Ser
                195                 200                 205

Val Met His Glu Ala Leu His Asn His Tyr Thr Gln Lys Ser Leu Ser
210                 215                 220

Leu Ser Pro Gly
225

<210> SEQ ID NO 41
<211> LENGTH: 228
<212> TYPE: PRT
<213> ORGANISM: Homo sapiens

<400> SEQUENCE: 41

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Ala Tyr Arg Val Val Ser Val Leu Pro Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
```

```
                180                 185                 190
Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
        210                 215                 220

Leu Ser Pro Gly
225

<210> SEQ ID NO 42
<211> LENGTH: 228
<212> TYPE: PRT
<213> ORGANISM: Homo sapiens

<400> SEQUENCE: 42

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Lys Tyr Arg Val Val Ser Val Leu Pro Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly
225

<210> SEQ ID NO 43
<211> LENGTH: 227
<212> TYPE: PRT
<213> ORGANISM: Homo sapiens

<400> SEQUENCE: 43

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
```

```
            35                  40                  45
Gln Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Tyr Arg Val Val Ser Val Leu Thr Val Leu His Gln Asp Trp Leu Asn
                     85                  90                  95

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly
225

<210> SEQ ID NO 44
<211> LENGTH: 230
<212> TYPE: PRT
<213> ORGANISM: Homo sapiens

<400> SEQUENCE: 44

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Asp Val Ser His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Lys Tyr Arg Val Val Ser Val Leu Thr Val Leu His Gln Asp
                     85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175
```

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly
225             230

<210> SEQ ID NO 45
<211> LENGTH: 231
<212> TYPE: PRT
<213> ORGANISM: Homo sapiens

<400> SEQUENCE: 45

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Thr Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 46
<211> LENGTH: 231
<212> TYPE: PRT
<213> ORGANISM: Homo sapiens

<400> SEQUENCE: 46

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
            35                  40                  45

Val Asp Phe Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly
225                 230

<210> SEQ ID NO 47
<211> LENGTH: 231
<212> TYPE: PRT
<213> ORGANISM: Homo sapiens

<400> SEQUENCE: 47

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Leu Val
            35                  40                  45

Thr Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly
225                 230

<210> SEQ ID NO 48
<211> LENGTH: 231
<212> TYPE: PRT
<213> ORGANISM: Homo sapiens

<400> SEQUENCE: 48

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Thr Asp Phe Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 49
<211> LENGTH: 229
<212> TYPE: PRT
<213> ORGANISM: Homo sapiens

<400> SEQUENCE: 49

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

-continued

```
Lys Asp Thr Leu Met Ile Ser Arg Thr Pro Glu Val Thr Cys Val Val
             35                  40                  45

Val Asp Val Ser Pro Asp Pro Val Lys Phe Asn Trp Tyr Val Asp Gly
 50                  55                  60

Val Glu Val His Asn Ala Lys Thr Lys Pro Arg Glu Glu Gln Tyr Asn
65                   70                  75                  80

Ser Lys Tyr Arg Val Val Ser Val Leu Thr Val Leu His Gln Asp Trp
                 85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly
225

<210> SEQ ID NO 50
<211> LENGTH: 229
<212> TYPE: PRT
<213> ORGANISM: Homo sapiens

<400> SEQUENCE: 50

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Leu Val
         35                  40                  45

Thr Asp Val Ser Pro Asp Pro Val Lys Phe Asn Trp Tyr Val Asp Gly
 50                  55                  60

Val Glu Val His Asn Ala Lys Thr Lys Pro Arg Glu Glu Gln Tyr Asn
65                   70                  75                  80

Ser Lys Tyr Arg Val Val Ser Val Leu Thr Val Leu His Gln Asp Trp
                 85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
```

```
                        165                 170                 175
Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly
225

<210> SEQ ID NO 51
<211> LENGTH: 231
<212> TYPE: PRT
<213> ORGANISM: Homo sapiens

<400> SEQUENCE: 51

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Leu Val
        35                  40                  45

Thr Asp Phe Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 52
<211> LENGTH: 444
<212> TYPE: PRT
<213> ORGANISM: Homo sapiens

<400> SEQUENCE: 52

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
```

```
                20                  25                  30
Tyr Met Tyr Trp Val Lys Gln Ala Pro Gly Gln Gly Leu Glu Trp Ile
            35                  40                  45
Gly Glu Ile Asn Pro Ser Asn Gly Asp Thr Asn Phe Asn Glu Lys Phe
        50                  55                  60
Lys Ser Lys Ala Thr Leu Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Ser Asp Gly Arg Asn Asp Met Asp Ser Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440
```

<210> SEQ ID NO 53
<211> LENGTH: 218
<212> TYPE: PRT
<213> ORGANISM: Homo sapiens

<400> SEQUENCE: 53

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 54
<211> LENGTH: 216
<212> TYPE: PRT
<213> ORGANISM: Homo sapiens

<400> SEQUENCE: 54

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

```
Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
        195                 200                 205

Asn Thr Lys Val Asp Lys Arg Val
    210                 215

<210> SEQ ID NO 55
<211> LENGTH: 228
<212> TYPE: PRT
<213> ORGANISM: Homo sapiens

<400> SEQUENCE: 55

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 56
<211> LENGTH: 228
<212> TYPE: PRT
```

<213> ORGANISM: Homo sapiens

<400> SEQUENCE: 56

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 57
<211> LENGTH: 228
<212> TYPE: PRT
<213> ORGANISM: Homo sapiens

<400> SEQUENCE: 57

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Ala Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro

```
                115                 120                 125
Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly
225

<210> SEQ ID NO 58
<211> LENGTH: 231
<212> TYPE: PRT
<213> ORGANISM: Homo sapiens

<400> SEQUENCE: 58

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Ala Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 59
<211> LENGTH: 227
```

```
<212> TYPE: PRT
<213> ORGANISM: Homo sapiens

<400> SEQUENCE: 59

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro
225

<210> SEQ ID NO 60
<211> LENGTH: 231
<212> TYPE: PRT
<213> ORGANISM: Homo sapiens

<400> SEQUENCE: 60

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

-continued

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 61
<211> LENGTH: 447
<212> TYPE: PRT
<213> ORGANISM: Homo sapiens

<400> SEQUENCE: 61

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Pro Ser Lys Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 62
<211> LENGTH: 447
<212> TYPE: PRT
<213> ORGANISM: Homo sapiens

<400> SEQUENCE: 62

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser

```
            180                 185                 190
Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asp Ser Lys Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

<210> SEQ ID NO 63
<211> LENGTH: 447
<212> TYPE: PRT
<213> ORGANISM: Homo sapiens

<400> SEQUENCE: 63

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Ser Asp Gly Arg Asn Asp Met Asp Ser Trp Gly Gln Gly Thr
        100                 105                 110
```

-continued

```
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Ser Ser Lys Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 64
<211> LENGTH: 444
<212> TYPE: PRT
<213> ORGANISM: Homo sapiens

<400> SEQUENCE: 64

Gln Val Gln Leu Val Gln Ser Gly Ala Glu Val Val Lys Pro Gly Ala
1               5                   10                  15
Ser Val Lys Leu Ser Cys Lys Ala Ser Gly Tyr Ile Phe Thr Ser Tyr
            20                  25                  30
Tyr Met Tyr Trp Val Lys Gln Ala Pro Gly Gln Gly Leu Glu Trp Ile
        35                  40                  45
```

Gly Glu Ile Asn Pro Ser Asn Gly Asp Thr Asn Phe Asn Glu Lys Phe
 50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Gln Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 65
<211> LENGTH: 228

```
<212> TYPE: PRT
<213> ORGANISM: Homo sapiens

<400> SEQUENCE: 65

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Lys Tyr Arg Val Val Ser Val Leu Pro Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Ser Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 66
<211> LENGTH: 231
<212> TYPE: PRT
<213> ORGANISM: Homo sapiens

<400> SEQUENCE: 66

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 67
<211> LENGTH: 447
<212> TYPE: PRT
<213> ORGANISM: Homo sapiens

<400> SEQUENCE: 67

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Asn Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 68
<211> LENGTH: 447
<212> TYPE: PRT
<213> ORGANISM: Homo sapiens

<400> SEQUENCE: 68

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
            180                 185                 190
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Arg Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 69
<211> LENGTH: 447
<212> TYPE: PRT
<213> ORGANISM: Homo sapiens

<400> SEQUENCE: 69

Gln Val Gln Leu Val Gln Ser Gly Ala Glu Val Lys Pro Gly Ala
1               5                   10                  15

Ser Val Lys Leu Ser Cys Lys Ala Ser Gly Tyr Ile Phe Thr Ser Tyr
                20                  25                  30

Tyr Met Tyr Trp Val Lys Gln Ala Pro Gly Gln Gly Leu Glu Trp Ile
            35                  40                  45

Gly Glu Ile Asn Pro Ser Asn Gly Asp Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110
```

```
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Glu Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 70
<211> LENGTH: 447
<212> TYPE: PRT
<213> ORGANISM: Homo sapiens

<400> SEQUENCE: 70

Gln Val Gln Leu Val Gln Ser Gly Ala Glu Val Lys Pro Gly Ala
1               5                   10                  15

Ser Val Lys Leu Ser Cys Lys Ala Ser Gly Tyr Ile Phe Thr Ser Tyr
                20                  25                  30

Tyr Met Tyr Trp Val Lys Gln Ala Pro Gly Gln Gly Leu Glu Trp Ile
            35                  40                  45
```

```
Gly Glu Ile Asn Pro Ser Asn Gly Asp Thr Asn Phe Asn Glu Lys Phe
 50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Phe Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 71
<211> LENGTH: 447
```

<212> TYPE: PRT
<213> ORGANISM: Homo sapiens

<400> SEQUENCE: 71

```
Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Gln Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 72
<211> LENGTH: 447
<212> TYPE: PRT
<213> ORGANISM: Homo sapiens

<400> SEQUENCE: 72

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Pro Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr

-continued

```
                325                 330                 335
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 73
<211> LENGTH: 444
<212> TYPE: PRT
<213> ORGANISM: Homo sapiens

<400> SEQUENCE: 73

Gln Val Gln Leu Val Gln Ser Gly Ala Glu Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Gln Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 74
<211> LENGTH: 227
<212> TYPE: PRT
<213> ORGANISM: Homo sapiens

<400> SEQUENCE: 74

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190
```

-continued

```
Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 75
<211> LENGTH: 231
<212> TYPE: PRT
<213> ORGANISM: Homo sapiens

<400> SEQUENCE: 75

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 76
<211> LENGTH: 231
<212> TYPE: PRT
<213> ORGANISM: Homo sapiens

<400> SEQUENCE: 76

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Asp Ser Lys Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 77
<211> LENGTH: 231
<212> TYPE: PRT
<213> ORGANISM: Homo sapiens

<400> SEQUENCE: 77

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
             20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Ser Ser Lys Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

```
                180                 185                 190
Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly
225                 230

<210> SEQ ID NO 78
<211> LENGTH: 231
<212> TYPE: PRT
<213> ORGANISM: Homo sapiens

<400> SEQUENCE: 78

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Pro Ser Lys Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 79
<211> LENGTH: 229
<212> TYPE: PRT
<213> ORGANISM: Homo sapiens

<400> SEQUENCE: 79

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Leu Val
```

```
                35                  40                  45
Thr Asp Phe Ser Pro Asp Pro Val Lys Phe Asn Trp Tyr Val Asp Gly
 50                  55                  60

Val Glu Val His Asn Ala Lys Thr Lys Pro Arg Glu Glu Gln Tyr Asn
 65                  70                  75                  80

Ser Lys Tyr Arg Val Ser Val Leu Thr Val Leu His Gln Asp Trp
                 85                  90                  95

Leu Asn Gly Lys Glu Tyr Lys Cys Lys Val Ser Asn Lys Ala Leu Pro
                100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
                180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
210                 215                 220

Ser Leu Ser Pro Gly
225

<210> SEQ ID NO 80
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 80

Glu Val Gln Leu Val Gln Ser Gly Ala Glu Val Lys Lys Pro Gly Ala
 1               5                  10                  15

Thr Val Lys Ile Ser Cys Lys Ala Ser Gly Phe Asn Ile Lys Asp Thr
             20                  25                  30

Tyr Met His Trp Val Gln Gln Ala Pro Gly Lys Gly Leu Glu Trp Met
         35                  40                  45

Gly Arg Ile Asp Pro Ala Ser Gly Asp Thr Lys Tyr Asp Pro Lys Phe
 50                  55                  60

Gln Val Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Asp Gly Met Trp Val Ser Thr Gly Tyr Ala Leu Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
            165                 170                 175
Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 81
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 81

Ser Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Thr Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Ala
65                  70                  75                  80

Glu Asp Val Ala Thr Tyr Phe Cys Gln Gln Asp Tyr Ser Ser Pro Tyr
```

```
                      85                  90                  95

Thr Phe Gly Gln Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 107
<212> TYPE: PRT
<213> ORGANISM: Homo sapiens

<400> SEQUENCE: 82

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 83
<211> LENGTH: 330
<212> TYPE: PRT
<213> ORGANISM: Homo sapiens

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
            85                  90                  95
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 84
<211> LENGTH: 327
<212> TYPE: PRT
<213> ORGANISM: Homo sapiens

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 326
<212> TYPE: PRT
<213> ORGANISM: Artificial Sequence
<220> FEATURE:
<223> OTHER INFORMATION: Synthetic Polypeptide

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Gln Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 86
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 86

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

-continued

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
            435                 440                 445

<210> SEQ ID NO 87
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 87

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 88
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 88

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

```
Tyr Met His Trp Val Gln Gln Ala Pro Gly Lys Gly Leu Glu Trp Met
         35                  40                  45

Gly Arg Ile Asp Pro Ala Ser Gly Asp Thr Lys Tyr Asp Pro Lys Phe
 50                  55                  60

Gln Val Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Asp Gly Met Trp Val Ser Thr Gly Tyr Ala Leu Asp Phe Trp Gly
             100                 105                 110

Gln Gly Thr Leu Val Thr Val Ser Ser Ala Ser Thr Lys Gly Pro Ser
         115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Ser Leu Gly Thr Lys Thr Tyr Thr Cys Asn Val Asp His
         195                 200                 205

Lys Pro Ser Asn Thr Lys Val Asp Lys Arg Val Glu Ser Lys Tyr Gly
     210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Asp Val Ser Gln Glu Asp Pro
             260                 265                 270

Glu Val Gln Phe Asn Trp Tyr Val Asp Gly Val Glu Val His Asn Ala
         275                 280                 285

Lys Thr Lys Pro Arg Glu Glu Gln Phe Asn Ser Thr Tyr Arg Val Val
     290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Gln Glu Glu Met Thr Lys Asn Gln Val Ser Leu Thr Cys
         355                 360                 365

Leu Val Lys Gly Phe Tyr Pro Ser Asp Ile Ala Val Glu Trp Glu Ser
     370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                 405                 410                 415

Arg Trp Gln Glu Gly Asn Val Phe Ser Cys Ser Val Met His Glu Ala
             420                 425                 430

Leu His Asn His Tyr Thr Gln Lys Ser Leu Ser Leu Ser Leu Gly
         435                 440                 445
```

<210> SEQ ID NO 89
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 89

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Ala Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
```

```
                 370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
                435                 440                 445

<210> SEQ ID NO 90
<211> LENGTH: 450
<212> TYPE: PRT
<213> ORGANISM: Artificial Sequence
<220> FEATURE:
<223> OTHER INFORMATION: Synthetic Polypeptide

<400> SEQUENCE: 90

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
                20                  25                  30

Tyr Met His Trp Val Gln Gln Ala Pro Gly Lys Gly Leu Glu Trp Met
            35                  40                  45

Gly Arg Ile Asp Pro Ala Ser Gly Asp Thr Lys Tyr Asp Pro Lys Phe
50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
```

Arg Val Ser Val Leu Thr Val Leu His Gln Asp Trp Leu Asn Gly
305             310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385             390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 91
<211> LENGTH: 702
<212> TYPE: DNA
<213> ORGANISM: Artificial Sequence
<220> FEATURE:
<223> OTHER INFORMATION: Synthesized DNA sequence

<400> SEQUENCE: 91
atggacttcg gcctgtccct ggtgttcctg gtgctgatcc tgaagggcgt gcagtgcagc        60
atcgtgatga cccagagccc cgacagcctg gccgtgagcc tgggcgagcg cgccaccatc       120
aactgcaagg ccagccagag cgtgaccaac gacgtggcct ggtatcagca gaagcccggc       180 cagccccca gctgctgat ctactacgcc agcaaccgct acaccggcgt gcccgaccgc        240
ttcagcggca gcggctacgg caccgacttc accttcacca tcagcagcct ccaggccgag       300
gacgtggcca cctacttctg ccagcaagac tacagcagcc cctacacctt cggccagggc       360
accaaggtgg agatcaagcg tacggtggct gcaccatctg tcttcatctt cccgccatct       420
gatgagcagt tgaaatctgg aactgcctct gttgtgtgcc tgctgaataa cttctatccc       480
agagaggcca agtacagtg gaaggtggat aacgccctcc aatcgggcaa ctcccaggag       540
agtgtcacag agcaggacag caaggacagc acctacagcc tcagctccac cctgacgctg       600
agcaaagcag actacgagaa acacaaagtc tacgcctgcg aagtcaccca tcagggcctg       660
tcctcgcccg tcacaaagag cttcaacagg ggagagtgtt aa                          702

<210> SEQ ID NO 92
<211> LENGTH: 233
<212> TYPE: PRT
<213> ORGANISM: Artificial Sequence
<220> FEATURE:
<223> OTHER INFORMATION: Synthetic amino acid sequence

<400> SEQUENCE: 92

Met Asp Phe Gly Leu Ser Leu Val Phe Leu Val Leu Ile Leu Lys Gly
1               5                   10                  15

Val Gln Cys Ser Ile Val Met Thr Gln Ser Pro Asp Ser Leu Ala Val
            20                  25                  30

Ser Leu Gly Glu Arg Ala Thr Ile Asn Cys Lys Ala Ser Gln Ser Val
        35                  40                  45

Thr Asn Asp Val Ala Trp Tyr Gln Gln Lys Pro Gly Gln Pro Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Tyr Gly Thr Asp Phe Thr Phe Thr Ile Ser Ser
                85                  90                  95

Leu Gln Ala Glu Asp Val Ala Thr Tyr Phe Cys Gln Gln Asp Tyr Ser
            100                 105                 110

Ser Pro Tyr Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 93
<211> LENGTH: 1410
<212> TYPE: DNA
<213> ORGANISM: Artificial Sequence
<220> FEATURE:
<223> OTHER INFORMATION: Synthetic DNA sequence

<400> SEQUENCE: 93
atggatatgc gcgtgcctgc ccaacttctc ggacttctcc tcctttggct gcctggagcc      60
cgatgtgagg tgcagctggt gcagagcggc gccgaggtga agaagcccgg cgccaccgtg     120
aagatcagct gcaaggccag cggcttcaac atcaaggaca cctacatgca ctgggtgcag     180 caggccccccg gcaagggcct ggagtggatg ggccgcatcg accccgccag cggcgacacc     240
aaatacgacc ccaagttcca agtccgggtg accatcaccg ccgacaccag caccgacacc     300
gcctacatgg agctgagcag cctgcgcagc gaggacaccg ccgtgtacta ctgcgccgac     360
ggcatgtggg tcagcaccgg ctacgccctg gacttctggg gccagggcac cctggtgacc     420
gtctcgagcg ctagtaccaa gggcccatcg gtcttccccc tggcgccctg ctccggagc      480 acctccgaga gcacagccgc cctgggctgc ctggtcaagg actacttccc cgaacctgtg     540
acggtgtcgt ggaactcagg cgccctgacc agcggcgtgc acaccttccc ggctgtccta     600
caatcctcag gactctactc cctctcttcc gtggtgaccg tgccctccag cagcttgggc     660
acgaagacct acacctgtaa cgtagatcac aagcccagca acaccaaggt ggacaagaga     720
gttgagtcca aatatggtcc cccatgccca ccttgcccag cacctgagtt cctggggga      780 ccatcagtct tcctgttccc cccaaaaccc aaggacactc tcatgatctc ccggacccct     840

-continued

```
gaggtcactt gcgtggtggt ggatgtgagc caggaagacc ccgaggtcca gtttaactgg     900
tacgtggatg gcgtggaagt ccacaatgcc aagacaaagc cgcgggagga gcagttccaa     960
agcacgtacc gtgtggtcag cgtcctcacc gtcctgcacc aagactggct gaacggcaag    1020
gagtacaagt gcaaggtgtc caacaaaggc ctcccgtcct ccatcgagaa aaccatctcc    1080
aaagccaaag ggcagccccg agaaccacag gtgtacaccc tgcccccatc gcgggatgag    1140
ctgaccaaga accaggtctc gctgacctgc ctggtcaaag gcttctatcc ctccgacatt    1200
gccgtggagt gggagagcaa tgggcagccg gagaacaact acaagaccac gcctcccgtg    1260
ttggactccg acggctcctt ctttctctac tccaaactca ccgtggacaa gagcaggtgg    1320
cagcagggga acgtcttctc atgctccgtg atgcatgagg ctctgcacaa ccactacacg    1380
caaaaaagcc tctccctcag cccgggctga                                     1410
```

<210> SEQ ID NO 94
<211> LENGTH: 469
<212> TYPE: PRT
<213> ORGANISM: Artificial Sequence
<220> FEATURE:
<223> OTHER INFORMATION: Synthetic amino acid sequence

<400> SEQUENCE: 94

```
Met Asp Met Arg Val Pro Ala Gln Leu Leu Gly Leu Leu Leu Leu Trp
1               5                   10                  15

Leu Pro Gly Ala Arg Cys Glu Val Gln Leu Val Gln Ser Gly Ala Glu
            20                  25                  30

Val Lys Lys Pro Gly Ala Thr Val Lys Ile Ser Cys Lys Ala Ser Gly
        35                  40                  45

Phe Asn Ile Lys Asp Thr Tyr Met His Trp Val Gln Gln Ala Pro Gly
    50                  55                  60

Lys Gly Leu Glu Trp Met Gly Arg Ile Asp Pro Ala Ser Gly Asp Thr
65                  70                  75                  80

Lys Tyr Asp Pro Lys Phe Gln Val Arg Val Thr Ile Thr Ala Asp Thr
                85                  90                  95

Ser Thr Asp Thr Ala Tyr Met Glu Leu Ser Ser Leu Arg Ser Glu Asp
            100                 105                 110

Thr Ala Val Tyr Tyr Cys Ala Asp Gly Met Trp Val Ser Thr Gly Tyr
        115                 120                 125

Ala Leu Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Lys Thr Tyr
    210                 215                 220

Thr Cys Asn Val Asp His Lys Pro Ser Asn Thr Lys Val Asp Lys Arg
225                 230                 235                 240

Val Glu Ser Lys Tyr Gly Pro Pro Cys Pro Pro Cys Pro Ala Pro Glu
                245                 250                 255
```

```
Phe Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
        275                 280                 285

Val Ser Gln Glu Asp Pro Glu Val Gln Phe Asn Trp Tyr Val Asp Gly
290                 295                 300

Val Glu Val His Asn Ala Lys Thr Lys Pro Arg Glu Glu Gln Phe Gln
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Gly Leu Pro
                340                 345                 350

Ser Ser Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly
465

<210> SEQ ID NO 95
<211> LENGTH: 84
<212> TYPE: PRT
<213> ORGANISM: Artificial Sequence
<220> FEATURE:
<223> OTHER INFORMATION: Synthetic peptide

<400> SEQUENCE: 95

Pro Ser Val Phe Pro Leu Thr Ala Ala Gly Cys Leu Val Lys Asp Tyr
1               5                   10                  15

Phe Pro Glu Pro Val Thr Val Ser Trp Asn Ser Gly Ala Leu Thr Ser
                20                  25                  30

Gly Val His Thr Phe Pro Ala Val Leu Gln Ser Ser Gly Leu Tyr Ser
                35                  40                  45

Leu Ser Ser Val Val Thr Val Pro Ser Ser Ser Leu Gly Thr Gln Thr
        50                  55                  60

Tyr Ile Cys Asn Val Asn His Lys Pro Ser Asn Thr Lys Val Asp Lys
65                  70                  75                  80

Arg Val Glu Ser

<210> SEQ ID NO 96
<211> LENGTH: 87
<212> TYPE: PRT
<213> ORGANISM: Artificial Sequence
<220> FEATURE:
<223> OTHER INFORMATION: Synthetic peptide

<400> SEQUENCE: 96
```

Pro Gln Val Tyr Thr Leu Gln Val Ser Thr Cys Leu Val Lys Gly Phe
1               5                   10                  15

Tyr Pro Ser Asp Ile Ala Val Glu Trp Glu Ser Asn Gly Gln Pro Glu
            20                  25                  30

Asn Asn Tyr Lys Thr Thr Pro Pro Val Leu Asp Ser Asp Gly Ser Phe
        35                  40                  45

Phe Leu Tyr Ser Lys Leu Thr Val Asp Lys Ser Arg Trp Gln Gln Gly
    50                  55                  60

Asn Val Phe Ser Cys Ser Val Met His Glu Ala Leu His Asn His Tyr
65                  70                  75                  80

Thr Gln Lys Ser Leu Ser Ser
                85

<210> SEQ ID NO 97
<211> LENGTH: 89
<212> TYPE: PRT
<213> ORGANISM: Artificial Sequence
<220> FEATURE:
<223> OTHER INFORMATION: Synthetic peptide

<400> SEQUENCE: 97

Pro Ser Val Phe Ile Phe Pro Pro Ser Val Val Cys Leu Leu Asn Asn
1               5                   10                  15

Phe Tyr Pro Arg Glu Ala Lys Val Gln Trp Lys Val Asp Asn Ala Leu
            20                  25                  30

Gln Ser Gly Asn Ser Gln Glu Ser Val Thr Glu Gln Asp Ser Lys Asp
        35                  40                  45

Ser Thr Tyr Ser Leu Ser Ser Thr Leu Thr Leu Ser Lys Ala Asp Tyr
    50                  55                  60

Glu Lys His Lys Val Tyr Ala Cys Glu Val Thr His Gln Gly Leu Ser
65                  70                  75                  80

Ser Pro Val Ile Lys Ser Phe Asn Cys
                85

<210> SEQ ID NO 98
<211> LENGTH: 89
<212> TYPE: PRT
<213> ORGANISM: Artificial Sequence
<220> FEATURE:
<223> OTHER INFORMATION: Synthetic peptide

<400> SEQUENCE: 98

Pro Ser Val Phe Leu Phe Thr Pro Glu Val Thr Cys Val Val Val Asp
1               5                   10                  15

Val Ser His Glu Asp Pro Glu Val Lys Phe Asn Trp Tyr Val Asp Gly
            20                  25                  30

Val Glu Val His Asn Ala Lys Thr Lys Pro Arg Glu Glu Gln Tyr Ser
        35                  40                  45

Ser Thr Tyr Arg Val Val Ser Val Leu Thr Val Leu His Gln Asp Trp
    50                  55                  60

Leu Asn Gly Lys Glu Tyr Lys Cys Lys Val Ser Asn Lys Ala Leu Pro
65                  70                  75                  80

Ala Pro Ile Glu Lys Thr Ile Ser Lys
                85

<210> SEQ ID NO 99
<211> LENGTH: 236
<212> TYPE: PRT
<213> ORGANISM: Artificial Sequence

```
<220> FEATURE:
<223> OTHER INFORMATION: Synthetic peptide

<400> SEQUENCE: 99

Met Asp Met Arg Val Pro Ala Gln Leu Leu Gly Leu Leu Leu Leu Trp
1               5                   10                  15

Phe Pro Gly Ser Arg Cys Ser Ile Val Met Thr Gln Ser Pro Asp Ser
            20                  25                  30

Leu Ala Val Ser Leu Gly Glu Arg Ala Thr Ile Asn Cys Lys Ala Ser
        35                  40                  45

Gln Ser Val Thr Asn Asp Val Ala Trp Tyr Gln Gln Lys Pro Gly Gln
    50                  55                  60

Pro Pro Lys Leu Leu Ile Tyr Tyr Ala Ser Asn Arg Tyr Thr Gly Val
65                  70                  75                  80

Pro Asp Arg Phe Ser Gly Ser Gly Tyr Gly Thr Asp Phe Thr Phe Thr
                85                  90                  95

Ile Ser Ser Leu Gln Ala Glu Asp Val Ala Thr Tyr Phe Cys Gln Gln
            100                 105                 110

Asp Tyr Ser Ser Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 100
<211> LENGTH: 466
<212> TYPE: PRT
<213> ORGANISM: Artificial Sequence
<220> FEATURE:
<223> OTHER INFORMATION: Synthetic peptide

<400> SEQUENCE: 100

Met Gly Trp Ser Leu Ile Leu Leu Phe Leu Val Ala Val Ala Thr Arg
1               5                   10                  15

Val Leu Ser Glu Val Gln Leu Val Gln Ser Gly Ala Glu Val Lys Lys
            20                  25                  30

Pro Gly Ala Thr Val Lys Ile Ser Cys Lys Ala Ser Gly Phe Asn Ile
        35                  40                  45

Lys Asp Thr Tyr Met His Trp Val Gln Gln Ala Pro Gly Lys Gly Leu
    50                  55                  60

Glu Trp Met Gly Arg Ile Asp Pro Ala Ser Gly Asp Thr Lys Tyr Asp
65                  70                  75                  80

Pro Lys Phe Gln Val Arg Val Thr Ile Thr Ala Asp Thr Ser Thr Asp
                85                  90                  95

Thr Ala Tyr Met Glu Leu Ser Ser Leu Arg Ser Glu Asp Thr Ala Val
```

```
                100             105             110
Tyr Tyr Cys Ala Asp Gly Met Trp Val Ser Thr Gly Tyr Ala Leu Asp
            115             120             125

Phe Trp Gly Gln Gly Thr Leu Val Thr Val Ser Ser Ala Ser Thr Lys
            130             135             140

Gly Pro Ser Val Phe Pro Leu Ala Pro Cys Ser Arg Ser Thr Ser Glu
145             150             155             160

Ser Thr Ala Ala Leu Gly Cys Leu Val Lys Asp Tyr Phe Pro Glu Pro
            165             170             175

Val Thr Val Ser Trp Asn Ser Gly Ala Leu Thr Ser Gly Val His Thr
            180             185             190

Phe Pro Ala Val Leu Gln Ser Ser Gly Leu Tyr Ser Leu Ser Ser Val
            195             200             205

Val Thr Val Pro Ser Ser Leu Gly Thr Lys Thr Tyr Thr Cys Asn
            210             215             220

Val Asp His Lys Pro Ser Asn Thr Lys Val Asp Lys Arg Val Glu Ser
225             230             235             240

Lys Tyr Gly Pro Pro Cys Pro Pro Cys Pro Ala Pro Glu Phe Leu Gly
            245             250             255

Gly Pro Ser Val Phe Leu Phe Pro Pro Lys Pro Lys Asp Thr Leu Met
            260             265             270

Ile Ser Arg Thr Pro Glu Val Thr Cys Val Val Val Asp Val Ser Gln
            275             280             285

Glu Asp Pro Glu Val Gln Phe Asn Trp Tyr Val Asp Gly Val Glu Val
            290             295             300

His Asn Ala Lys Thr Lys Pro Arg Glu Glu Gln Phe Gln Ser Thr Tyr
305             310             315             320

Arg Val Val Ser Val Leu Thr Val Leu His Gln Asp Trp Leu Asn Gly
            325             330             335

Lys Glu Tyr Lys Cys Lys Val Ser Asn Lys Gly Leu Pro Ser Ser Ile
            340             345             350

Glu Lys Thr Ile Ser Lys Ala Lys Gly Gln Pro Arg Glu Pro Gln Val
            355             360             365

Tyr Thr Leu Pro Pro Ser Arg Asp Glu Leu Thr Lys Asn Gln Val Ser
            370             375             380

Leu Thr Cys Leu Val Lys Gly Phe Tyr Pro Ser Asp Ile Ala Val Glu
385             390             395             400

Trp Glu Ser Asn Gly Gln Pro Glu Asn Asn Tyr Lys Thr Thr Pro Pro
            405             410             415

Val Leu Asp Ser Asp Gly Ser Phe Phe Leu Tyr Ser Lys Leu Thr Val
            420             425             430

Asp Lys Ser Arg Trp Gln Gln Gly Asn Val Phe Ser Cys Ser Val Met
            435             440             445

His Glu Ala Leu His Asn His Tyr Thr Gln Lys Ser Leu Ser Leu Ser
            450             455             460

Pro Gly
465

<210> SEQ ID NO 101
<211> LENGTH: 19
<212> TYPE: PRT
<213> ORGANISM: Artificial Sequence
<220> FEATURE:
<223> OTHER INFORMATION: Synthetic peptide
```

```
<400> SEQUENCE: 101

Glu Ser Lys Tyr Gly Pro Pro Cys Pro Pro Cys Pro Ala Pro Pro Val
1               5                   10                  15

Ala Gly Pro

<210> SEQ ID NO 102
<211> LENGTH: 5
<212> TYPE: PRT
<213> ORGANISM: Artificial Sequence
<220> FEATURE:
<223> OTHER INFORMATION: Synthetic peptide

<400> SEQUENCE: 102

Gly Gly Gly Gly Ser
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic peptide

<400> SEQUENCE: 103

Ser Gly Gly Gly Gly Ser
1               5
```

ANTI-VLA-4 ANTIBODIES HAVING REDUCED EFFECTOR FUNCTION

CROSS REFERENCE TO RELATED APPLICATION(S)

This application is a 35 U.S.C. § 371 National Phase Entry Application from PCT/US2019/034962, filed May 31, 2019, which claims the benefit of U.S. Provisional Application Nos. 62/680,466, filed Jun. 4, 2018, 62/782,876, filed Dec. 20, 2018, and 62/833,319, filed Apr. 12, 2019, the disclosures of which are incorporated by reference.

FIELD OF THE INVENTION

This invention relates to alpha-4 binding antibodies, and fragments thereof.

SEQUENCE LISTING

The instant application contains a Sequence Listing which has been submitted via Patent Center and is hereby incorporated by reference in its entirety. Said Sequence Listing, created on Oct. 17, 2023, is named 123429_60202_ST25 and is 224,372 bytes in size.

BACKGROUND OF THE INVENTION

Integrins are members of a large family of cell surface receptors that mediate cell-cell and cell-matrix interactions. They exist as non-covalent as heterodimers of different combinations of α and β chains and share extensive structural homology. Integrins mediate a wide variety of physiological processes and are relevant to a wide variety of pathological conditions. The α4 chain is largely leukocyte restricted and can associate with two β chains, β1 and β7.

VLA-4 (also called α4β1) and α4β7 play central roles in the pathophysiology of inflammatory diseases. VLA-4 is a member of the β1 integrin family of cell surface receptors. VLA-4 contains an α4 chain and a β1 chain and is involved in cell-cell interactions. Its expression is mainly restricted to lymphoid cells, including T lymphocytes, and myeloid cells including microglia cells and macrophages. VLA-4 binds the endothelial cell ligand VCAM-1 (Vascular Cell Adhesion Molecule-1), and can mediate T and B lymphocyte attachment to the heparin II binding fragment of human plasma fibronectin. VLA-4 regulates normal leukocyte trafficking (Lobb and Hemler, J. Clin. Invest. 94(5): 1722-1728, 1994) and provides a key co-stimulatory signal supporting cell activation (Clark and Brugge, Science 268(5208):233-9, 1995). During inflammatory responses, VLA-4 regulates leukocyte migration into the damaged tissues and thus has been recognized as an attractive therapeutic target. In vivo studies using blocking monoclonal antibodies (Lobb and Hemler, supra; Enders et al., Brain 121 (Pt 7):1257-66, 1998; Ramos-Barbon et al., Am J Respir Crit Care Med. 163(1):101-8. 2001), inhibitory peptides (Molossi et al., J Clin Invest. 95(6):2601-10, 1995; Abraham, 1997; van der Laan et al., J Neurosci Res. 2002 Jan. 15; 67(2):191-9, 2002), and small molecule antagonists (Kudlacz et al., J. Pharmacol. Exp. Ther. 301(2):747-52, 2002) have verified the critical role of α4β1 integrins in leukocyte-mediated inflammation.

α4β1 mediates cell adhesion by binding to either of two protein ligands, VCAM-1 or fibronectin (e.g., the alternatively spliced connecting segment 1 (CS1)-containing fibronectin variant) (Osborn et al., Cell 59(6):1203-11, 1989; Wayner et al., J. Cell Biol. 109(3):1321-30, 1989). Other potential ligands have been identified (Bayless et al., J. Cell Sci. 111 (Pt 9):1165-74, 1998); however, the biological significance of these interactions is less clear. The interactions between α4β1 and its ligands are of low affinity and binding presumably is modulated through multivalent interactions. While expression of α4β1 is constitutive, its interactions with ligands are strongly enhanced in an activated state that can be induced by various stimuli including antigen, anti-T-cell receptor mAbs, phorbol esters, the divalent cation $Mn^{2+}$, and certain β1-specific antibodies. These changes in affinity and/or avidity ultimately determine whether an interaction is productive and stabilizes the ligand/integrin complex (Humphries, Curr Opin Cell Biol. 8(5):632-40, 1996). α4β7 is expressed by a more restricted set of leukocytes, and is in part responsible for the homing of lymphocytes to mucosyl lymphoid tissues by binding the mucosal addressin MadCAM, but it also binds VCAM-1 and fibronectin. Certain monoclonal antibodies (mAbs) to α4 can block adhesive functions of both VLA4 and α4β7.

Humanized antibodies can be used as therapeutic agents in place of murine antibodies to avoid the undesirable immune response in humans termed the HAMA (Human Anti-Mouse Antibody) response. Humanized antibodies are generally constructed by replacing the complementarity determining regions (CDRs) of a human antibody with the CDRs of another species, typically a mouse antibody.

Antibodies have the ability to bind antigens through their variable regions. Once an antigen is bound by the antibody, the antigen is targeted for destruction, often mediated, at least in part, by the constant region or Fc region of the antibody. There are several effector functions or activities mediated by the Fc region of an antibody. One effector function is the ability to bind complement proteins which can assist in lysing the target antigen, for example, a cellular pathogen, in a process termed complement-dependent cytotoxicity (CDC). Another effector activity of the Fc region is to bind to Fc receptors (e.g., FcγRs) on the surface of immune cells, or so-called effector cells, which have the ability to trigger other immune effects. These immune effects (e.g., antibody-dependent cell cytotoxicity (ADCC) and antibody-dependent cell phagocytosis (ADCP)), act in the removal of pathogens/antigens by, for example, releasing immune activators and regulating antibody production, endocytosis, phagocytosis, and cell killing. In some clinical applications these responses are crucial for the efficacy of the antibody while in other cases they provoke unwanted side effects. One example of an effector-mediated side effect is the release of inflammatory cytokines causing an acute fever reaction. Another example is the long term deletion of antigen-bearing cells.

The effector function of an antibody can be avoided by using antibody fragments lacking the Fc region (e.g., such as a Fab, F(ab')$_2$, or single chain Fv (scFv)). However, these fragments have reduced half-lives due to rapid clearance through the kidneys. Fab and scFv fragments have only one antigen-binding site instead of two, potentially compromising any advantages due to binding avidity and presenting potential challenges in manufacturing. Alternative approaches aim to reduce the effector functions of a full-length antibody while retaining other valuable attributes of the Fc region (e.g., prolonged half-life and heterodimerization). One approach to reducing effector function is to generate so-called aglycosylated antibodies by eliminating sugars that are linked to particular residues in the Fc region. Aglycosylated antibodies can be generated by, for example, deleting or altering the residue to which the sugar is attached, removing the sugars enzymatically, producing the antibody in cells cultured in the presence of a glycosylation inhibitor, or by expressing the antibody in cells unable to glycosylate proteins (e.g., bacterial host cells). Another approach is to employ Fc regions from an IgG4 antibody, instead of IgG1. It is well known that IgG4 antibodies are characterized by having lower levels of complement activation and antibody-dependent cellular cytotoxicity than IgG1.

Monoclonal antibodies to human α4 bind to three functionally distinct topographical epitopes, A, B, and C (Pulido et al., J. Biol. Chem. 266:10241-10245, 1991; Schiffer et al., J. Biol. Chem. 270: 14270-14273, 1995). Epitope B is subdivided into B1 and B2 epitopes that are topographically indistinguishable but are defined by the ability of mAbs to induce cell aggregation. Anti-α4 mAbs directed to epitopes A and B2 can induce homotypic cell aggregation, but those directed against epitopes B1 and C do not.

SUMMARY OF THE INVENTION

The invention relates to anti-VLA-4 antibodies and binding fragments thereof comprising germline variable region frameworks, which can optimize CDR-grafted alpha-4 binding antibodies, such as anti-VLA-4 antibodies. Accordingly, the invention comprises anti-VLA-4 variable heavy (VH) and variable light (VL) chains and antibody molecules including such frameworks. In some embodiments, the VLA-4 is human VLA-4. In some embodiments, the VLA-4 comprises an α4 chain (e.g., a human α4 chain).

The antibodies can also contain modified Fc regions, which alter or reduce effector function and improve stability. The antibodies with modified Fc regions can improve the significant adverse effects observed in antibodies that lack oligosaccharides, particularly adverse effects on conformation and stability. The antibodies with modified Fc regions can also have altered or reduced effector function and improved stability. The invention further relates to methods of making the molecules described herein.

The antibodies can improve the problems of prior art "effector-less" antibodies by providing improved methods for enhancing the stability of an Fc region. For example, the invention provides stability-engineered Fc polypeptides, e.g., stabilized IgG antibodies or other Fc-containing binding molecules, which comprise stabilizing amino acids in the Fc region of the polypeptide. In one embodiment, the invention provides a method for introducing mutations at specific amino acid residue positions in the Fc region of a parental Fc polypeptide which result in the enhanced stability of the Fc region. In some embodiments, the stabilized Fc polypeptides have an altered or reduced effector function (as compared to a polypeptide which does not comprise the stabilizing amino acid(s)) and exhibits enhanced stability as compared to the parental Fc polypeptide. In some embodiments, the parental Fc polypeptide is human IgG1 (e.g., having the sequence of SEQ ID NO: 83). In some embodiments, the parental Fc polypeptide is human IgG4 (e.g., having the sequence of SEQ ID NO: 84).

Accordingly, the antibodies disclosed herein can offer several advantages which include, but are not limited to, the following:

providing stabilized aglycosylated Fc polypeptides comprising stabilized aglycosylated Fc regions, for example, stabilized fusion proteins or aglycosylated IgG antibodies, suitable as therapeutics because of their reduced effector function;

providing stabilized Fc polypeptides comprising Fc regions derived from IgG4 antibodies, for example, stabilized glycosylated or aglycosylated fusion proteins or IgG4 antibodies, suitable as therapeutics because of their reduced effector function;

an efficient method of producing stabilized Fc polypeptides with minimal alterations to the polypeptide (e.g., by introducing changes into an unstabilized parent polypeptide or by expressing a nucleic acid molecule encoding a stabilized Fc polypeptide);

a method of enhancing the stability of an Fc polypeptide while avoiding any increase in immunogenicity and/or effector function;

methods for enhancing the scalability, manufacturing, and/or long-term stability of an Fc polypeptide; and methods for treating a subject in need of therapy with a stabilized Fc polypeptide of the invention.

In one embodiment, the invention features an anti-α4 antibody VH chain having CDRs from a donor anti-α4 antibody, e.g., an anti-α4 antibody described herein, and a VH framework having regions 1, 2, 3, and 4 from the sequence of, or having no more than 5, 10 or 15 differences from a germline variable region sequence for the VH chain. In one embodiment, variable framework region 4 (FR4) is a human consensus sequence. In one embodiment, the complete VH chain framework regions FR1, FR2, FR3 and FR4, are present. In another embodiment, the chain is an antigen-binding fragment of a VH region.

In one embodiment, the germline sequence is human IGHV1-f (SEQ ID NO: 2), depicted in FIG. 1. In certain embodiments, the VH framework sequence can differ by at least one, but by no more than 2, 3, 4, 5, 10 or 15 amino acid residues from a germline sequence, e.g., SEQ ID NO: 2. In one embodiment, the VH framework further includes residues other than the corresponding human residues. For example, the VH chain includes non-canonical residues at one or more of framework positions 24, 67, 76, 80, and 94 (Kabat numbering) of SEQ ID NO: 2.

In one embodiment, at least one or more of the complementarity determining regions (CDRs) of the variable domains are derived from a donor non-human α4-binding antibody (i.e., a non-human antibody that specifically binds to α4). In one embodiment, the antigen binding regions of the CDR-grafted heavy chain variable domain include the CDRs corresponding to positions 26-34 (CDR1), 50-65 (CDR2) and 95-102 (CDR3) (Kabat numbering).

Thus, in one embodiment, the variable heavy chain (VH) framework has an acceptor sequence derived from human antibody germline sequence IGHV1-f.

In another embodiment, at least one amino acid, and less than 2, 3, 4, 5, or 10 amino acid residues, in the FR1 region of the VH is other than the corresponding human germline residue. One or more of such residues can, for example, be identical to the nonhuman antibody framework region from which the CDR sequences are derived. In one embodiment, the amino acid residue at Kabat position 24 is mutated to be identical to the nonhuman antibody framework region.

In another embodiment, at least one amino acid, and less than 2, 3, 4, 5, or 10 amino acid residues, in the FR2 region of the VH is other than the corresponding human germline residue. One or more of such residues can, for example, be identical to the nonhuman antibody framework region from which the CDR sequences are derived.

In yet another embodiment, at least one amino acid, and less than 2, 3, 4, 5, or 10 amino acid residues, in FR3 of the VH chain is other than the corresponding human germline residue. One or more of such residues can, for example, be identical to the nonhuman antibody framework region from which the CDR sequences are derived. In one embodiment, the amino acid residue at Kabat position 94 is identical to the nonhuman antibody framework region. In yet another embodiment, the amino acid residues at Kabat positions 67, 76, 80, and 94 are identical to the nonhuman antibody framework region.

In certain embodiments, the VH chain of the antibody has the sequence of SEQ ID NO: 3, SEQ ID NO: 4, or SEQ ID NO: 5.

In one aspect, the invention features, an anti-VLA-4 VL chain having CDRs from a donor anti-VLA-4 antibody, e.g., an anti-VLA-4 antibody described herein, and a VL framework having regions 1, 2, 3, and 4 from the sequence of, or having no more than 5, 10 or 15 differences (either per/region or in total) from, a germline variable region sequence for the VL chain. In one embodiment, variable framework region 4 (FR4) is a human consensus sequence. In one embodiment, the complete VL chain framework regions FR1, FR2, FR3 and FR4, are present. In another embodiment, the chain is an antigen-binding fragment of a VL region.

In another embodiment, the germline sequence is IGKV4-1 (SEQ ID NO: 7), depicted in FIG. 2. In yet other embodiments, the VL framework sequence can differ by at least one, but no more than 2, 3, 4, 5, 10 or 15 amino acid residues from a germline framework sequence, e.g., SEQ ID NO: 7. In another embodiment, the VL further includes other than the corresponding human amino acid residues. For example, the VL chain further includes non-human residues at one or more of framework positions 1, 73, and 87 (Kabat numbering) of SEQ ID NO: 7.

In one embodiment, the sequence is AAH7035.1 (SEQ ID NO: 12) or its germline engineered version (SEQ ID NO: 13), depicted in FIG. 2. In some embodiments, the VL framework sequence can differ by at least one, but not more than 5, 10, 15, 20, or 25 amino acid residues from a germline engineered framework sequence, e.g., SEQ ID NO: 13. In one embodiment, the VL chain includes other than the corresponding human residues. For example, the VL chain includes non-human residues at one or more of framework positions 1 and 87 (Kabat numbering) of SEQ ID NO: 12. In another embodiment, the VL includes amino acid substitutions in the framework regions to resemble a different human germline framework sequence, such as from germline sequence IGKV4-1. In certain embodiments, the VL framework sequence is altered to be identical to the IGKV4-1 germline sequence at positions 1-3, 5-23, 35-37, 39-42, 45-49, 57, 59-61, 63-64, 70-72, 74-84, 86-88, 99-106 (Kabat numbering) of SEQ ID NO: 12.

In one embodiment, at least one or more of the complementarity determining regions (CDRs) of the variable domains are derived from a donor non-human α4-binding antibody. In another embodiment, the antigen binding regions of the CDR-grafted heavy chain variable domain include the CDRs corresponding to positions 24-31 (CDR1), 50-56 (CDR2) and 89-97 (CDR3) (Kabat numbering). Thus, in one embodiment, the VL framework has an acceptor sequence constructed from IGKV4-1 germline sequence, from antibody AAH70335.1 or from germline engineered antibody AAH70335.1.

In yet another embodiment, at least one amino acid, and less than 2, 3, 4, 5, 10, or 15 residues, in FR1 of the VL chain is other than the corresponding human residue. One or more of such residues can, for example, be identical to the nonhuman antibody framework region from which the CDR sequences are derived. In one embodiment, the amino acid residue at the N-terminal position of FR1 is mutated to be identical to the nonhuman antibody framework region.

In another embodiment, at least one amino acid, and less than 2, 3, 4, 5, 10, or 15 residues, in FR2 of the VL chain is other than the corresponding human residue. One or more of such residues can, for example, be identical to the nonhuman antibody framework region from which the CDR sequences are derived.

In yet another embodiment, at least one amino acid, and less than 2, 3, 4, 5, 10, or 15 residues, in FR3 of the VL is other than the corresponding human residue. One or more of such residues can, for example, be identical to the nonhuman antibody framework region from which the CDR sequences are derived. In another embodiment, the amino acid residue at Kabat position 87 is mutated to be identical to the nonhuman antibody framework region. In yet another embodiment, the amino acid residues at Kabat positions 67 and 87 are mutated to be identical to the nonhuman antibody framework sequence. In yet another embodiment, the amino acid residues at Kabat positions 67, 73, and 87 of SEQ ID NO: 7 are mutated to be identical to the nonhuman antibody framework sequence.

In other embodiments, the VL chain of the antibody has the sequence of SEQ ID NO: 8, SEQ ID NO: 9, SEQ ID NO: 10, or SEQ ID NO: 11.

In one embodiment, the VH chain of the antibody has the sequence of SEQ ID NO: 4 and the VL chain of the antibody has the sequence of SEQ ID NO: 11.

In one embodiment, the CDRs of the VH and VL acceptor framework sequences are selected to resemble the CDR sequences of a nonhuman (e.g., murine) antibody sequence, where the nonhuman antibody binds integrin alpha-4 or a fragment thereof. In another embodiment, the sequences of the CDRs are selected to resemble the sequences of the CDRs of a non-human antibody that binds the B1 epitope of the VLA-4 α4 chain. In one embodiment, the CDRs are selected to resemble a murine monoclonal antibody, e.g., HP1/2, HP2/1, HP2/4, L25, P4C2, or 21.6 (Pulido et al., J. Biol. Chem. 266:10241-10245, 1991; U.S. Pat. No. 6,033,665). Modification can mean, e.g., excision and insertion or alteration, e.g., by directed mutagenesis.

In another aspect, the invention features an antibody, or antigen binding fragment thereof, including:
an anti-VLA-4 VL chain described herein, e.g., an anti-VLA-4 VL chain having CDR's from a donor anti-VLA-4 antibody, e.g., an anti-VLA-4 antibody described herein, and a VL framework having LC framework regions 1, 2 and 3 from the sequence of, or having no more than 5, 10, or 15 differences from, a germline variable region sequence for the VL chain. In one embodiment, variable region 4 is a human consensus sequence; and
an anti-VLA-4 VH chain described herein, e.g., an anti-VLA-4 VL chain having CDRS from a donor anti-VLA-4 antibody, e.g., an anti-VLA-4 antibody described herein, and a VL framework having LC framework regions 1, 2 and 3 from the sequence of, or having no more than 5, 10 or 15 differences from, a germline variable region sequence for the VL chain. In one embodiment, variable region 4 is a human consensus sequence.

In one embodiment, the antibody binds one or both of α4β1 and α4β7.

In another aspect, a VL or VH chain, or antibody, or fragment thereof, described herein is detectably labeled.

In another aspect, the invention provides a recombinant anti-alpha 4 antibody or an alpha 4-binding fragment thereof comprising: (a) a variable light chain comprising the sequence of SEQ ID NO: 11; (b) a variable heavy chain comprising the sequence of SEQ ID NO: 4; (c) a constant light chain of human kappa light chain (SEQ ID NO: 82); and (d) a constant heavy chain of human IgG1, said constant region comprising at least one mutation selected from S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, or deletion of K478 according to Kabat numbering scheme.

In some embodiments, the constant heavy chain of human IgG1 comprises, consists, or consists essentially of at least two mutations selected from S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, or deletion of K478 according to Kabat numbering scheme.

In some embodiments, the constant heavy chain of human IgG1 comprises, consists, or consists essentially of at least three mutations selected from S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, or deletion of K478 according to Kabat numbering scheme.

In some embodiments, the constant heavy chain of human IgG1 comprises, consists, or consists essentially of at least four, or at least five, or at least six, or at least seven, or at least eight, or at least nine, or at least ten or at least eleven, or at least twelve, or at least thirteen, or at least fourteen, or at least fifteen, or at least sixteen, or at least seventeen or at least eighteen or at least nineteen, or at least twenty, or at least twenty-one, or at least twenty-two, or at least twenty-three, or at least twenty-four mutations selected from S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, or deletion of K478 according to Kabat numbering scheme.

In some embodiments, the constant heavy chain of human IgG1 comprises, consists, or consists essentially of the following mutations: S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme.

In another aspect, the invention provides a recombinant anti-alpha 4 antibody or an alpha 4-binding fragment thereof comprising: (a) a variable light chain comprising the sequence of SEQ ID NO: 11; (b) a variable heavy chain comprising the sequence of SEQ ID NO: 4; (c) a constant light chain of human kappa light chain (SEQ ID NO: 82); and (d) a constant heavy chain of human IgG4, said constant region comprising at least one mutation selected from the group consisting of S241P, N314Q, Q376R, E377D, M381L, R440K, E450Q, L476P, and deletion of K478 according to Kabat numbering scheme.

In some embodiments, the constant heavy chain of human IgG4 comprises, consists, or consists essentially of at least two mutations selected from the group consisting of S241P, N314Q, Q376R, E377D, M381L, R440K, E450Q, L476P, and deletion of K478 according to Kabat numbering scheme.

In some embodiments, the constant heavy chain of human IgG4 comprises, consists, or consists essentially of at least three, or at least four, or at least five, or at least six, or at least seven, or at least eight, or at least nine mutations selected from the group consisting of S241P, N314Q, Q376R, E377D, M381L, R440K, E450Q, L476P, and deletion of K478 according to Kabat numbering scheme.

In some embodiments, the constant heavy chain of human IgG4 comprises, consists, or consists essentially of one or more of the following mutations: S241P, N314Q, Q376R, E377D, M381L, R440K, E450Q, L476P, and deletion of K478 according to Kabat numbering scheme.

Note that the C' terminal lysine residue (at position 478 according to the Kabat number scheme) is typically deleted post-translationally or by artifice. Thus, in some embodiments, the heavy chain of the antibodies (or Fc portions of domains thereof) described herein lack a lysine at the C terminus. In other words, in some embodiments, the lysine at position 478 (Kabat numbering) is deleted in the heavy chain of the antibodies (or Fc portions of domains thereof) described herein.

In some embodiments, the constant heavy chain of human IgG1 with no mutations or substitutions has the sequence of SEQ ID NO: 83.

In some embodiments, constant heavy chain of human IgG4 with no mutations or substitutions has the sequence of SEQ ID NO: 84.

In yet another aspect, the invention features a vector containing DNA encoding an antibody heavy chain, or an α4 binding fragment thereof, described herein. In some embodiments, the DNA of the vector encodes a VH having the sequence of SEQ ID NO: 3, SEQ ID NO: 4, or SEQ ID NO: 5.

In yet another aspect, the invention features a vector containing DNA encoding an antibody light chain, or an α4 binding fragment thereof, described herein. In some embodiments, the DNA of the vector encodes a VL chain having the sequence of SEQ ID NO: 8, SEQ ID NO: 9, SEQ ID NO: 10 or SEQ ID NO: 11.

In yet another aspect, the invention features a vector containing DNA encoding an antibody heavy chain, or an α4 binding fragment thereof, described herein and an antibody light chain, or an α4 binding fragment thereof, described herein.

In another aspect, the invention features a host cell containing a vector described herein, e.g., one capable of expressing a heavy and/or light chain antibody or antibody fragment described herein. In certain embodiment, the host cell is a Chinese hamster ovary (CHO) cell.

In one aspect, the invention features a method of making a recombinant anti-α4 antibody, or an α4-binding fragment thereof, by providing a host cell transfected with (a) a DNA sequence encoding an antibody heavy chain described herein, or an α4-binding fragment thereof, and (b) a DNA sequence encoding an antibody light chain, or an α4-binding fragment thereof, and culturing the transfected cell to produce the recombinant anti-α4 antibody molecule or α4 binding fragment thereof. The DNA encoding the antibody heavy and light chains can be on the same vector or on different vectors.

In one aspect, the invention features a method of making a recombinant anti-α4 antibody, or an α4-binding fragment thereof, by providing a host cell transfected with (a) a DNA sequence encoding an antibody heavy chain, or an α4-binding fragment thereof, e.g., where the DNA sequence has the sequence of SEQ ID NO: 4, and (b) a DNA sequence encoding an antibody light chain, or an α4-binding fragment thereof, e.g., wherein the DNA sequence has the sequence of SEQ ID NO: 11, and culturing the transfected cell line to produce the recombinant anti-α4 antibody molecule or α4 binding fragment thereof. The DNA encoding the antibody heavy and light chains can be on the same vector or on different vectors.

In another aspect, the invention features a method of treating a disease or disorder mediated by an α4 integrin, e.g., an α4β1 (VLA-4) or α4β7 integrin, by administering an α4 antibody or antibody fragment described herein, or a pharmaceutical composition containing the antibody or fragment, to a subject in need of such treatment. The subject can have or be at risk for developing, for example, inflammatory, immune, or autoimmune disorders (e.g., inflammation of the central nervous system, such as multiple sclerosis, meningitis, neuromyelitis optica, neurosarcoidosis, CNS vasculitis, encephalitis, and transverse myelitis), tissue or organ graft rejection or graft-versus-host disease, acute CNS injury, such as stroke, traumatic brain injury (TBI), or spinal cord injury (SCI); chronic renal disease; allergy, e.g., allergic asthma; type 1 diabetes mellitus; inflammatory bowel disorders, such as Crohn's disease, ulcerative colitis; myasthenia gravis; fibromyalgia; arthritic disorders, such as rheumatoid arthritis, psoriatic arthritis; inflammatory/immune skin disorders, such as psoriasis, vitiligo, dermatitis, lichen planus; systemic lupus erythematosus; Sjogren's Syndrome; hematological cancers, such as multiple myeloma, leukemia, lymphoma; solid cancers, such as sarcomas or carcinomas, e.g., of the lung, breast, prostate, brain; and fibrotic disorders, such as pulmonary fibrosis, myelofibrosis, liver cirrhosis, mesangial proliferative glomerulonephritis, crescentic glomerulonephritis, diabetic nephropathy, and renal interstitial fibrosis. In a preferred embodiment, the invention features a method of treating a patient suffering from multiple sclerosis or alleviating a symptom of a patient suffering from multiple sclerosis, such as clinically isolated syndrome, relapsing remitting multiple sclerosis, or active secondary progressive multiple sclerosis. In certain embodiments, the multiple sclerosis is a relapsing form of multiple sclerosis. In a preferred embodiment, the invention features a method of treating a patient having or at risk for developing epilepsy, including a drug-resistant epilepsy. In certain embodiments, the subject or patient is a human.

In another aspect, the invention features a method of treating a patient by administering to the patient an α4-binding antibody or antibody fragment. In one embodiment, the patient has a cancer, such as a solid tumor or a hematological malignancy. For example, a patient treated with an α4-binding antibody or antibody fragment can have acute myelogenous leukemia (AML) or multiple myeloma (MM).

In another embodiment, the patient has an inflammatory disorder, such as multiple sclerosis, asthma (e.g., moderate to severe asthma), rheumatoid arthritis, diabetes, or Crohn's disease. In another embodiment, the composition is administered as a regimen. In yet another embodiment, the method further includes selecting a patient suitable for treatment with the composition. A patient suitable for treatment, for example, has demonstrated a sign or symptom indicative of disease onset, such as a sign or symptom indicative of MS. In a preferred embodiment, the patient has epilepsy.

In certain embodiments, the patient is administered a therapeutically effective amount of an α4-binding antibody or antibody fragment. In certain embodiments, the patient is administered an α4-binding antibody or antibody fragment in an amount ranging from about 0.0003 mg/kg, 0.0004 mg/kg, 0.0005 mg/kg, 0.0006 mg/kg, 0.0007 mg/kg, 0.0008 mg/kg, 0.0009 mg/kg, 0.0010 mg/kg, 0.0015 mg/kg, or 0.0020 mg/kg to about 0.0025 mg/kg, 0.003 mg/kg, 0.005 mg/kg, 0.010 mg/kg, 0.0125 mg/kg, 0.025 mg/kg, 0.050 mg/kg, 0.0625 mg/kg, 0.080 mg/kg, 0.100 mg/kg, 0.200 mg/kg, 0.300 mg/kg, 0.3125 mg/kg, 0.40 mg/kg, 0.50 mg/kg, 0.6 mg/kg, 0.7 mg/kg, 0.8 mg/kg, 0.9 mg/kg, 1 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, or 10 mg/kg. In some embodiments, the patient is administered in an amount of about 0.025 mg/kg to about 10 mg/kg of an α4-binding antibody or antibody fragment. In some embodiments, the patient is administered in an amount of about 0.0625 mg/kg to about 8.0 mg/kg of an α4-binding antibody or antibody fragment. In some embodiments, the patient is administered in an amount of about 0.3 mg/kg to about 6.0 mg/kg of an α4-binding antibody or antibody fragment. In some embodiments, the patient is administered in an amount of about 0.5 mg/kg to about 5.0 mg/kg of an α4-binding antibody or antibody fragment.

In yet another embodiment, the method further includes administering to the patient a second therapeutic agent, such as, a chemotherapeutic agent, a thrombolytic agent, a neuroprotective agent, an anti-inflammatory agent, a steroid, a cytokine, or a growth factor.

In one embodiment, the patient is administered a humanized anti-VLA-4 antibody, or fragment thereof, described herein, such as HuHP1/2, H1L1, H1L2 or H1L3.

In one embodiment, the composition containing an α4-binding antibody is administered as a regimen, such at regular intervals. For example, the composition can be administered once daily, weekly or monthly; once per week, twice per week, three times per week, four times per week or more; or once every two weeks, once every three weeks, once every four weeks or more.

In one embodiment, dosing can be adjusted according to a patient's rate of clearance of a prior administration of anti-α4 antibody. For example, in one embodiment, a patient will not be administered a second or follow-on dose before the level of anti-α4 antibodies in the patient's system has dropped below a pre-determined level. In one embodiment, a sample from a patient (e.g., plasma, serum, blood or urine sample) is assayed for the presence of anti-α4 antibodies, and if the level of anti-α4 antibodies is above a pre-determined level, the patient will not be administered a second or follow-on dose. If the level of anti-α4 antibodies in the patient's system is below a pre-determined level, then the patient is administered a second or follow-on dose.

In one embodiment, the composition is administered continuously, e.g., over a period of more than 30 minutes but less than 1, 2, 4, or 12 hours. The composition containing the antibody and the second agent can be administered by any appropriate method, e.g., subcutaneously, intramuscularly, or intravenously.

In some embodiments, each of the antibody and the second agent is administered at the same dose as each is prescribed for monotherapy. In other embodiments, the antibody is administered at a dosage that is equal to or less than an amount required for efficacy if administered alone. Likewise, the second agent can be administered at a dosage that is equal to or less than an amount required for efficacy if administered alone.

Another aspect featured in the disclosure is a method of evaluating a patient by determining if the patient meets a preselected criterion, and if the patient meets the preselected criterion approving, providing, prescribing, or administering a VLA-4 binding antibody formulation described herein to the patient. In one embodiment, the preselected criterion is the failure of the patient to adequately respond to a prior alternate therapeutic treatment or regimen, e.g., for treatment of MS. In another embodiment, the preselected criterion is the absence of any signs or symptoms of progressive multifocal leukoencephalopathy (PML), or the absence of any diagnosis of PML. In some cases, the selection is based on the absence of a risk factor for PML, for example, the subject does not test positive for JC virus DNA or does not test positive for JC virus antibodies. In another embodiment, the criterion is as described in PCT/US07/75577 (published as WO2008/021954), hereby incorporated by reference, which describes methods and systems for drug distribution and for providing drugs to patients.

In another aspect, a method of distributing a composition described herein is provided. The composition contains an alpha-4 binding antibody. The method includes providing a recipient (e.g., an end user, patient, physician, retail or wholesale pharmacy, distributor, or pharmacy department at a hospital, nursing home clinic or HMO) with a package containing sufficient unit dosages of the drug to treat a patient for at least 6, 12, 24, 36, or 48 months. In another aspect, the invention features a method of evaluating the quality of a package or lot of packages (e.g., to determine if it has expired) of a composition described herein containing an alpha-4 binding antibody. The method includes evaluating whether the package has expired. The expiration date is at least 6, 12, 24, 36, or 48 months, e.g., greater than 24 or 36 months, from a preselected event, such as manufacturing, assaying, or packaging. In some embodiments, a decision or step is taken as a result of the analysis. For example, depending on the right analysis, the antibody in the package is used or discarded, classified, selected, released or withheld, shipped, moved to a new location, released into commerce, sold, or offered for sale, withdrawn from commerce or no longer offered for sale, depending on whether the product has expired.

In another aspect, the invention features a package containing at least two unit doses of an aqueous composition containing an α4 binding antibody. In one embodiment, all of the unit doses contain the same amount of antibody, and in other embodiments there are unit dosages of two or more strengths, or two or more different formulations, e.g., having different strengths or release properties.

In another aspect, the invention includes a method of instructing a recipient on the administration of a formulation containing α4 binding antibody. The method includes instructing the recipient (e.g., an end user, patient, physician, retail or wholesale pharmacy, distributor, or pharmacy department at a hospital, nursing home clinic or HMO) that the antibody should be administered to a patient according to a regimen described herein. The method can also include instructing the recipient that the antibody should be administered prior to the expiration date. The expiration date is at least 6, 12, 24, 36, or 48 months, e.g., greater than 24 or 36 months, from a preselected event, such as manufacturing, assaying, or packaging. In one embodiment, the recipient also receives a supply of the antibody, e.g., a supply of unit dosages of the antibody.

In one embodiment, the stabilized polypeptide comprising a chimeric Fc region, wherein said stabilized polypeptide comprises at least one constant domain derived from a human IgG4 antibody and at least one constant domain derived from a human IgG1 antibody.

In one embodiment, the Fc region is a glycosylated Fc region.

In one embodiment, the Fc region is an aglycosylated Fc region.

In one embodiment, the Fc region is an aglycosylated Fc region comprising a glutamine (Q) at position 297 (EU numbering), position 314 (Kabat numbering) of the Fc region.

In one embodiment, the chimeric Fc region comprises a CH2 domain from an IgG antibody of the IgG4 isotype and a CH3 domain from an IgG antibody of the IgG1 isotype. In some embodiments, the chimeric Fc region comprising a CH2 domain from an IgG antibody of the IgG4 isotype and a CH3 domain from an IgG antibody of the IgG1 isotype further comprises a glutamine (Q) residue at position 297 (EU numbering), position 314 (Kabat numbering) of the Fc region instead of the naturally occurring arginine (N) residue.

In one embodiment, the chimeric Fc region comprises a hinge, CH1 and CH2 domains from an IgG antibody of the IgG4 isotype and a CH3 domain from an IgG antibody of the IgG1 isotype, and wherein the antibody comprises a proline at amino acid position 228 (EU numbering), position 241 (Kabat numbering). In some embodiments, the chimeric Fc region comprises a hinge, CH1, and CH2 domain from an IgG antibody of the IgG4 isotype and a CH3 domain from an IgG antibody of the IgG1 isotype, and wherein the antibody comprises a proline at amino acid position 228 (EU numbering), position 241 (Kabat numbering), further comprises a glutamine (Q) residue at position 297 (EU numbering), position 314 (Kabat numbering) of the Fc region instead of the naturally occurring arginine (N) residue.

In one embodiment, the IgG antibody is a human antibody.

In one embodiment, the aglycosylated Fc region comprises a chimeric hinge domain.

In one embodiment, the chimeric hinge domain comprises a substitution with proline residue at amino acid position 228 (EU numbering), position 241 (Kabat numbering).

In one embodiment, the antibody comprises a VH chain having the sequence of SEQ ID NO: 4, a VL chain having the sequence of SEQ ID NO: 11, a chimeric Fc region comprising a hinge, CH1 and CH2 domains from an IgG antibody of the IgG4 isotype and a CH3 domain from an IgG antibody of the IgG1 isotype, and wherein the antibody comprises a substitution to a glutamine residue (Q) at position 297 (EU numbering), position 314 (Kabat numbering) in the CH2 region; a substitution to a proline residue (P) at amino acid position 228 (EU numbering), position 241 (Kabat numbering) in the hinge region; and a deletion of a lysine (K) at position 447 EU numbering (position 478 Kabat numbering) in the CH3 region.

In one embodiment, the antibody comprises a heavy chain having the sequence of SEQ ID NO: 80 and a light chain having the sequence of SEQ ID NO: 81.

In one embodiment, the antibody comprises the heavy chain of SEQ ID NO: 86, a HP1/2 H1 heavy chain for IgG4 (wildtype; glycosylated).

In one embodiment, the antibody comprises the heavy chain of SEQ ID NO: 87, a HP1/2 heavy chain for IgG4 S228P (EU numbering) (aka IgG4P; glycosylated).

In one embodiment, the antibody comprises the heavy chain of SEQ ID NO: 88, a HP1/2 H1 heavy chain for IgG4 S228P L235E (EU numbering) (aka IgG4PE; glycosylated).

In one embodiment, the antibody comprises the heavy chain of SEQ ID NO: 89, a HP1/2 H1 heavy chain for IgG4 S228P T299A (EU numbering) (aglycosyl).

In one embodiment, the antibody comprises the heavy chain of SEQ ID NO: 90, a HP1/2 H1 heavy chain for IgG1 N297Q (EU numbering) (aglycosyl).

In certain therapeutic antibodies, for example those having an IgG4 constant region, scrambling can result in a bispecific monoclonal antibody that is monovalent for the therapeutic antibody's target (e.g., VLA4) and monovalent for another antigen. In one embodiment, the antibody can eliminate scrambling or reduce the antibody's susceptibility to scrambling thereby reducing PK/PD variability. In certain embodiments, the antibody can increase potency with a bivalent monoclonal antibody and eliminate bispecificity due to scrambling. In certain embodiments, the antibody can exhibit higher binding affinity than their non-mutated counterparts and/or demonstrate a higher sustained receptor occupancy.

Other features and advantages of the invention will be apparent from the following detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 is the amino acid sequence of an IgG4 Fc (hinge+CH2+CH3 domain)(SEQ ID NO:14). The hinge region is depicted in bold, and the CH3 domain is underlined. The boxed "S" is Ser228 (EU numbering, which is Ser241, Kabat numbering). The circled "N" is Asn314 in Kabat numbering (which is Asn297, EU numbering).

FIG. 7A depicts inhibition of binding of HL60 and KG1 cells to FN-coated wells. FIG. 7B depicts inhibition of binding of KG1 cells to VCAM1-Ig-coated wells. FIG. 7C depicts inhibition of binding of HL60 cells to FN- and VCAM1-Ig-coated wells when incubated with 20 μg/mL HuHP1/2 (Solid bars). Clear bars indicate percent cell adhesion in the presence of an isotype control. "HP1/2" refers to humanized HP1/2.

FIG. 8A depicts inhibition of binding of U266 and H929 cells to FN-coated wells. FIG. 8B depicts inhibition of binding of U266 and H929 cells to VCAM1-Ig-coated wells. FIG. 8C depicts inhibition of binding of U266 cells to FN- and VCAM1-Ig-coated wells when incubated with 20 μg/mL HuHP1/2 (Solid bars). Clear bars indicate percent cell adhesion in the presence of an isotype control. "HP1/2" refers to humanized HP1/2.

FIG. 9A depicts inhibition of binding of Mec1 and JM1 cells to FN-coated wells. FIG. 9B depicts inhibition of binding of Mec1 and JM1 cells to VCAM1-Ig-coated wells. FIG. 9C depicts inhibition of binding of Mec1 cells to FN- and VCAM1-Ig-coated wells when incubated with 20 μg/mL HuHP1/2 (Solid bars). Clear bars indicate percent cell adhesion in the presence of an isotype control. "HP1/2" refers to humanized HP1/2.

FIG. 11A-11D depicts the two interacting CH3 domains (Panel A) from an IgG1 X-ray crystal structure (pdb code 1hzh). Highlighted are IgG1 residues K409/K440 (EU numbering/Kabat numbering) and D399/D427 (EU numbering/Kabat numbering). FIG. 11B depicts the alignment of human IgG1/kappa constant domain sequences using a structure-based HMM (Wang et al, 2009, Proteins 76: 99, 2009). huIgG1_CH1 is SEQ ID NO: 95; huIGG1_CH3 is SEQ ID NO: 96; hukappa_CL is SEQ ID NO: 97; huIgG1_CH2 is SEQ ID NO: 98. Residue positions of CL, CH1, and CH3 that are involved in inter-domain interactions and amino acid positions that covary strongly with those amino acids in direct contact with the carbohydrate are highlighted in grey. Kabat and EU number are provided below the alignment. FIG. 11C depicts the ribbon diagram of the structure of the IgG1-CH2 domain (Sondermann et al, 406(6793):267-73, 2000). The valine residues buried by the N-linked carbohydrate and the unique 6 amino acid loop within the CH2 domain are labeled. FIG. 11D depicts the alignment of the native IgG1-CH2 sequence and the fully modified IgG1-CH2 sequence. Residue positions that were modified are shown in black. The EU number of the modified positions is shown above the alignment.

FIG. 22A includes the nucleotide and amino acid sequences of HP1/2 hG4P agly(N297Q, EU Numbering) G1, kappa light chain (H1L3). The nucleotide sequence (DNA is shown corresponding to SEQ ID NO: 91) and amino acids 1-233 of the light chain sequence (SEQ ID NO: 92) is shown. Amino acids 1-19 (and encoding DNA sequence) shown in bold italics contain the synthetic LC signal peptide. The mature N-terminus begins with the amino acid at position 20 (S).

FIG. 22B includes the nucleotide and amino acid sequences of HP1/2 hG4P agly(N297Q, EU Numbering) G1, heavy chain (H1L3). The nucleotide sequence (DNA is shown and corresponds to SEQ ID NO: 93) and amino acids 1-469 of the heavy chain (SEQ ID NO: 94) are shown. Amino acids 1-22 (DNA sequence shown in italics) contain the recoded synthetic signal peptide. The mature N-terminus begins with amino acid at position 23 (E).

FIG. 23A includes the amino acid sequence, including the signal sequences (underlined) of HP1/2 hG4P agly(N297Q, EU Numbering; SEQ ID NO: 100) G1, kappa light chain (H1L3) (SEQ ID NO: 99).

FIG. 23B includes the amino acid sequence of HP1/2 hG4P agly(N297Q, EU Numbering) G1, kappa light chain (H1L3) having a mature light chain of SEQ ID NO: 81 and a mature heavy chain of SEQ ID NO: 80.

G1) (referred to as HP12 in the figure; open circles), 30 mg/kg HP12 (closed circles), and 3 mg/kg natalizumab (Tysabri®, closed triangles).

Figure 36:
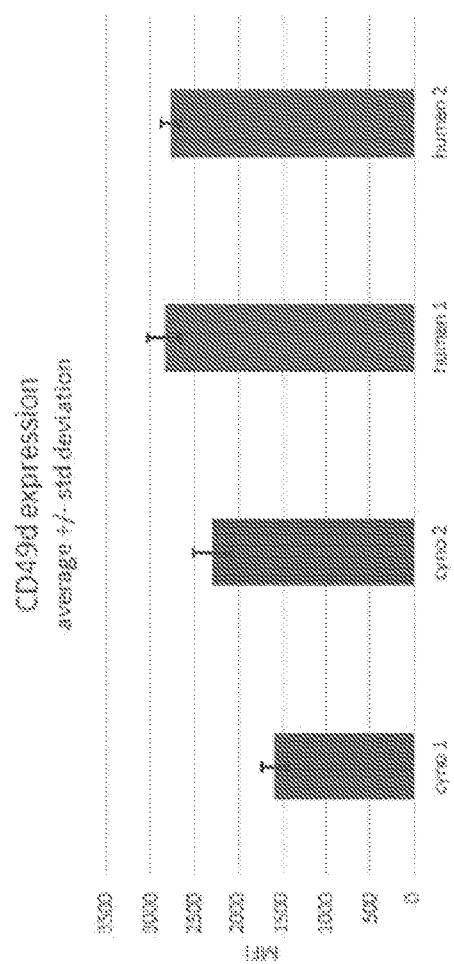
Figures 37A, 37B:
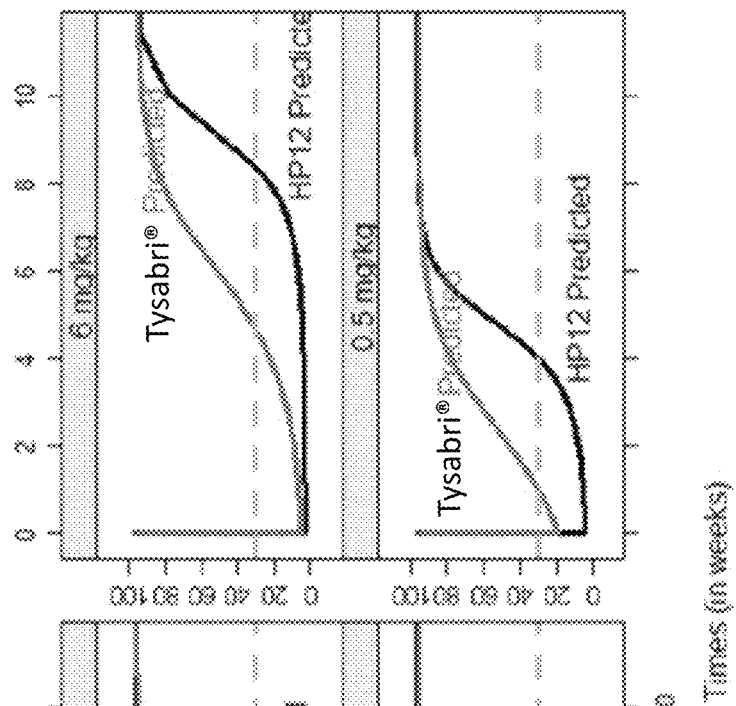
Figures 37C, 37D:
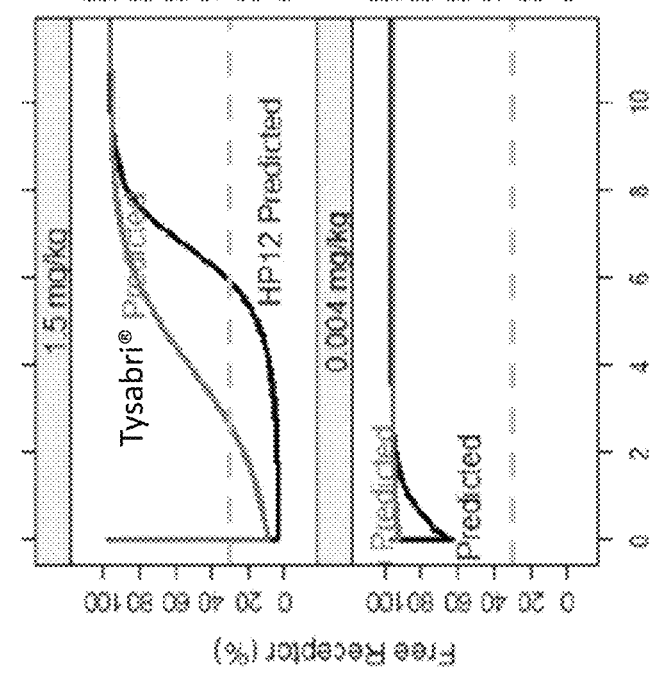

FIG. 36 is a bar graph showing CD49 (alpha-4 integrin) expression levels in humans (human 1 and human 2) and cynomolgus monkeys (cyno 1 and cyno 2).

FIGS. 37A-37D are line graphs showing the predicted receptor occupancy time-course after a single IV dose of natalizumab (red lines) and HP1/2 (black lines) at the indicated dosages.

Figure 38:
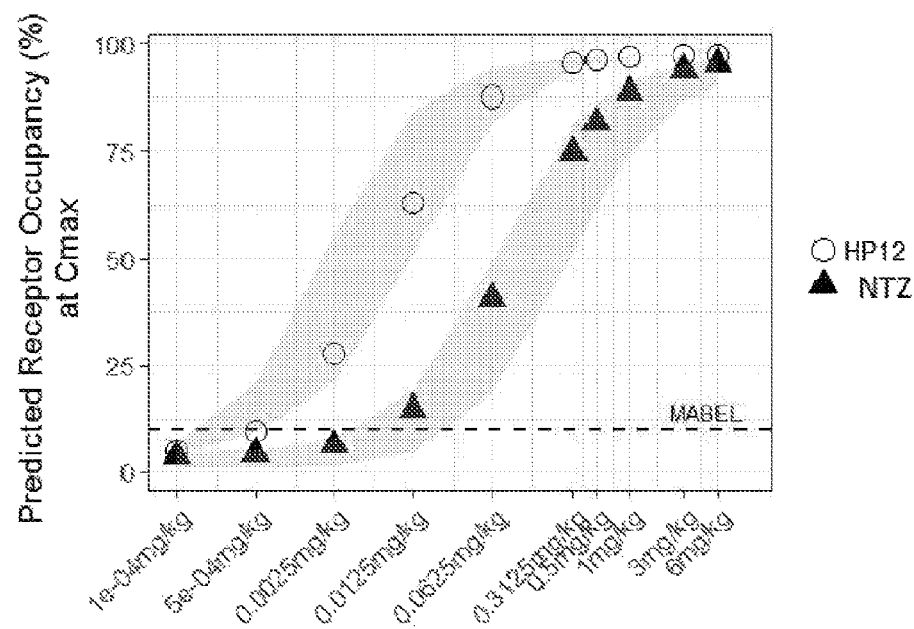

FIG. 38 provides a graph depicting the predicted receptor occupancy at Cmax following the administration of certain doses of HP1/2 (referred to as HP12 in the figure, open circles) and natalizumab (filled in triangles).

DETAILED DESCRIPTION

Antibodies against VLA-4 have been demonstrated to be useful in treating disease. For example, natalizumab (TYSABRI®), an anti-VLA-4 antibody, is used for treating relapsing multiple sclerosis and Crohn's disease. However, for treatment of certain conditions, for example acute conditions such as spinal cord injury (SCI) or traumatic brain injury (TBI), or treatments that are administered in a finite number such as treatment of cancer, it may be advantageous to treat with an anti-VLA-4 antibody that binds with an affinity different than that of natalizumab, e.g., a higher affinity, and/or a different pharmacologic profile (e.g., has with lower pharmacokinetic/pharmacodynamic variability in vivo). Such antibodies may also be useful for treating conditions such as multiple sclerosis in that less frequent treatment may be required or administration by means other than infusion may be more efficient. Enabling treatment with lower doses may also lower the risk of adverse events such as PML. Accordingly, the present invention provides antibodies having such desirable properties.

Certain antibodies of the invention disclosed herein have exhibited unexpected characteristics of newly designed humanized α4-binding antibodies that have a binding affinity for α4 that is 10-fold higher than that of the anti-α4 antibody natalizumab.

The antibodies also have stabilized Fc regions with reduced effector function, for example, by including one or more stabilizing amino acids in the Fc region of Fc polypeptide. In some embodiments, the stabilizing amino acids stabilize the Fc region of the polypeptide without the influencing the glycosylation and/or effector function of the polypeptide, and do not significantly alter other desired functions of the polypeptide (e.g., antigen binding affinity or half-life).

To provide a clear understanding of the specification and claims, the following definitions are conveniently provided below.

Definitions

As used herein, the term "effector function" refers to the functional ability of the Fc region or portion thereof to bind proteins and/or cells of the immune system and mediate various biological effects. Effector functions may be antigen-dependent or antigen-independent. A decrease in effector function refers to a decrease in one or more effector functions, while maintaining the antigen binding activity of the variable region of the antibody (or fragment thereof). Increase or decreases in effector function, e.g., Fc binding to an Fc receptor or complement protein, can be expressed in terms of fold change (e.g., changed by 1-fold, 2-fold, and the like) and can be calculated based on, e.g., the percent changes in binding activity determined using assays the are well-known in the art. As used herein, the term "antigen-dependent effector function" refers to an effector function which is normally induced following the binding of an antibody to a corresponding antigen. Typical antigen-dependent effector functions include the ability to bind a complement protein (e.g. C1q). For example, binding of the C1 component of complement to the Fc region can activate the classical complement system leading to the opsonization and lysis of cell pathogens, a process referred to as complement-dependent cytotoxicity (CDCC). The activation of complement also stimulates the inflammatory response and may also be involved in autoimmune hypersensitivity.

Other antigen-dependent effector functions are mediated by the binding of antibodies, via their Fc region, to certain Fc receptors ("FcRs") on cells. There are a number of Fc receptors which are specific for different classes of antibody, including IgG (gamma receptors, or IgγRs), IgE (epsilon receptors, or IgεRs), IgA (alpha receptors, or IgαRs) and IgM (mu receptors, or IgμRs). Binding of antibody to Fc receptors on cell surfaces triggers a number of important and diverse biological responses including endocytosis of immune complexes, engulfment and destruction of antibody-coated particles or microorganisms (also called antibody-dependent phagocytosis, or ADCP), clearance of immune complexes, lysis of antibody-coated target cells by killer cells (called antibody-dependent cell cytotoxicity, or ADCC), release of inflammatory mediators, regulation of immune system cell activation, placental transfer and control of immunoglobulin production. Certain Fc receptors, the Fc gamma receptors (FcγRs), play a critical role in either abrogating or enhancing immune recruitment. FcγRs are expressed on leukocytes and are composed of three distinct classes: FcγRI, FcγRII, and FcγRIII (Gessner et al., Ann. Hematol., (1998), 76: 231-48). Structurally, the FcγRs are all members of the immunoglobulin superfamily, having an IgG-binding α-chain with an extracellular portion composed of either two or three Ig-like domains. Human FcγRI (CD64) is expressed on human monocytes, exhibits high affinity binding (Ka=108-109 M-1) to monomeric IgG1, IgG3, and IgG4. Human FcγRII (CD32) and FcγRIII (CD16) have low affinity for IgG1 and IgG3 (Ka<107 M-1), and can bind only complexed or polymeric forms of these IgG isotypes. Furthermore, the FcγRII and FcγRIII classes comprise both "A" and "B" forms. FcγRIIa (CD32a) and FcγRIIIa (CD 16a) are bound to the surface of macrophages, NK cells and some T cells by a transmembrane domain while FcγRIIb (CD32b) and FcγRIIIb (CD 16b) are selectively bound to cell surface of granulocytes (e.g. neutrophils) via a phosphatidyl inositol glycan (GPI) anchor. The respective murine homologs of human FcγRI, FcγRII, and FcγRII are FcγRIIa, FcγRIIb/1, and FcγR1o.

As used herein, the term "antigen-independent effector function" refers to an effector function which may be induced by an antibody, regardless of whether it has bound its corresponding antigen. Typical antigen-independent effector functions include cellular transport, circulating half-life and clearance rates of immunoglobulins, and facilitation of purification. A structurally unique Fc receptor, the "neonatal Fc receptor" or "FcRn", also known as the salvage receptor, plays a critical role in regulating half-life and cellular transport. Other Fc receptors purified from microbial cells (e.g. Staphylococcal Protein A or G) are capable of binding to the Fc region with high affinity and can be used to facilitate the purification of the Fc-containing polypeptide.

Unlike FcγRs which belong to the Immunoglobulin superfamily, human FcRns structurally resemble polypeptides of Major Histocompatibility Complex (MHC) Class I (Ghetie and Ward, Immunology Today, (1997), 18(12): 592-8). FcRn is typically expressed as a heterodimer consisting of a transmembrane α or heavy chain in complex with a soluble β or light chain (β2 microglobulin). FcRn shares 22-29% sequence identity with Class I MHC molecules and has a non-functional version of the MHC peptide binding groove (Simister and Mostov, Nature, (1989), 337: 184-7. Like MHC, the a chain of FcRn consists of three extracellular domains (α1, α2, α3) and a short cytoplasmic tail anchors the protein to the cell surface. The α1 and α2 domains interact with FcR binding sites in the Fc region of antibodies (Raghavan et al, Immunity, (1994), 1: 303-15). FcRn is expressed in the maternal placenta or yolk sac of mammals and it is involved in transfer of IgGs from mother to fetus. FcRn is also expressed in the small intestine of rodent neonates, where it is involved in the transfer across the brush border epithelia of maternal IgG from ingested colostrum or milk. FcRn is also expressed in numerous other tissues across numerous species, as well as in various endothelial cell lines. It is also expressed in human adult vascular endothelium, muscle vasculature, and hepatic sinusoids. FcRn is thought to play an additional role in maintaining the circulatory half-life or serum levels of IgG by binding it and recycling it to the serum. The binding of FcRn to IgG molecules is strictly pH-dependent with an optimum binding at a pH of less than 7.0.

As used herein, the term "half-life" refers to a biological half-life of a particular binding polypeptide in vivo. Half-life may be represented by the time required for half the quantity administered to a subject to be cleared from the circulation and/or other tissues in the animal. When a clearance curve of a given binding polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the binding polypeptide in the intravascular space. Therefore, in a non-limiting embodiment, the term half-life as used herein refers to the half-life of the binding polypeptide in the β-phase. The typical § phase half-life of a human antibody in humans is 21 days. As used herein, the term "polypeptide" refers to a polymer of two or more of the natural amino acids or non-natural amino acids. The term "Fc polypeptide" refers to a polypeptide comprising an Fc region or a portion thereof (e.g., an Fc moiety). In some embodiments, the Fc polypeptide is stabilized according to the methods of the invention. In optional embodiments, the Fc polypeptide further comprises a binding site which is operably linked or fused to the Fc region (or portion thereof) of the Fc polypeptide.

As used herein, the term "protein" refers to a polypeptide (e.g., an Fc polypeptide) or a composition comprising more than one polypeptide. Accordingly, proteins may be either monomers (e.g., a single Fc polypeptide) or multimers. For example, in one embodiment, a protein of the invention is a dimer. In one embodiment, the dimers of the invention are homodimers, comprising two identical monomeric subunits or polypeptides (e.g., two identical Fc polypeptides). In another embodiment, the dimers of the invention are heterodimers, comprising two non-identical monomeric subunits or polypeptides (e.g., two non-identical Fc polypeptides or an Fc polypeptide and a second polypeptide other than an Fc polypeptide). The subunits of the dimer may comprise one or more polypeptide chains, wherein at least one of the polypeptide chains is an Fc polypeptide. For example, in one embodiment, the dimers comprise at least two polypeptide chains (e.g., at least two Fc polypeptide chains). In one embodiment, the dimers comprise two polypeptide chains, wherein one or both of the chains are Fc polypeptide chains. In another embodiment, the dimers comprise three polypeptide chains, wherein one, two or all of the polypeptide chains are Fc polypeptide chains. In another embodiment, the dimers comprise four polypeptide chains, wherein one, two, three, or all of the polypeptide chains are Fc polypeptide chains.

As used herein, the terms "linked," "fused," or "fusion," are used interchangeably. These terms refer to the joining together of two more elements or components, by whatever means including chemical conjugation or recombinant means. Methods of chemical conjugation (e.g., using heterobifunctional crosslinking agents) are known in the art. As used herein, the term "genetically fused" or "genetic fusion" refers to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. In some embodiments, the genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). Although the reading frame is thus made continuous throughout the fused genetic segments, the protein segments may be physically or spatially separated by, for example, an in-frame polypeptide linker.

As used herein, the term "Fc region" shall be defined as the portion of an immunoglobulin formed by two or more Fc moieties of antibody heavy chains. In certain embodiments, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties. In other embodiments, the Fc region is monomeric or "single-chain" Fc region (i.e., a scFc region). Single chain Fc regions are comprised of Fc moieties genetically linked within a single polypeptide chain (i.e., encoded in a single contiguous genetic sequence). Exemplary scFc regions are disclosed in PCT Application No. PCT/US2008/006260, filed May 14, 2008, which is incorporated by reference herein.

As used herein, the term "Fc moiety" refers to a sequence derived from the portion of an immunoglobulin heavy chain beginning in the hinge region just upstream of the papain cleavage site (i.e., residue 226, Kabat numbering/residue 216, EU numbering in IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. A complete Fc moiety comprises at least a hinge domain, a CH2 domain, and a CH3 domain (i.e., Kabat amino acid positions 226-477; EU amino acid positions 216-446). An additional lysine residue (K) is sometimes present at the extreme C-terminus of the Fc moiety, but is often cleaved from a mature antibody. Each of the amino acid positions within an Fc region have been numbered according to the art-recognized EU numbering system unless otherwise specified. In certain embodiments, an Fc moiety comprises at least one of: a hinge (e.g., upper, middle, and/or lower hinge region) domain, a CH2 domain, a CH3 domain, or a variant, portion, or fragment thereof. In some embodiments, an Fc moiety comprises at least a CH2 domain or a CH3 domain. In certain embodiments, the Fc moiety is a complete Fc moiety. In other embodiments, the Fc moiety comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a CH2 domain (or portion thereof), and (v) a CH3 domain or portion thereof.

It should be noted that amino acid residues in antibodies have their own numbering scheme. The publication Kabat et al., *Sequences of Proteins of Immunological Interest*, 5<sup>th</sup> ed., vol. 4, 1991, U.S. Department of Health and Human Services, NIH, USA, set forth a numbering scheme that is sometimes referred to as EU Index numbering as in Kabat et al. Over time, however, a new numbering system, called Kabat numbering, has emerged.

In a non-limiting example, the following table sets for a comparison of EU numbering and Kabat numbering of the heavy chain CH1, CH2, and CH3 domains of human IgG1. Note that the sequence of the constant region of human IgG1 is provided in SEQ ID NO: 83.

| CH1 of human IgG1 | | | CH2 of human IgG1 | | | CH3 of human IgG1 | | |
|---|---|---|---|---|---|---|---|---|
| Residue | EU | Kabat | Residue | EU | Kabat | Residue | EU | Kabat |
| A | 118 | 114 | A | 231 | 244 | G | 341 | 361 |
| S | 119 | 115 | P | 232 | 245 | Q | 342 | 363 |
| T | 120 | 116 | E | 233 | 246 | P | 343 | 364 |
| K | 121 | 117 | L | 234 | 247 | R | 344 | 365 |
| G | 122 | 118 | L | 235 | 248 | E | 345 | 366 |
| P | 123 | 119 | G | 236 | 249 | P | 346 | 367 |
| S | 124 | 120 | G | 237 | 250 | Q | 347 | 368 |
| V | 125 | 121 | P | 238 | 251 | V | 348 | 369 |
| F | 126 | 122 | S | 239 | 252 | Y | 349 | 370 |
| P | 127 | 123 | V | 240 | 253 | T | 350 | 371 |
| L | 128 | 124 | F | 241 | 254 | L | 351 | 372 |
| A | 129 | 125 | L | 242 | 255 | P | 352 | 373 |
| P | 130 | 126 | F | 243 | 256 | P | 353 | 374 |
| S | 131 | 127 | P | 244 | 257 | S | 354 | 375 |
| S | 132 | 128 | P | 245 | 258 | R | 355 | 376 |
| K | 133 | 129 | K | 246 | 259 | D | 356 | 377 |
| S | 134 | 130 | P | 247 | 260 | E | 357 | 378 |
| T | 135 | 133 | K | 248 | 261 | L | 358 | 381 |
| S | 136 | 134 | D | 249 | 262 | T | 359 | 382 |
| G | 137 | 135 | T | 250 | 263 | K | 360 | 383 |
| G | 138 | 136 | L | 251 | 264 | N | 361 | 384 |
| T | 139 | 137 | M | 252 | 265 | Q | 362 | 385 |
| A | 140 | 138 | I | 253 | 266 | V | 363 | 386 |
| A | 141 | 139 | S | 254 | 267 | S | 364 | 387 |
| L | 142 | 140 | R | 255 | 268 | L | 365 | 388 |
| G | 143 | 141 | T | 256 | 269 | T | 366 | 389 |
| C | 144 | 142 | P | 257 | 270 | C | 367 | 390 |
| L | 145 | 143 | E | 258 | 271 | L | 368 | 391 |
| V | 146 | 144 | V | 259 | 272 | V | 369 | 392 |
| K | 147 | 145 | T | 260 | 273 | K | 370 | 393 |
| D | 148 | 146 | C | 261 | 274 | G | 371 | 394 |
| Y | 149 | 147 | V | 262 | 275 | F | 372 | 395 |
| F | 150 | 148 | V | 263 | 276 | Y | 373 | 396 |
| P | 151 | 149 | V | 264 | 277 | P | 374 | 397 |
| E | 152 | 150 | D | 265 | 278 | S | 375 | 398 |
| P | 153 | 151 | V | 266 | 279 | D | 376 | 399 |
| V | 154 | 152 | S | 267 | 280 | I | 377 | 400 |
| T | 155 | 153 | H | 268 | 281 | A | 378 | 401 |
| V | 156 | 154 | E | 269 | 282 | V | 379 | 402 |
| S | 157 | 156 | D | 270 | 283 | E | 380 | 405 |
| W | 158 | 157 | P | 271 | 284 | W | 381 | 406 |
| N | 159 | 162 | E | 272 | 285 | E | 382 | 407 |
| S | 160 | 163 | V | 273 | 286 | S | 383 | 408 |
| G | 161 | 164 | K | 274 | 287 | N | 384 | 410 |
| A | 162 | 165 | F | 275 | 288 | G | 385 | 411 |
| L | 163 | 166 | N | 276 | 289 | Q | 386 | 414 |
| T | 164 | 167 | W | 277 | 290 | P | 387 | 415 |
| S | 165 | 168 | Y | 278 | 291 | E | 388 | 416 |
| G | 166 | 169 | V | 279 | 292 | N | 389 | 417 |
| V | 167 | 171 | D | 280 | 295 | N | 390 | 418 |
| H | 168 | 172 | G | 281 | 296 | Y | 391 | 419 |
| T | 169 | 173 | V | 282 | 299 | K | 392 | 420 |
| F | 170 | 174 | E | 283 | 300 | T | 393 | 421 |
| P | 171 | 175 | V | 284 | 301 | T | 394 | 422 |
| A | 172 | 176 | H | 285 | 302 | P | 395 | 423 |
| V | 173 | 177 | N | 286 | 303 | P | 396 | 424 |
| L | 174 | 178 | A | 287 | 304 | V | 397 | 425 |
| Q | 175 | 179 | K | 288 | 305 | L | 398 | 426 |
| S | 176 | 180 | T | 289 | 306 | D | 399 | 427 |
| S | 177 | 182 | K | 290 | 307 | S | 400 | 428 |
| G | 178 | 183 | P | 291 | 308 | D | 401 | 430 |
| L | 179 | 184 | R | 292 | 309 | G | 402 | 433 |
| Y | 180 | 185 | E | 293 | 310 | S | 403 | 434 |
| S | 181 | 186 | E | 294 | 311 | F | 404 | 435 |
| L | 182 | 187 | Q | 295 | 312 | F | 405 | 436 |
| S | 183 | 188 | Y | 296 | 313 | L | 406 | 437 |
| S | 184 | 189 | N | 297 | 314 | Y | 407 | 438 |
| V | 185 | 190 | S | 298 | 317 | S | 408 | 439 |
| V | 186 | 191 | T | 299 | 318 | K | 409 | 440 |
| T | 187 | 192 | Y | 300 | 319 | L | 410 | 441 |
| V | 188 | 193 | R | 301 | 320 | T | 411 | 442 |
| P | 189 | 194 | V | 302 | 321 | V | 412 | 443 |
| S | 190 | 195 | V | 303 | 322 | D | 413 | 444 |
| S | 191 | 196 | S | 304 | 323 | K | 414 | 445 |
| S | 192 | 197 | V | 305 | 324 | S | 415 | 446 |
| L | 193 | 198 | L | 306 | 325 | R | 416 | 447 |
| G | 194 | 199 | T | 307 | 326 | W | 417 | 448 |
| T | 195 | 200 | V | 308 | 327 | Q | 418 | 449 |
| Q | 196 | 203 | L | 309 | 328 | Q | 419 | 450 |
| T | 197 | 205 | H | 310 | 329 | G | 420 | 451 |
| Y | 198 | 206 | Q | 311 | 330 | N | 421 | 452 |
| I | 199 | 207 | D | 312 | 331 | V | 422 | 453 |
| C | 200 | 208 | W | 313 | 332 | F | 423 | 454 |
| N | 201 | 209 | L | 314 | 333 | S | 424 | 455 |
| V | 202 | 210 | N | 315 | 334 | C | 425 | 456 |
| N | 203 | 211 | G | 316 | 335 | S | 426 | 457 |
| H | 204 | 212 | K | 317 | 336 | V | 427 | 458 |
| K | 205 | 213 | E | 318 | 337 | M | 428 | 459 |
| P | 206 | 214 | Y | 319 | 338 | H | 429 | 460 |
| S | 207 | 215 | K | 320 | 339 | E | 430 | 461 |
| N | 208 | 216 | C | 321 | 340 | A | 431 | 462 |
| T | 209 | 217 | K | 322 | 341 | L | 432 | 463 |
| K | 210 | 218 | V | 323 | 342 | H | 433 | 464 |
| V | 211 | 219 | S | 324 | 343 | N | 434 | 465 |
| D | 212 | 220 | N | 325 | 344 | H | 435 | 466 |
| K | 213 | 221 | K | 326 | 345 | Y | 436 | 467 |
| K | 214 | 222 | A | 327 | 346 | T | 437 | 468 |
| V | 215 | 223 | L | 328 | 347 | Q | 438 | 469 |
| | | | P | 329 | 348 | K | 439 | 470 |
| | | | A | 330 | 349 | S | 440 | 471 |
| | | | P | 331 | 350 | L | 441 | 472 |
| | | | I | 332 | 351 | S | 442 | 473 |
| | | | E | 333 | 354 | L | 443 | 474 |

-continued

| CH1 of human IgG1 | | | CH2 of human IgG1 | | | CH3 of human IgG1 | | |
|---|---|---|---|---|---|---|---|---|
| Residue | EU | Kabat | Residue | EU | Kabat | Residue | EU | Kabat |
| | | | K | 334 | 353 | S | 444 | 475 |
| | | | T | 335 | 354 | P | 445 | 476 |
| | | | I | 336 | 355 | G | 446 | 477 |
| | | | S | 337 | 357 | K | 447 | 478 |
| | | | K | 338 | 358 | | | |
| | | | A | 339 | 359 | | | |
| | | | K | 340 | 360 | | | |

Note that the amino acid residues in the above table are those that naturally occur, or are canonical, in human IgG1. Thus, the canonical residue at position 297 (EU numbering) (which is position 314 in Kabat numbering) is Asparagine (N). Any change of an amino acid residue from a canonical residue will be referred to as a substitution or a mutation.

Note that due to the similarity of human IgG molecules (e.g., IgG1, IgG2, IgG3, IgG4), the constant regions of all IgG molecules start with an alanine residue at position 118 EU numbering (position 114 Kabat numbering) and end with a lysine residue at the C terminus at position 447 EU numbering (position 478 Kabat numbering).

The below table shows the correlation of EU numbering and Kabat numbering in the hinge of human IgG1, starting with the Glutamic Acid residue at position 216 in EU numbering (position 226 in Kabat numbering).

| Residue in human IgG1 hinge | E | P | K | S | C | D | K | T | H | T | C | P | P | C | P |
|---|---|---|---|---|---|---|---|---|---|---|---|---|---|---|---|
| EU | 216 | 217 | 218 | 219 | 220 | 221 | 222 | 223 | 224 | 225 | 226 | 227 | 228 | 229 | 230 |
| Kabat | 226 | 227 | 228 | 232 | 233 | 234 | 235 | 236 | 237 | 238 | 239 | 240 | 241 | 242 | 243 |

The below table shows the correlation of EU numbering and Kabat numbering in the hinge of human IgG4, starting with the Glutamic Acid residue at position 216 in EU numbering (position 226 in Kabat numbering).

| Residue in human IgG4 hinge | E | S | K | Y | G | P | P | C | P | S | C | P |
|---|---|---|---|---|---|---|---|---|---|---|---|---|
| EU | 216 | 217 | 218 | | | 224 | 225 | 226 | 227 | 228 | 229 | 230 |
| Kabat | 226 | 227 | 228 | 229 | 230 | 237 | 238 | 239 | 240 | 241 | 242 | 243 |

In some embodiments, where the substitutions referenced herein are in either naturally occurring IgG1 or IgG4, the EU or Kabat numbering indicating the substitution will refer to the numbering of the naturally occurring parent molecule (or domain thereof). For example, if the serine at position 228 in the hinge of IgG4 is being mutated to, for example, proline, the mutation would be denoted S228P in EU numbering and S241P in Kabat numbering.

The full-length sequence of the naturally occurring heavy chain of human IgG1 is provided herewith as SEQ ID NO: 83 starting with the canonical alanine residue at position 118 (EU numbering) which is position 114 (Kabat numbering).

The full length sequence of the naturally occurring heavy chain of human IgG1 is provided herewith as SEQ ID NO: 84 starting with the canonical alanine residue at position 118 (EU numbering) which is position 114 (Kabat numbering).

As set forth herein, it will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. For example, the Fc moiety may comprise or consist of at least the portion of an Fc moiety that is known in the art to be required for FcRn binding or extended half-life. In another embodiment, an Fc moiety comprises at least the portion known in the art to be required for FcγR binding. In one embodiment, an Fc region of the invention comprises at least the portion of known in the art to be required for Protein A binding. In one embodiment, an Fc moiety of the invention comprises at least the portion of an Fc molecule known in the art to be required for protein G binding. In certain embodiments, the Fc moieties of Fc region are of the same isotype.

For example, the Fc moieties may be derived from an immunoglobulin (e.g., a human immunoglobulin) of an IgG1 or IgG4 isotype. However, the Fc region (or one or more Fc moieties of an Fc region) may also be chimeric. A chimeric Fc region may comprise Fc moieties derived from different immunoglobulin isotypes. In certain embodiments, at least two of the Fc moieties of a dimeric or single-chain Fc region may be from different immunoglobulin isotypes. In additional or alternative embodiments, the chimeric Fc regions may comprise one or more chimeric Fc moieties. For example, the chimeric Fc region or moiety may comprise one or more portions derived from an immunoglobulin of a first isotype (e.g., an IgG1, IgG2, or IgG3 isotype) while the remainder of the Fc region or moiety is of a different isotype. For example, an Fc region or moiety of an Fc polypeptide may comprise a CH2 and/or CH3 domain derived from an immunoglobulin of a first isotype (e.g., an IgG1, IgG2 or IgG4 isotype) and a hinge region from an immunoglobulin of a second isotype (e.g., an IgG3 isotype). In another embodiment, the Fc region or moiety comprises a hinge and/or CH2 domain derived from an immunoglobulin of a first isotype (e.g., an IgG4 isotype) and a CH3 domain from an immunoglobulin of a second isotype (e.g., an IgG1, IgG2, or IgG3 isotype). In another embodiment, the chimeric Fc region comprises an Fc moiety (e.g., a complete Fc moiety) from an immunoglobulin for a first isotype (e.g., an IgG4 isotype) and an Fc moiety from an immunoglobulin of a second isotype (e.g., an IgG1, IgG2 or IgG3 isotype). In one exemplary embodiment, the Fc region or moiety comprises a CH2 domain from an IgG4 immunoglobulin and a CH3 domain from an IgG1 immunoglobulin. In another embodiment, the Fc region or moiety comprises a CH1 domain and a CH2 domain from an IgG4 molecule and a CH3 domain from an IgG1 molecule. In another embodiment, the Fc region or moiety comprises a portion of a CH2 domain from a particular isotype of antibody, e.g., Kabat positions 309-360, EU positions 292-340 of a CH2 domain. For example, in one embodiment, an Fc region or moiety comprises amino acids a positions 292-340 (EU numbering), 309-360 (Kabat numbering) of CH2 derived from an IgG4 moiety and the remainder of CH2 derived from an IgG1 moiety (alternatively, 292-340 (EU numbering) 309-360 (Kabat numbering) of CH2 may be derived from an IgG1 moiety and the remainder of CH2 derived from an IgG4 moiety).

In other embodiments, an Fc region or moiety can comprise a chimeric hinge region. The chimeric hinge may be derived, in part, from an IgG1, IgG2, or IgG4 molecule (e.g., an upper and lower middle hinge sequence) and, in part, from an IgG3 molecule (e.g., a middle hinge sequence). In another example, an Fc region or moiety can comprise a chimeric hinge derived, in part, from an IgG1 molecule and, in part, from an IgG4 molecule. In a particular embodiment, the chimeric hinge can comprise upper and lower hinge domains from an IgG4 molecule and a middle hinge domain from an IgG1 molecule. Such a chimeric hinge can be made by introducing a proline substitution (Ser228Pro (EU numbering); Ser241Pro (Kabat numbering)) at EU position 228, Kabat position 241 in the middle hinge domain of an IgG4 hinge region. In another embodiment, the chimeric hinge can comprise amino acids at Kabat positions 246-249 are from an IgG2 antibody and/or the Ser228Pro (EU numbering) Ser241Pro (Kabat numbering) mutation, wherein the remaining amino acids of the hinge are from an IgG4 antibody (e.g., a chimeric hinge of the sequence ESKYGPPCPPCPAPPVAGP; SEQ ID NO: 101). Additional chimeric hinges are described in U.S. patent application Ser. No. 10/880,320, which is incorporated by reference herein in its entirety.

Specifically included within the definition of "Fc region" is an "aglycosylated Fc region." By "aglycosylated Fc region" as used herein is Fc region that lacks a covalently linked oligosaccharide or glycan, e.g., at the N-glycosylation site at EU position 297, Kabat position 314, in one or more of the Fc moieties thereof. In certain embodiments the aglycosylated Fc region is fully aglycosylated, i.e., all of its Fc moieties lack carbohydrate. In other embodiments, the aglycosylation is partially aglycosylated (i.e., hemi-glycosylated). The aglycosylated Fc region may be a deglycosylated Fc region that is an Fc region for which the Fc carbohydrate has been removed, for example chemically or enzymatically. Alternatively, the aglycosylated Fc region may be nonglycosylated or unglycosylated, that is an antibody that was expressed without Fc carbohydrate, for example by mutation of one or residues that encode the glycosylation pattern, e.g., at the N-glycosylation site (e.g., Asn-X-Ser or Asn-X-Thr) at EU position 297 or 299, Kabat position 314 or 318, by expression in an organism that does not naturally attach carbohydrates to proteins, (e.g., bacteria), or by expression in a host cell or organism whose glycosylation machinery has been rendered deficient by genetic manipulation or by the addition of glycosylation inhibitors (e.g., glycosyltransferase inhibitors). In alternative embodiments, the Fc region is a "glycosylated Fc region," i.e., it is fully glycosylated at all available glycosylation sites.

The term "parental Fc polypeptide" includes a polypeptide containing an Fc region (e.g., an IgG antibody) for which stabilization is desired. In some embodiments, the parental Fc polypeptide is an effector-less Fc polypeptide. Stabilized Fc polypeptides with reduced effector function have been described (see, e.g., PCT Publication No. WO2010/085682, incorporated by reference herein in its entirety). Thus, the parental Fc polypeptide represents the original Fc polypeptide on which the methods of the instant invention are performed or which can be used a reference point for stability comparisons. The parental polypeptide may comprise a native (i.e. a naturally occurring) Fc region or moiety (e.g., a human IgG4 Fc region or moiety) or an Fc region with pre-existing amino acid sequence modifications (such as insertions, deletions and/or other alterations) of a naturally occurring sequence, but lacking one or more stabilizing amino acid.

The term "mutation" or "mutating" shall be understood to include physically making a mutation in a parental Fc polypeptide (e.g., by altering, e.g., by site-directed mutagenesis, a codon of a nucleic acid molecule encoding one amino acid to result in a codon encoding a different amino acid) or synthesizing a variant Fc region having an amino acid not found in the parental Fc region (e.g., by knowing the nucleotide sequence of a nucleic acid molecule encoding a parental Fc region and by designing the synthesis of a nucleic acid molecule comprising a nucleotide sequence encoding a variant of the parental Fc region without the need for mutating one or more nucleotides of a nucleic acid molecule which encodes a stabilized polypeptide of the invention).

In one exemplary embodiment, the parent Fc polypeptide comprises an Fc region from an effector-less Fc polypeptide. As used herein the term "effector-less Fc polypeptide" refers to an Fc polypeptide which has altered or reduced effector function as compared to a wild-type, aglycosylated antibody of the IgG1 isotype. In some embodiments, the effector function that is reduced or altered is an antibody-dependent effector function, e.g., ADCC and/or ADCP. In one embodiment, an effector-less Fc polypeptide has reduced effector function as a result of modified or reduced glycosylation in the Fc region of the Fc polypeptide, e.g., an aglycosylated Fc region. In another embodiment, the effector-less Fc polypeptide has reduced effector function due to the incorporation of an IgG4 Fc region or portion thereof (e.g., a CH2 and/or CH3 domain of an IgG4 antibody).

The terms "variant Fc polypeptide" or "Fc variant", include an Fc polypeptide derived from a parental Fc polypeptide. The Fc variant differs from the parental Fc polypeptide in that it comprises stabilizing one or more stabilizing amino acid residues, e.g., due to the introduction of at least one Fc stabilizing mutation. In certain embodiments, the Fc variants of the invention comprise an Fc region (or Fc moiety) that is identical in sequence to that of a parental polypeptide but for the presence of one or more stabilizing Fc amino acids. In some embodiments, the Fc variant will have enhanced stability as compared to the parental Fc polypeptide and, optionally, equivalent or reduced effector function as compared to the parental Fc polypeptide.

A polypeptide or amino acid sequence "derived from" a designated polypeptide or protein refers to the origin of the polypeptide. In some embodiments, the polypeptide or amino acid sequence which is derived from a particular sequence has an amino acid sequence that is essentially identical to that sequence or a portion thereof, wherein the portion consists of at least 10-20 amino acids, or at least 20-30 amino acids, or at least 30-50 amino acids, or which is otherwise identifiable to one of ordinary skill in the art as having its origin in the sequence. In the context of polypeptides, a "linear sequence" or a "sequence" is the order of amino acids in a polypeptide in an amino to carboxyl terminal direction in which residues that neighbor each other in the sequence are contiguous in the primary structure of the polypeptide. Polypeptides (e.g., variant Fc polypeptides) derived from another polypeptide (e.g., a parental Fc polypeptide) may have one or more mutations relative to the starting or parent polypeptide, e.g., one or more amino acid residues which have been substituted with another amino acid residue or which has one or more amino acid residue insertions or deletions. In some embodiments, the polypeptide comprises an amino acid sequence which is not naturally occurring. Such variants necessarily have less than 100% sequence identity or similarity with the starting polypeptide. In a non-limiting embodiment, the variant will have an amino acid sequence from about 75% to less than 100% amino acid sequence identity or similarity with the amino acid sequence of the starting polypeptide, or from about 80% to less than 100%, or from about 85% to less than 100%, or from about 90% to less than 100% (e.g., 91%, 92%, 93%, 94%, 95%, 96%, 97%, 98%, 99%) or from about 95% to less than 100%, e.g., over the entire length of the variant molecule or a portion thereof (e.g., an Fc region or Fc moiety). In one embodiment, there is one amino acid difference between a starting polypeptide sequence (e.g., the Fc region of a parental Fc polypeptide) and the sequence derived therefrom (e.g., the Fc region of a variant Fc polypeptide). In other embodiments, there are between two and ten amino acid differences between the starting polypeptide sequence and the variant polypeptide (e.g., about 2-20, about 2-15, about 2-10, about 5-20, about 5-15, about 5-10 amino acid differences). For example, there may be less than about 10 amino acid differences (e.g., two, three, four, five, six, seven, eight, nine, or ten amino acid differences). Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

Fc polypeptides of the invention may comprise an amino acid sequence (e.g., at least one Fc region or Fc moiety) derived from a human immunoglobulin sequence (e.g., an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc polypeptide. In some embodiments, Fc polypeptides of the invention are not immunogenic.

It will also be understood by one of ordinary skill in the art that the Fc polypeptides of the invention may be altered such that they vary in amino acid sequence from the parental polypeptides from which they were derived, while retaining one or more desirable activities (e.g., reduced effector function) of the parental polypeptides. In particular embodiments, nucleotide or amino acid substitutions which stabilize the Fc polypeptide are made. In one embodiment, an isolated nucleic acid molecule encoding an Fc variant can be created by introducing one or more nucleotide substitutions, additions or deletions into the nucleotide sequence of the parental Fc polypeptide such that one or more amino acid substitutions, additions or deletions are introduced into the encoded protein. Mutations (e.g., stabilizing mutations) may be introduced by standard techniques, such as site-directed mutagenesis and PCR-mediated mutagenesis.

As used herein the term "protein stability" refers to an art-recognized measure of the maintenance of one or more physical properties of a protein in response to an environmental condition (e.g. an elevated or lowered temperature). In one embodiment, the physical property is the maintenance of the covalent structure of the protein (e.g. the absence of proteolytic cleavage, unwanted oxidation or deamidation). In another embodiment, the physical property is the presence of the protein in a properly folded state (e.g. the absence of soluble or insoluble aggregates or precipitates). In one embodiment, stability of a protein is measured by assaying a biophysical property of the protein, for example thermal stability, pH unfolding profile, stable removal of glycosylation, solubility, biochemical function (e.g., ability to bind to a protein (e.g., a ligand, a receptor, an antigen, etc.) or chemical moiety, etc.), and/or combinations thereof. In another embodiment, biochemical function is demonstrated by the binding affinity of an interaction. In one embodiment, a measure of protein stability is thermal stability, i.e., resistance to thermal challenge. Stability can be measured using methods known in the art and/or described herein. For example, the "Tm", also referred to as the "transition temperature" may be measured. The Tm is the temperature at which 50% of a macromolecule, e.g., binding molecule, becomes denatured, and is considered to be the standard parameter for describing the thermal stability of a protein.

The term "amino acid" includes alanine (Ala or A); arginine (Arg or R); asparagine (Asn or N); aspartic acid (Asp or D); cysteine (Cy s or C); glutamine (Gln or Q); glutamic acid (Glu or E); glycine (Gly or G); histidine (His or H); isoleucine (He or I): leucine (Leu or L); lysine (Ly s or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" include amino acids that can have nonzero net charge on their side chains (e.g. R, K, H, E, D). These amino acids can participate in hydrophobic interactions and electrostatic interactions. As used herein the term "amino acids with sufficient steric bulk" includes those amino acids having side chains which occupy larger 3 dimensional space. Exemplary amino acids having side chain chemistries of sufficient steric bulk include tyrosine, tryptophan, argine, lysine, histidine, glutamic acid, glutamine, and methionine, or analogs or mimetics thereof.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions", can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence. As set forth above, these terms include actual changes to an existing physical nucleic acid molecule or changes made during a design process (e.g., on paper or on a computer) to an existing nucleic acid sequence. In certain embodiments, the polypeptides of the invention are binding polypeptides. As used herein, the term "binding polypeptide" (e.g., a binding antibody) refers to polypeptides (e.g., Fc polypeptides) that comprise at least one target binding site or binding domain that specifically binds to the indicated target molecule (such as an antigen or binding partner). For example, in one embodiment, a binding polypeptide of the invention comprises an immunoglobulin antigen binding site or the portion of a receptor molecule responsible for ligand binding or the portion of a ligand molecule that is responsible for receptor binding. The binding polypeptides of the invention comprise at least one binding site. In one embodiment, the binding polypeptides of the invention comprise at least two binding sites. In one embodiment, the binding polypeptides comprise two binding sites. In another embodiment, the binding polypeptides comprise three binding sites. In another embodiment, the binding polypeptides comprise four binding sites. In one embodiment, the binding sites are linked to each other in tandem. In other embodiments, the binding sites are located at different positions of the binding polypeptide, e.g., at one or more of the N- or C-terminal ends of the Fc region of an Fc polypeptide. For example, where the Fc region is a scFc region, a binding site may linked to N-terminal end, the C-terminal end, or both ends of the scFc region. Where the Fc region is a dimeric Fc region, binding sites may be linked to one or both N-terminal ends and/or one or both C-terminal ends.

The terms "binding domain," "binding site," or "binding moiety," as used herein, refers to the portion, region, or site of a binding polypeptide that has a biological activity (other than an Fc-mediated biological activity), e.g., which mediates specific binding with a target molecule (e.g. an antigen, ligand, receptor, substrate or inhibitor). Exemplary binding domains include biologically active proteins or moieties, an antigen binding site, a receptor binding domain of a ligand, a ligand binding domain of a receptor or an enzymatic domain. In another example, the term "binding moiety" refers to biologically active molecules or portions thereof which bind to components of a biological system (e.g., proteins in sera or on the surface of cells or in cellular matrix) and which binding results in a biological effect (e.g., as measured by a change in the active moiety and/or the component to which it binds (e.g., a cleavage of the active moiety and/or the component to which it binds, the transmission of a signal, or the augmentation or inhibition of a biological response in a cell or in a subject)).

The term "ligand binding domain" as used herein refers to a native receptor (e.g., cell surface receptor) or a region or derivative thereof retaining at least a qualitative ligand binding ability, and/or at least some of (or a majority of) the biological activity of the corresponding native receptor. The term "receptor binding domain" as used herein refers to a native ligand or region or derivative thereof retaining at least a qualitative receptor binding ability, and/or at least some of the biological activity of the corresponding native ligand. In one embodiment, the binding polypeptides of the invention have at least one binding domain specific for a molecule targeted for reduction or elimination, e.g., a cell surface antigen or a soluble antigen. In some embodiments, the binding domain comprises or consists of an antigen binding site (e.g., comprising a variable heavy chain sequence and variable light chain sequence or six CDRs from an antibody placed into alternative framework regions (e.g., human framework regions optionally comprising one or more amino acid substitutions). The term "binding affinity", as used herein, includes the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction.

The term "binding free energy" or "free energy of binding", as used herein, includes its art-recognized meaning, and, in particular, as applied to binding site-ligand or Fc-FcR interactions in a solvent. Reductions in binding free energy enhance affinities, whereas increases in binding free energy reduce affinities.

The term "specificity" includes the number of potential binding sites which specifically bind (e.g., immunoreact with) a given target. A binding polypeptide may be monospecific and contain one or more binding sites which specifically bind the same target (e.g., the same epitope) or the binding polypeptide may be multispecific and contain two or more binding sites which specifically bind different regions of the same target (e.g., different epitopes) or different targets. In one embodiment, multispecific binding polypeptide (e.g., a bispecific polypeptide) having binding specificity for more than one target molecule (e.g., more than one antigen or more than one epitope on the same antigen) can be made. In another embodiment, the multispecific binding polypeptide has at least one binding domain specific for a molecule targeted for reduction or elimination and at least one binding domain specific for a target molecule on a cell. In another embodiment, the multispecific binding polypeptide has at least one binding domain specific for a molecule targeted for reduction or elimination and at least one binding domain specific for a drug. In yet another embodiment, the multispecific binding polypeptide has at least one binding domain specific for a molecule targeted for reduction or elimination and at least one binding domain specific for a prodrug. In yet another embodiment, the multispecific binding polypeptides are tetravalent antibodies that have two binding domains specific for one target molecule and two binding sites specific for the second target molecule.

As used herein the term "valency" refers to the number of potential binding domains in a binding polypeptide or protein. Each binding domain specifically binds one target molecule. When a binding polypeptide comprises more than one binding domain, each binding domain may specifically bind the same or different molecules (e.g., may bind to different ligands or different antigens, or different epitopes on the same antigen). In one embodiment, the binding polypeptides of the invention are monovalent. In another embodiment, the binding polypeptides of the invention are multivalent. In another embodiment, the binding polypeptides of the invention are bivalent. In another embodiment, the binding polypeptides of the invention are trivalent. In yet another embodiment, the binding polypeptides of the invention are tetravalent. In certain aspects, the binding polypeptides of invention employ polypeptide linkers. As used herein, the term "polypeptide linkers" refers to a peptide or polypeptide sequence (e.g., a synthetic peptide or polypeptide sequence) which connects two domains in a linear amino acid sequence of a polypeptide chain. For example, polypeptide linkers may be used to connect a binding site to an Fc region (or Fc moiety) of an Fc polypeptide of the invention. In some embodiments, such polypeptide linkers provide flexibility to the polypeptide molecule. For example, in one embodiment, a VH domain or VL domain is fused or linked to a polypeptide linker and the N- or C-terminus of the polypeptide linker is attached to the C- or N-terminus of an Fc region (or Fc moiety) and the N-terminus of the polypeptide linker is attached to the N- or C-terminus of the VH or VL domain). In certain embodiments the polypeptide linker is used to connect (e.g., genetically fuse) two Fc moieties or domains of an scFc polypeptide. Such polypeptide linkers are also referred to herein as Fc connecting polypeptides. As used herein, the term "Fc connecting polypeptide" refers specifically to a linking polypeptide which connects (e.g., genetically fuses) two Fc moieties or domains. A binding molecule of the invention may comprise more than one peptide linker.

As used herein the term "properly folded polypeptide" includes polypeptides (e.g., binding polypeptides of the invention) in which all of the functional domains comprising the polypeptide are distinctly active. As used herein, the term "improperly folded polypeptide" includes polypeptides in which at least one of the functional domains of the polypeptide is not active. As used herein, a "properly folded Fc polypeptide" or "properly folded Fc region" comprises an Fc region (e.g., an scFc region) in which at least two component Fc moieties are properly folded such that the resulting Fc region comprises at least one effector function.

As used herein, the term "immunoglobulin" includes a polypeptide having a combination of two heavy and two light chains whether or not it possesses any relevant specific immunoreactivity.

As used herein, the term "antibody" refers to such assemblies (e.g., intact antibody molecules, antibody fragments, or variants thereof) which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "antibody" includes five distinct classes of antibody that can be distinguished biochemically. Fc moieties from each class of antibodies are clearly within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable domain.

Light chains of an immunoglobulin are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention.

Both the light and heavy chains are divided into regions of structural and functional homology. The term "region" refers to a part or portion of a single immunoglobulin (as is the case with the term "Fc region") or a single antibody chain and includes constant regions or variable regions, as well as more discrete parts or portions of said domains. For example, light chain variable domains include "complementarity determining regions" or "CDRs" interspersed among "framework regions" or "FRs", as defined herein. Certain regions of an immunoglobulin may be defined as "constant" (C) regions or "variable" (V) regions, based on the relative lack of sequence variation within the regions of various class members in the case of a "constant region", or the significant variation within the regions of various class members in the case of a "variable regions". The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, transplacental mobility, Fc receptor binding, complement binding, and the like. The subunit structures and three dimensional configuration of the constant regions of the various immunoglobulin classes are well known.

The constant and variable regions of immunoglobulin heavy and light chains are folded into domains. The term "domain" refers to an independently folding, globular region of a heavy or light chain polypeptide comprising peptide loops (e.g., comprising 3 to 4 peptide loops) stabilized, for example, by β-pleated sheet and/or intrachain disulfide bond. Constant region domains on the light chain of an immunoglobulin are referred to interchangeably as "light chain constant region domains", "CL regions" or "CL domains". Constant domains on the heavy chain (e.g. hinge, CH1, CH2 or CH3 domains) are referred to interchangeably as "heavy chain constant region domains", "CH" region domains or "CH domains". Variable domains on the light chain are referred to interchangeably as "light chain variable region domains", "VL region domains or "VL domains". Variable domains on the heavy chain are referred to interchangeably as "heavy chain variable region domains", "VH region domains" or "VH domains".

By convention the numbering of the variable and constant region domains increases as they become more distal from the antigen binding site or amino-terminus of the immunoglobulin or antibody. The N-terminus of each heavy and light immunoglobulin chain is a variable region and at the C-terminus is a constant region; the CH3 and CL domains actually comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation. Amino acid positions in a heavy chain constant region, including amino acid positions in the CH1, hinge, CH2, and CH3 domains, are numbered herein according to the EU index numbering system unless stated otherwise. In contrast, amino acid positions in a light chain constant region (e.g. CL domains) are numbered herein according to the Kabat index numbering system (see Kabat et al., ibid).

As used herein, the term "VH domain" includes the amino terminal variable domain of an immunoglobulin heavy chain, and the term "VL domain" includes the amino terminal variable domain of an immunoglobulin light chain according to the Kabat index numbering system.

As used herein, the term "CH1 domain" includes the first (most amino terminal) constant region domain of an immunoglobulin heavy chain that extends, e.g., from about EU positions 118-215. The CH1 domain is adjacent to the VH domain and amino terminal to the hinge region of an immunoglobulin heavy chain molecule, and does not form a part of the Fc region of an immunoglobulin heavy chain. In one embodiment, a binding polypeptide of the invention comprises a CH1 domain derived from an immunoglobulin heavy chain molecule (e.g., a human IgG1 or IgG4 molecule).

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "CH2 domain" includes the portion of a heavy chain immunoglobulin molecule that extends, e.g., from about EU positions 231-340. The CH2 domain is unique in that it is not closely paired with another domain. Rather, two N-linked branched carbohydrate chains are interposed between the two CH2 domains of an intact native IgG molecule. In one embodiment, a binding polypeptide of the invention comprises a CH2 domain derived from an IgG1 molecule (e.g. a human IgG1 molecule). In another embodiment, a binding polypeptide of the invention comprises a CH2 domain derived from an IgG4 molecule (e.g., a human IgG4 molecule). In an exemplary embodiment, a polypeptide of the invention comprises a CH2 domain (EU positions 231-340), or a portion thereof.

As used herein, the term "CH3 domain" includes the portion of a heavy chain immunoglobulin molecule that extends approximately 110 residues from N-terminus of the CH2 domain, e.g., from about position 341-446b (EU numbering system). An additional lysine residue (K) is sometimes present at the extreme C-terminus of the CH3 domain, but is often cleaved from a mature antibody. The CH3 domain typically forms the C-terminal portion of the antibody. In some immunoglobulins, however, additional domains may extend from CH3 domain to form the C-terminal portion of the molecule (e.g. the CH4 domain in the p chain of IgM and the a chain of IgE). In one embodiment, a binding polypeptide of the invention comprises a CH3 domain derived from an IgG1 molecule (e.g., a human IgG1 molecule). In another embodiment, a binding polypeptide of the invention comprises a CH3 domain derived from an IgG4 molecule (e.g., a human IgG4 molecule).

As used herein, the term "CL domain" includes the first (most amino terminal) constant region domain of an immunoglobulin light chain that extends, e.g. from about Kabat position 107A-216. The CL domain is adjacent to the VL domain. In one embodiment, a binding polypeptide of the invention comprises a CL domain derived from a kappa light chain (e.g., a human kappa light chain).

As indicated above, the variable regions of an antibody allow it to selectively recognize and thus specifically bind to epitopes on antigens. An antibody that specifically binds to a target may be referred to as a target binding antibody (e.g., an α4 binding antibody is an antibody that specifically binds to α4). By "specifically bind" means that the antibody (or variable regions thereof) specifically binds to its target (e.g., an epitope on the α4 integrin) with an equilibrium dissociation constant ($K_D$) of less than about $5\times10^{-5}$ (i.e., 50 uM), or less than about $1\times10^{-5}$ (i.e., 10 uM), or less than about $5\times10^{-6}$ (i.e., 5 uM), or less than about $1\times10^{-6}$ (i.e., 1 uM), or less than about $5\times10^{-7}$ (i.e., 500 nM), or less than about $1\times10^{-7}$ (i.e., 100 nM), or less than about $5\times10^{-8}$ (i.e., 50 nM), or less than about $1\times10^{-8}$ (i.e., 10 nM), or less than about $5\times10^{-9}$ (i.e., 5 nM), or less than about $1\times10^{-9}$ (i.e., 1 nM), or less than about $5\times10^{-10}$ (i.e., 500 pM), or less than about $1\times10^{-10}$ (i.e., 100 pM), or less than about $5\times10^{-11}$ (50 pM), or less than about $1\times10^{-11}$ (10 pM) or less than about $5\times10^{-12}$ (5 pM) or less than about $1\times10^{-12}$ (1 pm), or less than about $5\times10^{-13}$ (500 fM), or less than about $1\times10^{-13}$ (100 fM) or less than about $5\times10^{-14}$ (50 fM) or less than about $1\times10^{-14}$ (10 fM) or less than about $5\times10^{-15}$ (5 fM) or less than about 1×10-15 (1 fM). That is, the VL domain and VH domain of an antibody combine to form the variable region (Fv) that defines a three dimensional antigen binding site. This quaternary antibody structure forms the antigen binding site present at the end of each arm of the Y. More specifically, the antigen binding site is defined by three complementarity determining regions (CDRs) on each of the heavy and light chain variable regions.

As used herein, the term "antigen binding site" includes a site that specifically binds (immunoreacts with) an antigen such as a cell surface or soluble antigen). In one embodiment, the binding site includes an immunoglobulin heavy chain and light chain variable region and the binding site formed by these variable regions determines the specificity of the antibody. An antigen binding site is formed by variable regions that vary from one polypeptide to another. In one embodiment, a binding polypeptide of the invention comprises an antigen binding site comprising at least one heavy or light chain CDR of an antibody molecule (e.g., the sequence of which is known in the art or described herein). In another embodiment, a binding polypeptide of the invention comprises an antigen binding site comprising at least two CDRs from one or more antibody molecules. In another embodiment, a binding polypeptide of the invention comprises an antigen binding site comprising at least three CDRs from one or more antibody molecules. In another embodiment, a binding polypeptide of the invention comprises an antigen binding site comprising at least four CDRs from one or more antibody molecules. In another embodiment, a binding polypeptide of the invention comprises an antigen binding site comprising at least five CDRs from one or more antibody molecules. In another embodiment, a binding polypeptide of the invention comprises an antigen binding site comprising six CDRs from an antibody molecule. Exemplary antibody molecules comprising at least one CDR that can be included in the subject binding polypeptides are known in the art and exemplary molecules are described herein.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. In some embodiments, the term "CDR" is a CDR as defined by Kabat based on sequence comparisons.

| CDR Definitions | | | |
|---|---|---|---|
| | Kabat[1] | Chothia[2] | MacCallum[3] |
| $V_H$CDR1 | 31-35 | 26-32 | 30-35 |
| $V_H$CDR2 | 50-65 | 53-55 | 47-58 |
| $V_H$CDR3 | 95-102 | 96-101 | 93-101 |
| $V_L$CDR1 | 24-34 | 26-32 | 30-36 |
| $V_L$CDR2 | 50-56 | 50-52 | 46-55 |
| $V_L$CDR3 | 89-97 | 91-96 | 89-96 |

[1]Residue numbering follows the nomenclature of Kabat et al., supra.
[2]Residue numbering follows the nomenclature of Chothia et al., supra
[3]Residue numbering follows the nomenclature of MacCallum et al., supra The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al; framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In some embodiments, the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

In certain embodiments, the binding polypeptides of the invention comprise at least two antigen binding domains (e.g., within the same binding polypeptide (e.g., at both the N- and C-terminus of a single polypeptide) or linked to each component binding polypeptide of a mutimeric binding protein of the invention) that provide for the association of the binding polypeptide with the selected antigen. The antigen binding domains need not be derived from the same immunoglobulin molecule. In this regard, the variable region may or may not be derived from any type of animal that can be induced to mount a humoral response and generate immunoglobulins against the desired antigen. As such, the variable region may be, for example, of mammalian origin e.g., may be human, murine, non-human primate (such as cynomolgus monkeys, macaques, etc.), lupine, camelid (e.g., from camels, llamas and related species).

The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules may comprise an scFv linker interposed between the VH domain and the VL domain. ScFv molecules are known in the art and are described, e.g., in U.S. Pat. No. 5,892,019; Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837.

A "scFv linker" as used herein refers to a moiety interposed between the VL and VH domains of the scFv. scFv linkers may, in some embodiments, maintain the scFv molecule in an antigen binding conformation. In one embodiment, a scFv linker comprises or consists of an scFv linker peptide. In certain embodiments, a scFv linker peptide comprises or consists of a gly-ser polypeptide linker. In other embodiments, a scFv linker comprises a disulfide bond.

As used herein, the term "gly-ser polypeptide linker" refers to a peptide that consists of glycine and serine residues. An exemplary gly/ser polypeptide linker comprises the amino acid sequence (Gly4Ser)(SEQ ID NO: 102)n. In one embodiment, n=1. In one embodiment, n=2. In another embodiment, n=3, i.e., (Gly4 Ser)(SEQ ID NO: 102)3. In another embodiment, n=4, i.e., (Gly4 Ser)(SEQ ID NO: 102)4. In another embodiment, n=5. In yet another embodiment, n=6. In another embodiment, n=7. In yet another embodiment, n=8. In another embodiment, n=9. In yet another embodiment, n=10. Another exemplary gly/ser polypeptide linker comprises the amino acid sequence Ser(Gly4Ser)(SEQ ID NO: 103)n. In one embodiment, n=1. In one embodiment, n=2. In a some embodiment, n=3. In another embodiment, n=4. In another embodiment, n=5. In yet another embodiment, n=6.

A used herein, the term "native cysteine" shall refer to a cysteine amino acid that occurs naturally at a particular amino acid position of a polypeptide and which has not been modified, introduced, or altered by the hand of man. The term "engineered cysteine residue or analog thereof or "engineered cysteine or analog thereof shall refer to a non-native cysteine residue or a cysteine analog (e.g. thiol-containing analogs such as thiazoline-4-carboxylic acid and thiazolidine-4 carboxylic acid (thioproline, Th)), which is introduced by synthetic means (e.g. by recombinant techniques, in vitro peptide synthesis, by enzymatic or chemical coupling of peptides or some combination of these techniques) into an amino acid position of a polypeptide that does not naturally contain a cysteine residue or analog thereof at that position.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by native disulfide bonds and the two heavy chains are linked by two native disulfide bonds at positions corresponding to 239 and 242 using the Kabat numbering system (position 226 or 229, EU numbering system).

As used herein, the term "bonded cysteine" shall refer to a native or engineered cysteine residue within a polypeptide which forms a disulfide bond or other covalent bond with a second native or engineered cysteine or other residue present within the same or different polypeptide. An "intrachain bonded cysteine" shall refer to a bonded cysteine that is covalently bonded to a second cysteine present within the same polypeptide (i.e. an intrachain disulfide bond). An "interchain bonded cysteine" shall refer to a bonded cysteine that is covalently bonded to a second cysteine present within a different polypeptide (i.e. an interchain disulfide bond).

As used herein, the term "free cysteine" refers to a native or engineered cysteine amino acid residues within a polypeptide sequence (and analogs or mimetics thereof, e.g. thiazoline-4-carboxylic acid and thiazolidine-4 carboxylic acid (thioproline, Th)) that exists in a substantially reduced form. In some embodiments, free cysteines are capable of being modified with an effector moiety of the invention.

The term "thiol modification reagent" shall refer to a chemical agent that is capable of selectively reacting with the thiol group of an engineered cysteine residue or analog thereof in a binding polypeptide (e.g., within an polypeptide linker of a binding polypeptide), and thereby providing means for site-specific chemical addition or crosslinking of effector moieties to the binding polypeptide, thereby forming a modified binding polypeptide. In some embodiments, the thiol modification reagent exploits the thiol or sulfhydryl functional group which is present in a free cysteine residue. Exemplary thiol modification reagents include maleimides, alkyl and aryl halides, α-haloacyls, and pyridyl disulfides.

The term "functional moiety" includes moieties which, in some embodiments, add a desirable function to the binding polypeptide. In some embodiments, the function is added without significantly altering an intrinsic desirable activity of the polypeptide, e.g., the antigen-binding activity of the molecule. A binding polypeptide of the invention may comprise one or more functional moieties, which may be the same or different. Examples of useful functional moieties include, but are not limited to, an effector moiety, an affinity moiety, and a blocking moiety. Exemplary blocking moieties include moieties of sufficient steric bulk and/or charge such that reduced glycosylation occurs, for example, by blocking the ability of a glycosidase to glycosylate the polypeptide. The blocking moiety may additionally or alternatively, reduce effector function, for example, by inhibiting the ability of the Fc region to bind a receptor or complement protein. Non-limiting blocking moieties include cysteine adducts, cysteine, mixed disulfide adducts, and PEG moieties. Exemplary detectable moieties include fluorescent moieties, radioisotopic moieties, radiopaque moieties, and the like. With respect to conjugation of chemical moieties, the term "linking moiety" includes moieties which are capable of linking a functional moiety to the remainder of the binding polypeptide. The linking moiety may be selected such that it is cleavable or non-cleavable. Uncleavable linking moieties generally have high systemic stability, but may also have unfavorable pharmacokinetics.

The term "spacer moiety" is a non-protein moiety designed to introduce space into a molecule. In one embodiment a spacer moiety may be an optionally substituted chain of 0 to 100 atoms, selected from carbon, oxygen, nitrogen, sulfur, etc. In one embodiment, the spacer moiety is selected such that it is water soluble. In another embodiment, the spacer moiety is polyalkylene glycol, e.g., polyethylene glycol or polypropylene glycol.

The terms "PEGylation moiety" or "PEG moiety" includes a polyalkylene glycol compound or a derivative thereof, with or without coupling agents or derivatization with coupling or activating moieties (e.g., with thiol, triflate, tresylate, azirdine, oxirane, or with a maleimide moiety, e.g., PEG-maleimide). Other appropriate polyalkylene glycol compounds include, maleimido monomethoxy PEG, activated PEG polypropylene glycol, but also charged or neutral polymers of the following types: dextran, colominic acids, or other carbohydrate based polymers, polymers of amino acids, and bio tin derivatives. As used herein, the term "effector moiety" (E) may comprise diagnostic and therapeutic agents (e.g. proteins, nucleic acids, lipids, drug moieties, and fragments thereof) with biological or other functional activity. For example, a binding polypeptide comprising an effector moiety conjugated to a binding polypeptide has at least one additional function or property as compared to the unconjugated polypeptide. For example, the conjugation of a cytotoxic drug moiety (e.g., an effector moiety) to a binding polypeptide (e.g., via its polypeptide linker) results in the formation of a modified polypeptide with drug cytotoxicity as second function (i.e. in addition to antigen binding). In another example, the conjugation of a second binding polypeptide to the first binding polypeptide may confer additional binding properties. In one aspect, wherein the effector moiety is a genetically encoded therapeutic or diagnostic protein or nucleic acid, the effector moiety may be synthesized or expressed by either peptide synthesis or recombinant DNA methods that are well known in the art. In another aspect, wherein the effector is a non-genetically encoded peptide or a drug moiety, the effector moiety may be synthesized artificially or purified from a natural source.

As used herein, the term "drug moiety" includes anti-inflammatory, anticancer, anti-infective (e.g., anti-fungal, antibacterial, anti-parasitic, anti-viral, etc.), and anesthetic therapeutic agents. In a further embodiment, the drug moiety is an anticancer or cytotoxic agent. Compatible drug moieties may also comprise prodrugs.

As used herein, the term "prodrug" refers to a precursor or derivative form of a pharmaceutically active agent that is less active, reactive or prone to side effects as compared to the parent drug and is capable of being enzymatically activated or otherwise converted into a more active form in vivo. Prodrugs compatible with the invention include, but are not limited to, phosphate-containing prodrugs, amino acid-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. One skilled in the art may make chemical modifications to the desired drug moiety or its prodrug in order to make reactions of that compound more convenient for purposes of preparing modified binding proteins of the invention. The drug moieties also include derivatives, pharmaceutically acceptable salts, esters, amides, and ethers of the drug moieties described herein.

An "affinity resin" is a chemical surface capable of binding the affinity domain with high affinity to facilitate separation of the protein bound to the affinity domain from the other components of a reaction mixture. Affinity resins can be coated on the surface of a solid support or a portion thereof. Alternatively, the affinity resin can comprise the solid support. Such solid supports can include a suitably modified chromatography column, microtiter plate, bead, or biochip (e.g. glass wafer). Exemplary affinity resins are comprised of nickel, chitin, amylase, and the like. The term "vector" or "expression vector" is used herein to mean vectors used in accordance with the present invention as a vehicle for introducing into and expressing a desired polynucleotide in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

The ordinarily skilled artisan will understand that if a polynucleotide (e.g., a DNA sequence) encoding an antibody described herein (or fragment or chain thereof), is contained within an expression vector that also includes regulatory elements, such as a promoter, enhancer, and/or poly A tail, the polynucleotide will be expressed as a protein in a host cell into which the vector has been introduced. Thus, such a polynucleotide, inserted into an expression vector, can be referred to as being "positioned for expression" in the vector and thus in a host cell introduced with the vector. However, a polynucleotide (e.g., a DNA sequence) does not need be inserted into an expression vector to be positioned for expression in a host cell. Well known methods for having a polynucleotide be positioned for expression in a cell are known. For example, a DNA sequence could be inserted into the genome of a host cell using, for example, homologous recombination, such that the expression of the inserted DNA sequence is regulated by the host cell's endogenous promoter and other regulatory elements. Such techniques for homologous recombination are well known.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Exemplary vectors include those described in U.S. Pat. Nos. 6,159,730 and 6,413,777, and U.S. Patent Application No. 2003 0157641 A1. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., peiB, phoA, or ompA), can be fused in-frame to the N terminus of a polypeptide of the invention to obtain optimal secretion of the polypeptide. (Lei et al. (1988), Nature, 331:543; Better et al. (1988) Science, 240:1041; Mullinax et al, (1990). PNAS, 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression is, for example, of mammalian origin. Those skilled in the art are credited with ability to preferentially determine particular host cell lines which are best suited for the desired gene product to be expressed therein. Exemplary host cell lines include, but are not limited to, DG44 and DUXBII (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-IcIBPT (bovine endothelial cells), RAJI (human lymphocyte) and 293 (human kidney). CHO cells (and also variants thereof including the DHFR activity-lacking CHO-K1 cells) are useful host cells. Host cell lines are typically available from commercial services, the American Tissue Culture Collection or from published literature. The polypeptides of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available including *Pichia pastoris*. For expression in *Saccharomyces*, the plasmid YRp7, for example, (Stinchcomb et al, (1979), Nature, 282:39; Kingsman et al, (1979), Gene, 7:141; Tschemper et al, (1980), Gene, 10:157) is commonly used. This plasmid already contains the TRP1 gene which provides a selection marker for a mutant strain of yeast lacking the ability to grow in tryptophan, for example ATCC™ No. 44076 or PEP4-4 (Jones, (1977), Genetics, 85: 12). The presence of the trp1 lesion as a characteristic of the yeast host cell genome then provides an effective environment for detecting transformation by growth in the absence of tryptophan.

In vitro production allows scale-up to give large amounts of the desired altered binding polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

As used herein, the phrase "subject that would benefit from administration of a binding polypeptide" includes subjects, such as mammalian subjects, that would benefit from administration of binding polypeptides used, e.g., for detection of an antigen recognized and specifically bound a binding polypeptide of the invention (e.g., for a diagnostic procedure) and/or from treatment with a binding polypeptide to reduce or eliminate the target recognized and specifically bound by the binding polypeptide. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As discussed above, the binding polypeptide can be used in unconjugated form or can be conjugated, e.g., to a drug, prodrug, or an isotope, to form a modified binding polypeptide for administering to said subject.

The term "pegylation", "polyethylene glycol", or "PEG" includes a poly alky lene glycol compound or a derivative thereof, with or without coupling agents or derviatization with coupling or activating moieties (e.g., with thiol, triflate, tresylate, azirdine, oxirane, or with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin derivatives.

I. Variable Regions

The present invention provides alpha-4 binding antibodies, and fragments thereof, where the variable light chain (VL) and variable heavy chain (VH) frameworks have acceptor sequences constructed from germline or germline engineered antibody sequences, such as IGKV4-1 or geAAH70335.1 or IGHV1-f antibodies. The CDR sequences are derived from nonhuman anti-α4 binding antibodies such as the anti-VLA-4 antibody HP1/2. See PCT Publication No. WO2011/130603, incorporated by reference herein in its entirety. Antibodies described herein can have an increase of at least 1.5, 2.0, 2.5, 3.0 fold in affinity, e.g., relative to its murine parent. In one embodiment, the increase in affinity is at least 1.5, 2.0, 2.5, 3.0 fold but is respectively, less than 25, 20, or 15 fold.

The murine monoclonal antibody (mAb) HP1/2 is a member of the B1 subgroup of α4 mAbs, and inhibits cell adhesion in vitro to both VCAM1 and fibronectin with a potency of about 0.1 nM. The cryo-EM structure of HP1/2 Fab was solved in complex with the α4β1 ectodomain. HP1/2 binds to the α4 β-propeller domain outside the ligand binding groove and non-competitively antagonizes ligand binding. The epitope and conformation of the α4 integrin recognized and specifically bound by HP1/2 is similar to that observed in the natalizumab α4 integrin crystal structure.

mAbs to α4 integrins are effective blockers of lymphocyte, eosinophil and monocyte emigration into tissues and show disease modifying effects in vivo. In particular, mAb HP1/2 has been shown to be efficacious in animal models of allergic hyper-responsiveness in sheep (Lobb et al., Ann. N.Y. Acad. Sci 796: 113-123, 1996), bronchial airways hyper-reactivity in guinea pigs (Pretolani et al., J. Ex. Med. 180(3):795-805, 1994; Kraneveld et al., J. Allergy Clin. Immunol. 100(2):242-50, 1997), ulcerative colitis in primates (Podolsky et al., J. Clin Invest. 92(1):372-380, 1993), endarterectomized carotid artery intimal hyperplasia in NHP (Lumsden et al., J. Vasc. Surg. 26(1):87-93, 1997), reduces neoadventitial formation and subsequent luminal narrowing following balloon injury (Labinaz et al., Can J. Cardiol. 16(2):187-96, 2000), inflammatory response to stent implantation in rabbits (Ma et al., 2004), and prevent cardiac graft rejection in rabbits (Sadahiro et al., Am. J. Pathol. 142(3): 675-683, 1993). In addition, HP1/2 stimulates the peripheralization of hematopoietic progenitors from the bone marrow stroma in baboons (Papayannopoulou and Nakamoto, Proc. Natl. Acad. Sci 90(20): 9374-9378, 1993).

The HP1/2 antibody was raised in Balb/c mice injected with the JM (immature T-cell leukemia) cell line (Sanchez-Madrid et al., Eur. J. Immunol. 16: 1343-1349, 1986). Spleen cells from two mice were fused with SP2 or β3-X63Ag8.653 mouse myeloma cells. The antibody was humanized in 1993, but then rehumanized in 2010 to take advantage of advances in humanization design.

The alpha-4 binding antibody or fragment thereof can comprise a variable light chain having the sequence of SEQ ID NO: 8, 9, 10, or 11. The alpha-4 binding antibody or fragment thereof can comprise a variable heavy chain of SEQ ID NO: 3, 4 or 5.

In certain embodiments, the alpha-4 binding antibody comprises a variable light chain having the sequence of SEQ ID NO: 11 and a variable heavy chain having the sequence of SEQ ID NO: 4.

The alpha-4 binding antibody can further comprise a variant Fc region as discussed in further detail herein.

II. Parental Fc Polypeptides

The variant Fc polypeptides may be derived from parental or starting Fc polypeptide known in the art. In one embodiment, the parental Fc polypeptide is an antibody, such as an IgG immunoglobulin, which includes all subtypes of IgG and combinations of thereof. In some embodiments, the parental Fc polypeptide of an IgG antibody is of an IgG subtype, or a combination of different portions of the Fc regions of two or more IgG subtypes. In humans, IgG subtypes include IgG1, IgG2, IgG3, and IgG4. The parental Fc polypeptide comprises an Fc region derived from an immunoglobulin, but may optionally further comprise a binding site which is operably linked or fused to the Fc region. In some embodiments, the forgoing polypeptide binds to an antigen such as a ligand, cytokine, receptor, cell surface antigen, or cancer cell antigen. Although the Examples herein employ an IgG antibody, it is understood that the method can be equally applied to an Fc region within any Fc polypeptide. When the Fc polypeptide is an antibody, the antibody can be synthetic, naturally-derived (e.g., from serum), produced by a cell line (e.g., a hybridoma), or produced in a transgenic organism.

In certain embodiments, the Fc polypeptides of the invention comprise a single Fc moiety of an Fc region. In other embodiments, the Fc polypeptide is a dcFc polypeptide. A dcFc polypeptide refers to a polypeptide comprising a dimeric Fc (or dcFc) region. In other embodiments, the Fc polypeptides of the invention are scFc polypeptides. As used herein, the term scFc polypeptide refers to a polypeptide comprising a single-chain Fc (scFc) region, e.g., a scFc polypeptide comprising at least two Fc moieties that are genetically fused, e.g., via a flexible polypeptide linker interposed between at least two of the Fc moieties. Exemplary scFc regions are disclosed in PCT Application No. PCT/US2008/006260, filed May 14, 2008, which is incorporated by reference herein.

In certain embodiments, the polypeptides of the invention may comprise a Fc region comprising Fc moieties of the same, or substantially the same, sequence composition (herein termed a "homomeric Fc region"). In other embodiments, the polypeptides of the invention may comprise an Fc region comprising at least two Fc moieties which are of different sequence composition (i.e., herein termed a "heteromeric Fc region"). In certain embodiments, the binding polypeptides of the invention comprise a Fc region comprising at least one insertion or amino acid substitution. In one exemplary embodiment, the heteromeric Fc region comprises an amino acid substitution in a first Fc moiety, but not in a second Fc moiety.

In one embodiment, the binding polypeptide of the invention may comprise a Fc region having two or more of its constituent Fc moieties independently selected from the Fc moieties described herein. In one embodiment, the Fc moieties are the same. In another embodiment, at least two of the Fc moieties are different. For example, the Fc moieties of the Fc polypeptides of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc moieties may differ in sequence at or more amino acid positions. For example, at least two of the Fc moieties may differ at about 5 amino acid positions (e.g., 1, 2, 3, 4, or 5 amino acid positions), about 10 positions, about 15 positions, about 20 positions, about 30 positions, about 40 positions, or about 50 positions).

The parental Fc polypeptides may be assembled together or with other polypeptides to form multimeric Fc polypeptides or proteins (also, referred to herein as "multimers"). The multimeric Fc polypeptide or proteins of the invention comprise at least one parental Fc polypeptide of the invention. Accordingly, the parental polypeptide includes without limitation monomeric as well as multimeric (e.g., dimeric, trimeric, tetrameric, and hexameric) Fc polypeptides or proteins and the like. In certain embodiments, the constituent Fc polypeptides of said multimers are the same (i.e. homomeric multimers, e.g. homodimers, homotrimers, homotetramers). In other embodiments, at least two constituent Fc polypeptides of the multimeric proteins of the invention are different (i.e. heteromeric multimers, e.g. heterodimers, heterotrimers, heterotetramers). In certain embodiments, at least two of the Fc polypeptides are capable of forming a dimer.

In another embodiment, an Fc polypeptide of the invention comprises a dimeric Fc region (either a single chain polypeptide which forms a dimer or a two chain polypeptide which forms a dimer) and is monomeric with respect to the biologically active moiety present in the molecule. For example, such an Fc construct can comprise one biologically active moiety only. One or two chain stabilized Fc monomeric constructs are desirable, e.g., when cross-linking of target molecules is not desired (for example, in the case of certain antibodies, e.g., anti-CD40 antibodies). In another embodiment, such an Fc construct can comprise two different biologically active moieties. In yet another embodiment, such an Fc construct can comprise two of the same biologically active moieties. In yet another embodiment, such an Fc construct can comprise more than two of the same biologically active moieties.

A. Fc Moieties

Fc moieties useful for producing the parental Fc polypeptides of the present invention may be obtained from a number of different sources. In some embodiments, a Fc moiety of the binding polypeptide is derived from a human immunoglobulin. It is understood, however, that the Fc moiety may be derived from an immunoglobulin of another mammalian species, including for example, a rodent (e.g. a mouse, rat, rabbit, guinea pig) or non-human primate (e.g. chimpanzee, macaque) species. Moreover, the Fc may be derived from any immunoglobulin class, including IgM, IgG, IgD, IgA and IgE, and any immunoglobulin isotype, including IgG1, IgG2, IgG3 and IgG4. For example, the Fc may be from IgG1, but have specific mutations in the sequence. In some embodiments, the human isotype IgG1 or IgG4 is used. In some embodiments, the Fc may be a chimera, containing portions taken from one type of Ig immunoglobulin (e.g., the CH3 domain from IgG1) and other portions from another type of Ig immunoglobulin (e.g., the CH1 domain from IgG4).

A variety of Fc moiety gene sequences (e.g. human constant region gene sequences) are available in the form of publicly accessible deposits. Constant region domains comprising an Fc moiety sequence can be selected having a particular effector function (or lacking a particular effector function) or with a particular modification to reduce immunogenicity. Many sequences of antibodies and antibody-encoding genes have been published and suitable Fc moiety sequences (e.g. hinge, CH2, and/or CH3 sequences, or portions thereof) can be derived from these sequences using art recognized techniques. The genetic material obtained using any of the foregoing methods may then be altered or synthesized to obtain Fc polypeptides of the present invention. It will further be appreciated that the scope of this invention encompasses alleles, variants and mutations of constant region DNA sequences.

Fc moiety sequences can be cloned, e.g., using the polymerase chain reaction and primers which are selected to amplify the domain of interest. To clone an Fc moiety sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al.

1994. J. Immunol. Methods 173:33); antibody leader sequences (Larrick et al. 1989 Biochem. Biophys. Res. Commun. 160:1250). The cloning of antibody sequences is further described in Newman et al, U.S. Pat. No. 5,658,570, filed Jan. 25, 1995, which is incorporated by reference herein.

The parental Fc polypeptides of the invention may comprise a single Fc moiety or multiple Fc moieties. Where there are two or more Fc moieties (e.g., 2, 3, 4, 5, 6, 7, 8, 9, 10, or more Fc moieties, at least two of the Fc moieties associate to form a properly folded Fc region (e.g., a dimeric Fc region or a single chain Fc region (scFc)). In one embodiment, the Fc moieties may be of different types. In one embodiment, at least one Fc moiety present in the parental Fc polypeptide comprises a hinge domain or portion thereof. In another embodiment, the parental Fc polypeptide comprises at least one Fc moiety which comprises at least one CH2 domain or portion thereof. In another embodiment, the parental Fc polypeptide comprises at least one Fc moiety which comprises at least one CH3 domain or portion thereof. In another embodiment, the parental Fc polypeptide comprises at least one Fc moiety which comprises at least one CH4 domain or portion thereof. In another embodiment, the parental Fc polypeptide comprises at least one Fc moiety which comprises at least one hinge domain or portion thereof and at least one CH2 domain or portion thereof (e.g., in the hinge-CH2 orientation). In another embodiment, the parental Fc polypeptide comprises at least one Fc moiety which comprises at least one CH2 domain or portion thereof and at least one CH3 domain or portion thereof (e.g., in the CH2-CH3 orientation). In another embodiment, the parental Fc polypeptide comprises at least one Fc moiety comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the parental Fc polypeptide comprises at least one complete Fc region derived from one or more immunoglobulin heavy chains (e.g., an Fc moiety including hinge, CH2, and CH3 domains, although these need not be derived from the same antibody). In other embodiments, the parental Fc polypeptide comprises at least two complete Fc regions derived from one or more immunoglobulin heavy chains. In some embodiments, the complete Fc moiety is derived from a human IgG immunoglobulin heavy chain (e.g., human IgG1 or human IgG4).

In another embodiment, a parental Fc polypeptide comprises at least one Fc moiety comprising a complete CH3 domain (about amino acids 341-438 of an antibody Fc region according to EU numbering). In another embodiment, a parental Fc polypeptide comprises at least one Fc moiety comprising a complete CH2 domain (about amino acids 231-340 of an antibody Fc region according to EU numbering). In another embodiment, a parental Fc polypeptide comprises at least one Fc moiety comprising at least a CH3 domain, and at least one of a hinge region (about amino acids 216-230 of an antibody Fc region according to EU numbering), and a CH2 domain. In one embodiment, a parental Fc polypeptide comprises at least one Fc moiety comprising a hinge and a CH3 domain. In another embodiment, a parental Fc polypeptide comprises at least one Fc moiety comprising a hinge, a CH2, and a CH3 domain. In some embodiments, the Fc moiety is derived from a human IgG immunoglobulin heavy chain.

The constant region domains or portions thereof making up an Fc moiety may be derived from different immunoglobulin molecules. For example, a parental Fc polypeptide may comprise a hinge and/or CH2 domain or portion thereof derived from an IgG4 molecule and a CH3 region or portion thereof derived from an IgG1 molecule. In another embodiment, a parental Fc polypeptide can comprise a chimeric hinge domain. For example, the chimeric hinge can comprise a hinge domain derived, in part, from an IgG1 molecule and, in part, from an IgG3 molecule. In another embodiment, the chimeric hinge comprises a middle hinge domain from an IgG1 molecule and upper and lower hinge domains from an IgG4 molecule.

As set forth herein, it will be understood by one of ordinary skill in the art that a parental Fc moiety may be identical to the corresponding Fc moiety of naturally-occurring immunoglobulin or may be altered such that it varies in amino acid sequence. In certain embodiments, a parental Fc polypeptide is altered, e.g., by amino acid mutation (e.g., addition, deletion, or substitution). For example, the parental Fc polypeptide may be a Fc moiety having at least one amino acid substitution as compared to the wild-type Fc from which the Fc moiety is derived. For example, wherein the Fc moiety is derived from a human IgG1 antibody, a variant comprises at least one amino acid mutation (e.g., substitution) as compared to a wild type amino acid at the corresponding position of the human IgG1 Fc region.

The amino acid substitution(s) may be located at a position within the Fc moiety referred to as "corresponding" to the position number that that residue would be given in an Fc region in an antibody (as set forth using the EU numbering convention). One of skill in the art can readily generate alignments to determine what the EU number "corresponding" to a position in an Fc moiety would be.

In one embodiment, the substitution is at an amino acid position located in a hinge domain or portion thereof. In another embodiment, the substitution is at an amino acid position located in a CH2 domain or portion thereof. In another embodiment, the substitution is at an amino acid position located in a CH3 domain or portion thereof. In another embodiment, the substitution is at an amino acid position located in a CH4 domain or portion thereof.

In certain embodiments, the parental Fc polypeptide comprises more than one amino acid substitution. The parental Fc polypeptide may comprise, for example, 2, 3, 4, 5, 6, 7, 8, 9, 10 or more amino acid substitutions relative to a wild-type Fc region. In some embodiments, the amino acid substitutions are spatially positioned from each other by an interval of at least 1 amino acid position or more, for example, at least 2, 3, 4, 5, 6, 7, 8, 9, or 10 amino acid positions or more. In some embodiments, the engineered amino acids are spatially positioned apart from each other by an interval of at least 5, 10, 15, 20, or 25 amino acid positions or more.

In certain embodiments, the substitution confers an alteration of at least one effector function imparted by an Fc region comprising a wild-type Fc moiety (e.g., a reduction in the ability of the Fc region to bind to Fc receptors (e.g. FcγRI, FcγRII, or FcγRIII) or complement proteins (e.g. C1q), or to trigger antibody-dependent cell cytotoxicity (ADCC), phagocytosis, or complement-dependent cytotoxicity (CDC)).

The parental Fc polypeptides may employ art-recognized substitutions which are known to impart an alteration of effector function. Specifically, a parental Fc polypeptide of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/

09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, the portion of each of which pertaining to Fc mutations is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

In some embodiments, a parental Fc polypeptide may comprise an Fc moiety comprising an amino acid substitution at an amino acid position corresponding to EU amino acid position that is within the "15 Angstrom Contact Zone" of an Fc moiety. The 15 Angstrom Zone includes residues located at EU positions 243 to 261, 275 to 280, 282-293, 302 to 319, 336 to 348, 367, 369, 372 to 389, 391, 393, 408, and 424-440 of a full-length, wild-type Fc moiety.

In another embodiment, a parental Fc polypeptide comprises an Fc region comprising one or more truncated Fc moieties that are nonetheless sufficient to confer one or more functions to the Fc region. For example, the portion of an Fc moiety that binds to FcRn (i.e., the FcRn binding portion) comprises from about amino acids 282-438, EU numbering. Thus, an Fc moiety of a parental Fc polypeptide may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used. In certain embodiments, the FcRn binding portion is aglycosylated. In other embodiments, the FcRn binding portion is glycosylated.

In certain embodiments, a parental Fc polypeptide comprises an amino acid substitution to an Fc moiety which alters the antigen-independent effector functions of the antibody, in particular the circulating half-life of the antibody. Such polypeptides exhibit either increased or decreased binding to FcRn when compared to polypeptides lacking these substitutions and, therefore, have an increased or decreased half-life in serum, respectively. Parental Fc polypeptides with improved affinity for FcRn are anticipated to have longer serum half-lives, and such molecules have useful applications in methods of treating mammals where long half-life of the administered polypeptide is desired, e.g., to treat a chronic disease or disorder. In contrast, parental Fc polypeptides with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Parental Fc polypeptides with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the parental Fc polypeptides exhibit reduced transport across the epithelium of kidney glomeruli from the vasculature. In another embodiment, the binding polypeptides of the invention exhibit reduced transport across the blood brain barrier (BBB) from the brain, into the vascular space. In one embodiment, a parental Fc polypeptide with altered FcRn binding comprises at least one Fc moiety (e.g., one or two Fc moieties) having one or more amino acid substitutions within the "FcRn binding loop" of an Fc moiety. The FcRn binding loop is comprised of amino acid residues 280-299 (according to EU numbering) of a wild-type, full-length, Fc moiety. In other embodiments, a parental Fc polypeptide having altered FcRn binding affinity comprises at least one Fc moiety (e.g., one or two Fc moieties) having one or more amino acid substitutions within the 15 A FcRn "contact zone."

As used herein, the term 15 A FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In some embodiments, a parental Fc polypeptide having altered FcRn binding affinity comprises at least one Fc moiety (e.g., one or two Fc moieties) having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein. In other embodiments, a parental Fc polypeptide comprises at least one Fc moiety having engineered cysteine residue or analog thereof which is located at the solvent-exposed surface. In some embodiments, the engineered cysteine residue or analog thereof does not interfere with an effector function conferred by the Fc region. In some embodiments, the Fc polypeptides comprise an Fc moiety comprising at least one engineered free cysteine residue or analog thereof that is substantially free of disulfide bonding with a second cysteine residue. In some embodiments, the Fc polypeptides may comprise an Fc moiety having engineered cysteine residues or analogs thereof at one or more of the following positions in the CH3 domain: 349-371, 390, 392, 394-423, 441-446, and 446b (EU numbering). In more some embodiments, the Fc polypeptides comprise an Fc variant having engineered cysteine residues or analogs thereof at any one of the following positions: 350, 355, 359, 360, 361, 389, 413, 415, 418, 422, 441, 443, and EU position 446b (EU numbering). Any of the above engineered cysteine residues or analogs thereof may subsequently be conjugated to a functional moiety using art-recognized techniques (e.g., conjugated with a thiol-reactive heterobifunctional linker).

B. Effector-Less Fc Polypeptides

In certain embodiments, the parental Fc polypeptides are "effector-less" Fc polypeptides with altered or reduced effector function. In some embodiments, the effector function that is reduced or altered is an antigen-dependent effector function. For example, a parental Fc polypeptide may comprise a sequence variation (e.g., an amino acid substitution) which reduces the antigen-dependent effector functions of the polypeptide, in particular ADCC or complement activation, e.g., as compared to a wild type Fc polypeptide. Unfortunately, such parental Fc polypeptides often have reduced stability making them ideal candidates for stabilization according to the methods of the invention.

Fc polypeptides with decreased FcγR binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation. In one embodiment, the Fc polypeptide exhibits a reduction in at least one antigen-dependent effector function selected from the group consisting of opsonization, phagocytosis, complement dependent cytotoxicity, antibody-dependent cell cytotoxicity (ADCC), or effector cell modulation as compared to a Fc polypeptide comprising a wild type Fc region. In one embodiment the Fc polypeptide exhibits altered binding to an activating FcγR (e.g. FcγRI, FcγRIIa, or FcγRIIIa). In another embodiment, the Fc polypeptide exhibits altered binding affinity to an inhibitory FcγR (e.g. FcγRIIb). In other embodiments, an Fc polypeptide with decreased FcγR binding affinity (e.g. decreased FcγRI, FcγRII, or FcγRIIIa binding affinity) comprises at least one Fc moiety (e.g., one or two Fc moieties) having an amino acid substitution at an amino acid position corresponding to one or more of the following positions: 234, 236, 239, 241, 251, 252, 261, 265, 268, 293, 294, 296, 298, 299, 301, 326, 328, 332, 334, 338, 376, 378, and 435 (EU numbering). In other embodiments, an Fc polypeptide with decreased complement binding affinity (e.g. decreased C1q binding affinity) comprises an Fc moiety (e.g., one or two Fc moieties) having an amino acid substitution at an amino acid position corresponding to one or more of the following positions: 239, 294, 296, 301, 328, 333, and 376 (EU numbering).

Exemplary amino acid substitutions which altered FcγR or complement binding activity are disclosed in International PCT Publication No. WO05/063815 which is incorporated by reference herein. In certain embodiments, binding polypeptide of the invention may comprise one or more of the following specific substitutions: S239D, S239E, M252T, H268D, H268E, I332D, I332E, N434A, and N434K (i.e., one or more of these substitutions at an amino acid position corresponding to one or more of these EU numbered position in an antibody Fc region).

In certain exemplary embodiments, the effector function of the parental 'effector-less' polypeptide may be altered or reduced due to an aglycosylated Fc region within the parental Fc polypeptide. In certain embodiments, the aglycosylated Fc region is generated by an amino acid substitution which alters the glycosylation of the Fc region. For example, the asparagine at EU position 297 within the Fc region may altered (e.g., by substitution, insertion, deletion, or by chemical modification) to inhibit its glycosylation. In another exemplary embodiment, the amino acid residue at EU position 299 (e.g., Threonine (T)) is substituted with (e.g., with Alanine (A)) to reduce glycosylation at the adjacent residue 297. Exemplary amino acid substitutions which reduce or alter glycosylation are disclosed in International PCT Publication No. WO05/018572 and US Patent Publication No. 2007/0111281, which are incorporated by reference herein. In other embodiments, the aglycosylated Fc region is generated by enzymatic or chemical removal of oligosaccharide or expression of the Fc polypeptide in a host cell that is unable to glycosylate the Fc region (e.g., a bacterial host cell or a mammalian host cell with impaired glycosylation machinery).

In certain embodiments, the aglycosylated Fc region is partially aglycosylated or hemi-glycosylated. For example, the Fc region may comprise a first, glycosylated, Fc moiety (e.g., a glycosylated CH2 region) and a second, aglycosylated, Fc moiety (e.g., an aglycosylated CH2 region). In other embodiments, the Fc region may be fully aglycosylated, i.e., none of its Fc moieties are glycosylated.

The aglycosylated Fc region of an "effector-less" polypeptide may be of any IgG isotype (e.g., IgG1, IgG2, IgG3, or IgG4). In one exemplary embodiment, the parental Fc polypeptide may comprise the aglycosylated Fc region of an IgG4 antibody such as "agly IgG4.P". Agly IgG4.P is an engineered form of an IgG4 antibody that includes a proline substitution (Ser228Pro) in the hinge region and a Thr299Ala mutation in the CH2 domain to produce an aglycosylated Fc region (EU numbering). Agly IgG4.P has been shown to have no measurable immune effector function in vitro. In another exemplary embodiment, the parental Fc polypeptide comprises the aglycosylated Fc region of an IgG1 antibody, such as "agly IgG1". Agly IgG1 is an aglycosylated form of the IgG immunoglobulin IgG1 with a Thr299Ala mutation (EU numbering) that confers a low effector function profile. Both agly IgG4.P and agly IgG1 antibodies represent an important class of therapeutic reagents where immune effector function is not desired.

In certain exemplary embodiments, the "effector-less" parental Fc polypeptide comprises a Fc region which is derived from an IgG4 antibody. The IgG4 Fc region may be identical to the wild-type Fc region or it may have one or more modifications to the wild-type IgG4 sequence. Such IgG4-like Fc polypeptides have reduced effector function as a result of the inherently reduced ability of an IgG4 antibody to bind to complement and/or Fc receptors. Parental Fc polypeptides of the IgG4 isotype may be either glycosylated or aglycosylated. Furthermore, the Fc region of an IgG4-like Fc polypeptide may comprise the complete Fc moiety of an IgG4 antibody or it may comprise a chimeric Fc moiety wherein a portion of the Fc moiety is from an IgG4 antibody and the remainder is from an antibody of another isotype. In one exemplary embodiment, the chimeric Fc moiety comprises a CH3 domain from an IgG1 antibody and CH2 domain from an IgG4 antibody. In another embodiment, the IgG4 antibody comprises a chimeric hinge, wherein the upper and lower hinge domains are from an IgG4 antibody but the middle hinge domain is from an IgG1 antibody as a result of a proline substitution (Ser228Pro) in the hinge region. In yet another embodiment, the parental chimeric chimeric IgG4 antibody comprises a chimeric hinge, wherein the upper and lower hinge domains are from an IgG4 antibody but the middle hinge domain is from an IgG1 antibody as a result of a proline substitution (Ser228Pro) in the hinge region, a CH1 domain from an IgG1 or IgG4 antibody, a CH2 domain (or positions 292-340, EU numbering) from an IgG4 antibody, and a CH1 and/or CH3 domain from an IgG1 antibody.

In certain embodiments, the reduced effector function of an "effector-less" Fc polypeptide is reduced binding to an Fc receptor (FcR), such as the FcγRI, FcγRII, FcγRIII, and/or FcγRIIIb receptor or a complement protein, for example, the complement protein C1q. This change in binding can be by a factor of about 1 fold or more, e.g., by about 2, 3, 4, 5, 6, 7, 8, 9, 10, 15, 50, or 100-fold or more, or by any interval or range thereof. These decreases in effector function, e.g., Fc binding to an Fc receptor or complement protein, are readily calculated based on, e.g., the percent reductions in binding activity determined using the assays described herein or assays known in the art.

In one embodiment of the invention a stabilized Fc polypeptide comprises a single chain Fc region. Such single chain Fc regions are known in the art (see, e.g., WO200801243, WO2008131242; WO2008153954) and can be made using known methods. Stabilizing amino acids as taught herein may be incorporated into one or more Fc moieties of such constructs using methods known to those of skill in the art. Such single chain Fc regions or genetically-fused Fc regions are synthetic Fc region comprised of Fc domains (or Fc moieties) genetically linked within a single polypeptide chain (i.e., encoded in a single contiguous genetic sequence). Accordingly, a genetically-fused Fc region (i.e., a scFc region) is monomeric in that they comprise one polypeptide chain, yet the appropriate portions of the molecule dimerize to form n Fc region. It will be understood that the teachings herein with respect to Fc moieties are applicable to both two chain Fc dimers and single chain Fc dimers. For example, either type of Fc region construct may be derived from, e.g., an IgG1 or IgG4 antibody or may be chimeric (e.g., comprising a chimeric hinge and/or comprising a CH2 domain from an IgG4 antibody and a CH3 domain from an IgG1 antibody.

III. Variant Fc Polypeptides with Stabilized Fc Regions

In variant aspects, the invention provides variant Fc polypeptides which comprise amino acid sequences which are variants of any one of the parental Fc polypeptides described supra. In particular, the variant Fc polypeptides of the invention comprise an Fc region (or Fc moiety) with an amino acid sequence which is derived from the Fc region (or Fc moiety) of a parental Fc polypeptide. In some embodiments, the variant Fc polypeptide differs from the parental Fc polypeptide by the presence of at least one of the stabilizing Fc mutations described herein. In certain embodiments, the Fc variant may comprise additional amino acid sequence alterations. In some embodiments, the Fc variant will have enhanced stability as compared to the parent Fc polypeptide and, optionally, altered effector function as compared to the parental Fc polypeptide. For example, the variant Fc polypeptide may have an antigen-dependent effector function that is equivalent to or lower than the antigen-dependent effector function (e.g., ADCC and/or CDC) of the parental Fc polypeptide. Additionally or alternatively, the variant Fc polypeptide may have an antigen-independent effector function (e.g., extended half-life) relative to the parental Fc polypeptide.

In certain embodiments, the variant Fc polypeptide comprises an Fc region (or Fc moiety) that is essentially identical to the Fc region of a parental Fc polypeptide (Fc moiety) but for about one or more mutations (e.g., about 1 to about 20, about 1 to about 15, about 1 to about 10, about 1 to about 5, about 1 to about 4, about 1 to about 3, about 2 to about 20, about 2 to about 15, about 2 to about 10, about 5 to about 20, or about 5 to about 10) mutations relative to the starting or parent polypeptide, e.g., one or more amino acid residues which have been substituted with another amino acid residue or which has one or more amino acid residue insertions or deletions. In certain embodiments, the variant Fc polypeptide has 1, 2, 3, 4, 5, 6, 7, 8, 9, 10, 11, 12, 13, 14, 15, 16, 17, 18, 19 or 20 mutations relative to the starting polypeptide. In some embodiments, the variant polypeptide comprises an amino acid sequence which is not naturally occurring.

Such variants necessarily have less than 100% sequence identity or similarity with the starting polypeptide. In some embodiments, the variant will have an amino acid sequence from about 75% to less than 100% amino acid sequence identity or similarity with the amino acid sequence of the starting polypeptide, for example, from about 80% to less than 100%, or from about 85% to less than 100%, or from about 90% to less than 100% (e.g., 91-99%, 92-99%, 93-99%, 94-99%, 95-99%, 96-99%, 97-99%, 98-99%, or 99%) or from about 95% to less than 100%, e.g., over the entire length of the variant molecule or a portion thereof (e.g., an Fc region or Fc moiety). In one embodiment, there is one amino acid difference between a starting polypeptide sequence (e.g., the Fc region of a parental Fc polypeptide) and the sequence derived therefrom (e.g., the Fc region of a variant Fc polypeptide).

In certain embodiments, the variant Fc polypeptides of the invention are stabilized Fc polypeptides. That is, the stabilized polypeptides comprise at least one sequence variation or mutation that is stabilizing Fc mutation. As used herein, the term "stabilizing Fc mutation" includes a mutation within an Fc region of a variant Fc polypeptide which confers enhanced protein stability (e.g. thermal stability) variant Fc polypeptide as compared to the parental Fc polypeptide from which it is derived. In some embodiments, the stabilizing mutation comprises the substitution of a destabilizing amino acid in an Fc region with a replacement amino acid that confers enhanced protein stability (herein a "stabilizing amino acid") to the Fc region. In one embodiment, a stabilized Fc polypeptide of the invention comprises one or more amino acid stabilizing Fc mutations (e.g., 1, 2, 3, 4, 5, 6, 7, 8, 9, 10, 11, 12, 13, 14, 15, 16, 17, 18, 19 or 20 stabilizing mutations). Stabilizing Fc mutations may be introduced, for example, into a CH2 domain, a CH3 domain, or both CH2 and CH3 domains of an Fc region.

In certain exemplary embodiments, a variant Fc polypeptide of the invention is a stabilized variant of an "effector-less" parental Fc polypeptide described supra. That is, the stabilized variant has enhanced stability relative to the "effector-less parent Fc polypeptide". In one exemplary embodiment, the variant Fc polypeptide is a stabilized variant of a parental Fc polypeptide comprising the aglycosylated Fc region of an IgG1 antibody, e.g., an aglycosylated IgG1 Fc region comprising a T299A mutation (EU numbering). In another exemplary embodiment, the variant Fc polypeptide is a stabilized variant of a parental Fc polypeptide comprising the Fc region of a glycosylated or aglycosylated IgG4 antibody. For example, the variant Fc polypeptide may comprise a stabilizing mutation in an Fc region derived from an "agly IgG4.P" antibody.

In some embodiments, the stabilized Fc polypeptides of the invention exhibit enhanced stability when compared to the variant Fc polypeptide under identical measurement conditions. It will be recognized, however, that the degree to which the stability of Fc variant polypeptide is enhanced relative to its parent Fc polypeptide may vary under the chosen measurement conditions. For example, the enhancement of stability may be observed at a particular pH, e.g., an acidic, neutral or basic pH. In one embodiment, the enhanced stability is observed at an acidic pH of less than about 6.0 (e.g., about 6.0, about 5.5, about 5.0, about 4.5, or about 4.0). In another embodiment, the enhanced stability is observed at a neutral pH of about 6.0 to about 8.0 (e.g., about 6.0, about 6.5, about 7.0, about 7.5, about 8.0). In another embodiment, the enhanced stability is observed at a basic pH of about 8.0 to about 10.0 (e.g., about 8.0, about 8.5, about 9.0, about 9.5, about 10.0).

The enhanced thermal stability of the variant Fc polypeptide can be evaluated, e.g., using any of the methods described below. In certain embodiments, the stabilized Fc polypeptides have Fc regions (or Fc moieties) with a thermal stability (e.g., a melting temperature or Tm) that is greater than about 0.1, about 0.25, about 0.5, about 0.75, about 1, about 1.25, about 1.5, about 1.75, about 2, about 3, about 4, about 5, about 6, about 7, about 8, about 9, about 10, about 11, about 12, about 13, about 14, about 15, about 16, about 17, about 18, about 19, about 20, about 25, about 30, about 40 or about 50 degrees Celsius higher than that of the parental polypeptide from which it is derived. In certain embodiments, stabilized Fc polypeptide variants of the invention are expressed as a monomeric, soluble protein of which is no more than 25% in dimeric, tetrameric, or otherwise aggregated form (e.g., less than about 25%, about 20%, about 15%, about 10%, or about 5%).

In another embodiment, stabilized Fc polypeptides have a TSO of greater than 40° C. (e.g., 40, 41, 42, 43, 44, 45, 46, 47, 48, 49° C., or more) in a thermal challenge assay (see U.S. patent application Ser. No. 11/725,970, which is incorporated by reference herein, as well as Example 4 infra). In some embodiments, stabilized Fc molecules of the invention have a T50 of greater than 50° C. (e.g., 50, 51, 52, 53, 54, 55, 56, 57, 58° C. or more). In some embodiments, stabilized Fc molecules of the invention have a T50 of greater than 60° C. (e.g., 60, 61, 62, 63, 64, 65° C., or more). In yet further embodiments, stabilized Fc molecules of the invention have a T50 of greater than 65° (e.g., 65, 66, 67, 68, 69, 70° C., or more). In further embodiments, stabilized Fc molecules of the invention have a T50 of greater than 70° C. (e.g., 70, 71, 73, 74, 75° C., or more).

In certain embodiments, stabilized Fc molecules of the invention have CH2 domains with Tm values greater than about 60° C. (e.g., about 61, 62, 63, 64, 65° C. or higher), greater than 65° C. (e.g., 65, 66, 67, 68, 69° C. or higher), or greater than about 70° C. (e.g., 71, 72, 73, 74, 75° C. or higher). In other embodiments, stabilized Fc molecules of the invention have CH3 domains with Tm values greater than about 70° C. (e.g., 71, 72, 73, 74, 75° C. or higher), greater than about 75° C. (e.g., 76, 77, 78, 79, 80° C. or higher), or greater than 80° C. (e.g., 81, 82, 83, 84, 85° C. or higher). In particular embodiments, said stabilized Fc polypeptides are variants of a parental Fc polypeptide comprising an aglycosylated or glycosylation Fc region of an IgG4 antibody (e.g., agly IgG4.P). In other embodiments, said stabilized Fc polypeptides are variants of a parental Fc polypeptide comprising an aglycosylated Fc region of an IgG1 antibody (e.g., agly IgG1). In yet other embodiments, the stabilized Fc molecule of the invention has a Fc region or Fc moiety (e.g., a CH2 and/or CH3 domain) with a thermal stability that is substantial the same or greater than that of a glycosylated IgG1 antibody.

In certain embodiments, variant Fc polypeptides of the invention result in reduced aggregation as compared to the parental Fc polypeptides from which they are derived. In one embodiment, a stabilized Fc molecule produced by the methods of the invention has a decrease in aggregation of at least 1% relative to the parental Fc molecule. In other embodiments, the stabilized Fc polypeptide has a decrease in aggregation of at least 2%, at least 5%, at least 10%, at least 20%, at least 30%, at least 50%, at least 75%, or at least 100%, relative to the parental molecule.

In other embodiments, stabilized Fc polypeptides of the invention result in increased long-term stability or shelf-life as compared to parental Fc polypeptides from which they are derived. In one embodiment, a stabilized Fc molecule produced by the methods of the invention has an increase in shelf life of at least 1 day relative to the unstabilized binding molecule. This means that a preparation of stabilized Fc polypeptides has substantially the same amount of biologically active variant Fc polypeptides as present on the previous day, and the preparation does not have any appreciable aggregation or decomposition of the variant polypeptide. In other embodiments, the stabilized Fc molecule has an increase in shelf life of at least 2 days, at least 5 days, at least 1 week, at least 2 weeks, at least 1 month, at least 2 months, at least 6 months, or at least 1 year, relative to the unstabilized Fc molecule.

In certain embodiments, stabilized Fc polypeptides of the invention are expressed at increased yield as compared to their parental Fc polypeptides. In one embodiment, a stabilized Fc polypeptide of the invention has an increase in yield of at least 1% relative to the parent Fc molecule. In other embodiments, the stabilized Fc polypeptide has an increase in yield of at least 2%, at least 5%, at least 10%, at least 20%, at least 30%, at least 50%, at least 75%, at least 80%, at least 90%, at least 95%, at least 98% or at least 100%, relative to the parental Fc molecule.

In exemplary embodiments, stabilized Fc polypeptides of the invention are expressed at increased yields (as compared to their parental Fc polypeptides) in a host cell, e.g., a bacterial or eukaryotic (e.g., yeast or mammalian) host cell. Exemplary mammalian host cells which can be used to express a nucleic acid molecule encoding a stabilized Fc polypeptide of the invention include Chinese Hamster Ovary (CHO) cells, HELA (human cervical carcinoma) cells, CVI (monkey kidney line) cells, COS (a derivative of CVI with SV40 T antigen) cells, R1610 (Chinese hamster fibroblast) cells, BALBC/3T3 (mouse fibroblast) cells, HAK (hamster kidney line) cells, SP2/O (mouse myeloma) cells, BFA-1c1BPT cells (bovine endothelial cells), RAJI (human lymphocyte) cells, PER.C6® (human retina-derived cell line, Crucell, The Netherlands) and 293 cells (human kidney).

In other embodiments, the stabilized Fc polypeptides of the invention are expressed at increased yields (relative to their parental Fc polypeptides) in a host cell under large-scale (e.g., commercial scale) conditions. In exemplary embodiments, the stabilized Fc molecule have increased yield when expressed in at least 10 liters of culture media. In other embodiments, a stabilized Fc binding molecule has an increase in yield when expressed from a host cell in at least 20 liters, at least 50 liters, at least 75 liters, at least 100 liters, at least 200 liters, at least 500 liters, at least 1000 liters, at least 2000 liters, at least 5,000 liters, or at least 10,000 liters of culture media. In an exemplary embodiment, at least 10 mg (e.g., 10 mg, 20 mg, 50 mg, or 100 mg) of a stabilized Fc molecule are produced for every liter of culture media.

(i) Stabilizing Fc Amino Acids

In certain embodiments, a stabilized Fc polypeptide of the invention comprises a CH2 domain (or amino acids 292-340 thereof) of an IgG4 molecule and a CH3 domain from an IgG1 molecule, having a Gln (Q) residue at position 297. In another embodiment, a stabilized Fc polypeptide of the invention comprises a CH2 and CH3 domain of an IgG1 molecule and a Lys (K) residue at position 299, either alone or in combination with an Asp (D) residue at position 297.

(ii) Exemplary Stabilized Fc Moieties

Exemplary stabilized Fc moieties of the invention can be found throughout the application, Examples, and sequence listing.

In certain exemplary embodiments, a stabilized Fc polypeptide of the invention comprises a stabilized IgG4 Fc region comprising one, two or more of the Fc amino acid sequences set forth in Table 1.1 below. Stabilizing Fc mutations are underlined in bold.

TABLE 1.1

Stabilized IgG4 Fc moieties

| Fc Moiety (Fc mutation(s), glycosylation state) | Sequence | |
|---|---|---|
| pCN579: (T299K, aglycosylated) | ESKYGPPCPPCPAPEFLGGPSVFLFPPKPKDTLMISR TPEVTCVVVDVSQEDPEVQFNWYVDGVEVHNAK TKPREEQFNSKYRVVSVLTVLHQDWLNGKEYKCK VSNKGLPSSIEKTISKAKGQPREPQVYTLPPSQEEM TKNQVSLTCLVKGFYPSDIAVEWESNGQPENNYK TTPPVLDSDGSFFLYSRLTVDKSRWQEGNVFSCSV MHEALHNHYTQKSLSLSLG | SEQ ID NO: 16 |
| EC301 (T299K, IV427F aglycosylated) | ESKYGPPCPPCPAPEFLGGPSVFLFPPKPKDTLMISR TPEVTCVVVDVSQEDPEVQFNWYVDGVEVHNAK TKPREEQFNSKYRVVSVLTVLHQDWLNGKEYKCK VSNKGLPSSIEKTISKAKGQPREPQVYTLPPSQEEM TKNQVSLTCLVKGFYPSDIAVEWESNGQPENNYK TTPPVLDSDGSFFLYSRLTVDKSRWQEGNVFSCSE MHEALHNHYTQKSLSLSLG | SEQ ID NO: 17 |
| EC302 (T299K, D399S, aglycosylated) | ESKYGPPCPPCPAPEFLGGPSVFLFP PKPKDTLMISRTPEVTCVVVDVSQE DPEVQFNWYVDGVEVHNAKTKPRE EQFNSKYRVVSVLTVLHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSVMHEALHNHYTQKSLSLSL G | SEQ ID NO: 18 |
| EC303 (T307P, V427F glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVLHQDWLNGKE YKCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSFMHEALHNHYTQKSLSLS LG | SEQ ID NO: 19 |
| EC304 (T307P, D399S, glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVLHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSVMHEALHNHYTQKSLSLSL G | SEQ ID NO: 20 |
| EC305 (T299K, D399S, V427F aglycosylated) | ESKYGPPCPPCPAPEFLGGPSVFLFP PKPKDTLMISRTPEVTCVVVDVSQE DPEVQFNWYVDGVEVHNAKTKPRE EQFNSKYRVVSVLTVLHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSFMHEALHNHYTQKSLSLSL G | SEQ ID NO: 21 |
| EC306: (T307P, D399S, V427F glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVLHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSFMHEALHNHYTQKSLSLSL G | SEQ ID NO: 22 |

TABLE 1.1-continued

Stabilized IgG4 Fc moieties

| Fc Moiety (Fc mutation(s), glycosylation state) | Sequence | |
|---|---|---|
| EC307 (T299K, V348F, V427F aglycosylated) | ESKYGPPCPPCPAPEFLGGPSVFLFP PKPKDTLMISRTPEVTCVVVDVSQE DPEVQFNWYVDGVEVHNAKTKPRE EQFNSKYRVVSVLTVLHQDWLNGKE YKCKVSNKGLPSSIEKTISKAKGQPR EPQFYTLPPSQEEMTKNQVSLTCLV KGFYPSDIAVEWESNGQPENNYKTT PPVLDSDGSFFLYSRLTVDKSRWQE GNVFSCSEMHFALHNHYTQKSLSLS LG | SEQ ID NO: 23 |
| EC308 (T307P, V323F glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVLHQDWLNGKE YKCKFSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LG | SEQ ID NO: 24 |
| EC309 (V240F glycosylated) | ESKYGPPCPPCPAPEFLGGPSFFLFPP KPKDTLMISRTPEVTCVVVDVSQED PEVQFNWYVDGVEVHNAKTKPREE QFNSTYRVVSVLTVLHQDWLNGKEY KCKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL G | SEQ ID NO: 25 |
| EC300 (T307P glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVLHQDWLNGKE YKCKVSNKGLPSSIEKTISKAKGQPR EPQVYTLPPSQEEMTKNQVSLTCLV KGFYPSDIAVEWESNGQPENNYKTT PPVLDSDGSFFLYSRLTVDKSRWQE GNVFSCSVMHEALHNHYTQKSLSLS LG | SEQ ID NO: 26 |
| EC321 (L309P, D399S glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLTVPHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSVMHEALHNHYTQKSLSLSL G | SEQ ID NO: 27 |
| EC322 (L309M, D399S glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLTVMHQDWLNGK EYKCKVSNKGLPSSIEKTISKAKGQ REPQVYTLPPSQEEMTKNQVSLTCL VKGFYPSDIAVEWESNGQPENNYKT TPPVLSDGSFFLYSRLTVDKSRWQE GNVFSCCVMHEALHNHYTQKSLSLS LG | SEQ ID NO: 28 |
| EC323 (L309K, D399S glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLTVKHQDWLNGKE YKCKVSNKGLPSSIEKTISKAKGQPR EPQVYTLPPSQEEMTKNQVSLTCLV KGFYPSDIAVEWESNGQPENNYKTT | SEQ ID NO: 29 |

TABLE 1.1-continued

Stabilized IgG4 Fc moieties

| Fc Moiety (Fc mutation(s), glycosylation state) | Sequence | |
|---|---|---|
| | PPVLSDGSFFLYSRLTVDKSRWQEG NVFSCSVMHEALHNHYTQKSLSLSL G | |
| EC324 (T307P, L309P, D399S glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVKHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSVMHEALHNHYTQKSLSLSL G | SEQ ID NO: 30 |
| EC325 (T307P, L309M, D399S glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVMHQDWLNGK EYKCK VSNKGLPSSIEKTIS KAKGQP REPQVYTLPPSQEEMTKNQVSLTCL VKGFYPSDIAVEWESNGQPENNYKT TPPVLSDGSFFLYSRLTVDKSRWQE GNVFSCSVMHEALHNHYTQKSLSLS LG | SEQ ID NO: 31 |
| EC326 (T307P, L309K, D399S glycosylated) | ESKYGPPCPPCPAPEFLGGPSVFLFP PKPKDTLMISRTPEVTCVVVDVSQE DPEVQFNWYVDGVEVHNAKTKPRE EQFNSTYRVVSVLPVKHQDWLNGKE YKCKVSNKGLPSSIEKTISKAKGQPR EPQVYTLPPSQEEMTKNQVSLTCLV KGFYPSDIAVEWESNGQPENNYKTT PPVLSDGSFFLYSRLTVDKSRWQEG NVFSCSVMHEALHNHYTQKSLSLSL G | SEQ ID NO: 32 |
| YC401 (T299A, T307P, D399S aglycosylated) | ESKYGPPCPPCPAPEFLGGPSVFLFPPKPKDTLMISR TPEVTCVVVDVSQEDPEVQFNWYVDGVEVHNAK TKPREEQFNSAYRVVSVLPVLHQDWLNGKEYKCK VSNKGLPSSIEKTISKAKGQPREPQVYTLPPSQEEM TKNQVSLTCLVKGFYPSDIAVEWESNGQPENNYK TTPPVLSDGSFFLYSRLTVDKSRWQEGNVFSCSV MHEALHNHYTQKSLSLSLG | SEQ ID NO: 33 |
| YC402 (T299A, L309K, D399S aglycosylated) | ESKYGPPCPPCPAPEFLGGPSVFLFPPKPKDTLMISR TPEVTCVVVDVSQEDPEVQFNWYVDGVEVHNAK TKPREEQFNSAYRVVSVLTKHQDWLNGKEYKCK VSNKGLPSSIEKTISKAKGQPREPQVYTLPPSQEEM TKNQVSLTCLVKGFYPSDIA VEWESNGQPENNYK TTPPVLSDGSFFLYSRLTVDKSRWQEGNVFSCSV MHEALHNHYTQKSLSLSLG | SEQ ID NO: 34 |
| YC403 (T299A, T307P, L309K, D399S aglycosylated) | ESKYGPPCPPCPAPEFLGGPSVFLFPPKPKDTLMISR TPEVTCVVVDVSQEDPEVQFNWYVDGVEVHNAK TKPREEQFNSAYRVVSVLPVKHQDWLNGKEYKCK VSNKGLPSSIEKTISKAKGQPREPQVYTLPPSQEEM TKNQVSLTCLVKGFYPSDIAVEWESNGQPENNYK TTPPVLSDGSFFLYSRLTVDKSRWQEGNVFSCSV MHEALHNHYTQKSLSLSLG | SEQ ID NO: 35 |
| YC404 (T299K, T307P, D399S aglycosylated) | ESKYGPPCPPCPAPEFLGGPSVFLFPPKPKDTLMISR TPEVTCVVVDVSQEDPEVQFNWYVDGVEVHNAK TKPREEQFNSKYRVVSVLPVLHQDWLNGKEYKCK VSNKGLPSSIEKTISKAKGQPREPQVYTLPPSQEEM TKNQVSLTCLVKGFYPSDIAVEWESNGQPENNYK TTPPVLSDGSFFLYSRLTVDKSRWQEGNVFSCSV MHEALHNHYTQKSLSLSLG | SEQ ID NO: 36 |
| YC405 (T299K, L309K, D399S aglycosylated) | ESKYGPPCPPCPAPEFLGGPSVFLFPPKPKDTLMISR TPEVTCVVVDVSQEDPEVQFNWYVDGVEVHNAK TKPREEQFNSKYRVVSVLTKHQDWLNGKEYKCK VSNKGLPSSIEKTISKAKGQPREPQVYTLPPSQEEM | SEQ ID NO: 37 |

TABLE 1.1-continued

Stabilized IgG4 Fc moieties

| Fc Moiety (Fc mutation(s), glycosylation state) | Sequence | |
|---|---|---|
| | TKNQVSLTCLVKGFYPSDIAVEWESNGQPENNYK TTPPVLSDGSFFLYSRLTVDKSRWQEGNVFSCSV MHEALHNHYTQKSLSLSLG | |
| YC406 (T299K, T307P, L309K, D399S aglycosylated) | ESKYGPPCPPCPAPEFLGGPSVFLFPPKPKDTLMISR TPEVTCVVVDVSQEDPEVQFNWYVDGVEVHNAK TKPREEQFNSKYRVVSVLPVKHQDWLNGKEYKCK VSNKGLPSSIEKTISKAKGQPREPQVYTLPPSQEEM TKNQVSLTCLVKGFYPSDIAVEWESNGQPENNYK TTPPVLSDGSFFLYSRLTVDKSRWQEGNVFSCSV MHEALHNHYTQKSLSLSLG | SEQ ID NO: 38 |

In certain exemplary embodiments, a stabilized Fc polypeptide of the invention comprises a stabilized chimeric Fc region with one, two or more of the chimeric Fc moiety amino acid sequences set forth in Table 1.2 below.

TABLE 1.2

Stabilized Chimeric Fc Moieties

| Fc Moiety (Fc mutation(s), glycosylation state) | Sequence | |
|---|---|---|
| EAG2296 (T299A, IgG4 CH2/IgG1 CH3 chimera) | ESKYGPPCPPCPAPEFLGGPSVFLFPPKPKDTLMI SRTPEVTCVVVDVSQEDPEVQFNWYVDGVEVH NAKTKPREEQFNSAYRVVSVLTVLHQDWLNGK EYKCKVSNKGLPSSIEKTISKAKGQPREPQVYTL PPSRDELTKNQVSLTCLVKGFYPSDIAVEWESN GQPENNYKTTPPVLDSDGSFFLYSKLTVDKSRW QQGNVFSCSVMHEALHNHYTQKSLSLSPG | SEQ ID NO: 39 |
| EAG2287 (T299K, IgG4 CH2/IgG1 CH3 chimera) | ESKYGPPCPPCPAPEFLGGPSVFLFPPKPKDTLMI SRTPEVTCVVVDVSQEDPEVQFNWYVDGVEVH NAKTKPREEQFNSKYRVVSVLTVLHQDWLNGK EYKCKVSNKGLPSSIEKTISKAKGQPREPQVYTL PPSRDELTKNQVSLTCLVKGFYPSDIAVEWESN GQPENNYKTTPPVLDSDGSFFLYSKLTVDKSRW QQGNVFSCSVMHEALHNHYTQKSLSLSPG | SEQ ID NO: 40 |
| EC330 (T299A, T307P IgG4 CH2/IgG1 CH3 chimera) | ESKYGPPCPPCPAPEFLGGPSVFLFPPKPKDTLMI SRTPEVTCVVVDVSQEDPEVQFNWYVDGVEVH NAKTKPREEQFNSAYRVVSVLPVLHQDWLNGK EYKCKVSNKGLPSSIEKTISKAKGQPREPQVYTL PPSRDELTKNQVSLTCLVKGFYPSDIAVEWESN GQPENNYKTTPPVLDSDGSFFLYSKLTVDKSRW QQGNVFSCSVMHEALHNHYTQKSLSLSPG | SEQ ID NO: 41 |
| EC331 (T299K, T307P IgG4 CH2/IgG1 CH3 chimera) | ESKYGPPCPPCPAPEFLGGPSVFLFPPKPKDTLMI SRTPEVTCVVVDVSQEDPEVQFNWYVDGVEVH NAKTKPREEQFNSKYRVVSVLPVLHQDWLNGK EYKCKVSNKGLPSSIEKTISKAKGQPREPQVYTL PPSRDELTKNQVSLTCLVKGFYPSDIAVEWESN GQPENNYKTTPPVLDSDGSFFLYSKLTVDKSRW QQGNVFSCSVMHEALHNHYTQKSLSLSPG | SEQ ID NO: 42 |
| pEAG2300 (IgG4 chimeric hinge + IgG1 CH3) | ESKYGPPCPPCPAPPVAGPSVFLFPPKPKDTLMIS RTPEVTCVVVDVSQEDPEVQFNWYVDGVEVHN AKTKPREEQFNSTYRVVSVLTVLHQDWLNGKE YKCKVSNKGLPSSIEKTISKAKGQPREPQVYTLP PSRDELTKNQVSLTCLVKGFYPSDIA VEWESNG QPENNYKTTPPVLDSDGSFFLYSKLTVDKSRWQ QGNVFSCSVMHEALHNHYTQKSLSLSPG | SEQ ID NO: 43 |

TABLE 1.2-continued

Stabilized Chimeric Fc Moieties

| Fc Moiety (Fc mutation(s), glycosylation state) | Sequence | |
|---|---|---|
| (N297Q, IgG4 Ch2/IgG1 CH3 chimera) | ESKYGPPCPPCPAPP<u>PVAG</u>PSVFLFPPKPKDTLMIS RTPEVTCVVVDVS<u>Q</u>EDPEVQFNWYVDGVEVHN AKTKPREEQFQSTYRVVSVLTVLHQDWLNGKE YKCKVSNKGLPSSIEKTISKAKGQPREPQVYTLP PSRDELTKNQVSLTCLVKGFYPSDIA VEWESNG QPENNYKTTPPVLDSDGSFFLYSKLTVDKSRWQ QGNVFSCSVMHEALHNHYTQKSLSLSPG | SEQ ID NO: 74 |

In other exemplary embodiments, a stabilized Fc polypeptide of the invention comprises a stabilized aglycosylated IgG1 Fc region with one, two or more of the IgG1 Fc moiety amino acid sequences set forth in Table 1.3 below.

TABLE 1.3

Stabilized Aglycosylated IgG1 Fc Moieties

| Fc Moiety (Fc mutation(s), glycosylation state) | Sequence | |
|---|---|---|
| SDE1 (T299K, V262L aglycosylated) | EPKSCDKTHTCPPCPAPELLGGPSVFLFPPKPKDT LMISRTPEVTCVVVDVSHEDPEVKFNWYVDGVE VHNAKTKPREEQYNS<u>K</u>YRVVSVLTVLHQDWLN GKEYKCKVSNKALPA<u>P</u>IEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 44 |
| SDE2 (T299K, V264T, aglycosylated) | EPKSCDKTHTCPPCPAPELLGGPSVFLFPPKPKDT LMISRTPEVTCVV<u>T</u>DVSHEDPEVKFNWYVDGVE VHNAKTKPREEQYNS<u>K</u>YRVVSVLTVLHQDWLN GKEYKCKVSNKALPA<u>P</u>IEKTISKAKGQPREPQVY TLPPSRDELTKNQVSLTCLVKGFYPSDIA VEWES NGQPENNYKTTPPVLDSDGSFFLYSKLTVDKSR WQQGNVFSCSVMHEALHNHYTQKSLSLSPG | SEQ ID NO: 45 |
| SDE3 (T299K, V266F, aglycosylated) | EPKSCDKTHTCPPCPAPELLGGPSVFLFPPKPKDT LMISRTPEVTCVVVD<u>F</u>SHEDPEVKFNWYVDGVE VHNAKTKPREEQYNS<u>K</u>YRVVSVLTVLHQDWLN GKEYKCKVSNKALPA<u>P</u>IEKTISKAKGQPREPQVY TLPPSRDELTKNQVSLTCLVKGFYPSDIA VEWES NGQPENNYKTTPPVLDSDGSFFLYSKLTVDKSR WQQGNVFSCSVMHEALHNHYTQKSLSLSPG | SEQ ID NO: 46 |
| SDE4 (T299K, V262L, V264T, aglycosylated) | EPKSCDKTHTCPPCPAPELLGGPSVFLFPPKPKDT LMISRTPEVTC<u>LVT</u>DVSHEDPEVKFNWYVDGVE VHNAKTKPREEQYNS<u>K</u>YRVVSVLTVLHQDWLN GKEYKCKVSNKALPA<u>P</u>IEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 47 |
| SDE5 (T299K, V264T, V266F, aglycosylated) | EPKSCDKTHTCPPCPAPELLGGPSVFLFPPKPKDT LMISRTPEVTCVV<u>TDF</u>SHEDPEVKFNWYVDGVE VHNAKTKPREEQYNS<u>K</u>YRVVSVLTVLHQDWLN GKEYKCKVSNKALPA<u>P</u>IEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 48 |
| SDE6 (T299K, Loop replacement, aglycosylated) | EPKSCDKTHTCPPCPAPELLGGPSVFLFPPKPKDT LMISRTPEVTCVVVDS__PDP_VKFNWYVDGVE VHNAKTKPREEQYNS<u>K</u>YRVVSVLTVLHQDWLN GKEYKCKVSNKALPA<u>P</u>IEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 49 |

TABLE 1.3-continued

Stabilized Aglycosylated IgG1 Fc Moieties

| Fc Moiety (Fc mutation(s), glycosylation state) | Sequence | |
|---|---|---|
| SDE7 (T299K, Loop replacement, V262L/V264T, aglycosylated) | EPKSCDKTHTCPPCPAPELLGGPSVFLFPPKPKDT LMISRTPEVTCLVTDVS__PDP_VKFNWYVDGVE VHNAKTKPREEQYNSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 50 |
| SDE8 (T299K, V262L, V264T, V266F, aglycosylated) | EPKSCDKTHTCPPCPAPELLGGPSVFLFPPKPKDT LMISRTPEVTCLVTDFSHEDPEVKFNWYVDGVE VHNAKTKPREEQYNSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 51 |
| SDE9 (T299K, Loop replacement, V262L/V264T/ V266F, aglycosylated) | EPKSCDKTHTCPPCPAPELLGGPSVFLFPPKPKDT LMISRTPEVTCLVTDFS__PDP_VKFNWYVDGVE VHNAKTKPREEQYNSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 79 |
| CN578 (T299K) | EPKSCDKTHTCPPCPAPELLGGPSVFLFPPKPKDT LMISRTPEVTCVVVDVSHEDPEVKFNWYVDGVE VHNAKTKPREEQYNSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 75 |
| CN647 (T299K + N297D) | EPKSCDKTHTCPPCPAPELLGGPSVFLFPPKPKDT LMISRTPEVTCVVVDVSHEDPEVKFNWYVDGVE VHNAKTKPREEQYDSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 76 |
| CN646 (T299K + N297S) | EPKSCDKTHTCPPCPAPELLGGPSVFLFPPKPKDT LMISRTPEVTCVVVDVSHEDPEVKFNWYVDGVE VHNAKTKPREEQYSSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 77 |
| CN645 (T299K + N297P) | EPKSCDKTHTCPPCPAPELLGGPSVFLFPPKPKDT LMISRTPEVTCVVVDVSHEDPEVKFNWYVDGVE VHNAKTKPREEQYPSKYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPG | SEQ ID NO: 78 |

IV. Methods for Stabilizing Variant Fc Polypeptides

In certain aspects, the invention pertains to a method of stabilizing a polypeptide comprising an Fc region (e.g., an aglycosylated Fc region), the method comprising: (a) selecting one or more amino acid positions within at least one Fc moiety of a starting Fc region for mutation; and (b) mutating the one or more amino acid positions selected for mutation, thereby stabilizing the polypeptide.

In one embodiment, the starting Fc region is an IgG1 Fc region. In another embodiment, the starting Fc region is an IgG4 Fc region. In another embodiment, the starting Fc region is a chimeric Fc region. In one embodiment, the starting Fc region is an aglycosylated IgG1 Fc region. In another embodiment, the starting Fc region is an aglycosylated IgG4 Fc region.

In some embodiments, an Fc region of an antibody (or fragment thereof) as described herein has the sequence set forth in SEQ ID NO: 85.

In one embodiment, an amino acid position selected for mutation is in an extended loop in the Fc region of a starting IgG molecule (e.g., an IgG4 molecule). In another embodiment, the amino acid position selected for mutation resides in the interface between CH3 domains. In another embodiment, an amino acid position selected for mutation is near a contact site with the carbohydrate in the 1hzh crystal structure (e.g., V264, R292 or V303). In other embodiments, the amino acid position may be near the CH3/CH2 interface, or near the CH3/CH2 interface (e.g., H310). In another embodiment, one or more mutations that alter the overall surface charge of the Fc region, e.g., in one or more of a set of surface exposed glutamine residues (Q268, Q274 or Q355) may be made. In another embodiment, the amino acid positions are valine residues found in the "valine core" of CH2 and CH3. The "valine core" in CH2 is five valine residues (V240, V255, V263, V302 and V323) that all are orientated into the same proximal interior core of the CH2 domain. A similar "valine core" is observed for CH3 (V348, V369, V379, V397, V412 and V427). In another embodiment, an amino acid position selected for mutation is at a position that is predicted to interact with or contact the N-linked carbohydrate at amino acid 297. Such amino acid positions can be identified by examining a crystal structure of the Fc region bound to a cognate Fc receptor (e.g., FcγRIIIa). Exemplary amino acids which form interactions with N297 include a loop formed by residues 262-270.

Exemplary amino acid positions include amino acid positions 240, 255, 262-266, 267-271, 292-299, 302-309, 379, 397-399, 409, 412 and 427 according to the EU numbering convention. In certain embodiments, the one or more amino acid positions selected for mutation are one or more amino acid positions selected from the group consisting of: 240, 255, 262, 263, 264, 266, 268, 274, 292, 299, 302, 303, 307, 309, 323, 348, 355, 369, 379, 397, 399, 409, 412 and 427. In certain embodiments, the one or more amino acid positions selected for mutation are one or more amino acid positions selected from the group consisting of: 240, 262, 264, 266, 297, 299, 307, 309, 399, 409 and 427. In another embodiment, the one or more amino acid positions are one or more amino acid positions selected from the group consisting of: 297, 299, 307, 309, 409 and 427. In another embodiment, the one or more amino acid positions are selected from amino acid residues 240, 262, 264, and 266. In another embodiment, at least one of the amino acid positions is at EU position 297. In another embodiment, at least one of the amino acid positions is at EU position 299. In another embodiment, at least one of the amino acid positions is at EU position 307. In another embodiment, at least one of the amino acid positions is at EU position 309. In another embodiment, at least one of the amino acid positions is at EU position 399. In another embodiment, at least one of the amino acid positions is at EU position 409. In another embodiment, at least one of the amino acid positions is at EU position 427.

In certain embodiments, the Fc region is an IgG1 Fc region. In certain embodiments, wherein the Fc region is an IgG1 Fc region, the one or more amino acid positions are selected from amino acid residues 240, 262, 264, 299, 297, and 266, according to EU numbering. In other embodiments, wherein the Fc region is an IgG4 Fc region, the one or more amino acid positions are selected from amino acid residues 297, 299, 307, 309, 399, 409 and 427, according to EU numbering.

In one embodiment, the mutation reduces the size of the amino acid side chain at the amino acid position (e.g., a substitution with an alanine (A), a serine (S) or threonine (T)). In another embodiment, the mutation is a substitution with an amino acid having a non-polar side chain (e.g., a substitution with a glycine (G), an alanine (A), a valine (V), a leucine (L), an isoleucine (I), a methionine (M), a proline (P), a phenylalanine (F), and a tryptophan (W)). In another embodiment, a mutation adds hydrophobicity to the CH3 interface, e.g., to increase the association between the two interacting domains (e.g., Y349F, T350V and T394V) or increase bulk in the side chains of the interface (e.g., F405Y). In another embodiment, one or more amino acids of the "valine core" are substituted with isoleucines or phenylalanines in order to increase their stability. In another embodiment, amino acids (e.g., L351 and/or L368) are mutated to higher branched hydrophobic sidechains.

In one embodiment, the mutation is a substitution with an alanine (A). In one embodiment, the mutation is a substitution with a phenylalanine (F). In another embodiment, the mutation is a substitution with a leucine (L). In one embodiment, the mutation is a substitution with a threonine (T). In another embodiment, the mutation is a substitution with a lysine (K). In one embodiment, the mutation is a substitution with a proline (P). In one embodiment, the mutation is a substitution with a phenylalanine (F).

In one embodiment, the mutating comprises one or more of the mutations or substitutions set forth in Table 5.1, Table 5.2, Table 5.3, and/or Table 5.4 infra.

In certain embodiments, the mutating comprises one or more substitutions selected from the group consisting of: 240F, 262L, 264T, 266F, 297Q, 297S, 297D, 299A, 299K, 307P, 309K, 309M, 309P, 323F, 399S, 409M and 427F (EU Numbering Convention). In another embodiment, the mutating comprises one or more substitutions selected from the group consisting of: 299 A, 299K, 307P, 309K, 309M, 309P, 323F, 399E, 399S, 409K, 409M and 427F. In another embodiment, the one or more amino acid positions are selected from amino acid residues 240F, 262L, 264T, and 266F. In another embodiment, at least one of the substitutions is 299A. In another embodiment, at least one of the substitutions is 299K. In another embodiment, at least one of the substitutions is 307P. In another embodiment, at least one of the substitutions is 309K. In another embodiment, at least one of the substitutions is 309M. In another embodiment, at least one of the substitutions is 309P. In another embodiment, at least one of the substitutions is 323F. In another embodiment, at least one of the substitutions is 399S. In another embodiment, at least one of the substitutions is 399E. In another embodiment, at least one of the substitutions is 409K. In another embodiment, at least one of the substitutions is 409M. In another embodiment, at least one of the substitutions is 427F.

In another embodiment, the mutating comprises two or more substitutions (e.g., 2, 3, 4, or 5). In another embodiment, the mutating comprises three or more substitutions (e.g., 3, 4, 5, or 6). In yet another embodiment, the stabilized Fc region comprises four or more substitutions (e.g., 4, 5, 6, or 7).

In another aspect, the invention pertains to a method of making a stabilized binding molecule comprising a stabilized Fc region, the method comprising genetically fusing a polypeptide comprising stabilized Fc region of the invention to the amino terminus or the carboxy terminus of a binding moiety. In certain embodiments, the stabilized Fc region is stabilized according to the methods of the invention.

In another embodiment, the therapeutic antibody can eliminate scrambling or reduce the antibody's susceptibility to scrambling. Certain antibodies, for example, those having a wild type IgG4 constant region (e.g., including the hinge region)_can be susceptible to scrambling with endogenous IgG4 antibodies to produce two copies of a functionally monovalent product (see, e.g., Aalberse and Schuurman, Immunology 105: 9-19, 2002). The rate of scrambling can be dependent on the endogenous levels of IgG4 and this is variable. As a result, a therapeutic antibody with a wild-type human IgG4 constant region has a variable pharmacokinetic/pharmacodynamic (PK/PD) profile. The scrambling of an antibody with a wild-type IgG4 constant region can result in a bispecific antibody that is monovalent for VLA4 and monovalent for another antigen. Thus, in some embodiments, the therapeutic antibody described herein has a more consistent PK profile than an antibody with the same specificity (e.g., specific binding to α4), but with a wild-type IgG4 constant region. In some embodiments, the more consistent PK profile of the therapeutic antibody described herein may increase the safety, increase the purity, and/or increase the potency of the antibody described herein as compared to an antibody with the same specificity (e.g., specific binding to α4), but with a wild-type IgG4 constant region.

In some embodiments, the therapeutic antibody comprising a heavy chain hinge and Fc region that is a chimeric or a hybrid between human IgG1 and human IgG4 antibodies can reduce or eliminate scrambling that occurs with an antibody comprising a hinge and Fc region from a human IgG4 molecule. In one embodiment, the antibody described herein having a chimeric or hybrid heavy chain constant region can eliminate scrambling or reduce the antibody's susceptibility to scrambling thereby reducing PK/PD variability. In some embodiments, the therapeutic antibody described herein has lower PK/PD variability than an antibody with the same specificity (e.g., specific binding to α4), but with a wild-type IgG4 constant region. In certain embodiments, the antibody described herein can increase potency with a bivalent monoclonal antibody and/or eliminate bispecificity due to scrambling. In certain embodiments, the antibody described herein can exhibit higher binding affinity than their non-mutated counterparts or than an antibody with the same specificity (e.g., specific binding to α4), but with a wild-type IgG4 constant region and/or demonstrate a higher sustained receptor occupancy. In some embodiments, the therapeutic antibody described herein having lower PK/PK variability, and/or higher binding affinity and/or reduced or eliminated scrambling may increase the safety, increase the purity, and/or increase the potency of the antibody described herein as compared to an antibody with the same specificity (e.g., specific binding to α4), but with a wild-type IgG4 constant region. In a preferred embodiment, the antibody that eliminate scrambling or reduce the antibody's susceptibility to scrambling is a recombinant anti-alpha 4 antibody comprising: (a) a heavy chain comprising, consisting essentially of, or consisting of the sequence of SEQ ID NO: 80; and (b) a light chain comprising, consisting essentially of, or consisting of the sequence of SEQ ID NO: 81.

V. Methods of Evaluating Protein Stability

The stability properties of the compositions of the invention can be analyzed using methods known in the art. Stability parameters acceptable to those in the art may be employed. Exemplary parameters are described in more detail below. In exemplary embodiments, thermal stability is evaluated. In some embodiments, the expression levels (e.g., as measured by % yield) of the compositions of the invention are evaluated. In some embodiments, the aggregation levels of the compositions of the invention are evaluated.

In certain embodiments, the stability properties of an Fc polypeptide are compared with that of a suitable control. Exemplary controls include a parental Fc polypeptide such as a wild-type Fc polypeptide, wild-type (glycosylated) IgG1 or IgG4 antibody. Another exemplary control is an aglycosylated Fc polypeptide, an aglycosylated IgG1 or IgG4 antibody. In one embodiment, one or more parameters described below are measured.

In one embodiment, one or more of these parameters is measured following expression in a mammalian cell. In one embodiment, one or more parameters described below are measured under large scale manufacturing conditions (e.g., expression of Fc polypeptide or molecules comprising Fc polypeptide in a bioreactor).

A. Thermal Stability

The thermal stability of the compositions of the invention may be analyzed using a number of non-limiting biophysical or biochemical techniques known in the art. In certain embodiments, thermal stability is evaluated by analytical spectroscopy. An exemplary analytical spectroscopy method is Differential Scanning Calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fc polypeptide (or a CH2 or CH3 domain thereof) unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol, 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

In other embodiments, the thermal stability of a composition of the invention is measured biochemically. An exemplary biochemical method for assessing thermal stability is a thermal challenge assay. In a "thermal challenge assay", a composition of the invention is subjected to a range of elevated temperatures for a set period of time. For example, in one embodiment, test Fc polypeptide comprising Fc regions are subject to an range of increasing temperatures, e.g., for 1-1.5 hours. The ability of the Fc region to bind an Fc receptor (e.g., an FcγR, Protein A, or Protein G) is then assayed by a relevant biochemical assay (e.g., ELISA or DELFIA). An exemplary thermal challenge assay is described in Example 4 infra.

In one embodiment, such an assay may be done in a high-throughput format. In another embodiment, a library of Fc variants may be created using methods known in the art. Fc expression may be induced and Fc may be subjected to thermal challenge. The challenged test samples may be assayed for binding and those Fc polypeptides which are stable may be scaled up and further characterized.

In certain embodiments, thermal stability is evaluated by measuring the melting temperature (Tm) of a composition of the invention using any of the above techniques (e.g. analytical spectroscopy techniques). The melting temperature is the temperature at the midpoint of a thermal transition curve wherein 50% of molecules of a composition are in a folded state.

In other embodiments, thermal stability is evaluated by measuring the specific heat or heat capacity (Cp) of a composition of the invention using an analytical calorimetric technique (e.g. DSC). The specific heat of a composition is the energy (e.g. in kcal/mol) required to raise by 1° C., the temperature of 1 mol of water. As large Cp is a hallmark of a denatured or inactive protein composition. In certain embodiments, the change in heat capacity (ΔCp) of a composition is measured by determining the specific heat of a composition before and after its thermal transition. In other embodiments, thermal stability may be evaluated by measuring or determining other parameters of thermodynamic stability including Gibbs free energy of unfolding (ΔG), enthalpy of unfolding (ΔH), or entropy of unfolding (ΔS).

In other embodiments, one or more of the above biochemical assays (e.g. a thermal challenge assay) is used to determine the temperature (i.e. the Tc value) at which 50% of the composition retains its activity (e.g. binding activity).

B. % Aggregation

In certain embodiments, the stability of a composition of the invention is determined by measuring its propensity to aggregate. Aggregation can be measured by a number of non-limiting biochemical or biophysical techniques. For example, the aggregation of a composition of the invention may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition of the invention can be determined by comparing the concentration of a fraction with the total concentration of protein applied to the gel. Stable compositions elute from the column as essentially a single fraction and appear as essentially a single peak in the elution profile or chromatogram.

In some embodiments, SEC is used in conjunction with in-line light scattering (e.g. classical or dynamic light scattering) to determine the % aggregation of a composition. In certain embodiments, static light scattering is employed to measure the mass of each fraction or peak, independent of the molecular shape or elution position. In some embodiments, dynamic light scattering is employed to measure the hydrodynamic size of a composition. Other exemplary methods for evaluating protein stability include High-Speed SEC (see e.g. Corbett et al., Biochemistry. 23(8):1888-94, 1984).

In a non-limiting embodiment, the % aggregation is determined by measuring the fraction of protein aggregates within the protein sample. In some embodiments, the % aggregation of a composition is measured by determining the fraction of folded protein within the protein sample.

C. % Yield

In other embodiments, the stability of a composition of the invention is evaluated by measuring the amount of protein that is recovered (herein the "% yield") following expression (e.g. recombinant expression) of the protein. For example, the % yield can be measured by determining milligrams of protein recovered for every ml of host culture media (i.e. mg/ml of protein). In some embodiments, the % yield is evaluated following expression in a mammalian host cell (e.g. a CHO cell).

D. % Loss

In yet other embodiments, the stability of a composition of the invention is evaluated by monitoring the loss of protein at a range of temperatures (e.g. from −80 to 25° C.) following storage for a defined time period. The amount or concentration of recovered protein can be determined using any protein quantification method known in the art, and compared with the initial concentration of protein. Exemplary protein quantification methods include SDS-PAGE analysis or the Bradford assay for (Bradford, et al., Anal. Biochem. 72, 248, (1976)). Non-limiting methods for evaluating % loss employs any of the analytical SEC methods described supra. It will be appreciated that % Loss measurements can be determined under any desired storage condition or storage formulation, including, for example, lyophilized protein preparations.

E. % Proteolysis

In still other embodiments, the stability of a composition of the invention is evaluated by determining the amount of protein that is proteolyzed following storage under standard conditions. In an exemplary embodiment, proteolysis is determined by SDS-PAGE a sample of the protein wherein the amount of intact protein is compared with the amount of low-molecular weight fragments which appear on the SDS-PAGE gel. In another exemplary embodiment, proteolysis is determined by Mass Spectrometry (MS), wherein the amount of protein of the expected molecular weight is compared with the amount of low-molecular weight protein fragments within the sample.

F. Binding Affinity

In still other embodiments, the stability of a composition of the invention may be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore™ system (Pharmacia Biosensor AB, Uppsala, Sweden and Piscataway, NJ). For further descriptions, see Jonsson, U., et al. (1993) Ann. Biol. Clin. 51:19-26; Jonsson, U., et al. (1991) Biotechniques 11:620-627; Johnsson, B., et al. (1995)/. MoI. Recognit. 8:125-131; and Johnnson, B., et al. (1991) Anal. Biochem. 198:268-277.

G. Other Binding Studies

In yet other embodiments, the stability of a composition of the invention may be assessed by quantifying the binding of a labeled compound to denatured or unfolded portions of a binding molecule. Such molecules may be hydrophobic, as they will likely bind or interact with large hydrophobic patches of amino acids that are normally buried in the interior of the native protein, but which are exposed in a denatured or unfolded binding molecule. An exemplary labeled compound is the hydrophobic fluorescent dye, 1-anilino-8-naphthaline sulfonate (ANS).

VI. Stabilized Binding Polypeptides Comprising Stabilized Fc Regions

In one embodiment, a polypeptide of the invention comprises a CH1 domain from an IgG4 antibody, a CH2 domain from an IgG4 antibody and a CH3 domain from an IgG1 antibody. In one embodiment, the polypeptide further comprises a Ser228Pro substitution. The polypeptide may further comprise a mutation at amino acid 297 and/or 299, e.g., 297Q and/or 299K or 297S and/or 299K. The polypeptide may also comprise a CH1 domain from an IgG1 or an IgG4 antibody, a CH2 domain from an IgG4 antibody and a CH3 domain from an IgG1 antibody; which polypeptide may comprise one or more of a Ser228Pro, 297Q or 299K substitutions. The amino acid sequence of an Fc region consisting of a CH1 domain from an IgG4 molecule (with an Ser228Pro substitution), a CH2 domain from an IgG4 antibody and a CH3 domain from an IgG1 antibody is provided in SEQ ID NO: 43. In one embodiment, a stabilized Fc polypeptide of the invention comprises the amino acid sequence set forth in SEQ ID NO: 40. In one embodiment, a stabilized Fc polypeptide of the invention comprises the amino acid sequence set forth in SEQ ID NO: 74. In one embodiment, a stabilized Fc polypeptide of the invention comprises the amino acid sequence set forth in SEQ ID NO: 75. In one embodiment, a stabilized Fc polypeptide of the invention comprises the amino acid sequence set forth in SEQ ID NO: 76. In one embodiment, a stabilized Fc polypeptide of the invention comprises the amino acid sequence set forth in SEQ ID NO: 77.

In one embodiment, the Fc region of a polypeptide of the invention is a single chain (scFc). In one embodiment, a molecule comprising an Fc region described in this paragraph is monovalent. In one embodiment, the molecule comprising an Fc region described in this paragraph is monovalent and the Fc region is a scFc. Molecules comprising an Fc region described herein may also comprise an scFv.

VII. Stabilized Fc-Containing Polypeptides Comprising Functional Moieties

The variant Fc-containing polypeptides of the invention may be further modified to provide a desired effect. For example, the Fc region of the variant Fc-polypeptide may be linked, for example, covalently linked, to an additional moiety, i.e., a functional moiety such as, for example, a blocking moiety, a detectable moiety, a diagnostic moiety, and/or a therapeutic moiety. Exemplary functional moieties are first described below followed by useful chemistries for linking such functional moieties to the different amino acid side chain chemistries.

Examples of useful functional moieties include, but are not limited to, a blocking moiety, a detectable moiety, a diagnostic moiety, and a therapeutic moiety. Exemplary blocking moieties include moieties of sufficient steric bulk and/or charge such that effector function is reduced, for example, by inhibiting the ability of the Fc region to bind a receptor or complement protein. Non-limiting blocking moieties include a polyalkylene glycol moiety, for example, a PEG moiety or a PEG-maleimide moiety. Non-limiting pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA) and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 Daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. In addition, pegylation can increase the solubility of a biologically-active molecule.

Pegylated antibodies and antibody fragments may generally be used to treat conditions that may be alleviated or modulated by administration of the antibodies and antibody fragments described herein. Generally the pegylated aglycosylated antibodies and antibody fragments have increased half-life, as compared to the nonpegylated aglycosylated antibodies and antibody fragments. The pegylated aglycosylated antibodies and antibody fragments may be employed alone, together, or in combination with other pharmaceutical compositions. Examples of detectable moieties which are useful in the methods and polypeptides of the invention include fluorescent moieties, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei (13C, 15N, 2H, 125I, 123I, 99Tc, 43K, 52Fe, 67Ga, 68Ga, 111In and the like). Other useful moieties are known in the art.

Examples of diagnostic moieties which are useful in the methods and polypeptides of the invention include detectable moieties suitable for revealing the presence of a disease or disorder. Typically a diagnostic moiety allows for determining the presence, absence, or level of a molecule, for example, a target peptide, protein, or proteins, that is associated with a disease or disorder. Such diagnostics are also suitable for prognosing and/or diagnosing a disease or disorder and its progression.

Examples of therapeutic moieties which are useful in the methods and polypeptides of the invention include, for example, anti-inflammatory agents, anti-cancer agents, anti-neurodegenerative agents, and anti-infective agents. The functional moiety may also have one or more of the above-mentioned functions.

Exemplary therapeutics include radionuclides with high-energy ionizing radiation that are capable of causing multiple strand breaks in nuclear DNA, and therefore suitable for inducing cell death (e.g., of a cancer). Exemplary high-energy radionuclides include: 90Y, 125I, 131I, 123I, 111In, 105Rh, 153Sm, 67Cu, 67Ga, 166Ho, 177Lu, 186Re and 188Re. These isotopes typically produce high energy $\alpha$- or $\beta$-particles which have a short path length. Such radionuclides kill cells to which they are in close proximity, for example neoplastic cells to which the conjugate has attached or has entered. They have little or no effect on non-localized cells and are essentially non-immunogenic.

Exemplary therapeutics also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary therapeutics also include alkylating agents such as the anthracycline family of drugs (e.g. adriamycin, carminomycin, cyclosporin-A, chloroquine, methopterin, mithramycin, porfiromycin, streptonigrin, porfiromycin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum(II) dichloride (cisplatin), melphalan, mitoxantrone, and oxaliplatin. Exemplary therapeutics also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone E09, diaziridinyl-benzoquinone methyl DZQ, triethylenephosphoramide, and nitrosourea compounds (e.g. carmustine, lomustine, semustine).

Exemplary therapeutics also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)); anti-angiogenesis compounds such as Angiostatin K1-3, DL-α-difluoromethyl-omithine, endostatin, fumagillin, genistein, minocycline, staurosporine, and (±)-thalidomide. Exemplary therapeutics also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutics also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879. Exemplary therapeutics also include gene regulators such as 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutics also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof. Other types of functional moieties are known in the art and can be readily used in the methods and compositions of the present invention based on the teachings contained herein.

Chemistries for linking the foregoing functional moieties be they small molecules, nucleic acids, polymers, peptides, proteins, chemotherapeutics, or other types of molecules to particular amino acid side chains are known in the art (for a detailed review of specific linkers see, for example, Hermanson, G. T., Bioconjugate Techniques, Academic Press (1996)).

VIII. Pharmaceutical Compositions

An α4 binding agent, such as a VLA-4 binding antibody having a stabilized Fc region, can be formulated as a pharmaceutical composition. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The antibody compositions described herein can be formulated according to methods known in the art. Pharmaceutical formulation is a well-established art, and is further described in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, the α4 antibody can be formulated with excipient materials, such as sodium chloride, sodium dibasic phosphate heptahydrate, sodium monobasic phosphate, and polysorbate 80. In another embodiment, the α4 antibody can be formulated in a citrate buffer, e.g., at pH 5, 5.5, 6, 6.5, 7, or 7.5. In yet another embodiment, the α4 antibody can be formulated in a solution including 2, 4, 5, 6, 8, 10, 12, 14, or 15% sucrose. It can be provided, for example, in a buffered solution at a concentration of about 20 mg/ml and can be stored at 2-8° C.

Pharmaceutical compositions may also be in a variety of other forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. A pharmaceutical composition can also be tested to insure it meets regulatory and industry standards for administration.

The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

IX. Administration

An α4 binding antibody having a stabilized Fc region can be administered to a subject, e.g., a human subject, by a variety of methods. For many applications, the route of administration is one of: intravenous injection or infusion, subcutaneous injection, or intramuscular injection. An α4 binding antibody can be administered as a fixed dose, or in a mg/kg dose. The antibody can be administered intravenously (IV) or subcutaneously (SC). For example, the antibody can be administered at a fixed unit dose of between about 50-600 mg IV, e.g., every 4 weeks, or between about 50-100 mg SC (e.g., 75 mg), e.g., at least once a week (e.g., twice a week). In one embodiment, the antibody is administered IV at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more. Administration of the IV dose can be once or twice or three times or more per week, or once every two, three, four, or five weeks, or less frequently.

In one embodiment, the antibody is administered SC at a fixed unit dose of 50 mg, 60 mg, 70 mg, 75 mg, 80 mg, 100 mg, or 120 mg or more. Administration of the SC dose can be once or twice or three times or more per week, or once every two, three, four, or five weeks, or less frequently.

An anti-α4 antibody having a stabilized Fc region can also be administered in a bolus at a dose of between about 1 and 10 mg/kg, e.g., about 6.0 mg/kg, 4.0 mg/kg, 3.0 mg/kg, 2.0 mg/kg, 1.0 mg/kg. Modified dose ranges include a dose that is less than about 600 mg/subject, about 400 mg/subject, about 300 mg/subject, about 250 mg/subject, about 200 mg/subject, or about 150 mg/subject, typically for administration every fourth week or once a month. The α4 binding antibody can be administered, for example, every three to five weeks, e.g., every fourth week, or monthly.

Dosing can be adjusted according to a patient's rate of clearance of a prior administration of anti-α4 antibody. For example, a patient may not be administered a second or follow-on dose before the level of anti-α4 antibodies in the patient's system has dropped below a pre-determined level. In one embodiment, a sample from a patient (e.g., plasma, serum, blood, urine, or cerebrospinal fluid (CSF)) is assayed for the presence of anti-α4 antibodies, and if the level of anti-α4 antibodies is above a pre-determined level, the patient will not be administered a second or follow-on dose. If the level of anti-α4 antibodies in the patient's system is below a pre-determined level, then the patient is administered a second or follow-on dose. A patient whose anti-α4 levels are determined to be too high (above the pre-determined level) can be tested again after one or two or three days, or a week, and if the level of anti-α4-antibody in the patient samples has dropped below the pre-determined level, the patient may be administered a second or follow-on dose of antibody.

The dose can also be chosen to reduce or avoid production of antibodies against the α4 binding antibody, to achieve greater than 40, 50, 70, 75, or 80% saturation of the α4 subunit, to achieve less than 80, 70, 60, 50, or 40% saturation of the α4 subunit, or to prevent an increase in the level of circulating white blood cells In certain embodiments, the active agent may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Controlled Drug Delivery (Drugs and the Pharmaceutical Sciences), Second Edition, J. Robinson and V. H. L. Lee, eds., Marcel Dekker, Inc., New York, 1987.

Pharmaceutical compositions can be administered with a medical device. For example, pharmaceutical compositions can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules are discussed in, e.g., U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules are also known.

This disclosure also features a device for administering a first and second agent. The device can include, for example, one or more housings for storing pharmaceutical preparations, and can be configured to deliver unit doses of the first and second agent. The first and second agents can be stored in the same or separate compartments. For example, the device can combine the agents prior to administration. It is also possible to use different devices to administer the first and second agent.

Dosage regimens are adjusted to provide the desired response, such as a therapeutic response or a combinatorial therapeutic effect. Generally, any combination of doses (either separate or co-formulated) of the VLA-4 binding agent and the second agent can be used in order to provide a subject with both agents in bioavailable quantities.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent.

A pharmaceutical composition may include a "therapeutically effective amount" of an agent described herein. Such effective amounts can be determined based on the combinatorial effect of the administered first and second agent. A therapeutically effective amount of an agent may also vary according to factors such as the disease state, age, sex, and weight of the individual, and the ability of the compound to elicit a desired response in the individual, such as amelioration of at least one disorder parameter, e.g., a multiple sclerosis parameter, or amelioration of at least one symptom of the disorder, e.g., a symptom of multiple sclerosis, such as muscle atrophy, ataxia, and tremors. A therapeutically effective amount is also one in which any toxic or detrimental effects of the composition are outweighed by the therapeutically beneficial effects.

X. Devices and Kits

Formulations containing an antibody described herein can be administered with a medical device. The device can be designed with features such as portability, room temperature storage, and ease of use so that it can be used in emergency situations, such as by an untrained subject or by emergency personnel in the field, removed to medical facilities and other medical equipment. The device can include, for example, one or more housings for storing pharmaceutical preparations that include an α4-binding antibody, and can be configured to deliver one or more unit doses of the agent.

For example, the pharmaceutical composition can be administered with a transcutaneous delivery device, such as a syringe, including a hypodermic or multichamber syringe. Other suitable delivery devices include stents, catheters, microneedles, and implantable controlled release devices. The composition can be administered intravenously with standard IV equipment, including, e.g., IV tubings, with or without in-line filters. In certain embodiments, the device will be a syringe for use in SC or IM administration.

Pharmaceutical compositions can be administered with medical devices. For example, pharmaceutical compositions can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules are described in, e.g., U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. The therapeutic composition can also be in the form of a biodegradable or nonbiodegradable sustained release formulation for subcutaneous or intramuscular administration. Methods for such compositions are known in the art. Continuous administration can also be achieved using an implantable or external pump. The administration can also be conducted intermittently, such as by single daily injection, or continuously at a low dose, such as in a sustained release formulation. The delivery device can be modified to be optimally suited for administration of an α4-binding antibody. For example, a syringe can be siliconized to an extent that is optimal for storage and delivery of the antibody. Of course, many other such implants, delivery systems, and modules are also known.

This disclosure also features a device for administering a first and second agent (e.g., an antibody and a second agent). The device can include, for example, one or more housings for storing pharmaceutical preparations, and can be configured to deliver unit doses of the first and second agent. The first and second agents can be stored in the same or separate compartments. In one embodiment, the device combines the agents prior to administration. In some embodiments, the first and second agents are administered by different devices.

An α4-binding antibody can be provided in a kit. In one embodiment, the kit includes (a) a container that contains a composition that includes a high concentration of VLA-4-binding antibody, optionally (b) a container that contains a composition that includes a second agent, and optionally (c) informational material. The informational material can be descriptive, instructional, marketing or other material that relates to the methods described herein and/or the use of the agents for therapeutic benefit. In one embodiment, the kit also includes a second agent. For example, the kit includes a first container that contains a composition that includes the α4-binding antibody, and a second container that includes the second agent.

The informational material of the kits is not limited in its form. In one embodiment, the informational material can include information about production of the antibody, concentration, date of expiration, batch or production site information, and so forth. In one embodiment, the informational material relates to methods of administering the α4-binding antibody, e.g., in a suitable dose, dosage form, or mode of administration (e.g., a dose, dosage form, or mode of administration described herein), to treat a subject who has an acute disorder such as a spinal cord injury or traumatic brain injury, or an inflammatory disease (e.g., MS), or who is at risk for experiencing an episode associated with an inflammatory disease. The information can be provided in a variety of formats, including printed text, computer readable material, video recording, or audio recording, or information that provides a link or address to substantive material.

In addition to the agent, the composition in the kit can include other ingredients, such as a solvent or buffer, a stabilizer, or a preservative. The agent can be provided in any form, e.g., liquid, dried or lyophilized form, and substantially pure and/or sterile. When the agents are provided in a liquid solution, the liquid solution typically is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the α4 binding antibody and the second agent, such as in a desired ratio. For example, the kit can include a plurality of syringes, ampoules, foil packets, blister packs, or medical devices each containing, for example, a single combination unit dose. The containers of the kits can be air tight, waterproof (e.g., impermeable to changes in moisture or evaporation), and/or light-tight.

The kit optionally includes a device suitable for administering the composition, e.g., a syringe or other suitable delivery device. The device can be provided pre-loaded with one or both of the agents or can be empty but suitable for loading.

XI. Oncology

The α4-binding antibodies and methods described herein can be used to treat cancer, including solid cancers and hematological malignancies. Exemplary solid cancers include sarcomas and carcinomas, such as of the lung, breast, pancreas, colon, prostate, bladder and brain. Hematological malignancies include cancers such as multiple myeloma, leukemia, and lymphoma.

Methods are provided for treating a patient having a hematological malignancy with a composition containing an α4-binding antibody, such as anti-VLA-4 antibody described herein. Hematological malignancies are cancers of the body's blood-forming and immune systems. Cancers of this type affect the blood, bone marrow, and/or lymph nodes. Hematological malignancies include leukemias, such as acute lymphoblastic leukemia (ALL), acute myelogenous leukemia (AML), chronic myelogenous leukemia (CML), chronic lymphocytic leukemia (CLL), acute promyelocytic leukemia, acute erythroleukemia, and hairy cell leukemia (HCL); lymphomas, such as Hodgkin's disease and Non-Hodgkin's lymphoma; and multiple myeloma; Waldenstrom's macroblobulinemia; myelodysplastic syndrome (MDS) (which can culminate in AML); a myeloproliferative disease, such as polycythemia vera (also called PV, PCV or polycythemia rubra vera (PRV)), Essential thrombocytosis (ET), myelofibrosis, heavy chain disease; and amyloid due to light-chain disease.

Patients having a hematological malignancy may be identified by analysis of blood count and blood film by, for example, light microscopy, which is useful for identifying malignant cells. A biopsy, such as from bone marrow, can also be used to identify malignant cells, and a biopsy from a lymph node can be useful for identifying a lymphadenopathy.

An α4-binding antibody (e.g., a humanized anti-VLA-4 antibody, such as HuHP1/2, H1L0, H1L1, H1L2 or H1L3) is useful for the treatment of a leukemia, such as AML. Leukemias are cancers that originate in the bone marrow, where the malignant cells are white blood cells (leukocytes). AML (also called acute myelocytic leukemia, acute myeloblastic leukemia, acute granulocytic leukemia, and acute nonlymphocytic leukemia) is a malignancy that arises in either granulocytes or monocytes. AML is characterized by the uncontrolled, exaggerated growth and accumulation of cells called leukemic blasts, which fail to function as normal blood cells, and the blockade of the production of normal marrow cells, leading to a deficiency of red cells (anemia), and platelets (thrombocytopenia) and normal white cells (especially neutrophils, i.e., neutropenia) in the blood.

All subtypes of AML are suitable for treatment with a VLA-4 binding antibody. The subtypes of AML are classified based on the stage of development myeloblasts have reached at the time of diagnosis. The categories and subsets allow the physician to decide what treatment works best for the cell type and how quickly the disease may develop. The subsets are: M0, myeloblastic, on special analysis; M1, Myeloblastic, without maturation; M2, Myeloblastic, with maturation; M3, Promyelocytic; M4, Myelomonocytic; M5, Monocytic; M6, Erythroleukemia; and M7, Megakaryocytic. A VLA-4 antibody can be administered with a secondary agent that is particularly suited to the subtype of AML. For example, acute promyelocytic leukemia (APL) and acute monocytic leukemia are subtypes of AML that need different treatment than other subtypes of AML. A second agent for treatment of APL can include all-trans retinoic acid (ATRA) or an antimetabolite, such as cytarabine. A second agent for treatment of acute monocytic leukemia can include a deoxyadenosine analog, such as 2-chloro-2'-deoxyadenosine (2-CDA).

Risk factors of AML include the presence of certain genetic disorders, such as Down syndrome, Fanconi anemia, Shwachman-Diamond syndrome and others. A patient having AML and a genetic disorder can be administered a VLA-4 binding antibody and a second agent to treat a symptom of the genetic disorder. For example, a patient with AML and Fanconi anemia can be administered a VLA-4 binding antibody and an antibiotic.

Other risk factors for AML include chemotherapy or radiotherapy for treatment of a different cancer, tobacco smoke, and exposure to large amounts of benzene.

Other cancers suitable for treatment with an α4-binding antibody include, solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, small cell lung carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

XI. Other Disorders

The formulations and methods described herein can also be used to treat other inflammatory, immune, or autoimmune disorders, e.g., inflammation of the central nervous system (e.g., in addition to multiple sclerosis, meningitis, neuromyelitis optica, neurosarcoidosis, CNS vasculitis, encephalitis, and transverse myelitis); tissue or organ graft rejection or graft-versus-host disease; acute CNS injury, e.g., stroke or spinal cord injury (SCI); chronic renal disease; allergy, e.g., allergic asthma, moderate to severe allergic rhinitis, ocular allergy; type 1 diabetes mellitus; inflammatory bowel disorders, e.g., Crohn's disease, ulcerative colitis (e.g., for treatment or maintenance of remission); epilepsy; eosinophilic gastroenteritis; myasthenia gravis; fibromyalgia; disorders associated with rheumatology/immunology, such as arthritic disorders, e.g., rheumatoid arthritis, psoriatic arthritis; dermatological disorders, such as inflammatory/immune skin disorders, e.g., psoriasis, vitiligo, dermatitis (e.g., atopic dermatitis), lichen planus, moderate to severe chronic urticaria; systemic lupus erythematosus (SLE; e.g., lupus nephritis); scleroderma (e.g., Progressive Systemic Sclerosis (PSS), such as PSS of the lung); acute or chronic primary eosinophilic pneumonia; Sjogren's Syndrome; acute coronary syndrome (ACS); acute myocardial infarction; atherosclerosis; and fibrotic disorders, e.g., pulmonary fibrosis (e.g., idiopathic pulmonary fibrosis), lung fibrosis (e.g., XRT induced), myelofibrosis, liver cirrhosis, mesangial proliferative glomerulonephritis, crescentic glomerulonephritis, diabetic nephropathy, and renal interstitial fibrosis. In a preferred embodiment, the formulation can be used to treat epilepsy.

The formulations and methods described herein can also be used to treat neurological disorders, such as cerebral ischemia, including prevention in patients with transient ischemic attacks and/or arterial stenosis. Other exemplary neurological disorders include chronic inflammatory demyelinating polyneuropathy (CIDP); Guillian-Barre Syndrome (GBS); ocular diseases, such as macular degeneration (e.g., wet macular degeneration), and anteriorischemic optic neuropathy; neuropathic pain (e.g., symptomatic neuropathic pain); Alzheimer's Disease; Amyotrophic Lateral Sclerosis (ALS) (e.g., disease modifying ALS)' and Parkinson's Disease.

The formulations and methods described herein can also be used to treat patients who have undergone transplantation, such as renal, heart, or bone marrow transplantation.

XIII. Multiple Sclerosis

Formulations containing an alpha-4 binding antibody described herein are useful for the treatment of inflammatory diseases, such as multiple sclerosis (MS). Multiple sclerosis is a central nervous system disease that is characterized by inflammation and loss of myelin sheaths.

Patients having MS may be identified by criteria establishing a diagnosis of clinically definite MS as defined by the workshop on the diagnosis of MS (Poser et al., Ann. Neurol. 13:227, 1983). For example, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. (McDonald et al., 2001, "Recommended diagnostic criteria for multiple sclerosis: guidelines from the International Panel on the Diagnosis of Multiple Sclerosis," Ann. Neurol. 50:121-127). The McDonald criteria include the use of MRI evidence of CNS impairment over time to be used in diagnosis of MS, in the absence of multiple clinical attacks. Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a method for grading clinical impairment due to MS (Kurtzke, Neurology 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step indicates an effective treatment (Kurtzke, Ann. Neurol. 36:573-79, 1994). Patients may also be diagnosed using other criteria used by those in the art.

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., Neurology 34:1368, 1984). An annual exacerbation rate and proportion of exacerbation-free patients are determined.

Therapy can be deemed to be effective if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy. Efficacy may also be assessed using any method used in the art, for example to assess symptoms of MS, including mobility improvement using a timed walk test used alone or in combination with other criteria.

Efficacy of administering a first agent and, optionally, a second agent, can also be evaluated based on one or more of the following criteria: frequency of MBP reactive T cells determined by limiting dilution, proliferation response of MBP reactive T cell lines and clones, cytokine profiles of T cell lines and clones to MBP established from patients. Efficacy is indicated by decrease in frequency of reactive cells, a reduction in thymidine incorporation with altered peptide compared to native, and a reduction in TNF and IFN-α.

Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images.

MRI can be used to measure active lesions using gadolinium-DTPA-enhanced imaging (McDonald et al. Ann. Neurol. 36:14, 1994) or the location and extent of lesions using T2-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of MS lesions can be determined by radiologists. Areas of lesions can be outlined and summed slice by slice for total lesion area. Three analyses may be done: evidence of new lesions, rate of appearance of active lesions, percentage change in lesion area (Paty et al., Neurology 43:665, 1993). Improvement due to therapy can be established by a statistically significant improvement in an individual patient compared to baseline or in a treated group versus a placebo group.

Exemplary symptoms associated with multiple sclerosis, which can be treated with the methods described herein, include: optic neuritis, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction. anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoff's symptom, gastroesophageal reflux, and sleeping disorders.

Each case of MS displays one of several patterns of presentation and subsequent course. Most commonly, MS first manifests itself as a series of attacks followed by complete or partial remissions as symptoms mysteriously lessen, only to return later after a period of stability. This is called relapsing-remitting (RR) MS. Clinically isolated syndrome (CIS) is another of the relapsing forms of MS. CIS refers to a first episode of neurologic symptoms that lasts at least 24 hours and is caused by inflammation or demyelination (loss of the myselin that covers the nerve cells) in the central nervous system (CNS). Primary-progressive (PP) MS is characterized by a gradual clinical decline with no distinct remissions, although there may be temporary plateaus or minor relief from symptoms. Active primary progressive MS occurs when a patient experiences occasional relapses or there is evidence of new lesions on an MRI. "Not active" or "with progression" means there is evidence that a symptom is worsening over time with or without relapse or with or without new lesions are shown on an MRI. Secondary-progressive (SP) MS begins with a relapsing-remitting course followed by a later primary-progressive course. Active secondary progressive MS is considered one of the relapsing forms of MS. Rarely, patients may have a progressive-relapsing (PR) course in which the disease takes a progressive path punctuated by acute attacks. PP, SP, and PR are sometimes lumped together and called chronic progressive MS.

Thus, a relapsing form of multiple sclerosis (or simply relapsing multiple sclerosis) includes, without limitation, clinically isolated syndrome (CIS), relapsing remitting multiple sclerosis (RRMS), and active secondary progressive multiple sclerosis (active SPMS).

A few patients experience malignant MS, defined as a swift and relentless decline resulting in significant disability or even death shortly after disease onset. This decline may be arrested or decelerated by administration of a therapy described herein.

Administration of an anti-α4 antibody featured herein can be effective to relieve one or more symptoms of MS, such as one or more of the symptoms described above. For example, administration of an anti-α4 antibody described herein can be used to treat primary or secondary progressive multiple sclerosis (PPMS or SPMS, respectively), and treatment with an anti-α4 antibody can be effective to prevent relapse.

In addition to or prior to human studies, an animal model can be used to evaluate the efficacy of using the two agents. An exemplary animal model for multiple sclerosis is the experimental autoimmune encephalitis (EAE) mouse model, e.g., as described in (Tuohy et al. (J. Immunol. (1988) 141: 1126-1130), Sobel et al. (J. Immunol. (1984) 132: 2393-2401), and Traugott (Cell Immunol. (1989) 119: 114-129). Mice can be administered a first and second agent described herein prior to EAE induction. Then the mice are evaluated for characteristic criteria to determine the efficacy of using the two agents in the model.

XIV. Epilepsy

Formulations containing an alpha-4 binding antibody described herein are useful for the treatment of epilepsy.

Epileptic seizures are paroxysmal episodes resulting from abnormally discharging neurons that may be detected through electroencephalographic or clinical means, with the particular site of the brain affected influencing clinical expression. Epileptic seizures fundamentally arise from an imbalance in the basic excitability of neurons that may be related to the neuronal membrane or excitatory and inhibitory processes. See also Holmes et al., Epilepsia 45(12): 1568-1579, 2004). Epilepsy is conceptually defined as a disorder of the brain characterized by an enduring predisposition to generate epileptic seizures and by the neurobiologic, cognitive, psychological, and social consequences of this condition (Fisher R. S., Curr Opin Neurol. 28(2):130-5, 2015). A recent review of the prevalence and incidence of epilepsy reported a lifetime prevalence of 7.6 per 1000 persons and annual cumulative incidence of 67.77 per 100, 000 persons (Fiest et al., Neurology 88(3):296-303, 2017).

Prior to the present invention, the common therapy for patients with epilepsy was antiepileptic drugs (AEDs), and it is estimated that approximately 70% of patients achieve good seizure control with AED therapy. Patients who fail adequate trials of 2 (or more) tolerated and appropriately chosen and used AEDs are defined as having drug-resistant epilepsy (see Kwan et al., *Epilepsia*. 51(6):1069-77, 2010; and erratum in *Epilepsia*. 51(9):1922, 2010). For these patients, other therapies are considered, including epilepsy surgery, neurostimulation devices, specialized diets, behavioral therapies, and other experimental treatments. AEDs typically work through modulation of voltage-dependent or ligand-gated ion channels or through effects on inhibitory or excitatory neurotransmitter systems. Currently, there are over 20 AEDs available commercially. Despite the launch of many newer AEDs in recent years, both new and old drugs remain generally equally effective in managing epilepsy, and it is still rare for prior drug-resistant epilepsy patients to become seizure free with the newer therapies.

There still remains a high unmet need to develop therapies that improve seizure control or eliminate seizures in drug-resistant epilepsy. Targeting the potential role of the immune system and inflammation in the pathogenesis of epilepsy represents an underexplored area in AED development and clinical studies. Evidence from both experimental models of epilepsy and human patients with epilepsy suggest a role for inflammation.

The formulations disclosed herein can be used to treat epilepsy. For example, a formulation comprising a recombinant anti-alpha 4 antibody or an alpha 4-binding fragment thereof comprising: (a) a heavy chain comprising the sequence of SEQ ID NO: 80; and (b) a light chain comprising the sequence of SEQ ID NO: 81, can be administered to a patient suffering from epilepsy. It is hypothesized that blocking $\alpha_4$ integrin will reduce leukocyte-vascular interactions and stabilize BBB integrity. Additionally, it is hypothesized that epilepsy-reducing leukocyte-vascular interactions induced by seizures will reduce the frequency and severity of seizures.

XV. Antibody Generation

Recombinant antibodies that bind to alpha-4 can be generated by in vivo or in vitro methods such as phage display. The methods can be used to supply anti-α4 CDRs for use in CDR grafted antibodies described herein. In addition, methods such as phage display can be used to select such CDRs in the context of the germline frameworks disclosed herein, such as by using a library where the framework is a germline framework.

EP 239 400 (Winter et al.) describes altering antibodies by substitution (within a given variable region) of their complementarity determining regions (CDRs) for one species with those from another. CDR-substituted antibodies can be less likely to elicit an immune response in humans compared to true chimeric antibodies because the CDR-substituted antibodies contain considerably less non-human components. (Riechmann et al., 1988, Nature 332, 323-327; Verhoeyen et al., 1988, Science 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the heavy and light chain genes can be co-expressed in mammalian cells to produce soluble antibody. Large nonimmunized phage display libraries may also be used to isolate high affinity antibodies that can be developed as human therapeutics using standard phage technology (see, e.g., Hoogenboom et al. (1998) Immunotechnology 4:1-20; and Hoogenboom et al. (2000) Immunol Today 2:371-8; U.S. 2003-0232333).

An anti-α4 antibody or antibody fragment described herein can recognize and specifically bind to epitopes of the α4 subunit that are involved in binding to a cognate ligand, e.g., VCAM-1 or fibronectin. In some embodiments, the anti-α4 antibody or antibody fragment thereof recognizes and specifically binds to a B epitope of the α4 integrin. Binding of the antibodies described herein can inhibit binding of the α4 integrin to one or more of the cognate ligands (e.g., VCAM-1 and fibronectin).

In some embodiments, the antibodies featured herein, can interact with VLA-4 on cells, e.g., lymphocytes, but do not cause cell aggregation.

An exemplary α4 binding antibody has one or more CDRs, e.g., all three heavy chain (HC) CDRs and/or all three light chain (LC) CDRs of a particular antibody disclosed herein, or CDRs that are, in sum, at least 80, 85, 90, 92, 94, 95, 96, 97, 98, 99% identical to such an antibody. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70, 80, 85, 90, 92, 95, 97, 98, 99, or 100% identical to the amino acid sequence of the HC and/or LC variable domain of an antibody described herein. The amino acid sequence of the HC and/or LC variable domain sequence can differ by at least one amino acid, but no more than ten, eight, six, five, four, three, or two amino acids from the corresponding sequence of an antibody described herein. For example, the differences may be primarily or entirely in the framework regions.

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of an antibody described herein. In one embodiment, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and non-aqueous methods are described in that reference and either can be used.

High stringency hybridization conditions include hybridization in 6×SSC at about 45° C., followed by one or more washes in 0.2×SSC, 0.1% SDS at 65° C., or substantially similar conditions.

XVI. Antibody Production

Antibodies can be produced in prokaryotic and eukaryotic cells. In one embodiment, the antibodies (e.g., scFvs) are expressed in a yeast cell such as *Pichia* (see, e.g., Powers et al. (2001) J. Immunol. Methods 251:123-35), Hanseula, or *Saccharomyces*.

In one embodiment, antibodies, particularly full length antibodies, e.g., IgGs, are produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). Exemplary selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G. For example, purified α4-binding antibodies can be concentrated to about 100 mg/mL to about 200 mg/mL using protein concentration techniques that are known in the art.

Antibodies may also include modifications, e.g., modifications that alter Fc function, e.g., to decrease or remove interaction with an Fc receptor or with C1q, or both. For example, the human IgG4 constant region can have a Ser to Pro mutation at residue 228 to fix the hinge region. The amino acid sequence of an IgG4 Fc (hinge+CH2+CH3 domain) is provided in FIG. 5.

In another example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. In another example, the Fc domain of IgG molecules is glycosylated at asparagine 297 in the CH2 domain (see FIG. 5). This asparagine is the site for modification with biantennary-type oligosaccharides. This glycosylation participates in effector functions mediated by Fc(receptors and complement C1q (Burton and Woof (1992) Adv. Immunol. 51:1-84; Jefferis et al. (1998) Immunol. Rev. 163:59-76). The Fc domain can be produced in a mammalian expression system that appropriately glycosylates the residue corresponding to asparagine 297. The Fc domain can also include other eukaryotic post-translational modifications.

Other suitable Fc domain modifications include those described in WO2004/029207. For example, the Fc domain can be an XMAB® Fc (Xencor, Monrovia, CA). The Fc domain, or a fragment thereof, can have a substitution in an Fcγ Receptor (FcγR) binding region, such as the domains and fragments described in WO05/063815. In some embodiments, the Fc domain, or a fragment thereof, has a substitution in a neonatal Fc Receptor (FcRn) binding region, such as the domains and fragments described in WO05047327. In other embodiments, the Fc domain is a single chain, or fragment thereof, or modified version thereof, such as those described in WO2008143954. Other suitable Fc modifications are known and described in the art.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted therein, the antibody of interest, e.g., an antibody described herein. The antibody can be purified from the milk, or for some applications, used directly.

Antibodies can be modified, e.g., with a moiety that improves its stabilization and/or retention in circulation, e.g., in blood, serum, lymph, bronchoalveolar lavage, or other tissues, e.g., by at least 1.5, 2, 5, 10, or 50 fold.

For example, a VLA-4 binding antibody can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 daltons (or about 1,000 to about 15,000, and 2,000 to about 12,500) can be used.

For example, a VLA-4 binding antibody can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

XVII. Exemplary Second Agents

In some cases, the formulations described herein, e.g., formulations containing an alpha-4 binding antibody, include a second agent, or are administered in combination with a formulation containing a second agent.

In one implementation, the α4 binding antibody and second agent is provided as a co-formulation, and the co-formulation is administered to the subject. It is further possible, e.g., at least 24 hours before or after administering the co-formulation, to administer separately one dose of the α4 binding antibody formulation and then one dose of a formulation containing the second agent. In another implementation, the antibody and the second agent are provided as separate formulations, and the step of administering includes sequentially administering the antibody and the second agent. The sequential administrations can be provided on the same day (e.g., within one hour of one another or at least 3, 6, or 12 hours apart) or on different days.

Generally, the antibody and the second agent are each administered as a plurality of doses separated in time. The antibody and the second agent are generally each administered according to a regimen. The regimen for one or both may have a regular periodicity. The regimen for the antibody can have a different periodicity from the regimen for the second agent, e.g., one can be administered more frequently than the other. In one implementation, one of the antibody and the second agent is administered once weekly and the other once monthly. In another implementation, one of the antibody and the second agent is administered continuously, e.g., over a period of more than 30 minutes but less than 1, 2, 4, or 12 hours, and the other is administered as a bolus. The antibody and the second agent can be administered by any appropriate method, e.g., subcutaneously, intramuscularly, or intravenously.

In some embodiments, each of the antibody and the second agent is administered at the same dose as each is prescribed for monotherapy. In other embodiments, the antibody is administered at a dosage that is equal to or less than an amount required for efficacy if administered alone. Likewise, the second agent can be administered at a dosage that is equal to or less than an amount required for efficacy if administered alone.

Non-limiting examples of second agents for treating multiple sclerosis in combination with an α4 binding antibody include:

interferons, e.g., human interferon beta-1a (e.g., AVONEX® or REBIF®)) and interferon beta-1b (BETASERON™; human interferon beta substituted at position 17; Berlex/Chiron);

glatiramer acetate (also termed Copolymer 1, Cop-1; COPAXONE™; Teva Pharmaceutical Industries, Inc.);

RITUXAN® (rituximab) or another anti-CD20 antibody, including an antibody that competes with or binds an overlapping epitope with rituximab;

mixtoxantrone (NOVANTRONE®, Lederle);

a remyelinating agent such as opicinumab;

a chemotherapeutic, e.g., clabribine (LEUSTATIN®), azathioprine (IMURAN®), cyclophosphamide (CYTOXAN®), cyclosporine-A, methotrexate, 4-aminopyridine, and tizanidine;

a corticosteroid, e.g., methylprednisolone (MEDRONE®, Pfizer), prednisone;

an immunoglobulin, e.g., RITUXAN® (rituximab); CTLA4 Ig; alemtuzumab (MABCAMPATH®) or daclizumab (an antibody that binds CD25);

statins; and

TNF antagonists.

Glatiramer acetate is a protein formed from a random chain of amino acids-glutamic acid, lysine, alanine and tyrosine (hence GLATiramer). Glatiramer acetate can be synthesized in solution from these amino acids at a ratio of approximately 5 parts alanine to 3 parts lysine, 1.5 parts glutamic acid and 1 part tyrosine using N-carboxyamino acid anhydrides.

Additional second agents include antibodies or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. Still other exemplary second agents include antibodies to cell surface molecules such as CD2, CD3, CD4, CD8, CD25, CD28, CD30, CD40, CD45, CD69, CD80, CD86, CD90 or their ligands. For example, daclizubmab is an anti-CD25 antibody that may ameliorate multiple sclerosis.

Still other exemplary antibodies include antibodies that provide an activity of an agent described herein, such as an antibody that engages an interferon receptor, e.g., an interferon beta receptor. Typically, in implementations in which the second agent includes an antibody, it specifically binds to a target protein other than VLA-4 or other than α4 integrin, or at least to an epitope on VLA-4 other than one recognized and specifically bound by the first agent.

Still other additional exemplary second agents include: FK506, rapamycin, mycophenolate mofetil, leflunomide, non-steroidal anti-inflammatory drugs (NSAIDs), for example, phosphodiesterase inhibitors, adenosine agonists, antithrombotic agents, complement inhibitors, adrenergic agents, agents that interfere with signaling by proinflammatory cytokines as described herein, IL-1β converting enzyme inhibitors (e.g., Vx740), anti-β7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, anti-inflammatory cytokines (e.g. IL-4, IL-10, IL-13 and TGF).

In some embodiments, a second agent may be used to treat one or more symptoms or side effects of MS. Such agents include, e.g., amantadine, baclofen, papaverine, meclizine, hydroxyzine, sulfamethoxazole, ciprofloxacin, docusate, pemoline, dantrolene, desmopressin, dexamethasone, tolterodine, phenytoin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline. Many second agents that are small molecules have a molecular weight between 150 and 5000 Daltons.

Examples of TNF antagonists include chimeric, humanized, human or in vitro generated antibodies (or antigen-binding fragments thereof) to TNF (e.g., human TNFα), such as D2E7, (human TNFα antibody, U.S. Pat. No.

6,258,562; BASF), CDP-571/CDP-870/BAY-10-3356 (humanized anti-TNFα antibody; Celltech/Pharmacia), cA2 (chimeric anti-TNFα antibody, REMICADE™, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, ENBREL™; Immunex; see e.g., Arthritis & Rheumatism (1994) Vol. 37, S295; J. Invest. Med. (1996) Vol. 44, 235A), p55 kdTNFR-IgG (55 kD TNF receptor-IgG fusion protein (LENERCEPT™)); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see e.g., Arthritis & Rheumatism (1996) Vol. 39, No. 9 (supplement), S284; Amer. J. Physiol.—Heart and Circulatory Physiology (1995) Vol. 268, pp. 37-42).

In addition to a second agent, it is also possible to deliver other agents to the subject. However, in some embodiments, no protein or no biologic, other than the α4 binding antibody and second agent, are administered to the subject as a pharmaceutical composition. The α4 binding antibody and the second agent may be the only agents that are delivered by injection. In embodiments in which the second agent is a recombinant protein, the α4 binding antibody and second agent may be the only recombinant agents administered to the subject, or at least the only recombinant agents that modulate immune or inflammatory responses. In still other embodiments, the α4 binding antibody alone is the only recombinant agent or the only biologic administered to the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Unless otherwise indicated, all amino acid numbering in these Examples uses EU numbering.

Example 1. Variant Anti-VLA-4 Antibodies are More Potent than Humanized HP1/2

Anti-VLA-4 antibodies were constructed using the germline framework IGKV4-1 (or design L1 and L2) or germline-engineered AAH7033.1 (for design L3) for the VL chain and germiline framework IGHV1-f for VH. These antibodies had fewer back mutations than the humanized HP1/2 antibody described in U.S. Pat. No. 6,602,503.

Heavy Chain Variations

Figure 1:
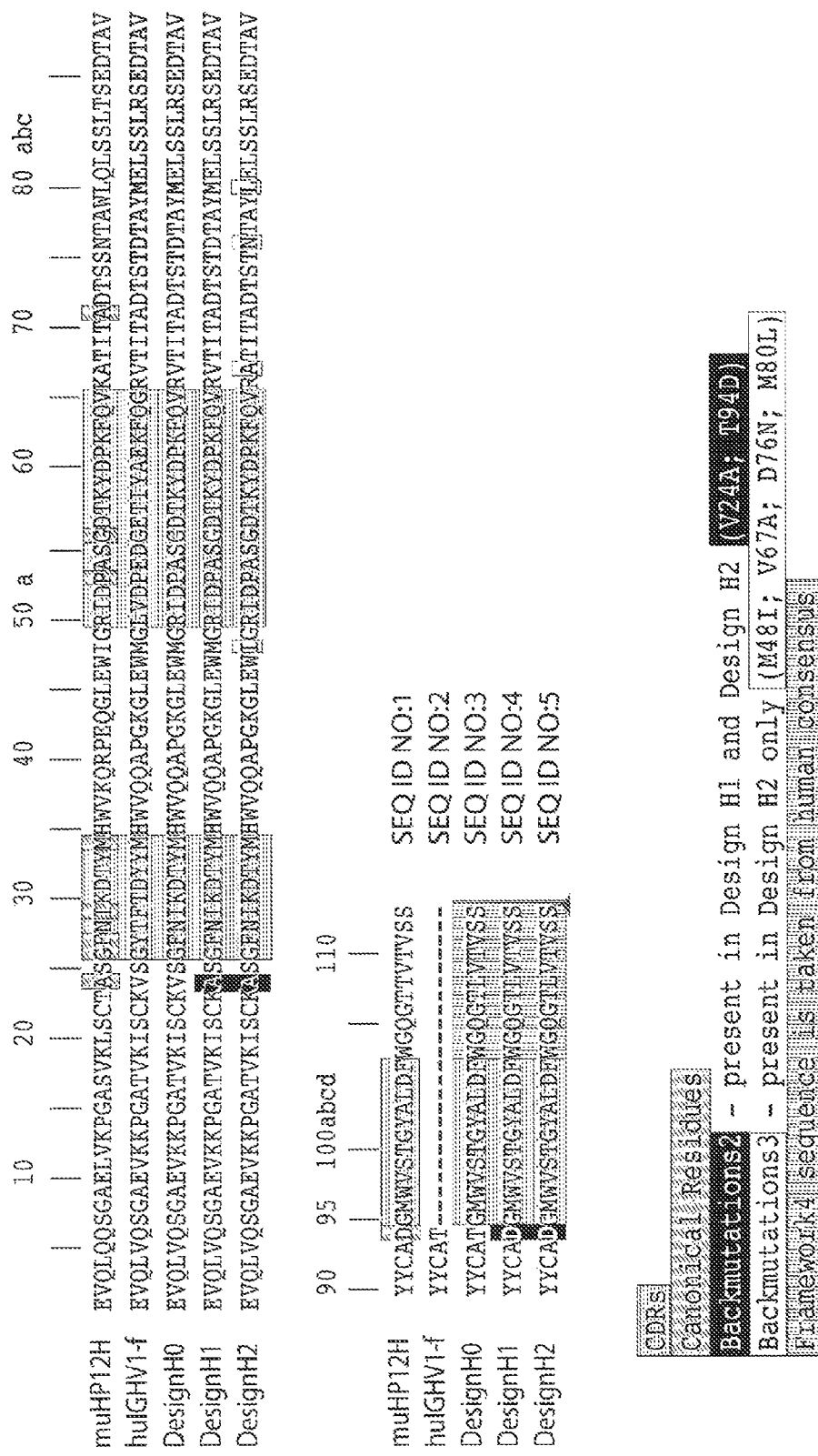
FIG. 1 illustrates the three sequence variants of HP1/2 heavy chain (SEQ ID NO: 1) to a human heavy germline IGHV1-f (SEQ ID NO: 2). The lower case letters above the sequence represent insertions according to the Kabat numbering scheme.

The sequences of three variations of the heavy chain are shown in FIG. 1 as Design H0, Design H1 and Design H2. Each design has the CDR's of murine HP1/2 grafted into the IGHV1-f framework. Design H0 includes no back mutations of the framework regions, while Designs H1 and H2 have various degrees of back mutations in the framework regions sequences to optimize the affinity of the humanized antibody.

Light Chain Variations

Figure 2:
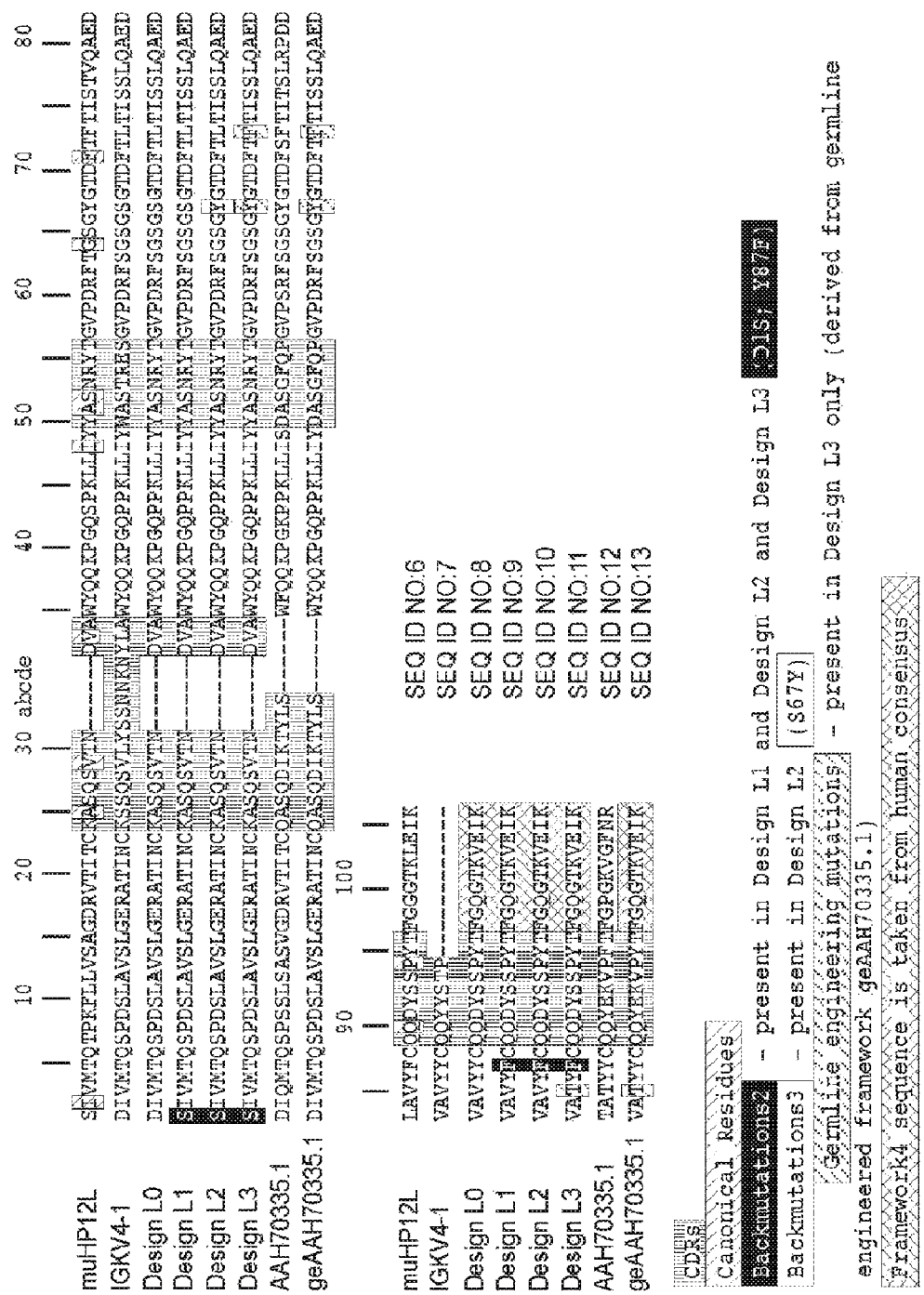
FIG. 2 illustrates the four sequence variants of HP1/2 light chain (SEQ ID NO: 6) to a germline IGKV4-1 antibody sequence (SEQ ID NO: 7) (Design L0—SEQ ID NO: 8, L1—SEQ ID NO: 9, and L2—SEQ ID NO: 10) or human kappa germline engineered AAH7033.1 antibody sequence (SEQ ID NO: 12) (Design L3—SEQ ID NO: 11). The lower case letters above the sequence represent insertions according to the Kabat numbering scheme.

The sequences of four variations of the light chain are shown in FIG. 2 as Design L0, Design L1, Design L2 and Design L3 (also called L0, L1, L2, L3). Each design has the CDR's of murine HP1/2 grafted into the germline framework. The IGKV4-1 germline framework was used for Designs L0, L1, and L2, and the AAH70335 germline engineered framework was used for Design L3. Design L0 includes no back mutations of the framework regions, while Designs L1, L2, and L3 have various degrees of back mutations in the framework regions to optimize the affinity of the humanized antibody.

Figure 3:
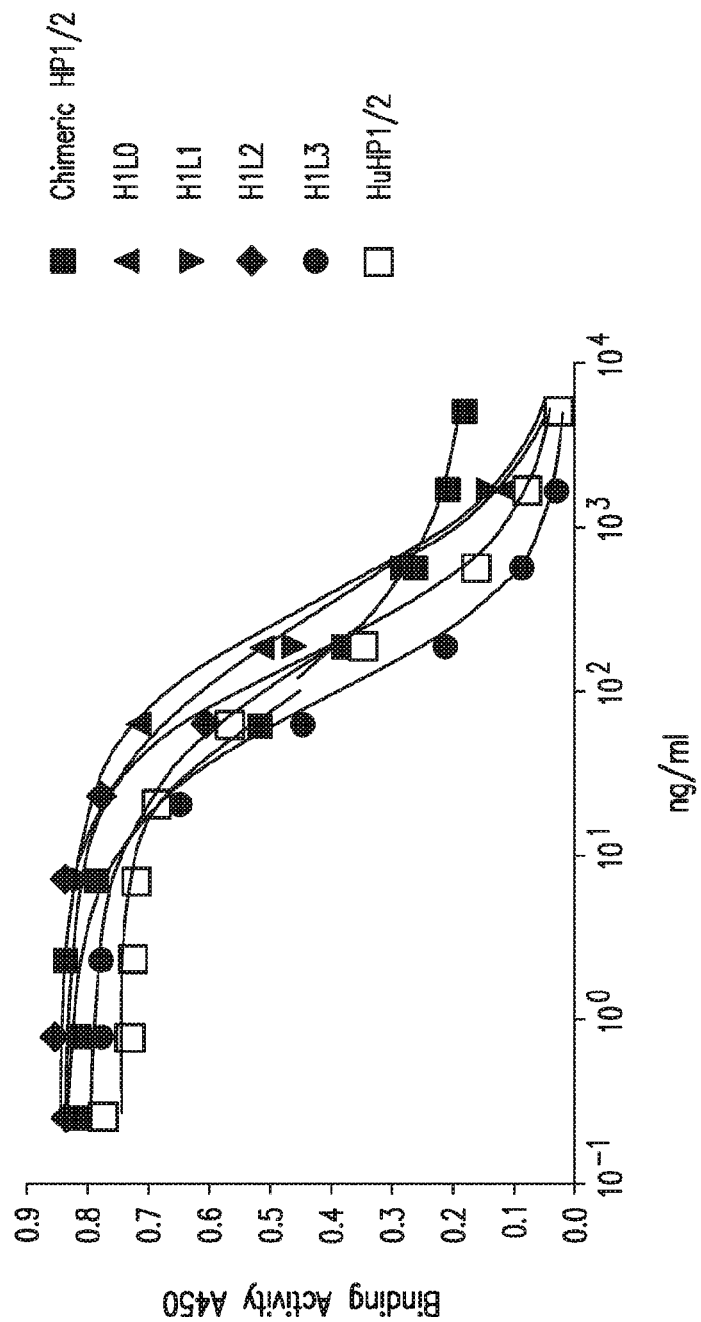
FIG. 3 is a graph depicting the results of ELISA assays.

The results of competition ELISA assays are shown in Table 2 and FIG. 3. In this experiment α4β1 was preincubated with testing mAb and then murine HP1/2 was used as competing reagent. The results of this experiment indicated that the antibodies having light chains L2 or L3 were more potent than the antibody described in U.S. Pat. No. 6,602,503. The results are shown in Table 2 below, and in FIG. 3. The heavy chain (H1) in the antibodies for this assay had the "Design H1" sequence shown in FIG. 1, whereas L1 refers to Design L1 in FIG. 2.

TABLE 2

| Competition Assay by ELISA | |
|---|---|
| mAb | IC50 nM |
| Chimeric HP1/2 | 1.06 |
| H1L0 | 1.87 |
| H1L1 | 1.67 |
| H1L2 | 0.9 |
| H1L3 | 0.49 |
| HuHP1/2 | 1.05 |

In Table 2, the chimeric mAb is chimerized HP1/2 antibody, where murine variable heavy and light chains are genetically fused to human IgG1 constant regions. This antibody is essentially identical in binding affinity to the original murine HP1/2 antibody (Sanchez-Madrid et al., Eur. J. Immunol. 16:1343-1349, 1996). The results of the experiment indicate that it is possible to improve the affinity of the monoclonal antibody relative to its murine parental sequence through humanization on germline-engineered acceptor framework.

Figure 4:
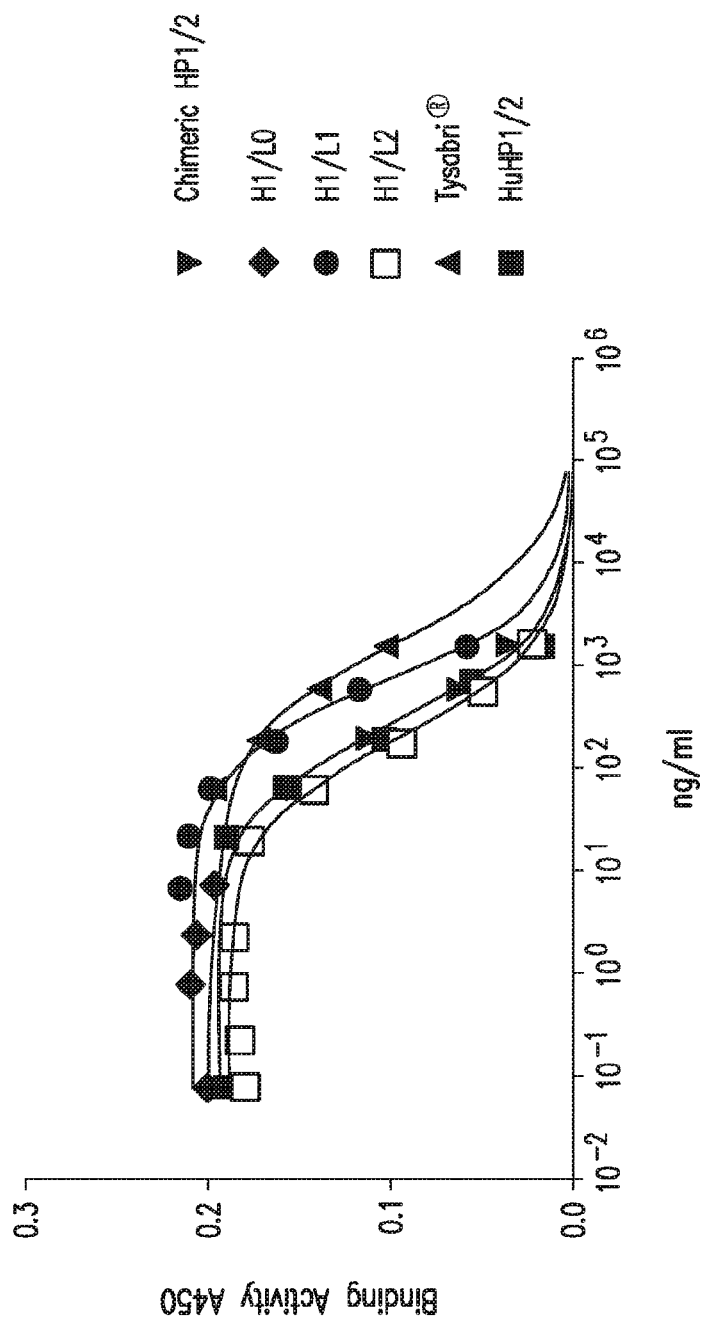
FIG. 4 is a graph depicting the results of ELISA assays.

Another competition assay compares the binding affinity of the new antibodies with the humanized 21.6 anti-α4 antibody (TYSABRI® (natalizumab)) described in U.S. Pat. No. 5,840,299. In this experiment the binding of mixture of mouse HP1/2 with testing mAb to α4131 was assayed. The results of this experiment are shown in FIG. 4 and in Table 3 below, and indicate that the newly designed antibodies are about 10-fold more potent than natalizumab.

TABLE 3

| Competition Assay by ELISA | |
|---|---|
| mAb | IC50 nM |
| Chimeric HP1/2 | 1.64 |
| H1L0 | 4.46 |
| H1L1 | 4.55 |

TABLE 3-continued

Competition Assay by ELISA

| mAb | IC50 nM |
|---|---|
| H1L2 | 1.34 |
| HuHP1/2 | 1.41 |
| TYSABRI® | 10.9 |

Example 2. Humanized HP1/2 (HuHP1/2) Binds VLA-4 on Tumor Cell Lines

Figure 6:
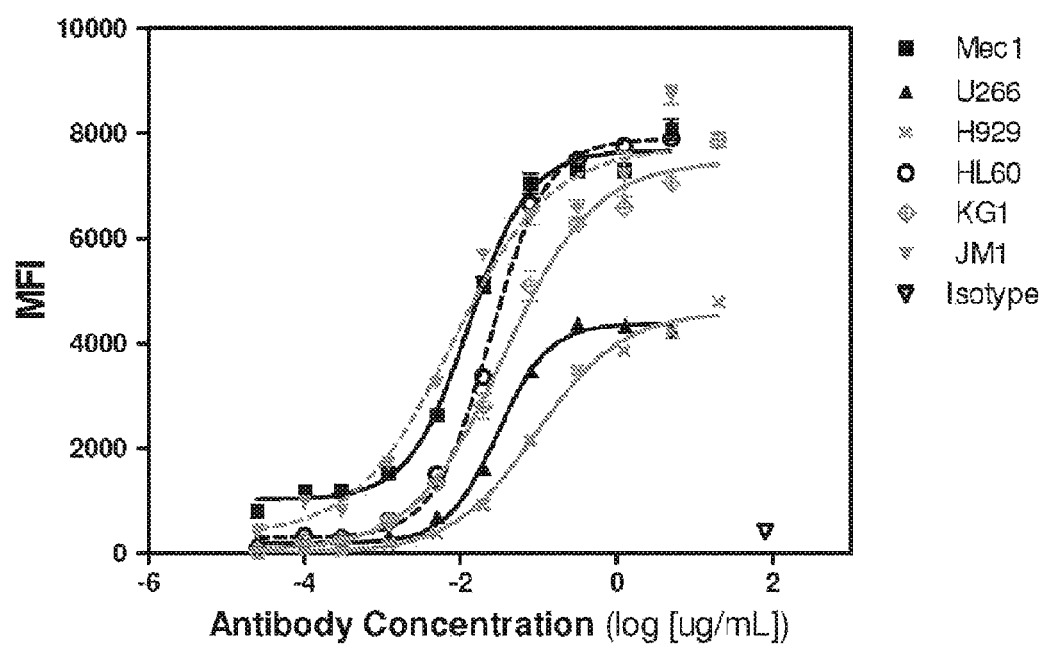
FIG. 6 is a graph depicting flow cytometry data from binding of HuHP1/2 to various tumor cell lines. "HP1/2" refers to humanized HP1/2.

Binding of anti-VLA-4 antibody HuHP1/2 to a variety of cell lines was tested by flow cytometry. Binding was tested on CLL (chronic lymphocytic leukemic) cell lines Mec1 and JM1; on MM (multiple myeloma) cell lines U266 and H929; and on AML (acute myelogenous leukemic) cell lines HL60 and KG1. HuHP1/2 bound all tumor cell lines tested (FIG. 6). The flow cytometry data was used to calculate the EC50 values for antibody binding to each of the different cell lines. This information is shown below in Table 4.

Figure 7A:
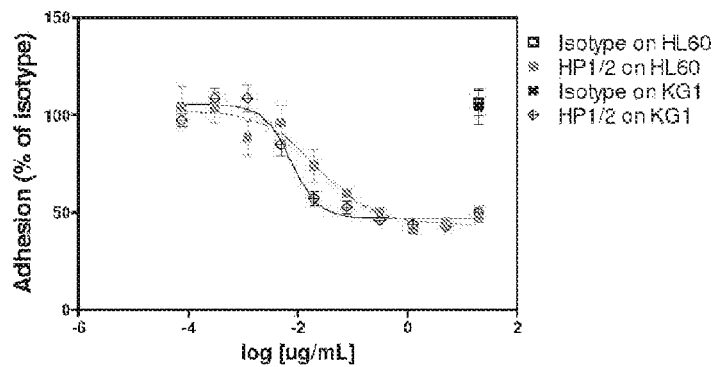
FIGS. 7A-7C is a panel of graphs depicting inhibition of binding of AML cell lines to fibronectin or VCAM1-Ig coated wells by HuHP1/2.
Figure 7B:
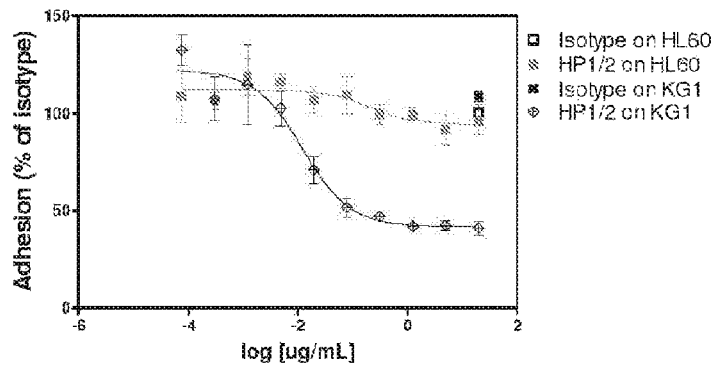
Figure 7C:
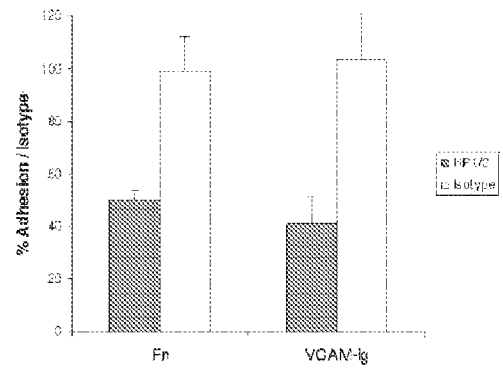

HuHP1/2 was also found to block adhesion of AML cell lines to fibronectin (FN) and VCAM1-Ig fusion protein. To test whether the antibody could block adhesion, AML cell lines HL60 or KG1 were allowed to adhere to FN-coated wells (FIG. 7A) or VCAM1-Ig-coated wells (FIG. 7B) in the presence of increasing concentrations of HP1/2 or isotype control antibody. HuHP1/2 blocked adhesion of both cell types to FN-coated wells and VCAM1-Ig-coated wells. The maximal inhibition of HL60 cell binding to both ligands was achieved with 20 ug/ml HuHP1/2 (FIG. 7C).

Figure 8A:
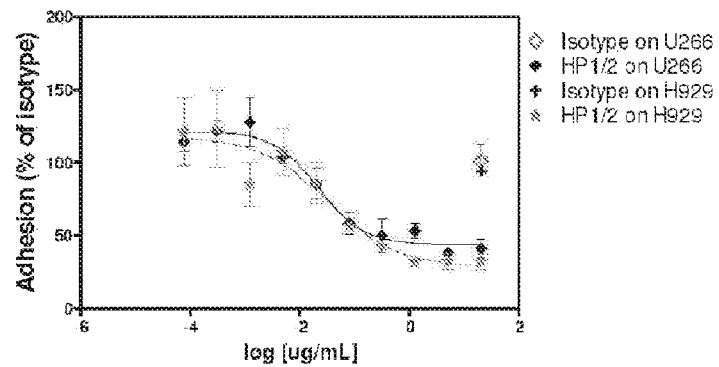
FIGS. 8A-8C make up a panel of graphs depicting inhibition of binding of MM cell lines to fibronectin or VCAM1-Ig coated wells by HuHP1/2.
Figure 8B:
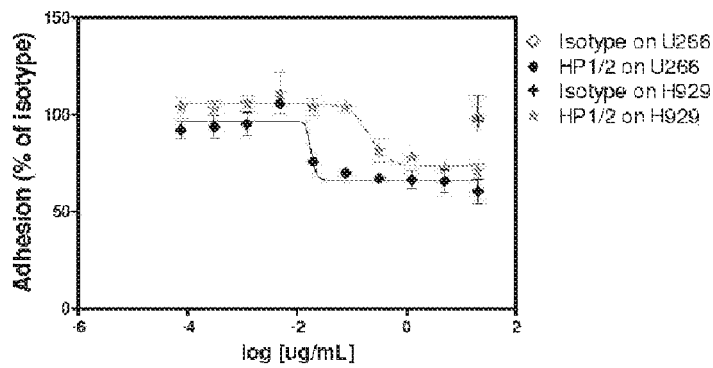
Figure 8C:
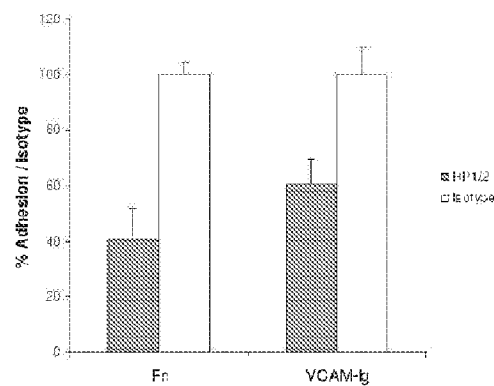

HuHP1/2 was also found to block adhesion of MM cell lines to FN and VCAM1-Ig fusion protein. The MM cell lines U266 and H929 were allowed to adhere to FN-coated wells (FIG. 8A) or VCAM1-Ig-coated wells (FIG. 8B) in the presence of increasing concentrations of HP1/2 or isotype control antibody. HuHP1/2 blocked adhesion of both types of cell lines to FN- and VCAM1-Ig-coated wells. The maximal inhibition of U266 cell binding to both ligands was achieved with 20 µg/mL HuHP1/2 (FIG. 8C).

Figure 9A:
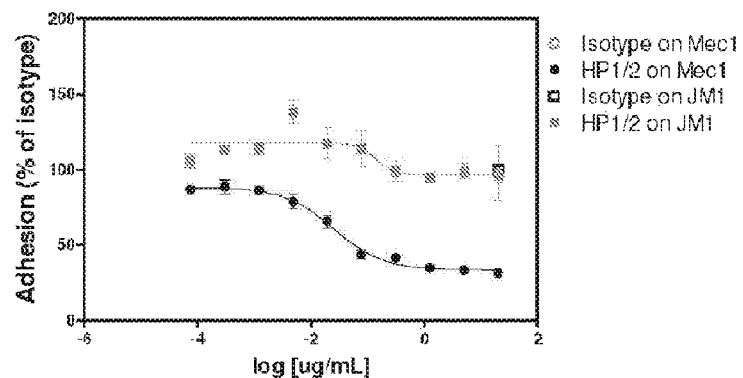
FIGS. 9A-9C makes up a panel of graphs depicting inhibition of binding of CLL cell lines to fibronectin or VCAM1-Ig coated wells by HuHP1/2.
Figure 9B:
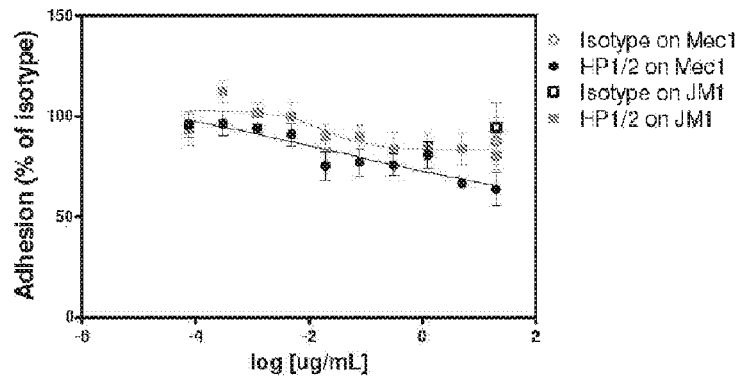
Figure 9C:
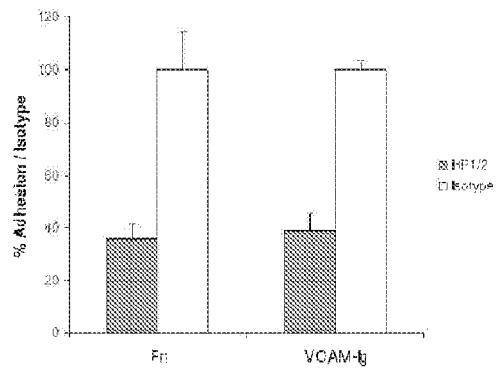

HuHP1/2 was also found to block adhesion of CLL cell lines to FN and VCAM1-Ig fusion protein. The CLL cell lines Mec1 and JM1 were allowed to adhere to FN-coated wells (FIG. 9A) or VCAM1-Ig-coated wells (FIG. 9B) in the presence of increasing concentrations of HP1/2 or isotype control antibody. HuHP1/2 blocked adhesion of both types of cell lines to FN- and VCAM1-Ig-coated wells. The maximal inhibition of Mec1 cell binding to both ligands was achieved with 20 µg/ml HuHP1/2 (FIG. 9C).

The IC50 values for HuHP1/2 binding to the tumor cell lines were calculated from the data shown in FIGS. 7-9. These data are shown in Table 4.

TABLE 4

Quantitation of HuHP1/2 on tumor cell lines

| | | | $IC_{50}$ (nM) | |
|---|---|---|---|---|
| | | $EC_{50}$ (nM) | Fibronectin | VCAM |
| CLL | Mec1 | 0.11 | 0.10 | 0.07 |
| | JM1 | 0.21 | — | 0.12 |
| MM | U266 | 0.46 | 0.14 | 0.13 |
| | H929 | 0.91 | 0.21 | 1.35 |

TABLE 4-continued

Quantitation of HuHP1/2 on tumor cell lines

| | | | $IC_{50}$ (nM) | |
|---|---|---|---|---|
| | | $EC_{50}$ (nM) | Fibronectin | VCAM |
| AML | HL60 | 0.11 | 0.16 | 0.91 |
| | KG1 | 0.19 | 0.05 | 0.1 |

Materials and Methods for Examples 3-13

Throughout Examples 3-13, the following materials and methods were used unless otherwise stated.

In general, the practice of the present invention employs, unless otherwise indicated, conventional techniques of chemistry, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al, C.S.H.L. Press, Pub. (1999); and Current Protocols in Molecular Biology, eds. Ausubel et al., John Wiley & Sons (1992).

Parental Antibodies

For producing the stabilized antibodies disclosed herein, polynucleotides encoding either a model human antibody (e.g., hu5c8), variant antibodies thereof, or corresponding Fc regions, were introduced into standard expression vectors. The human antibody hu5c8 and variants thereof are described in, e.g., U.S. Pat. Nos. 5,474,771 and 6,331,615. The amino acid sequences are provided below for, respectively, the hu5c8 IgG4 heavy chain (SEQ ID NO: 52), hu5c8 light chain (SEQ ID NO: 53), hu5c8 Fab (SEQ ID NO: 54), complete Fc moiety from parental IgG4 antibody (SEQ ID NO: 55), parental IgG4 Fc moiety with S228P mutation (SEQ ID NO: 56), and parental aglycosylated IgG4 Fc moiety with S228P/T299A mutations (SEQ ID NO: 57). The leader sequence for the heavy chain was MDWTWRVFCL-LAVAPGAHS. Also provided is the heavy chain (SEQ ID NO: 58) and Fc moiety (SEQ ID NO: 59) sequences of a parental IgG1 aglycosylated hu5c8 antibody.

Hu 5c8 IgG4 heavy chain (EAG1807)
(SEQ ID NO: 52)
QVQLVQSGAEVVKPGASVKLSCKASGYIFTSYYMYWVK
QAPGQGLEWIGEINPSNGDTNFNEKFKSKATLTVDKSAS
TAYMELSSLRSEDTAVYYCTRSDGRNDMDSWGQGTLVT
VSSASTKGPSVFPLAPCSRSTSESTAALGCLVKDYFPEPV
TVSWNSGALTSGVHTFPAVLQSSGLYSLSSVVTVPSSSLG
TKTYTCNVDHKPSNTKVDKRVESKYGPPCPPCPAPEFLG
GPSVFLFPPKPKDTLMISRTPEVTCVVVDVSQEDPEVQFN
WYVDGVEVHNAKTKPREEQFNSTYRVVSVLTVLHQDWL
NGKEYKCKVSNKGLPSSIEKTISKAKGQPREPQVYTLPPS
QEEMTKNQVSLTCLVKGFYPSDIAVEWESNGQPENNYKT
TPPVLDSDGSFFLYSRLTVDKSRWQEGNVFSCSVMHEAL
HNHYTQKSLSLSLG Hu 5c8 light chain
(SEQ ID NO: 53)
DIVLTQSPATLSVSPGERATISCRASQRVSSSTYSYMHWYQQKPGQPPK
LLIKYASNLESGVPARFSGSGSGTDFTLTISSVEPEDFATYYCQHSWEI
PPTFGGGTKLEIKRTVAAPSVFIFPPSDEQLKSGTASVVCLLNNFYPRE
AKVQWKVDNALQSGNSQESVTEQDSKDSTYSLSSTLTLSKAD YEKHKV
YACEVTHQGLSSPVTKSFNRGEC -continued Hu 5c8 VH/CH1 domains
(SEQ ID NO: 54)
QVQLVQSGAEVVKPGASVKLSCKASGYIFTSYYMYWVK
QAPGQGLEWIGEINPSNGDTNFNEKFKSKATLTVDKSAS
TAYMELSSLRSEDTAVYYCTRSDGRNDMDSWGQGTLVT
VSSASTKGPSVFPLAPCSRSTSESTAALGCLVKDYFPEPV
TVSWNSGALTSGVHTFPAVLQSSGLYSLSSVVTVPSSSLG
TKTYTCNVDHKPSNTKVDKRV Parental IgG4 Fc moiety
(SEQ ID NO: 55)
ESKYGPPCPSCPAPEFLGGPSVFLFPPKPKDTLMISRTPEV
TCVVVDVSQEDPEVQFNWYVDGVEVHNAKTKPREEQFN
STYRVVSVLTVLHQDWLNGKEYKCKVSNKGLPSSIEKTI
SKAKGQPREPQVYTLPPSQEEMTKNQVSLTCLVKGFYPS
DIAVEWESNGQPENNYKTTPPVLDSDGSFFLYSRLTVDK
SRWQEGNVFSCSVMHEALHNHYTQKSLSLSLG Parental IgG4 Fc moiety with S228P mutation
(SEQ ID NO: 56)
ESKYGPPCPPCPAPEFLGGPSVFLFPPKPKDTLMISRTPEV
TCVVVDVSQEDPEVQFNWYVDGVEVHNAKTKPREEQFN
STYRVVSVLTVLHQDWLNGKEYKCKVSNKGLPSSIEKTI
SKAKGQPREPQVYTLPPSQEEMTKNQVSLTCLVKGFYPS
DIAVEWESNGQPENNYKTTPPVLDSDGSFFLYSRLTVDK
SRWQEGNVFSCSVMHEALHNHYTQKSLSLSLG Parental IgG4 Aglycosylated Fc moiety with S228P/
T299A mutations (YC407)
(SEQ ID NO: 57)
ESKYGPPCPPCPAPEFLGGPSVFLFPPKPKDTLMISRTPEVTCVVVDVS
QEDPEVQFNWYVDGVEVHNAKTKPREEQFNSAYRVVSVLTVLHQDWLNG
KEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDK
SRWQEGNVFSCSVMHEALHNHYTQKSLSLSLG Parental IgG1 Aglycosylated Fc moiety
(SEQ ID NO: 58)
EPKSCDKTHTCPPCPAPELLGGPSVFLFPPKPKDTLMISRTPEVTCVVV
DVSHEDPEVKFNWYVDGVEVHNAKTKPREEQYNSAYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG Parental IgG4 Aglycosylated Fc with S228P/N297Q
mutations (EAG2412)
(SEQ ID NO: 59)
ESKYGPPCPPCPAPEFLGGPSVFLFPPKPKDTLMISRTPEVTCVVVDVS
QEDPEVQFNWYVDGVEVHNAKTKPREEQFQSTYRVVSVLTVLHQDWLNG
KEYKCKVSNKGLPSSIEKTISKAKGQPREPQVYTLPPSRDELTKNQVSL
TCLVKGFYPSDIAVEWESNGQPENNYKTTPPVLDSDGSFFLYSKLTVDK
SRWQQGNVFSCSVMHEALHNHYTQKSLSLSP Parental IgG1
(SEQ ID NO: 60)
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPG Example 3. Rational Design of Gain-in-Stability IgG Fc Mutations Aglycosylated antibodies represent an important class of therapeutic reagents where immune effector function is not desired. However, it is well established that removal of the CH2 associated oligosaccharides in IgG1 and IgG4 affects antibody conformation and stability. Loss of antibody stability can present process development challenges adversely impacting program timelines and resources. Here we detail a number of methods utilized to design a library of amino acid positions in CH2 and CH3 to generate increased stability for IgG Fc. All the numbering indicated in this Example is EU numbering.

A. Covariation and Residue Frequency Designs for Effector-Less IgGs: IgG4 CH2 Domain Covariation analyses with the diverse CI-class Ig-fold sequence database were performed as described previously (see, e.g., PCT Publication No. WO2007109254; Wang et al, 2009, Proteins 76: 99, 2009). Compilation and structure/HMM-based alignment of CI-class Ig-fold sequences was also performed as described previously (PCT Publication No. WO2007109254, incorporated herein by reference in its entirety). The covariation analyses consist of a dataset of correlation coefficients, φ-values, relating how a pair of amino acids is or is not found to be co-conserved within particular protein sequences, φ-values range from −1.0 to 1.0. A φ-value of 1.0 indicates that when an amino acid is found at one position within a subset of sequences, another amino acid at a different residue position is also always found to be present in that subset. A φ-value of −1.0 indicates that when an amino acid is found at one position within a subset of sequences, another amino acid at a different residue position is never present in that sequence subset. Absolute φ-values greater than 0.2 were found to be statistically significant for the dataset that was analyzed (PCT Publication No. WO2007109254; Wang et al., 2009, supra). Based on experience with the dataset, φ-values>0.25 were deemed to be meaningful (i.e., there is likely to be a physical reason for the co-existence of the amino acid pair), while φ-values>0.5 were deemed to be very strong and likely co-conserved for important functional or structural reasons.

For this study, the CH2 sequence from IgG4 was used as a query sequence and a φ-values>0.3 was used as a cut-off to identify mutations by covariation. The residues identified from the covariation analysis are listed in Table 5.1 (all subsequent residues detailed throughout the rest of Example 3 are listed in Table 5.1). In Table 5.1, each residue gives reference to desired amino acid substitutions at that position according to the EU numbering system. "Rationale" refers to the design method employed. Covariation and Residue Frequency are described in detail in U.S. patent application Ser. No. 11/725,970. The number of additional covariation links refers to the additional covariation relationships formed by mutation to the listed amino acid type at a given position minus the number of covariation relationships lost by making this substitution. The number of additional covariation links is meant to be an additional measure of the quality of the suggested covariation mutation. In the case where multiple amino acid substitutions are suggested with no predominant associated additional number of covariation links, a library approach was used at this position in which all 20 amino acids were screened using the Delphia thermal challenge assay (detailed in Example 4). Using this methodology, six amino acid positions were identified with specific covariation mutations suggested: L242P (meaning L at position 242 changed to a P), Q268D, N286T, T307P, Y319F and S330A. In addition, five residue positions were identified to have multiple desirable (positive additional covariation links) substitutions, and a library approach was utilized. These positions are: D270, P271, E294, A299, and N315.

The methods for improving stability based on residue frequency analysis at individual positions within a protein fold has been successfully used (Steipe, 2004; Demarest et al, 2006)—and described previously in the patent application BGNA242-1 "STABILIZED POLYPEPTIDES AND METHODS FOR EVALUATING AND INCREASING THE STABILITY OF SAME" for identification of library positions within the anti-LTβR antibody BHA10 VH and VL-domains. Residue frequency analysis was used to identify five residue positions for gain-in-stability mutations: N276S, K288R, V308I, S324N, and G327A. In addition, two residues were generated by PCR error in the production of the covariation and residue frequency mutations: L309 and N325.

TABLE 5.1

Residues for Gain-in-Stability Mutations and Rationale

| EU# | IgG4 Residue | Most Frequent Residue | Residue Frequency | Covariation 0.3 | # of add'l covariation links | Mutations Made | Rationale |
|---|---|---|---|---|---|---|---|
| 242 | L | I | 0.27 | P | 1 | P | Covariation |
| 268 | Q | Q | 1.00 | D | 1 | D | Covariation |
| 270 | D | D | 1.00 | * | library | nnk | Covariation |
| 271 | P | P | 1.00 | * | library | nnk | Covariation |
| 286 | N | T | 0.17 | T | 10 | T | Covariation |
| 294 | E | E | 1.00 | * | library | nnk | Covariation |
| 299 | A | T | 1.00 | * | library | K, Y, L | Covariation |
| 307 | T | P | 0.35 | P | 5 | P | Covariation |
| 315 | N | N | 1.00 | * | library | nnk | Covariation |
| 319 | Y | F | 0.27 | F | 1 | F | Covariation |
| 330 | S | A | 1.00 | A | 10 | A | Covariation |
| 276 | N | S | 0.70 | | | S | Residue Frequency |
| 288 | K | R | 0.91 | | | R | Residue Frequency |
| 308 | V | I | 0.35 | | | I | Residue Frequency |
| 324 | S | N | 0.21 | | | H, N | Residue Frequency |
| 327 | G | A | 1.00 | | | A | Residue Frequency |
| 309 | L | | | | | M, K, P | Screening |
| 325 | N | | | | | H | Screening |
| 269 | E | | | | | library | Structural Analysis: In extended loop |
| 349 | Y | | | | | F | Structural Analysis: Interface |
| 350 | T | | | | | V | Structural Analysis: Interface |
| 394 | T | | | | | V | Structural Analysis: Interface |
| 399 | D | | | | | E, S | Structural Analysis: Interface |
| 405 | F | | | | | Y | Structural Analysis: Interface |
| 409 | R | | | | | K, M, I | Structural Analysis: Interface |
| 266 | V | | | | | F, Y | Structural Analysis: Interior Bulk |
| 264 | V | | | | | K, T, N | Structural Analysis: Near carbohydrate |
| 292 | R | | | | | S, F | Structural Analysis: Near carbohydrate |
| 303 | V | | | | | S | Structural Analysis: Near carbohydrate |
| 310 | H | | | | | K, S, A | Structural Analysis: Near CH3 |
| 268 | Q | | | | | H | Structural Analysis: Residue Charge |
| 274 | Q | | | | | H, R | Structural Analysis: Residue Charge |

TABLE 5.1-continued

Residues for Gain-in-Stability Mutations and Rationale

| EU# | IgG4 Residue | Most Frequent Residue | Residue Frequency | Covariation 0.3 | # of add'l covariation links | Mutations Made | Rationale |
|---|---|---|---|---|---|---|---|
| 355 | Q | | | | | R, H | Structural Analysis: Residue Charge |
| 419 | E | | | | | Q, K | Structural Analysis: Residue Charge |
| 240 | V | | | | | I | Structural Analysis: Thermostable |
| 255 | V | | | | | I | Structural Analysis: Thermostable |
| 263 | V | | | | | I | Structural Analysis: Thermostable |
| 302 | V | | | | | I | Structural Analysis: Thermostable |
| 323 | V | | | | | I | Structural Analysis: Thermostable |
| 348 | V | | | | | I | Structural Analysis: Thermostable |
| 35 | L | | | | | I | Structural Analysis: Thermostable |
| 363 | V | | | | | I | Structural Analysis: Thermostable |
| 368 | L | | | | | I | Structural Analysis: Thermostable |
| 369 | V | | | | | I | Structural Analysis: Thermostable |
| 379 | V | | | | | I | Structural Analysis: Thermostable |
| 397 | V | | | | | I | Structural Analysis: Thermostable |
| 412 | V | | | | | I | Structural Analysis: Thermostable |
| 427 | V | | | | | I, F | Structural Analysis: Thermostable |

B. Structural Analysis Designs for Effector-Less IgGs

In additional to the design of mutations by covariation and residue frequency analysis, structure analysis of the published crystal structure of intact human IgG b.12 antibody (pdb code: 1hzh; ref: Saphire, E. O., et al. (2001) Crystal structure of a neutralizing human IGG against HIV-I: a template for vaccine design. Science 293:1155-1159). The structural analysis identified specific structural qualities that could be modified to improve the stability of IgG molecules. In order to shift the stability of an IgG4 molecule closer to the stability of an IgG 1, a number of mutations were made to compensate for the structural differences in between IgG1 and IgG4 molecules. One such mutation is located in an extended loop in IgG4, E269. A library approach was used to screen for residues that might compensate for the additional length of this loop. This loop was also the subject to additional changes as detailed in part C. of this Example.

Figure 11A:
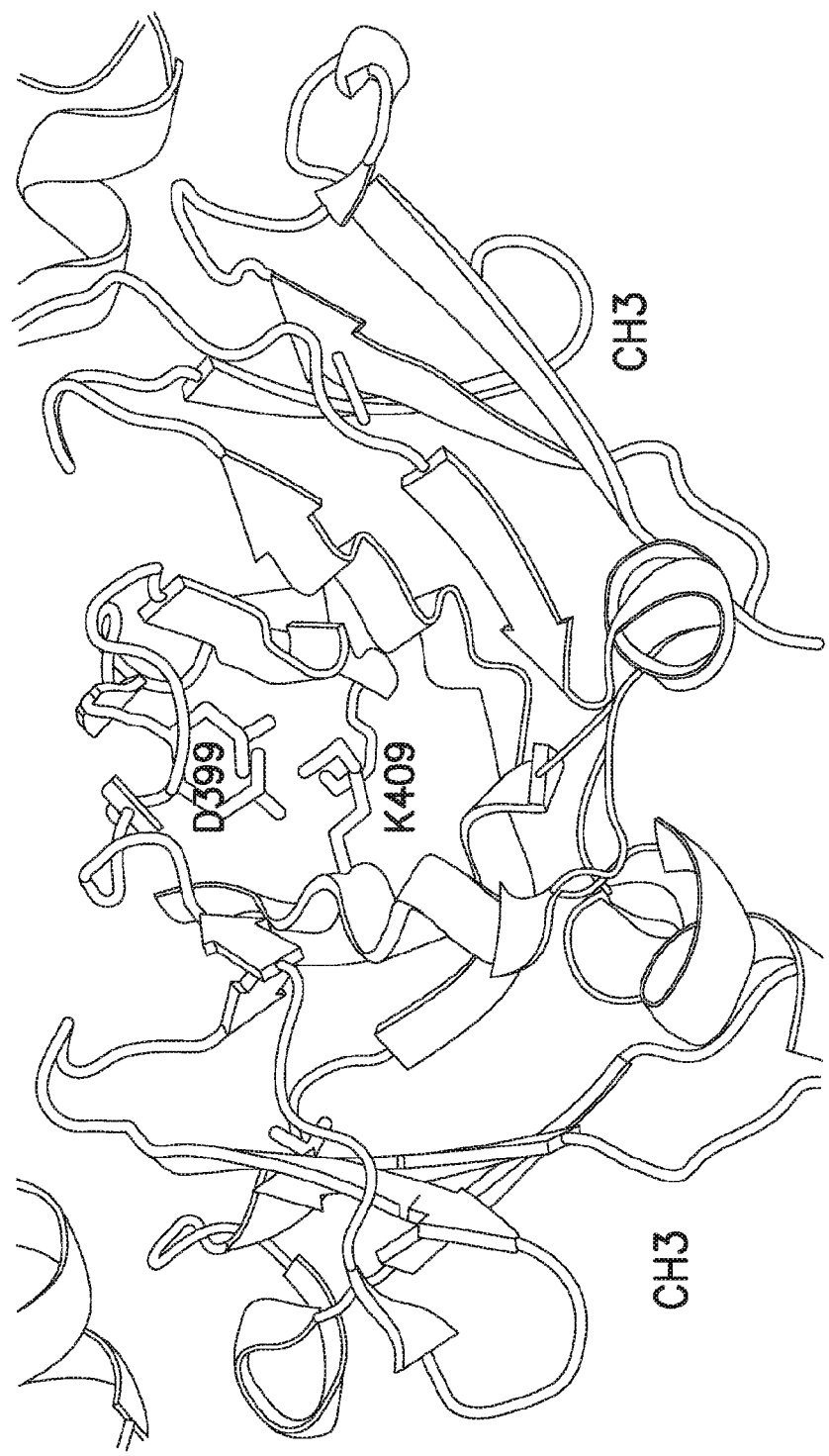
Figures 11C, 11D:
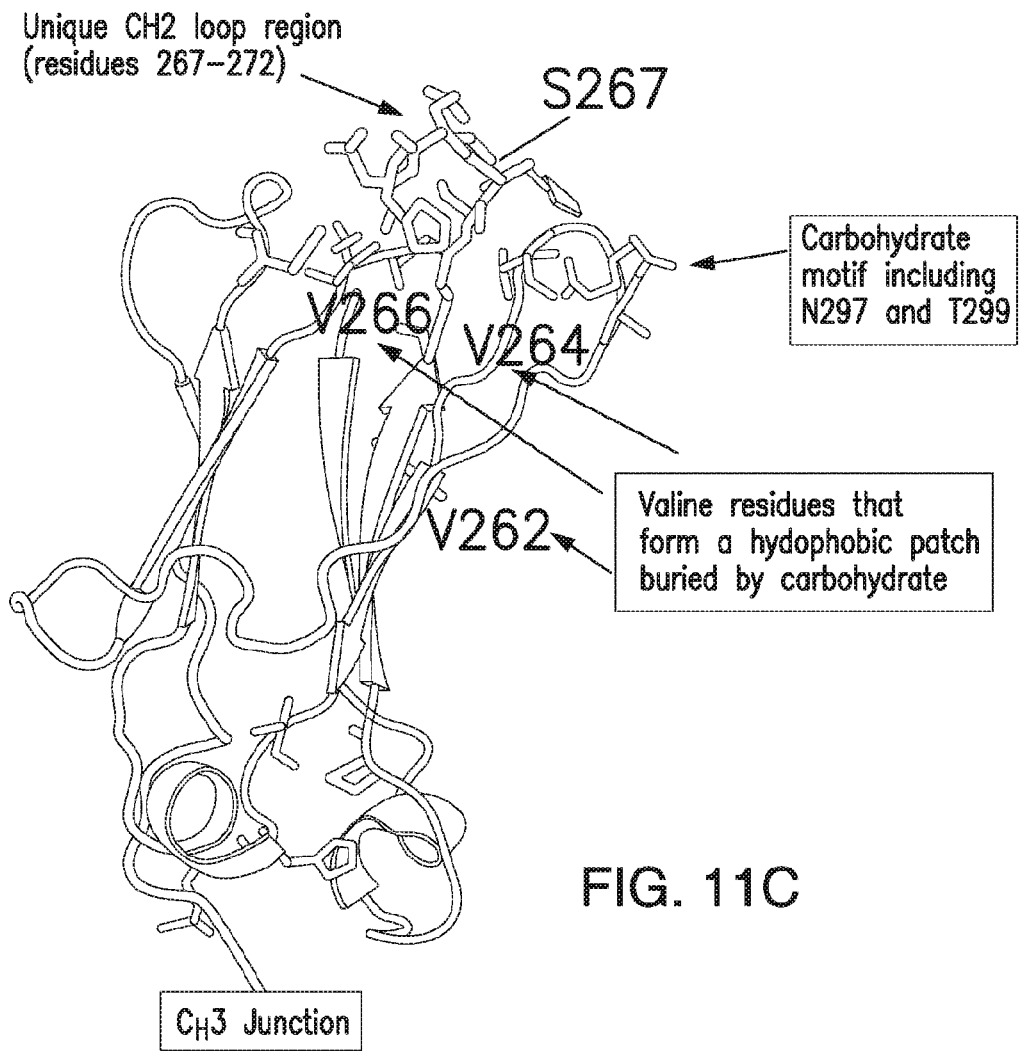

The interface between the CH3 domains constitutes the largest protein-protein contact area in the Fc domain of IgG molecules. A single substitutional difference in this interface between IgG1 and IgG4 is located at residue 409. In IgG1, a lysine is located at position 409 and in IgG4 molecules an arginine is located at position 409. Substitution of R409 in IgG4 to the IgG1 K409 was designed to introduce the superior stability qualities observed for the IgG1 CH3. R409M and R409I were also designed to test this theory. To better accommodate the added bulk of the arginine in the IgG4 CH3 interface, a number of mutations were made at the contacting residue D399 from the opposite CH3 domain: D399E and D399S (FIG. 11A). By substituting a smaller side chain at this position, the opposite CH3 domain could better accommodate the added bulk of the arginine and increase the overall stability of the CH3 domain. Another approach was used in designing mutations that added hydrophobicity to the CH3 interface to increase the association between the two interacting domains (Y349F, T350V and T394V) as well as increase bulk in the side chains of the interface (F405Y). Mutations were also designed to test for stabilization in residues that were located near contact sites with the carbohydrate in the 1hzh crystal structure (V264, R292, V303) as well as H310 near the CH3/CH2 interface. A set of surface exposed glutamine residues (Q268, Q274 and Q355) were also the focus of a number of mutations to alter the overall surface charge. The same approach was used for E419.

Finally, one of the most common mechanisms used to explain the increased thermostability of thermophilic proteins involves tighter packing of the interior core of the protein (ref: Jaenicke, R. and Zavodszky, P. 1990. Proteins under extreme physical conditions. FEBS Lett. 268: 344-349). To recapitulate this phenomenon, valine residues found in the "valine core" of CH2 and CH3 were substituted with isoleucines or phenylalanines. Increase in stability was predicted from the additional branched side chains and greater associated bulk. The "valine core" in CH2 is five valine residues (V240, V255, V263, V302 and V323) that all are orientated into the same proximal interior core of the CH2 domain. A similar "valine core" is observed for CH3 (V348, V369, V379, V397, V412 and V427). In addition, L351 and L368 were mutated to higher branched hydrophobic sidechains.

C. Covariation Designs for Effector-Less IgGs: Concerted Mutations Near the CH2 Glycosylation Site Based on Covariation Patterns Observed in Other C-Class Ig-Domains.

The IgG CH2 domain co-conserves many residues to maintain interactions with both the N-linked carbohydrate at EU position N297 and interactions with the various FcγR forms of CD 16, CD32, and CD64. Removal of the carbohydrate leads to a dramatic reduction in FcγR-binding by IgG-Fcs (Taylor and Garber, 2005). For the designs described here, the co-mutability of residues near the N-linked carbohydrate within the IgG-Fc was investigated by substituting with amino acids found to be co-conserved in other C-class Ig-fold domains. The affect these co-mutations would have on FcγR-binding and on the stability of the CH2 domain in the presence and absence of the N-linked carbohydrate was investigated, as it was possible these modifications might be both particularly well tolerated within an aglycosly-Fc and may reduce the interactions with FcγRs in both aglycosyl and glycosylated Fc moieties.

Residues important for potentially interacting with the N-linked carbohydrate were the focus of this study. IgG1-Cˆ residues that make direct contact with the carbohydrate at N297 were identified using a published crystal structure of IgG1-Fc bound to FcγRIIIa and the program MOLMOL (Sondermann, P., Huber, R., Oosthuizen, V., Jacob, U. (2000) The 3.2 A crystal structure of the human IgG1 Fc fragment-FcgRIII complex. Nature, 406: 267-273; Koradi, R., Billeter, M. & Wuthrich, K. (1996) MOLMOL: a program for display and analysis of macromolecular structures. J. Mol. Graph. 14: 51-55). It was these amino acids that were the focus of the covariation analyses and designs.

Compilation and structure/HMM-based alignment of Cl-class Ig-fold sequences was performed as described previously (PCT Publication No. WO2007109254). Covariation analyses with the diverse Cl-class Ig-fold sequence database were also performed as described previously (PCT Publication No. WO2007109254; Wang et al., 2009, supra). The covariation analyses consist of a dataset of correlation coefficients, φ-values, relating how a pair of amino acids is or is not found to be co-conserved within particular protein sequences, φ-values range from −1.0 to 1.0. A φ-value of 1.0 indicates that when an amino acid is found at one position within a subset of sequences, another amino acid at a different residue position is also always found to be present in that subset. An φ-value of −1.0 indicates that when an amino acid is found at one position within a subset of sequences, another amino acid at a different residue position is never present in that sequence subset. Absolute q-values greater than 0.2 were found to be statistically significant for the dataset that was analyzed (PCT Publication No. WO2007109254; Wang et al., 2009, supra). Based on experience with the dataset, φ-values>0.25 were deemed to be meaningful (i.e., there is likely to be a physical reason for the co-existence of the amino acid pair), while φ-values>0.5 were deemed to be very strong and likely co-conserved for important functional or structural reasons.

Based on structural analyses, it was found that hydrophobic residues V262 and V264 form a hydrophobic patch on the surface of the CH2 domain that is sequestered from solvent by the N-linked carbohydrate. Additionally, V266 is a residue in the proximity of V262 and V264 and is unique to CH2 domains, although it exists in a loop and buries itself into the interior of the domain. V262, V264, and V266 were found to be highly co-conserved within the IgG-Cˆ domain with highly significant correlation coefficients between one another (q-values: V262-V264=0.44; V262−V26=0.40; V264−V266=0.54). The residues are highlighted in our structure-based sequence alignment of the IgG constant domains (FIG. 11B).

The three valine residues (262, 264, and 266) also have strong correlation coefficients with residues that form a unique loop structure in CR2 domains (residues 267-271). This loop is two amino acids longer than the consensus loops formed by the other IgG constant domains CL, CH1, and CH3. The specific correlations are between V262 and E269 and D270 (φ-values=0.38 and 0.31, respectively), V264 and S267, D268, and E269 (φ-values=0.27, 0.44, and 0.52, respectively), and V266 and S267 (φ-value=0.30). Based on these correlations, we surmised that this loop may be important for positioning the loop containing N297 and its carbohydrate as well as positioning the loop containing residues 325-330 that is known to be important for interactions with FcγRs (Sondermann et al, 2000; Shields et al, 2001).

Based on these observations, we generated designs to investigate the tolerability (i.e., impact on the folding and stability of the CH2 domain) of other amino acid types at these positions, particularly in aglycosyl-IgG. Another aspect we wished to observe was the affect modification at these sites might have on the FcγR-binding properties of an IgG. The amino acid changes that were made within the CH2 domain based on these observations are listed in Table 5.2 and are shown on the structure of IgG-Fc in FIG. 11C (Sondermann, P., Huber, R., Oosthuizen, V., Jacob, U. (2000) The 3.2 A crystal structure of the human IgG1 Fc fragment-FcgRIII complex. Nature, 406: 267-273). An alignment of the native sequence against the sequence (SDE9) containing all the mutations is shown in FIG. 11D.

TABLE 5.2

Mutations to aglycosyl-IgG1 CH2 domain.

| Construct | Native Amino Acid(s)/EU#/Mutant Amino Acid |
|---|---|
| SD401 | A299K[a], V262L |
| SD402 | A299K[a], V264T |
| SD403 | A299K[a], V264T |

TABLE 5.2-continued Mutations to aglycosyl-IgG1 CH2 domain.

| Construct | Native Amino Acid(s)/EU#/Mutant Amino Acid |
|---|---|
| SD404 | A299K[a], V262L, V264T |
| SD405 | A299K[a], V264T, V266F |
| SDE8 | A299K[a], V262L, V264T, V266F |
| SD407 | A299K[a], Loop Replace (6 a. acids)-267SHEDPE272 with (4 a. acids)-PDPV |
| SDE7 | A299K[a], V262L, V264T, Loop Replace (6 a. acids)-267SHEDPE272 with (4 a. acids)-PDPV |
| SDE9[b] | A299K[a], V262L, V264T, Loop Replace (6 a. acids)-267SHEDPE272 with (4 a. acids)-PDPV |

Figure 10:
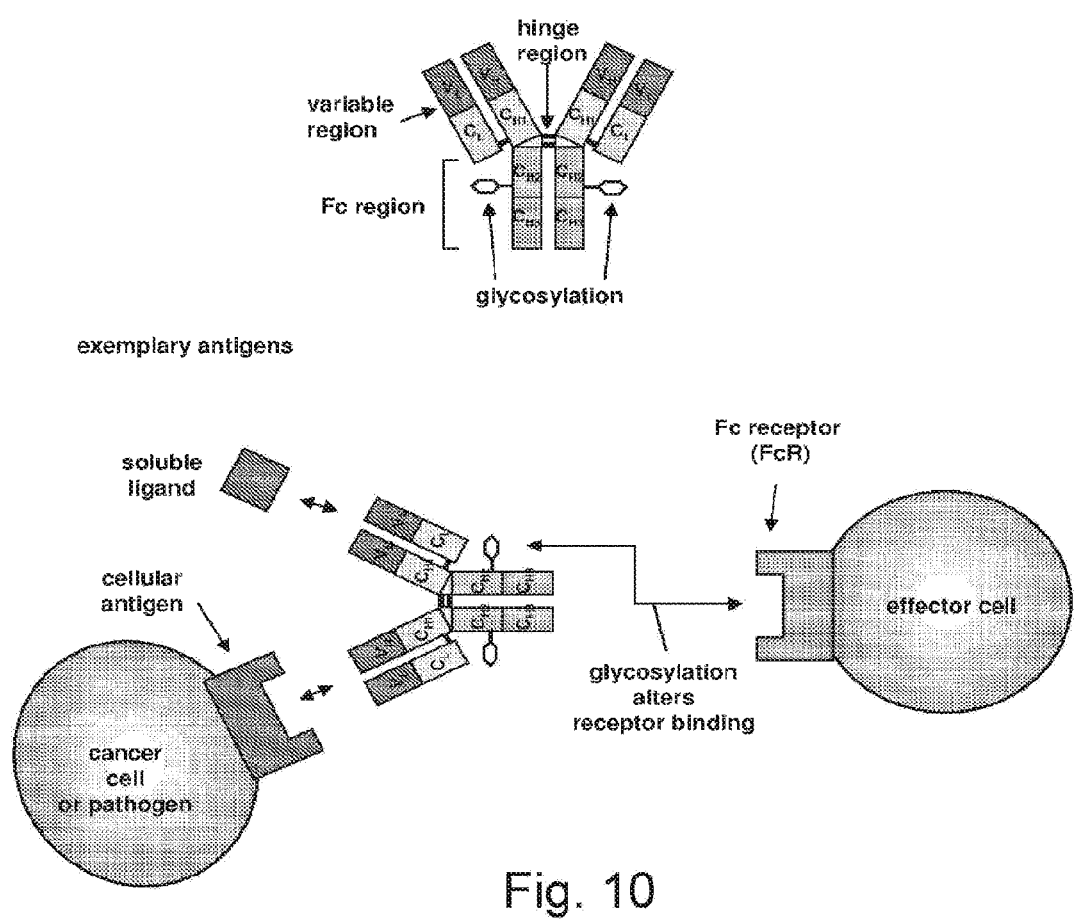
FIG. 10 depicts the structure of a typical antigen binding polypeptide (IgG antibody) and the functional properties of antigen binding and effector function (e.g., Fc receptor (FcR) binding) of an antibody. Also shown is how the presence of sugars (glycosylation) in the CH2 domain of the antibody alters effector function (FcR binding) but does not affect antigen binding.

[a]A299K mutation was made to interrupt the N-linked glycosylation motif resulting in an aglycosyl-IgG.
[b]An alignment of the native sequence against the fully modified sequence is shown in FIG. 10D.

D. Supporting Mutations

In order to test the specificity of a particular type of mutation at a given residue position, we have designed a series of additional mutations. These include testing different amino acid types (polar, hydrophobic, and charged) at residue positions that were shown to increase stability. We will also test the application of all gain-in-stability mutations to various IgG isotypes and glycosylation states. These mutations are listed in Table 5.3.

TABLE 5.3

Supporting mutations

| Number Positional | Format | Constructs (using EU numbering) IgG4.P agly | Already Made |
|---|---|---|---|
| 1 | | T299D | |
| 2 | | T299R | |
| 3 | | T299F | |
| 4 | | T299E | |
| 5 | | T299P | |
| 6 | | T299Q | |
| 7 | | T299N | |
| 8 | | T299S | |
| 9 | | T307V | |
| 10 | | T307D | |
| 11 | | T307K | |
| 12 | | T307S | |
| 13 | | L309I | |
| 14 | | L309D | |
| 15 | | L309R | |
| 16 | | L309T | |
| 17 | | D399A | |
| 18 | | D399K | EC311 |
| 19 | | T307P, L309K, T299K, R409K | EC310 |
| 20 | | T307P, L309K, T299K, R409M | |
| 21 | | T307P, L309K, T299K, R409M, D399N | |
| 22 | | T307P, L309K, T299K, R409M, D399E | |
| Isotype | IgG1 agly | | |
| 23 | | T307P | |
| 24 | | L309K | |
| 25 | | T307P, L309K | |
| 26 | | T307P, L309K, T299K | |
| Isotype | IgG1 | | |
| 27 | | T307P | |
| 28 | | L309K | |
| 29 | | T307P, L309K | |
| Variable | BIIB022 | | |
| 30 | | EC326 | |
| 31 | | EC331 | |
| 32 | | pEAG2300 | |

E. Additional Multiple Mutation Constructs

In order to reduce potential T-cell epitopes generated from peptides with stability mutation T299K and to utilize the T307P and D399S stability mutations in combination with other mutations that result in an aglycosylated IgG1 and IgG4, we will also generate the following constructs (Table 5.4).

TABLE 5.4

Additional multiple mutation constructs

| Number | Format | Constructs |
|---|---|---|
| | T-cell epitope | |
| 1 | IgG1 agly | N297P, T299K |
| 2 | IgG1 agly | N297D, T299K |
| 3 | IgG1 agly | N297S, T299K |
| | Additional effectorless, stability engineered | |
| 4 | IgG4.P agly | N297Q, T307P, D399S |
| 5 | IgG4.P agly/IgG1 Chimeric | N297Q, T307P/IgG1 CH3 |

Example 4. Thermal Stability Screening of IgQ Fc Antibody Domains Produced in *E. coli*

A modified thermal challenge assay described in U.S. patent application Ser. No. 11/725,970 was employed as a stability screen to determine the amount of soluble IgG Fc protein at 40° C. retained following a thermal challenge event at pH 4.5.

*E. coli* strain W3110 (ATCC™, Manassas, Va. Cat. #27325) was transformed with plasmids encoding pBRM012 (IgG1) and pBRM013 (IgG4 with S228P, T299A mutations) Fc's plus C-terminal Histidine tag under the control of an inducible ara C promoter. Transformants were grown overnight in expression media consisting of SB (Teknova, Half Moon Bay, Ca. Cat. #S0140) supplemented with 0.6% glycine, 0.6% Triton™ X100, 0.02% arabinose, and 50 µg/ml carbenicillin at 30° C. Bacteria was pelleted by centrifugation and supernatants harvested for further treatment.

After thermal challenge, the aggregated material was removed by centrifugation and soluble Fc samples remaining in the treated, cleared supernatant were assayed for binding to Protein A (Sigma β7837) by DELFIA assay. Two 96-well plates (MaxiSorp™, Nalge Nunc, Rochester, NY, Cat. #437111) were coated for one hour at 37° C. with Protein A at 0.5 µg/ml in PBS, and then blocked with DELFIA assay buffer (DAB, 10 mM Tris™ HCl, 150 mM NaCl, 20 pM EDTA, 0.5% BSA, 0.02% Tween™ 20, 0.01% NaN3, pH 7.4) for one hour with shaking at room temperature. The plate was washed 3 times with DAB without BSA (Wash buffer), and 10 µl of supernatant were added to 90 µl of DAB to achieve a final volume of 100 µl (reference plate). 10 µl of 10% HOAc was next added to each supernatant in a polypropylene plate to achieve a sample pH of 4.5. The plate was incubated for 90 minutes at 40° C. and denatured proteins were removed by centrifugation at 1400×g. 10 µl of acid and heat treated supernatant were added to in another DELFIA plate containing 90 µl of DAB supplemented with 100 mM Tris™, pH 8.0 (challenge plate). The DELFIA plates were incubated at room temperature with shaking for one hour, and washed 3 times as before. Bound Fc was detected by addition of 100 µl per well of DAB containing 250 ng/ml of Eu-labeled anti-His6 antibody (Perkin Elmer, Boston, MA, Cat. #AD0109) and incubated at room temperature with shaking for one hour. The plate was washed 3 times with Wash buffer, and 100 μl of DELFIA enhancement solution (Perkin Elmer, Boston, MA, Cat. #4001-0010) was added per well. Following incubation for 15 minutes, the plate was read using the Europium method on a Victor 2™ (Perkin Elmer, Boston, MA). Data was analyzed by ranking the ratio of Eu-fluorescence between the reference and challenge plates for the various constructs at 40° C. Fluorescence values greater than the value for pBRM013 were interpreted as an increase in stability over the target construct (IgG4.P agly). Data is shown in Table 6.1.

TABLE 6.1

Delphia Thermal Challenge Assay Results

| EU# | IgG4 Residue | Mutant | Rationale | normAvgF (T = 40° C.) |
|---|---|---|---|---|
| 242 | L | P | Covariation | <4.33 |
| 242 | L | I | Residue Frequency | <4.33 |
| 268 | Q | D | Covariation | <4.33 |
| 268 | Q | H | Residue Charge | <4.33 |
| 270 | D | nnk | Covariation | <4.33 |
| 271 | P | nnk | Covariation | <4.33 |
| 274 | Q | H | Residue Charge | <4.33 |
| 274 | Q | R | Residue Charge | <4.33 |
| 276 | N | S | Residue Frequency | <4.33 |
| 286 | N | T | Covariation | <4.33 |
| 288 | K | R | Residue Frequency | <4.33 |
| 294 | E | nnk | Covariation | <4.33 |
| 299 | A | K | Covariation | 4.83 |
| 299 | A | Y | Covariation | 4.71 |
| 299 | A | L | Covariation | <4.33 |
| 307 | T | P | Covariation | 5.43 |
| 308 | V | I | Residue Frequency | <4.33 |
| 309 | L | M | | 5.17 |
| 309 | L | K | | <4.33 |
| 309 | L | P | | <4.33 |
| 315 | N | nnk | Covariation | <4.33 |
| 319 | Y | F | Covariation | <4.33 |
| 324 | S | H | Residue Frequency | <4.33 |
| 324 | S | N | Residue Frequency | <4.33 |
| 327 | G | A | Residue Frequency | <4.33 |
| 330 | S | A | Residue Frequency | <4.33 |
| 355 | Q | R | Residue Charge | <4.33 |
| 355 | Q | H | Residue Charge | <4.33 |
| 419 | E | Q | Residue Charge | <4.33 |
| 419 | E | K | Residue Charge | <4.33 |
| | wt IgG1 agly | | | 5.45 |
| | wt IgG4.P agly | | | 4.33 |
| | Combinations | | | |
| 276 | N | S | | 5.49 |
| 307 | T | P | | |
| 286 | N | T | | 5.31 |
| 307 | T | P | | |
| 276 | N | S | | 5.25 |
| 286 | N | T | | |
| 307 | T | P | | |
| 308 | V | I | | 4.99 |
| 309 | L | K | | |

Example 5. Production of Stabilized IgG Fc Antibodies

A. Mutagenesis, Transient Expression of Stabilized IgG Fc Moieties in *E. coli* and Purification Stability mutations were incorporated into an the BRM 13 construct previously detailed in Example 4, by Site-Directed mutagenesis using a Stratagene Quik-Change Lightning mutagenesis kit. Primers were designed between 36-40 bases in length with the mutation in the middle with 10-15 bases of correct sequence on both sides, at least 40% GC content, starting and terminating in one or more C/G bases. All mutant constructs are listed in Table 7.1 below.

TABLE 7.1

IgG-Fc constructs Expressed and Purified from *E. coli*

Final AA Substitution using EU numbering

| | |
|---|---|
| BRM013 | IgG4.P S228P, T299A |
| BRM023 | S228P, T299A, T307P |
| BRM030 | S228P, T299K |
| CR103 | S228P, T299A, R409K |
| CR104 | S228P, T299A, R409M |
| CR105 | S228P, T299A, R409L |
| CR106 | S228P, T299A, R409I |
| CR107 | S228P, T299A, D399S |
| CR108 | S228P, T299A, D399N |
| CR109 | S228P, T299A, D399E |
| CR110 | S228P, T299A, V369I |
| CR111 | S228P, T299A, V379I |
| CR112 | S228P, T299A, V397I |
| CR113 | S228P, T299A, V427I |
| CR114 | S228P, T299A, V427F |
| CR115 | S228P, T299A, V240I |
| CR116 | S228P, T299A, V263I |
| CR117 | S228P, T299A, V273I |
| CR118 | S228P, T299A, V302I |
| CR119 | S228P, T299A, V323I |

Following the PCR using the primers that would introduce the mutation, each mutagenesis was digested with a Dpn I restriction enzyme at 37° C. for 5 minutes in order to completely digest the parental plasmid. The mutagenesis reactions were then transformed into XL1-Blue *E. Coli* ultracompetent cells. Ampicillin resistant colonies were screened and DNA sequencing was used to confirm the right sequence from the mutagenesis reaction.

Sequence confirmed DNA was transform into 3110 cells by electroporation using the EC3 program. Unique colonies were picked and grown in a starter culture in 10 ml LB-amp overnight. This preculture was transferred to 1 L expression media [SB+0.02% arabinose+amp/carb 50 mg/L] and grown overnight at 32° C. Cells were spun down in a centrifuge and resuspended completely in the 100 ml of spheroplast buffer (20% sucrose, 1 mM EDTA, 10 mM Tris™-HCl pH 8.0, and lysozyme (0.01% w/v)). Cells were spun down and resultant protein was in supernatant.

The IgG-Fc constructs were purified by batch-purification using Protein A Sepharose™ FF (GE Healthcare). The Fc molecule was eluted from the Protein A Sepharose™ using 0.1 M glycine at pH 3.0, neutralized with Tris™ base, and finally dialyzed into PBS using the Pierce 10 ml dialysis cassettes (10,000 MWCO cutoff).

B. Mutagenesis, Transient Expression of Stabilized Antibodies in CHO Cells, Antibody Purification, and Characterization Stability mutations were incorporated into an IgG4.P antibody (a VH construct already containing a proline hinge mutation at amino acid 228) by Site-Directed mutagenesis using a Stratagene Quik-Change Lightning mutagenesis kit. The antigen recognizing Fab was from the anti-CD40 antibody 5c8. Primers were designed between 36-40 bases in length with the mutation in the middle with 10-15 bases of correct sequence on both sides, at least 40% GC content, starting and terminating in one or more C/G bases. All glycosylated and aglycosylated mutant constructs are listed in Table 7.2.

TABLE 7.2

Protein yield from IL culture and % Monomer as measured by Analytical Size-Exclusion Chromatography (IgG1 constructs in italics)

| | Final AA Substitution using EU numbering | yield (mg) | % monomer |
|---|---|---|---|
| I. Glycosylated | | | |
| EC301 | S228P, A299K, V427F | 2.2 | 53% |
| EC302 | S228P, A299K, D399S | 4.3 | 98.60% |
| EC303 | S228P, T307P, V427F | 1.7 | 98.20% |
| EC304 | S228P, T307P, D399S | 2.9 | 99.00% |
| EC305 | S228P, A299K, V427F, D399S | 5 | 99.10% |
| EC306 | S228P, T307P, V427F, D399S | 15.3 | 28% |
| EC307 | S228P, A299K, V427F, V348F | 0 | — |
| EC308 | S228P, T307P, V323F | 9 | 99.50% |
| EC309 | S228P, V240F | 15.75 | 98.10% |
| EC321 | S228P, D399S, L309P | 13.3 | 97.80% |
| EC322 | S228P, D399S, L309M | 13.3 | 97.50% |
| EC323 | S228P, D399S, L309K | 13.41 | 98.40% |
| EC324 | S228P, T307P, D399S, L309P | 15.66 | 97% |
| EC325 | S228P, T307P, D399S, L309M | 8.1 | 97.80% |
| EC326 | S228P, T307P, D399S, L309K | 21.1 | 98.60% |
| EC300 | S228P, T307P | 16 | 98.30% |
| II. Aglycosylated | | | |
| EC330 | S228P/T299A/T307/IgG1-CH3 | 21.42 | 98.10% |
| EC331 | S228P/T299K/T307/IgG1-CH3 | 7 | 98.70% |
| YC401 | S228P, T299A, T307P, D399S | 3 | 96% |
| YC402 | S228P, T299A, L309K, D399S | 3 | 95% |
| YC403 | S228P, T299A, T307P, D399S, L309K | 4 | 95.10% |
| YC404 | S228P, T299K, T307P, D399S | 5 | 97.22% |
| YC405 | S228P, T299K, L309K, D399S | 4.5 | 95% |
| YC406 | S228P, T299K, T307P, D399S, L309K | 3.5 | 96% |
| YC407 | S228P, T299A | 4.07 | 96.90% |
| CN578 | T299K (IgG1) | 9.38 | 100% |
| CN579 | S228P,T299K | 11.55 | 90% |
| pEAG2296 | S228P/T299A/IgG1-CH3 | 7.24 | 98% |
| pEAG2287 | S228P/T299K/IgG1-CH3 | 14.2 | 100% |
| SDE1 | A299K, V262L | 4.91 | 100% |
| SDE2 | A299K, V264T | 2.8 | 100% |
| SDE3 | A299K, V266F | 8.96 | 95.15% |
| SDE4 | A299K, V262L, V264T | 2.6 | 95.20% |
| SDE5 | A299K, V264T, V266F | 3.93 | 95.40% |
| SDE6 | A299K, Loop Replacement | 2.11 | 95.95% |
| SDE7 | A299K, Loop + V262L/V264T | 8.54 | 99.10% |
| SDE8 | A299K, V262L, V264T, V266F | 6.83 | 98.90% |
| SDE9 | A299K, Loop + V262L/V264T/V266F | 6.46 | 99.20% |

Following the PCR using the primers that would introduce the mutation, each mutagenesis was digested with a Dpn I restriction enzyme at 37° C. for 5 minutes in order to completely digest the parental plasmid. The mutagenesis reactions were then transformed into XL10-Gold® E. Coli ultracompetent cells. Ampicillin resistant colonies were screened and DNA sequencing was used to confirm the right sequence from the mutagenesis reaction.

DNA from confirmed sequences were scaled up and transformed into TOP10 E. coli competent cells (Invitrogen Corporation, Carlsbad, CA). E. coli colonies transformed to ampicillin drug resistance were screened for presence of inserts. Colonies were then cultured into large scale culture of 250 ml. A Qiagen HiSpeed® Maxiprep kit was used to extract and purify the DNA from the bacterial culture for transient transfection. The DNA was quantified using an E280 to measure DNA concentration to be used for transfection.

The mutant plasmids along with an equal amount of 5c8 VL plasmid were then used to co-transfect CHO—S cells for transient expression of antibody protein. The amount of DNA to be used for the transfection was 0.5 mg/L of the VH and 0.5 mg/L of the VL. The transfection media (CHO—S-SFMII from Invitrogen with LONG R4IGF-1 from SAFC) was prepared at 5% of the transfection volume with 1 mg/ml of PEI (Polysciences Cat. #23966) in a ratio of 3 mg of PEI to 1 mg of DNA. DNA was added to the transfection media/PEI solution and swirled then sat at room temperature for 5 minutes. The mixture was then added to 500 ml of CHO—S cells at Ie6 cells/mi. After 4 hours at 37° C. at 5% C02, 1× volume of expansion media (CHOM37+20 g/l PDSF+Penstrep/amphostericin) was added for a final culture volume of 1 L. On day 1, 10 ml of cotton hydrolysate at 200 g/L was added and the temperature was dropped to 28° C. Culture viability was monitored until the viability dropped below 70% (8-12 days). Titers for protein expression were also checked at this point using the Octet® (ForteBio) in measuring binding to anti-IgG tips. The cells were harvested by spinning down the culture sat 2400 rpm for 10 minutes, and then the supernatant filtered through 0.2 um ultrafilters.

The 5C8 antibody was captured from the supernatant using Protein A Sepharose™ FF (GE Healthcare) on AKTA™ (Amersham Biosciences). The antibody molecule was eluted from the Protein A using 0.1 M glycine at pH 3.0, neutralized with Tris™ base, dialyzed into PBS using the Pierce 10 ml dialysis cassettes (10,000 MWCO cutoff), concentrated to 1 ml final volume, and the further purified using preparative size exclusion chromatography (TOSO-HASS, TOSOH Biosciences). The κC8 molecule was dialyzed into a 20 mmol citrate, 150 mmol NaCl solution at pH 6.0. Purity and percentage of monomer antibody product was assessed by 4-20/a Tris™-glycine SDS-PAGE and analytical size-exclusion HPLC, respectively.

C. Confirmation of Protein Sequences and Post-Translational Modifications of Stability Engineering Antibodies Using Mass Spectral Analysis The samples were analyzed under reducing conditions. Reduction took place in 100 mM DTT in the presence of 4M guanidine HCl for 1 hour at 37° C. Prior to injection, the samples were diluted 1:1 with PBS. Glacial acetic acid was added to the mix to a final concentration of 2% (v/v). 5 µg of each sample was injected onto a phenyl column and analyzed by ESI-TOF. A bind and elute method was used. Buffer A contains 0.03% TFA in water and buffer B contains 0.025% TFA in acetonitrile. Flow rate was kept constant at 100 µl per minute. Spectra were obtained from the Analyst software and deconvoluted using MaxEntl. After reduced analysis, 3 of the samples were detected as glycoforms, therefore, deglycosylation was performed on the 3 samples: EC323, EC326 and EAG2300. Deglycosylation was performed under reducing condition: 1 mU of N-glycanase/2 µg of protein in the presence of 20 mM DTT, 10 mM Tris™ pH 7.0. The samples were deglycosylated at 37° C. After 2 hours, an additional 30 mM of DTT was added to the samples in the presence of 2.7M guanidine HCl and incubated at 37° C. for an additional 30 minutes. 5 µg of each reduced, deglycosylated sample were injected onto a phenyl column and analyzed as detailed above.

Results confirmed the identities of all 13 samples with conversion of the N-terminal glutamine (Q) of the heavy chain to pyroglutamic acid (PE). Table 7.3 lists the masses obtained for all samples, glycosylated and deglycosylated.

All light chains and heavy chains contained low levels of glycation of 1% or less. Masses corresponding to the unmodified N-terminal glutamine were observed in each of the samples at a relative intensity of ~20-40%. All light chain deconvoluted spectra were identical as expected.

TABLE 7.3

Masses Detected

| Sample ID | Probable Assignment | Detected Mass | Theoretical Mass |
|---|---|---|---|
| YC401 | LC 1-218 | 23857 | 23858 |
|  | HC 1-444 Q PE | 48640 | 48641 |
| YC402 | LC 1-218 | 23857 | 23858 |
|  | HC 1-444 Q PE | 48659 | 48660 |
| YC403 | LC 1-218 | 23857 | 23858 |
|  | HC 1-444 Q PE | 48655 | 48656 |
| YC404 | LC 1-218 | 23857 | 23858 |
|  | HC 1-444 Q PE | 48697 | 48698 |
| YC405 | LC 1-218 | 23857 | 23858 |
|  | HC 1-444 Q PE | 48716 | 48717 |
| YC406 | LC 1-218 | 23857 | 23858 |
|  | HC 1-444 Q PE | 48712 | 48713 |
| YC407 | LC 1-218 | 23857 | 23858 |
|  | HC 1-444 Q PE | 48672 | 48673 |
| EC323 | LC 1-218 | 23857 | 23858 |
|  | HC 1-444 Q PE, G0F | 50134 | 50135 |
|  | HC 1-444 Q PE, G1F | 50297 | 50297 |
|  | HC 1-444 Q PE, G2F | 50459 | 50459 |
|  | HC 1-444 Q PE, G0 (Minus fucose) | 49988 | 49989 |
| EC323 Deglycosylated | LC 1-218 | 23857 | 23858 |
|  | HC 1-444 Q PE | 48690 | 48690 |
| EC326 | LC 1-218 | 23857 | 23858 |
|  | HC 1-444 Q PE, G0F | 50130 | 50131 |
|  | HC 1-444 Q PE, G1F | 50293 | 50293 |
|  | HC 1-444 Q PE, G2F | 50454 | 50455 |
|  | HC 1-444 Q PE, G0 (Minus fucose) | 49984 | 49985 |
| EC326 Deglycosylated | LC 1-218 | 23857 | 23858 |
|  | HC 1-444 Q PE | 48685 | 48686 |
| EC331 | LC 1-218 | 23857 | 23858 |
|  | HC 1-444 Q PE | 48676 | 48677 |
| EAG2300 | LC 1-218 | 23857 | 23858 |
|  | HC 1-443 Q PE, G0F | 49919 | 49920 |
|  | HC 1-443 Q PE, G1F | 50081 | 50082 |
|  | HC 1-443 Q PE, G2F | 50243 | 50244 |
| EAG2300 Deglycosylated | LC 1-218 | 23857 | 23858 |
|  | HC 1-443 Q PE | 48473 | 48475 |
| CN578 | LC 1-218 | 23857 | 23858 |
| CN578 | HC 1-447 Q PE | 48885 | 48885 |
| CN579 | LC 1-218 | 23857 | 23858 |
|  | HC 1-444 Q PE | 48729 | 48730 |

It should be noted that post-translational modifications can vary widely in the antibodies described herein. For example, glycation (the non-enzymatic modification caused by reaction of amino groups on proteins with glucose) is routinely detected in proteins and levels vary widely depending on cell culture conditions. Certainly, glycation levels can be much higher than the 1% described above on each of the heavy and light chains. For example, the level of glycation of an intact antibody as described herein can be 10%, or 20%, or 30%, or 40%, or higher than 40%. Likewise, other post-translational modifications, such as deamination and glycosylation, may vary depending upon generation and purification methods of the antibodies described herein.

Samples EC323, EC326 and EAG2300 contained the usual G0F, G1F, G2F biantennary glycans with the G0F as the most abundant species followed by G1F then G2F. Samples EC323 and EC326 contained a peak at −146 Da from the G0F peak which corresponds to a G0F glycan missing a core fucose (G0). For EC323, the relative percentage intensity of G0 (minus fucose) was 2% while that of the EC326 sample was 23%. All 3 glycosylated samples contained low levels (<1%) of sialic acid on the G2F glycan.

All sample chains contained a ~18 Da peak which has been shown to be an instrument artifact related to elevated gas temperature of the ESI-TOF. A temperature of 350° C. was used to eliminate TFA adducts.

Example 6. Thermal Stability of Aglycosylated IgG Fc Antibodies

Protein stability is a central issue for the development and scale up of protein therapeutics. Insufficient stability may lead to a number of development issues ranging from unsuitability for scale-up production in bioreactors, difficulties in protein purification, and unsuitability for pharmaceutical preparation and use. In order to generate an effector-function deficient Fc backbone, mutations were introduced into agly IgG4.P (S228P) to increase the overall stability of the CH2 and CH3 domains. The goal of this study was to investigate whether the designed mutations increase thermal stability. Therefore, the thermostability of each construct was assessed using differential scanning calorimetry (DSC). Both the E. coli produced Fc-domain constructs and full length antibody constructs were assessed by DSC. The expression and purification methods for the E. coli produced Fc-domain constructs and the full length antibody constructs are detailed in Example 5.

The antibodies were dialyzed against a 25 mM sodium citrate, 150 mM NaCl buffer at pH 6.0. Antibodies were concentration to 1 mg/mL and measured by UV absorbance. Scans were performed using an automated capillary DSC (MicroCal, LLC, Northampton, MA). Two buffer scans were performed for baseline subtraction. Scans ran from 20-105° C. at 1° C./min using the medium feedback mode. Scans were then analyzed using the software Origin (MicroCal LLC, Northampton, MA). Nonzero baselines were corrected using a third-order polynomial and the unfolding transitions of each antibody were fit using the non-two-state unfolding model. To further asses the stability of these constructs, the full length antibodies were dialyzed against a 25 mM sodium phosphate, 25 mM sodium citrate, 150 nM NaCl buffer at pH 4.5. The same DSC protocol was used as detailed above. E. coli expressed Fc-domain constructs lacking the Fab domain were used to test stability enhancement of the mutations identified in the Delphia thermal challenge assay as detailed in Example 2. The constructs BRM023, BRM030 and CR103-119 are listed along with their melting temperatures in Table 8.1.

TABLE 8.1

Melting Temperatures of E. coli Expressed IgG Fc constructs as measured by DSC.

| DSC | Final AA Substitution using EU numbering | Tm (° C.) CH2 | Tm (° C.) CH3 | Fab | Source |
|---|---|---|---|---|---|
| BRM012 | IgG1 (agly b/c expressed in E. coli) | 65.9 | 82.6 | n/a | E.coli |
| BRM013 | IgG4.P S228P, T299A | 62.3 | 71.15 | n/a | E.coli |
| BRM023 | S228P, T299A, T307P | 66.2 | 69.9 | n/a | E.coli |
| BRM030 | S228P, T299K | 65.7 | 70 | n/a | E.coli |
| CR103 | S228P, T299A, R409K | 58.3 | 83.2 | n/a | E.coli |
| CR104 | S228P, T299A, R409M | 60.9 | 77.7 | n/a | E.coli |
| CR105 | S228P, T299A, R409L | — | — | n/a | E.coli |
| CR106 | S228P, T299A, R409I | X | X | n/a | E.coli |
| CR107 | S228P, T299A, D399S | 58.4 | 74.9 | n/a | E.coli |

TABLE 8.1-continued

Melting Temperatures of E. coli Expressed IgG Fc constructs as measured by DSC.

| DSC | Final AA Substitution using EU numbering | Tm (° C.) CH2 | CH3 | Fab | Source |
|---|---|---|---|---|---|
| CR108 | S228P, T299A, D399N | 57.2 | 70.4 | n/a | E.coli |
| CR109 | S228P, T299A, D399E | 58.4 | 66.9 | n/a | E.coli |
| CR109 2 | S228P, T299A, D399E | 57.1 | 68.1 | n/a | E.coli |
| CR110 | S228P, T299A, V369I | 60.5 | 65.6 | n/a | E.coli |
| CR111 | S228P, T299A, V379I | 57.7 | 66.8 | n/a | E.coli |
| CR112 | S228P, T299A, V397I | 59.7 | 72 | n/a | E.coli |
| CR113 | S228P, T299A, V427I | X | X | n/a | E.coli |
| CR114 | S228P, T299A, V427F | 61.6 | 75.3 | n/a | E.coli |
| CR115 | S228P, T299A, V240I | X | X | n/a | E.coli |
| CR116 | S228P, T299A, V263I | X | X | n/a | E.coli |
| CR117 | S228P, T299A, V273I | X | X | n/a | E.coli |
| CR118 | S228P, T299A, V302I | 59.7 | 71.7 | n/a | E.coli |
| CR119 | S228P, T299A, V323I | 59.1 | 59.1 | n/a | E.coli |

As depicted in Table 8.1, the agly IgG1 and IgG4.P (S228P, T299A) Fc moiety controls had melting temperatures of 65.9° C. and 62.3° C. respectively for CH2 and 82.6° C. and 71.2° C., respectively for CH3. Of the single site mutations, BRM023 (T307P) and BRM030 (T299K) showed a 3.4-3.9° C. increase in CH2 melting temperature over the agly IgG4.P (S228P, T299A) control. Substitution at position R409 with Lysine or Methionine, showed an increase of 12 and 6.6° C. in the CH3 melting temperature. Substitution to smaller, hydrophobic side chains (Leu and Ile) did not confer increased stability for CH3. This position represents the single difference in the CH3 interface between IgG1 and IgG4. Mutations at position D399 were made to compensate for the added bulk of the Arginine side chain at position 409 in the IgG4 CH3 interface (as detailed in Example 3). A substitution of a smaller side chain (Ser) facilitated an increase in melting temperature of ~4° C. Substitution to either a side chain with same size but lacking charge (Asp) or to a larger side chain with same charge (Glu) both showed no increase in stability. Substitutions in the hydrophobic valine core as detailed in Example 3, showed either no effect or a decrease in melting temperature with the exception of V427F which showed an increase in CH3 melting temperature of ~4° C.

To evaluate single and combinations of multiple mutations, full length IgG molecules were utilized. Mutations were incorporated into full length 5c8 antibodies as detailed in Example 5. The effects of the mutations on the melting temperatures of the CH2 and CH3 domains as measured by DSC at pH 6.0 and pH 4.5 are summarized in Table 8.2 below.

TABLE 8.2

Melting Temperatures of Full Length IgG constructs as measured by DSC

| DSC | Final AA Substitution using EU numbering | Tm (° C.) pH 6.0 | | | pH 4.5 | | | Source |
|---|---|---|---|---|---|---|---|---|
| | | CH2 | CH3 | Fab | CH2 | CH3 | Fab | |
| | IgG4.P agly (S228P, T299A) | 53.8 | 70 | 76.67 | 38.5 | 60.2 | 69 | CHO |
| | IgG4.P (S228P) | 64.14 | 73.66 | 77.2 | 51.04 | 63.23 | 68.84 | CHO |
| | IG1 agly (T299A) | 58.8 | 85.3 | 77.2 | | | | CHO |
| | S228P, T299K | 71.5 | 84.9 | 77.5 | 60 | 75.5 | 69 | CHO |
| EC301 | S228P, T299K, V427F | 44.8 | 54.77 | 76.26 | | | | CHO |
| EC302 | S228P, T299K, D399S | 60.4 | 74.4 | 77 | 42.8 | 66.37 | 69.61 | CHO |
| EC303 | S228P, T307P, V427F | 63 | 75 | 76.6 | | | | CHO |
| EC304 | S228P, T307P, D399S | 67.4 | 75.4 | 77.6 | 54.46 | 66.74 | 69.85 | CHO |
| EC305 | S228P, T299K, V427F, D399S | 47.1 | 74.81 | 77.1 | | | | CHO |
| EC306 | S228P, T307P, V427F, D399S | 52.8 | 75 | 77.4 | | | | CHO |
| EC307 | S228P, T299K, V427F, V348F | | | | | | | CHO |
| EC308 | S228P, T307P, V323F | 63.47 | 73.71 | 77.15 | | | | CHO |
| EC309 | S228P, V240F | 50.1 | 73.5 | 77.3 | | | | CHO |
| EC321 | S228P, D399S, L309P | 60.2 | 75.1 | 77.5 | | | | CHO |
| EC322 | S228P, D399S, L309M | 62.1 | 74.8 | 77.4 | | | | CHO |
| EC323 | S228P, D399S, L309K | 64.7 | 74.8 | 77.5 | 53.11 | 66.6 | 69.82 | CHO |
| EC324 | S228P, T307P, D399S, L309P | 62.7 | 74.8 | 77.5 | | | | CHO |
| EC325 | S228P, T307P, D399S, L309M | 65.21 | 74.98 | 77.5 | | | | CHO |
| EC326 | S228P, T307P, D399S, L309K | 67.5 | 75.23 | 77.6 | 56.48 | 66.73 | 69.95 | CHO |
| EC300 | S228P, T307P | 62.5 | 74.8 | 77.4 | | | | CHO |
| EC330 | S228P/T299A/T307/IgG1-CH3 | 60.5 | 84.5 | 76.8 | 43 | 77.36 | 68.75 | CHO |
| EC331 | S228P/T299K/T307/IgG1-CH3 | 65.5 | 84.77 | 76.6 | 47.4 | 77.1 | 68.2 | CHO |
| YC401 | S228P, T299A, T307P, D399S | 61.55 | 75 | 77.15 | 46.35 | 71.31 | 68.04 | CHO |
| YC402 | S228P, T299A, L309K, D399S | 59.95 | 75.52 | 77.02 | 47.14 | 72.54 | 69.32 | CHO |
| YC403 | S228P, T299A, T307P, D399S, L309K | 62.21 | 74.77 | 77.1 | 51.64 | 73.53 | 70.44 | CHO |

TABLE 8.2-continued

Melting Temperatures of Full Length IgG constructs as measured by DSC

| DSC | Final AA Substitution using EU numbering | Tm (° C.) pH 6.0 CH2 | CH3 | Fab | pH 4.5 CH2 | CH3 | Fab | Source |
|---|---|---|---|---|---|---|---|---|
| YC404 | S228P, T299K, T307P, D399S | 63.44 | 75.14 | 77.2 | 50.8 | 71.93 | 68.76 | CHO |
| YC405 | S228P, T299K, L309K, D399S | 63.16 | 74.81 | 77.16 | 49.4 | 71.92 | 68.66 | CHO |
| YC406 | S228P, T299K, T307P, D399S, L309K | 66.2 | 74.1 | 77.23 | 53.53 | 72.3 | 69.25 | CHO |
| YC407 | S228P, T299A | 55.8 | 73.05 | 76.78 | 41.52 | 72.52 | 67.53 | CHO |
| CN578 | T299K (IgG1) | 65.4 | 85.2 | 77.7 | 47.6 | 72.2 | 67.8 | CHO |
| CN579 | S228P, T299K | 60.9 | 73.7 | 77.2 | 42.1 | 61.1 | 68.6 | CHO |
| pEAG2296 | S228P/T299/IgG1-CH3 | 54.6 | 85.2 | 76.4 | 35.1 | 77.5 | 68.1 | CHO |
| pEAG2287 | S228P/T299K/IgG1-CH3 | 60 | 85.2 | 76.4 | 41.4 | 77.4 | 68.1 | CHO |
| SDE1 | T299K, V262L | | | | | | | CHO |
| SDE2 | T299K, V264T | 64.81 | 85.12 | 77.32 | 50.61 | 73.72 | 70.01 | CHO |
| SDE3 | T299K, V266F | 58.03 | 85.25 | 77.3 | | | | CHO |
| SDE4 | T299K, V262L, V264T | 63.24 | 85.11 | 77.22 | | | | CHO |
| SDE5 | T299K, V264T, V266F | 58.3 | 84.95 | 77.35 | | | | CHO |
| SDE6 | T299K, Loop Replacement | 61.68 | 85.16 | 77.16 | | | | CHO |
| SDE7 | T299K, ILoop + V13L/V15T | 59.2 | 84.89 | 76.97 | | | | CHO |
| SDE8 | T299K, V262L, V264T, V266F | 56.98 | 85.21 | 77.13 | | | | CHO |
| SDE9 | T299K, Loop + V13L/V15T/V17F | 53.45 | 85.04 | 77.03 | | | | CHO |

As depicted in Table 8.2, the D399S mutation increased the thermal stability of the CH3 domain in agly IgG4.P on average by 2° C. at pH 6.0 and by as much as 10° C. at pH 4.5. The mutant T299K is used to generate an aglycosylated CH2. The lysine substitution at position 299 increases the melting temperature by 5° C. at pH 6.0 and by 11° C. at pH 4.5 in the IgG4.P molecule over a substitution of alanine in this position. The T299K mutation also increases the Tm for IgG1 CH2 by 6° C. at pH 6.0. The T307P mutation showed an increase of 4C for the glycosylated IgG4.P CH2 domain when used in combination with D399S. By itself, T307P did not increase the melting temperature in the glycosylated IgG4.P form. In the aglycosylated form, the T307P mutation increased the CH2 Tm by 6° C. When combined with the T299K mutation, the Tm for CH2 increased by 8° C. The L309K mutation conferred a 1° C. increase in stability for the aglycosylated IgG4.P when in combination with T307P and T299A. However, in combination of T307P and T299K, the L309K mutation conferred an increase of 3° C. In the glycosylated form of IgG4.P, the L309K mutation increases the Tm for CH2 by 2° C. The L309K mutation conferred a 1° C. increase in stability for the aglycosylated IgG4.P when in combination with T307P and T299A. However, in combination of T307P and T299K, the L309K mutation conferred an increase of 3° C. at pH 4.5. The V323F mutation in CH2 showed no effect on the melting temperature of the CH2 domain while a V240F mutation decreased the melting temperature by 13° C. In addition, the V427F mutation also showed a decrease in the Tm of 13° C. for CH2.

The most dramatic increase in melting temperatures is observed in the combination of T299K, T307P, L309K and D399S in IgG4.P. This construct shows an increase in the Tm for CH2 of 11° C. (pH 6.0) and 12° C. (pH 4.5) when compared to T299A IgG4.P. In fact the T299K mutation increases the Tm by 2-3° C. when in combination with T307P, L309K and D399S over the T299A mutation. Additionally, the introduction of T299K into the IgG4.P CH2 in combination with the conversion of the CH3 of the IgG4.P isotype to the CH3 from IgG1 resulted in an increase of 6C and 15° C., for the CH2 and CH3 domains respectively over the agly IgG4.P.

Mutations identified in covariation studies of CH2 glycosylation show none to little effect on the Tm for IgG1 CH2 (V262L, and V264T in combination with V262L, Loop replacement), or a decreased effect of 7° C. (V266F, V264T & V266F, Loop & V264T & V266F). A large decrease in melting Tm of 10-12° C. was observed for the combination of V262L, V264T and V266F.

In summary, T299K, T307P, L309K showed the ability to increase the thermal stability of the CH2 domain either as single mutations or in combinations with each other. D399S conferred stability to the CH3 domain of IgG4.P.

Example 7: Agitation and PH Hold Step Studies of IgG Fc Antibodies

It is highly desirable for a protein therapeutic to have a long shelf life, with minimal changes to the physical or chemical properties of the protein during manufacturing production and storage. Evaluating related stresses is an important part of formulation development and two types of associated stress were evaluated for the IgG Fc mutants.

A. Agitation Stress

Agitation mimics stresses encountered during manufacturing and processing as well as simulates the stress during actual shipping (i.e. shipment of the drug product vials to test site). Therefore, agitation stability was analyzed over the course of 48 hours, and protein aggregation or precipitation was monitored using analytical size exclusion chromatography (SEC) and turbidity was measured by monitoring absorbance at 320 nM. Turbidity is a measure of light scattering due to aggregation and precipitant formation that makes the protein/buffer solution cloudy or even opaque in extreme cases. The following method was used consistently in each set of experiments: 1 ml of each sample at 0.5 mg/ml was shaken in a 3 ml formulation tube at 650 rpm, sealed with a rubber stopper, and sealed again with parafilm. 100 µl of sample were extracted at the necessary time points (0, 6, 24, and 48 hours) and spun down at 14,000 rpm for 5 minutes to spin down aggregates or precipitants formed. The samples were then run and analyzed on an analytical SEC column. Aggregated protein elutes at shorter retention times and protein degradation products elute at longer retention times in the SEC elution profile. Therefore the percentage of monomer species was used to monitor the overall stability of the protein at a given time point.

Constructs with the highest thermal stabilization (see Example 6) were chosen for the agitations studies. For the aglycosylated IgG4 molecules, YC401 through YC403 (all aglycosylated IgG4.P T299A and D399S [plus T307P, L309K, and T307P/L309K respectively], YC404 through YC406 (all aglycosylated IgG4.P T299K and D399S [plus T307P, L309K, and T307P/L309K respectively], YC407 as the wild-type IgG4.P aglycosylated (T299A) control, CN578 (aglycosylated IgG1 A299K), EC331 (which is the aglycosylated IgG4.P T299K and T307P with an IgG1 CH3 domain), an aglycosylated IgG1 (T299A), aglycosylated IgG4.P (T299A) and an aglycosylated IgG1 (T299A) were selected for study. For the glycosylated molecules, EC304 (glycosylated IgG4.P T307P, D399S), EC323 (glycosylated IgG4.P D399S, L309K), EC326 (glycosylated IgG4.P T307P, D399S, L309K), glycosylated IgG4.P T299A, and glycosylated IgG1 were selected for study.

Figure 12A:
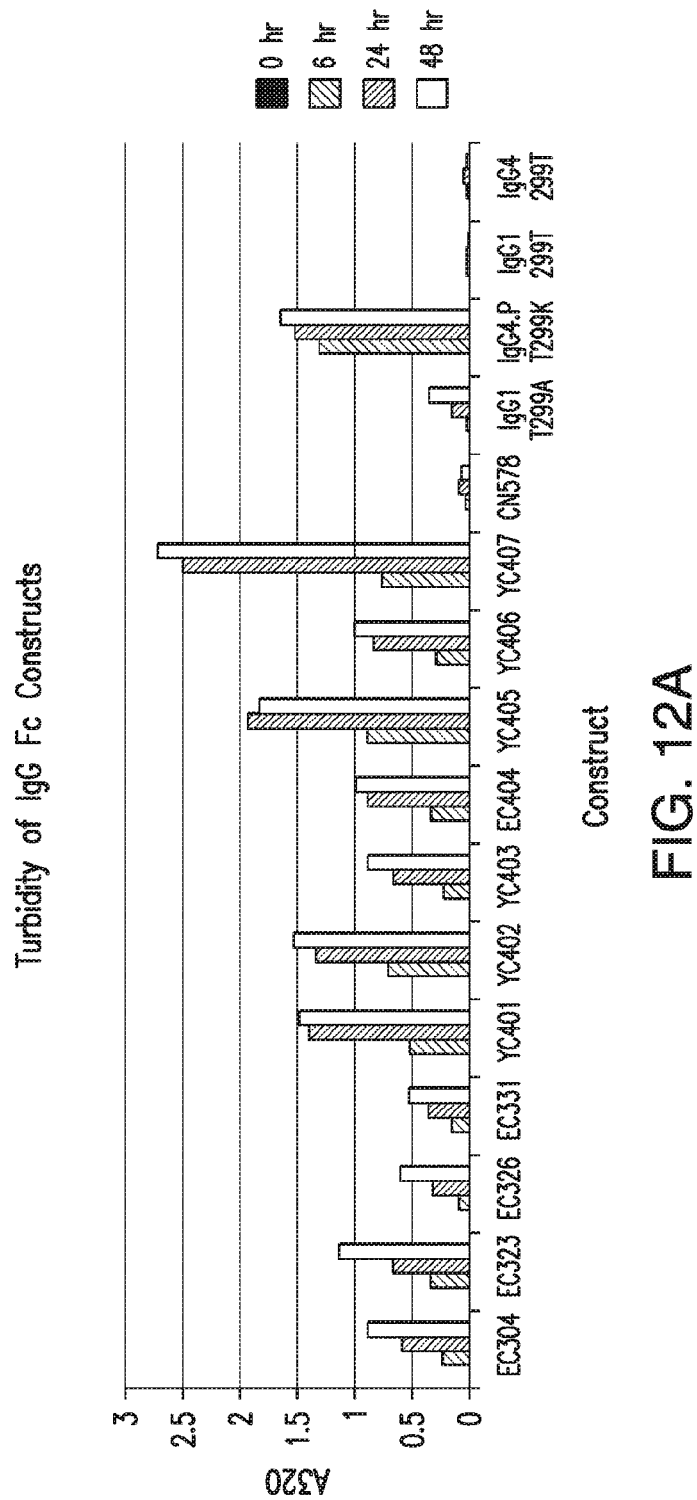
FIG. 12 depicts the turbidity (Panel A) and % monomer content (Panel B) of exemplary IgG Fc constructs of the invention following agitation.

Comparing the aglycosylated mutants in terms of turbidity (see Table 9.1 below and FIG. 12A), YC403 (aglycosylated IgG4.P T299A, T307P, L309K, and D399S) and YC406 (aglycosylated IgG4.P T299K, T307P, L309K, and D399S) showed the lowest amount of turbidity compared to the wild type YC407 (aglycosylated IgG4.P T299A). Both constructs consistently show one-third of the turbidity compared to the wild-type at each time point. The only difference between the two constructs is T299A (YC403) and T299K (YC406).

TABLE 9.1

Turbidity of Constructs at Time Points During Agitation

| Time | 0 hr | 6 hr | 24 hr | 48 hr |
|---|---|---|---|---|
| EC304 | 0 | 0.232 | 0.584 | 0.89 |
| EC323 | 0 | 0.333 | 0.672 | 1.139 |
| EC326 | 0 | 0.088 | 0.316 | 0.595 |
| EC331 | 0 | 0.157 | 0.343 | 0.54 |
| YC401 | 0 | 0.51 | 1.406 | 1.49 |
| YC402 | 0 | 0.717 | 1.331 | 1.54 |
| YC403 | 0 | 0.221 | 0.675 | 0.892 |
| YC404 | 0 | 0.334 | 0.884 | 0.977 |
| YC405 | 0 | 0.885 | 1.94 | 1.841 |
| YC406 | 0 | 0.29 | 0.838 | 0.993 |
| YC407 | 0 | 0.772 | 2.5 | 2.709 |
| CN578 | 0 | 0.029 | 0.078 | 0.072 |
| IgG1 T299A | 0 | 0.019 | 0.144 | 0.348 |
| IgG4.P T299K | 0 | 1.322 | 1.51 | 1.657 |

TABLE 9.1-continued

Turbidity of Constructs at Time Points During Agitation

| Time | 0 hr | 6 hr | 24 hr | 48 hr |
|---|---|---|---|---|
| IgG1 299T | 0 | 0.009 | 0.01 | 0.008 |
| IgG4 299T | 0 | 0.009 | 0.0465 | 0.0185 |

In comparing the % monomer (see Table 9.2 below and FIG. 12B, all of the mutant construct showed reduced aggregation over time. At the 24 hour time point, all the mutant constructs were better than the wild-type, and at the 48 hour time point, most constructs were at least 2 fold better. However, the construct that retained the highest % monomer was YC403, followed by YC402 (aglycosylated IgG4.P T299A, L309K and D399S), and then YC406 (aglycosylated IgG4.P T299K, T307P, L309K, and D399S). These constructs showed the least gradual loss in % monomer over time. The common mutation seen amongst the best ranking constructs is the L309K mutation. This data demonstrates that the mutations chosen improve the overall stability in a mechanical stress context. Comparing both agitation measurements for the aglycosylated IgG4.P constructs, the YC403 (aglycosylated IgG4.P T299A, T307P, L309K, and D399S) and YC406 (aglycosylated IgG4.P T299K, T307P, L309K, and D399S) constructs best resist the mechanical stress over time. Both molecules show additive mutations (T307P/L309K) that enable the thermal and structural stability to improve.

TABLE 9.2

% Monomer of constructs at time points during agitation

| Time | 0 hr | 6 hr | 24 hr | 48 hr |
|---|---|---|---|---|
| EC304 | 100 | 96.5 | 90.52 | 87.22 |
| EC323 | 100 | 98.16 | 96.29 | 94.37 |
| EC326 | 100 | 98.11 | 95.89 | 93.35 |
| EC331 | 100 | 100 | 100 | 100 |
| YC401 | 96.5 | 90.17 | 73.63 | 71.07 |
| YC402 | 96.6 | 89.45 | 85.49 | 80.88 |
| YC403 | 95 | 95.382 | 90.03 | 84.75 |
| YC404 | 97 | 95.45 | 83.78 | 73.5 |
| YC405 | 92.7 | 87.46 | 76.72 | 72.1 |
| YC406 | 95.5 | 94.12 | 83.89 | 74.8 |
| YC407 | 97 | 95.88 | 72.3 | 33.4 |
| CN578 | 99.73 | 100 | 100 | 99.3 |
| IgG1 T299A | 100 | 100 | 100 | 100 |
| IgG4.P T299K | 96.7 | 100 | 0 | 0 |
| IgG1 299T | 100 | 99.01 | 98.85 | 99 |
| IgG4 299T | 80.51 | 80.2 | 80.35 | 78.06 |

For IgG1 aglycosylated molecules, CN578 (aglycosylated IgG1 A299K) showed minimal turbidity and it also showed essentially no aggregation throughout the entire experiment. CN578 performs better than the IgG1 T299A and also the wild-type IgG1 299T molecule, thus showing that the A299K mutation has minimal effect on agitation for an aglycosylated IgG1 molecule. CN578 is 5-fold better in the turbidity study than the IgG1 T299A. The CN578 molecule also shows no aggregation over a 48 hour time span, which is the same result as both aglycosylated IgG1 T299A and glycosylated IgG1 299T. EC331 (which is the aglycosylated IgG4.P T299K and T307P with an IgG1 CH3 domain) performed very well compared to the other constructs, as it also maintained 100% monomer throughout the agitation study. It showed a 2-fold improvement in turbidity compared to the IgG4.P agly constructs (YC series). This data suggests that the IgG1 CH3 portion greatly aids in both the thermal and structural stability of the molecule.

Figure 12B:
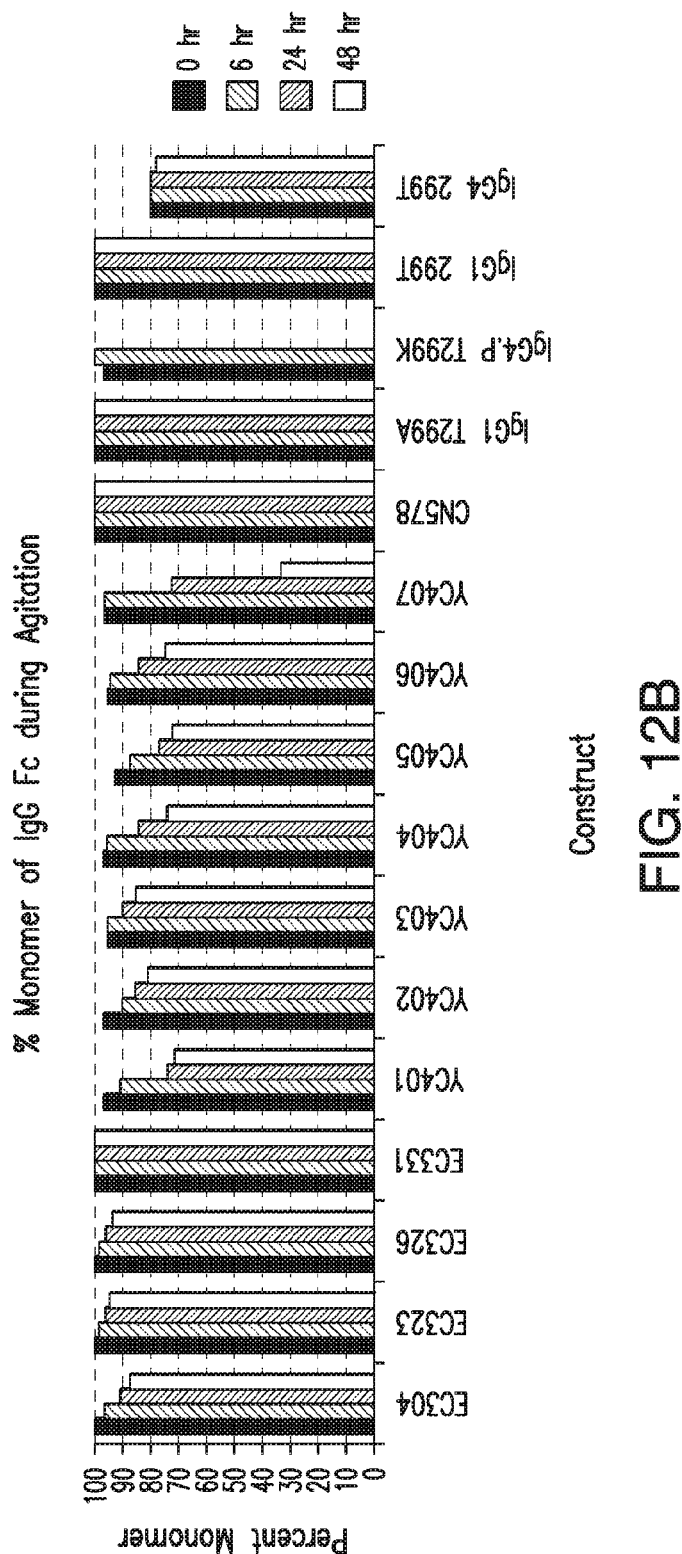

Among the glycosylated molecules, EC304 (glycosylated IgG4.P T307P, D399S), EC323 (glycosylated IgG4.P D399S, L309K), EC326 (glycosylated IgG4.P T307P, D399S, L309K), there is an improvement in % monomer over the course of the aggregation study compared to the wild-type glycosylated IgG4.P molecule (See Table 9.2 and FIG. 12B. Yet the turbidity greatly increases at every time point even up to 75-fold. Consistently, each molecule contains a D399S, so it may be possible that this mutation destabilizes the structural stability as the data shows.

B. Low pH Hold Step Studies

Figure 13:
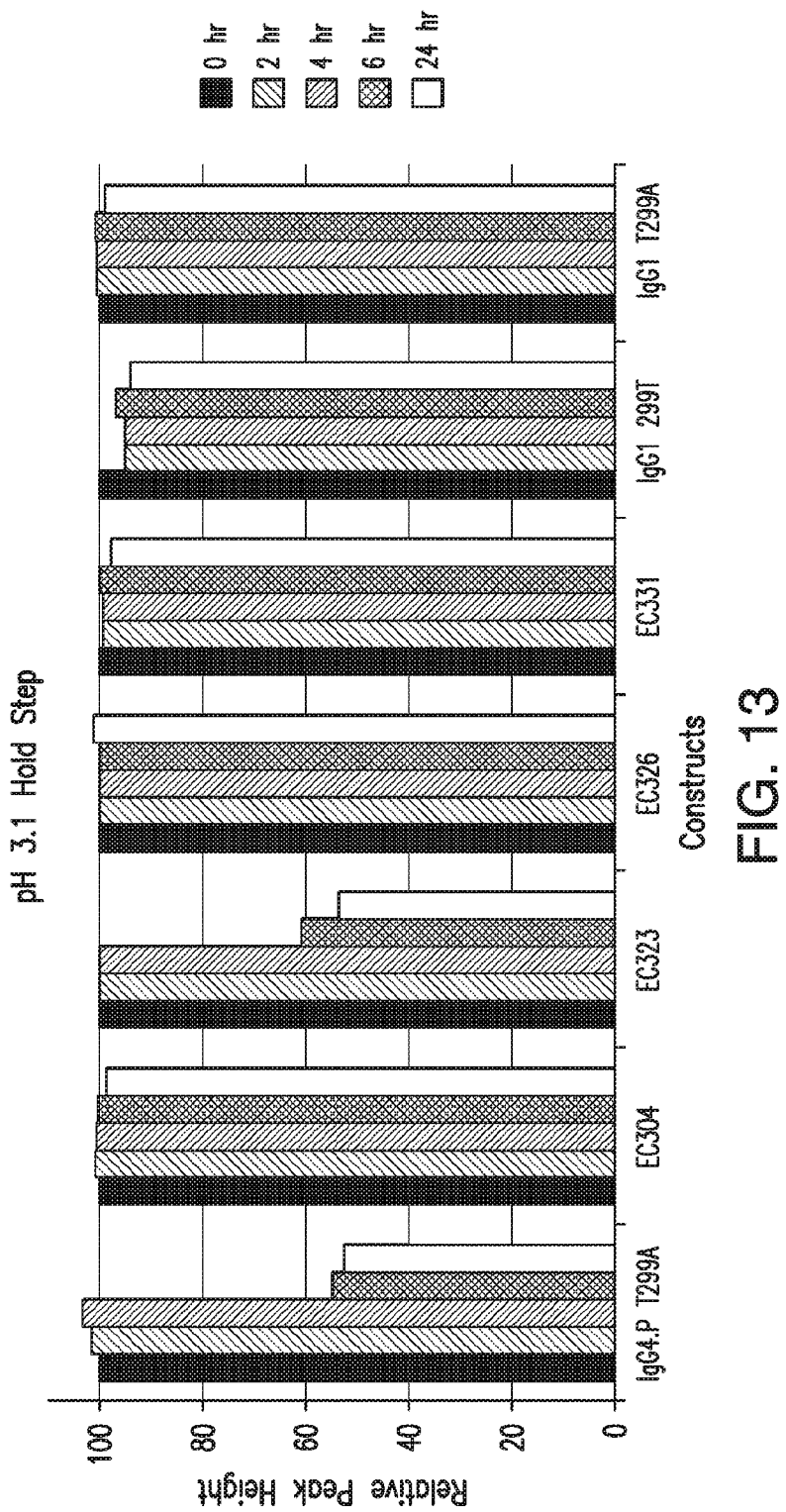
FIG. 13 depicts relative peak height over time of IgG Fc constructs at a low pH hold (pH 3.1).

It is highly desirable for a protein therapeutic to have manufacturability and scalability. Performing a pH hold step study is essential for process development. A pH hold study mimics the process development during the production and purification stages of the protein. For the production stage, reproducibility and consistency in the protein are essential for quality assurance. This method can be used to measure stability of a protein at either a high or low pH. For the study, 1 mg of protein was loaded onto a protein-A column using an AKTA™ (Pharmacia Biotech, now GE Healthcare) and eluted with acetate buffer at pH 3.1. The protein was held at the low pH for 2 hour intervals up to 6 hours. A 100 µl aliquot was taken and then run on analytical SEC to measure loss of protein due to degradation and aggregation. The results are summarized in Table 9.3 (see below) and FIG. 13.

TABLE 9.3

Relative Peak Height over time of IgG Fc's at low pH hold

| Time | 0 hr | 2 hr | 4 hr | 6 hr | 24 hr |
|---|---|---|---|---|---|
| EC304 | 100 | 100.74 | 100.53 | 100.18 | 98.82 |
| EC323 | 100 | 99.66 | 99.99 | 60.8 | 53.47 |
| EC326 | 100 | 100.83 | 99.8 | 100.16 | 101.27 |
| EC331 | 100 | 99.22 | 99.09 | 100.82 | 97.79 |
| IgG1 299T | 100 | 95.15 | 95.12 | 96.76 | 94.08 |
| IgG1 T299A | 100 | 100.39 | 100.5 | 100.91 | 99.01 |
| IgG4.P T299A | 100 | 101.68 | 103.33 | 54.84 | 52.53 |

For this study, EC304 (glycosylated IgG4.P T307P, D399S), EC323 (glycosylated IgG4.P D399S, L309K), EC326 (glycosylated IgG4.P T307P, D399S, L309K), glycosylated IgG4.P T299A, EC331 (which is the aglycosylated IgG4.P T299K and T307P with an IgG1 CH3 domain), an aglycosylated IgG1 (T299A), aglycosylated IgG4.P (T299A) and glycosylated IgG1 were selected for study. From the data, EC331 is shown to be able to withstand the low pH hold for at least 6 hours without losing much yield. This is an improvement compared to the aglycosylated IgG4 wild type control that was run. It is predicted that the other aglycosylated constructs will not lose any protein due to degradation as this construct was able to withstand the low pH hold. With both being glycosylated, EC304 and EC326 also maintain their yields, which is also comparable to the glycosylated IgG1 wild-type. EC323, which is also glycosylated, did not fare so well over time. It is hypothesized that the L309K mutation alone needs to be stabilized together with a T307P mutation, which is seen in the more stabilized EC326 construct.

Example 8. Fc Receptor Binding of Stability Engineered IgG Fc Antibodies

The effector function of the aglycosylated variant antibodies of the invention were characterized by their ability to bind Fc receptors or a complement molecule such as C1q.

A. Solution Phase Competition Biacore™ Experiments

Figure 14:
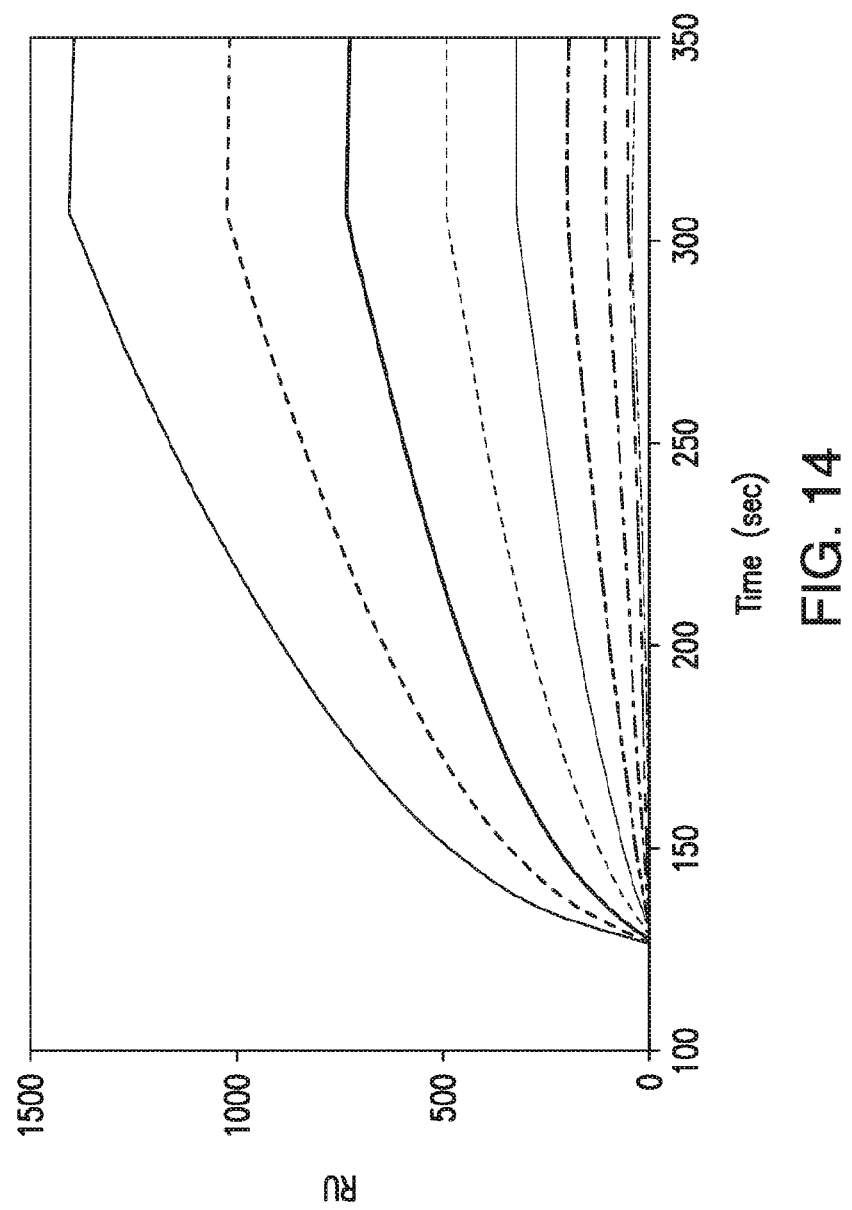
FIG. 14 depicts initial binding rates of exemplary IgG1 and IgG4 Fc constructs of the invention to Fcγ receptors as measured by solution affinity surface plasmon resonance.
Figure 15A:
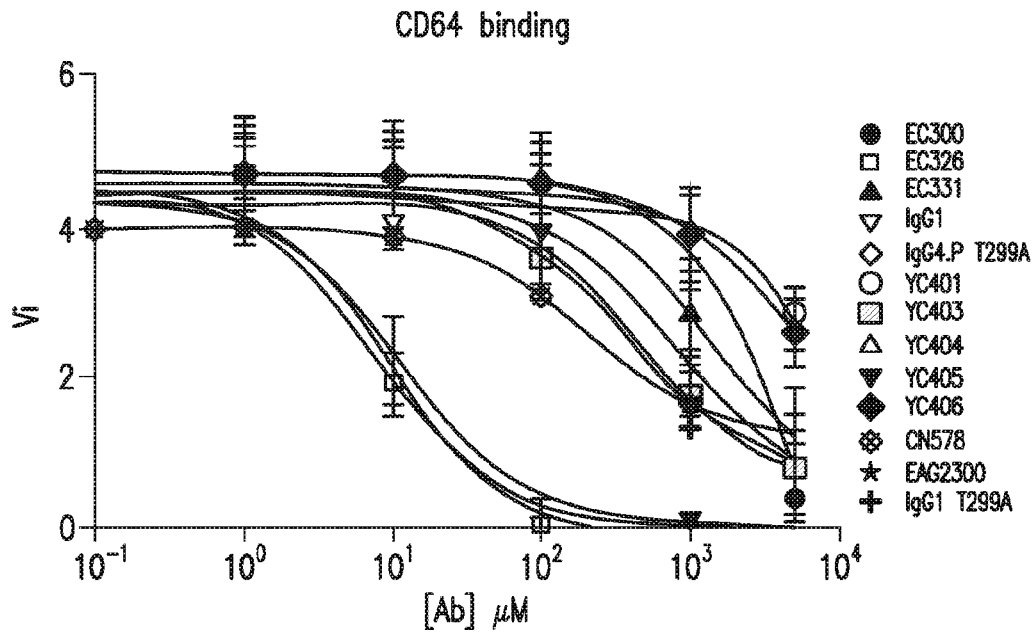
FIGS. 15A and 15B depict the titration curves used to calculate IC50s for binding of exemplary IgG1 and IgG4 Fc constructs of the invention to CD64 (FcγRI) (FIG. 15A) and CD16 (FcγRIIIa V158) (FIG. 15B).
Figure 15B:
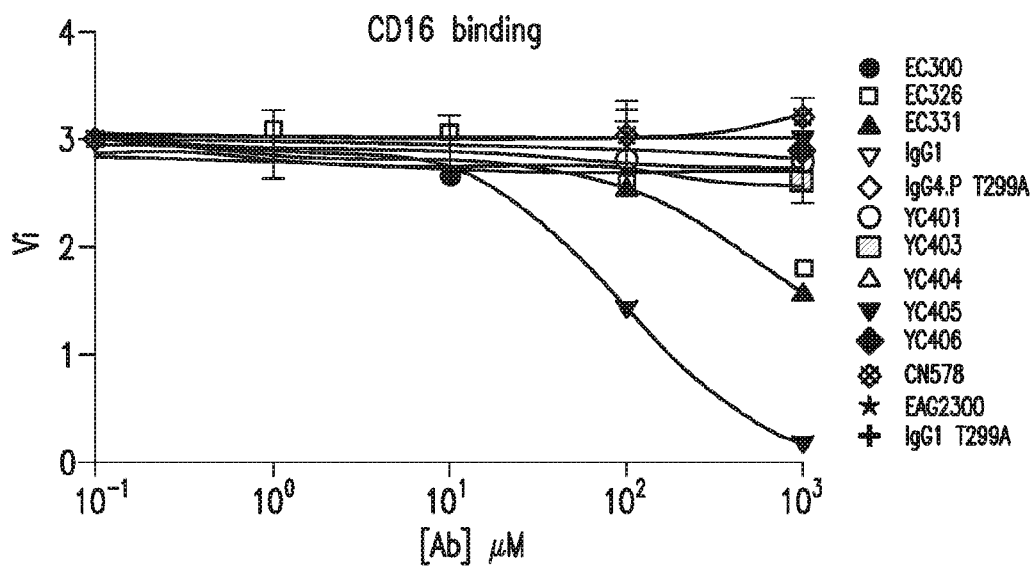

Binding to Fcγ receptors was analyzed using solution affinity surface plasmon resonance (ref Day E S, Cachero T G, Qian F, Sun Y, Wen D, Pelletier M, Hsu Y M, Whitty A. Selectivity of BAFF/BLyS and APRIL for binding to the TNF family receptors BAFFR/BR3 and BCMA. Biochemistry. 2005 Feb. 15; 44(6):1919-31.) The method utilizes conditions of so-called "mass-transport-limited" binding, in which the initial rate of ligand binding (protein binding to the senor chip) is proportional to the concentration of ligand in solution (ref BIApplications Handbook (1994) Chapter 6: Concentration measurement, pp 6-1-6-10, Pharmacia Biosensor AB). Under these conditions, binding of the soluble analyte (protein flowing over chip surface) to the immobilized protein on the chip is fast compared to the diffusion of the analyte into the dextran matrix on the chip surface. Therefore, the diffusion properties of the analyte and the concentration of analyte in solution flowing over the chip surface determine the rate at which analyte binds to the chip. In this experiment, the concentration of free Fc receptor in solution is determined by the initial rate of binding to a CM5 Biacore™ chip containing an immobilized IgG1 MAb. Into these Fc receptor solutions were titrated the stability engineered constructs (see Table 10.1 below). The half maximal (50%) inhibitory concentration ($IC_{50}$) of these constructs was demonstrated by their ability to inhibit Fc receptor from binding to the immobilized IgG1 antibody immobilized on the surface of the sensor chip. Initial binding rates were obtained from raw sensorgram data (FIG. 14). The titration curves that were used to calculate IC50's are shown in FIG. 15A for CD64 (FcγRI) and FIG. 15B for CD16 (FcγRIIIa V158). The results are shown in Table 10.1 and reported as the average of two titrations.

TABLE 10.1

FcγR affinity characterization of Fc variants

| | $IC_{50}$(uM) | |
|---|---|---|
| | CD64 | CD16 |
| EC300 | 11.19 | 563.5 |
| EC326 | 7.558 | 380.5 |
| EC331 | 2595 | >1000 |
| YC401 | 377.4 | >1000 |
| YC403 | 433.7 | >1000 |
| YC404 | >5000 | >1000 |
| YC405 | >5000 | >1000 |
| YC406 | >5000 | >1000 |
| CN578 | 1425 | >1000 |
| EAG2300 | 3021 | >1000 |
| IgG1 | 9.636 | 100.2 |
| IgG1 T299A | 205.3 | >1000 |
| IgG4.P T299A | 739 | >1000 |

Figure 16A:
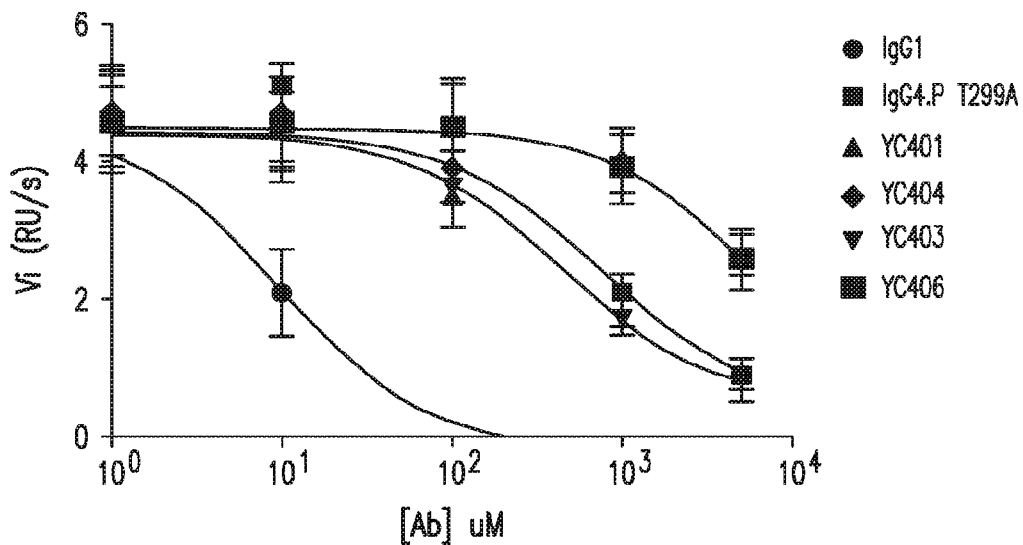
FIGS. 16A and 16B depict the titration curves highlighting the reduction in binding of the IgG1 T318K (Kabat numbering) (T299K, EU numbering) compared to IgG1 T318A (Kabat numbering) (T299A, EU numbering) and IgG1 wild type for CD64 (FcγRI) (FIG. 16A) and the binding of exemplary IgG4 Fc constructs incorporating the T318K (Kabat numbering) (T299K, EU numbering) mutation compared to other exemplary IgG4 Fc constructs incorporating the T318A (Kabat numbering) (T299A, EU numbering) mutation and IgG1 wild type for CD64 (FcγRI) (FIG. 16B).
Figure 16B:
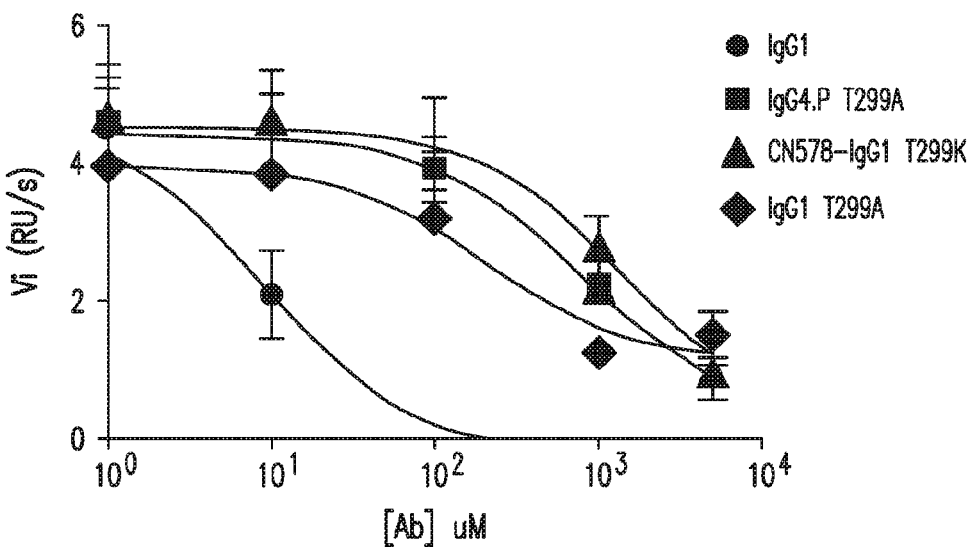

In the CD64 binding assay, the IgG1 control antibody had an $IC_{50}$ of 9.6 µM, while the IgG1 T299A (agly) and IgG4.P T299A (agly) had $IC_{50}$'s of 205 and 739 µM respectively. As expected, the IgG1 molecules have greater affinity for CD64 than the IgG4 molecule, and the aglycosylated IgG1 showed a reduced affinity compared to the glycosylated IgG1. The stability engineered glycosylated IgG4.P molecules (EC300 and EC326) had $IC_{50}$ values at about 8 µM, compared to the stability engineered aglycosylated IgG4.P molecules (EC331 and YC400 series) which ranged from 440 to >5000 µM. The $IC_{50}$'s for the stability engineered IgG4.P glycosylated molecules (EC300, EC326) were equivalent to the glycosylated IgG1 control, and the stability engineered aglycosylated IgG4.P with T299A (YC401, YC403) had the log equivalent $IC_{50}$'s as the aglycosylated IgG4.P T299A control. The stability engineered aglycosylated IgG4.P with T299K, however, showed a 1 to 2 logs greater reduction in affinity compared to the equivalent molecules with a T299A substitution FIG. 7A. This result was also observed for the stability engineered aglycosylated IgG1 T299K (CN578) that showed a log reduction in affinity compared to the aglycosylated IgG1 T299A control (FIG. 16B). In fact, the T299K substitution shifts the aglycosylated IgG1 (T299A) molecule from having greater affinity for CD64 than the aglycosylated IgG4.P T299A control, to having reduced affinity for the aglycosylated IgG1 (T299K) compared to the aglycosylated IgG4.P control (FIG. 16B). In summary, the T299K mutation reduces the affinity for CD64 in both IgG1 and IgG4 molecules.

Figure 17:
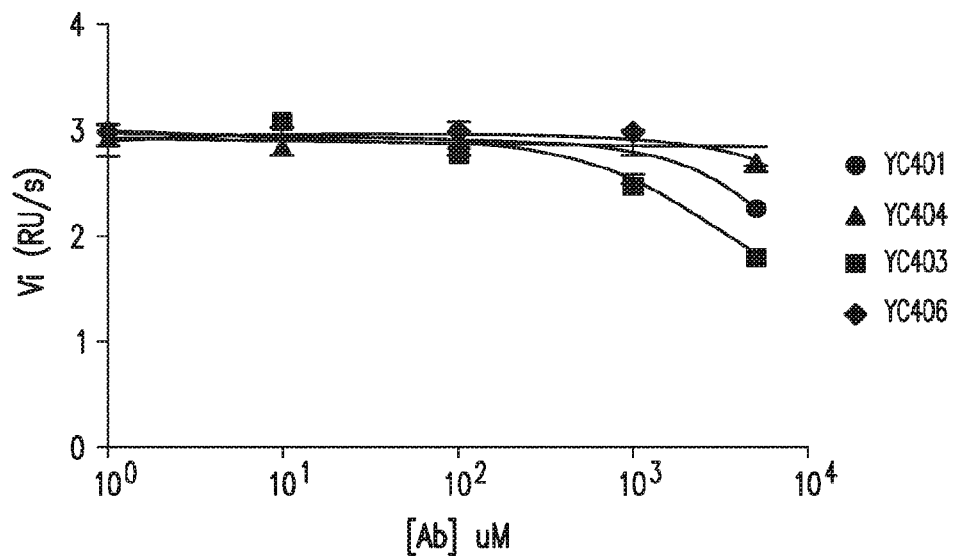
FIG. 17 depicts the binding of exemplary IgG4 Fc constructs incorporating the T299K mutation compared to other exemplary IgG4 Fc constructs incorporating the T299A mutation and IgG1 wild type for CD16 (FcγRIIIa V158).

For the CD16 assay, the IgG1 control had an $IC_{50}$ of 105 µM, while the aglycosylated IgG4.P T299A and IgG1 T299A both had $IC_{50}$'s>1000 µM. The glycosylated stability engineered IgG4.P molecules had $IC_{50}$ values at the log equivalent to the IgG1 control, and all of the stability engineered aglycosylated molecules (both IgG4.P and IgG1) had $IC_{50}$'s>1000 µM. To investigate whether T299K further reduced affinity to CD 16, two sets of constructs with the T299K substitution as the only difference (YC401, YC404 and YC403, YC406) were tested at high concentrations of antibody (5 µM). The binding curves show a reduction in the affinity to CD16 caused by the T299K mutation at the high concentration (FIG. 17). In summary, the T299K mutation reduces the affinity for CD 16 in IgG molecules.

B. C1q Binding ELISA

The C1q binding assay was be performed by coating 96 well Maxisorb™ ELISA plates (Nalge-Nunc Rochester, NY, USA) with 50 µl recombinant soluble human CD40 ligand at 10 ug/ml overnight at 4° C. in PBS. The wells were aspirated and washed three times with wash buffer (PBS, 0.05% Tween® 20) and blocked for 1 hour with 200 µl/well of block/diluent buffer (0.1 M Na2HP04, pH 7.0, 1 M NaCl, 0.05% Tween® 20, 1% gelatin). The antibodies were diluted in block/diluent buffer with 3-fold dilutions and incubated for 2 hours at room temperature.

After aspirating and washing as above, 50 J. well of 2 J. gel of Sigma human C1q (C0660) diluted in block/diluent buffer were added and incubated for 1.5 h at room temperature.

After aspirating and washing as above, 50 pll/well of sheep anti C1q (Serotec AHP033), diluted 3, 560-fold in block/diluent buffer, were added. After incubation for 1 h at room temperature, the wells were aspirated and washed as above. 50 pll/well of donkey anti-sheep IgG HRP conjugate (Jackson ImmunoResearch 713-035-147) diluted to 1:10,000 in block/diluent were then added, and the wells incubated for 1 h at room temperature.

After aspirating and washing as above, 100 all TMB substrate (420 plM TMB, 0.004% H2O2 in 0.1 M sodium acetate/citric acid buffer, pH 4.9) were added and incubated for 2 min before the reaction was stopped with 100 ul 2 N sulfuric acid. The absorbance was read at 450 nm with a Softmax® PRO instrument, and Softmax® software was used to determine the relative binding affinity (C value) with a 4-parameter fit.

The results of the experiment show both CN578 (IgG1 T299K) and YC406 (aglycosylated IgG4.P T299K, T307P, L309K, and D399S) have no measurable binding of C1q (FIG. 17) while IgG1 T299A has some residual binding.

Example 9. IgG1 CH3 Stabilizes Aglycosylated IgG4 CH2 with No Effector Function

The proteins described in section derive from the 5c8 antibody and, unless indicated otherwise, comprise a CH1 region from IgG4, a CH2 domain from IgG4 and a CH3 domain from an IgG1 or IgG4 antibody (as indicated). Protein was produced and purified as described in Example 3. The thermostability of the CH2 and CH3 domains of the modified antibodies were measured by DSC at pH 6.0 and pH 4.5 (detailed in Example 6). The effect of agitation stress was measured by analytical SEC and by turbidity measurements at A320 nm (Example 7). The effector function of the aglycosylated variant antibodies of the invention were characterized by their ability to bind Fc receptors or a complement molecule such as C1q. Binding to Fcγ receptors was analyzed using solution affinity surface plasmon resonance and binding to complement factor C1q was analyzed by ELISA (Example 6). Finally, the serum half-life was determined by pharmacokinetic studies conducted in Sprague-Dawley rats (Example 9).

The IgG4-CH2/IgG1-CH3 aglycosylated constructs were expressed in CHO as detailed in Example 5, with yields ranging from 7 to 14 mg per 1 liter culture. The introduction of the IgG1-CH3 seems to impart a greater yield (~1.5x) compared to the same construct with the CH3 from IgG4 (Table 8.1). In addition, the IgG1aglycosyl IgG4-CH2/IgG1-CH3 had increased thermal stability in the CH3 domain (Tm=85° C.) compared to the stability of the CH3 domain of the wild-type aglycosyl IgG4 (Tm=74° C., Table 12.2 and 8.2). An interesting observation is that the IgG1 CH3 is the determining feature in agitation stability (Table 12.3) because it had been previously thought that the loss of the glycans in the CH2 domain would be the dominating factors in stability.

It is observed that the EAG2412 construct (N297Q IgG4-CH2/IgG1-, i.e., 5c8 variable region (IgG1 framework), IgG4 CH1, IgG4 CH2, IgG1 CH3 with N297Q and Ser228Pro substitutions) shows a better effector function profile, with the lowest binding for CD64 and CD32, compared to the T299A and T299K IgG4-CH2/IgG1-CH3. The IgG1-CH3 was found to have no effect on the binding to the Fc γ receptors. All of the aglycosyl IgG4-CH2 domain-containing constructs do not bind to C1q.

Pharmacokinetic studies were conducted in Sprague-Dawley rats to address the stability and serum half-life of the stability engineered IgG4/IgG1 molecules. Rats were maintained in accordance with the Biogen Idec Institutional Animal Care and Use Committee, and city, state, and federal guidelines for the humane treatment and care of laboratory animals. A single bolus injection of 1 mg/kg (1 mg/ml) of the antibody diluted in phosphate-buffered saline (PBS) was administered by IV into male Sprague-Dawley rats. Rats were sacrificed at 0, 0.25, 0.5, 1, 2, 6, 24, 48, 96, 168, 216, 264, and 336 hours post-injection. Serum samples were prepared for analysis to quantify levels of the antibody. The samples were diluted in DAB supplemented with 5% normal mouse serum (Jackson ImmunoResearch 015-000-120), and the detection reagent was an Eu-labeled mouse anti-Human Fc antibody (Perkin Elmer 1244-330) used at a final concentration of 250 ng/ml. Quantitation was performed by using Excel's TREND function in comparison to a standard curve of purified antibody.

Figure 19A:
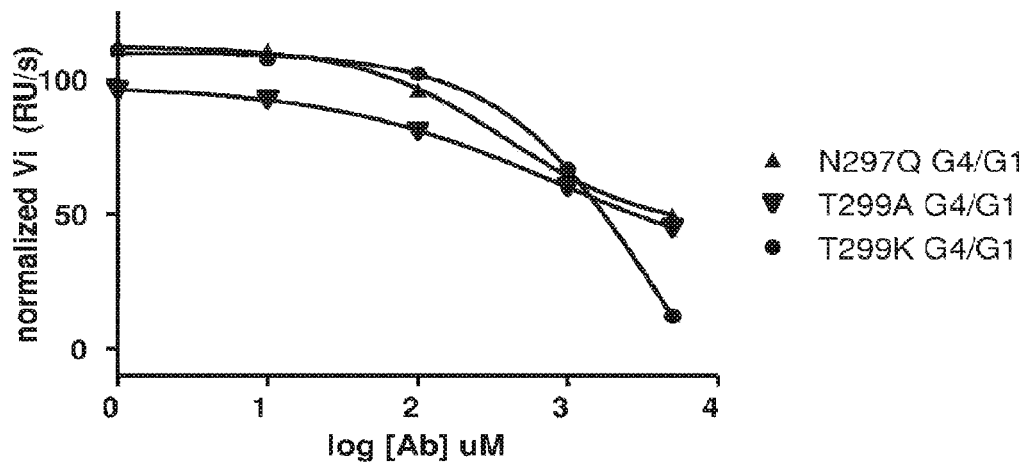
FIG. 19 panels A and B illustrate the titration curves used to evaluate binding of various Fc constructs to CD64 and CD 16, respectively. Panel C illustrates that the N314Q (Kabat numbering) (N297Q, EU numbering) IgG4-CH2/IgG1-CH3 has the same half-life as the T318A (Kabat numbering) (T299A, EU numbering) antibody (which was slightly shorter than the aglycosylated IgG1).
Figure 19B:
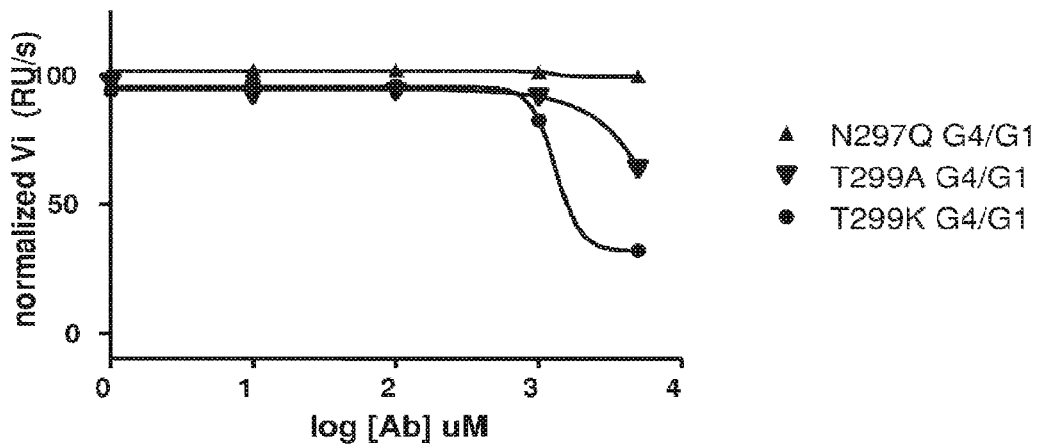
Figure 19C:
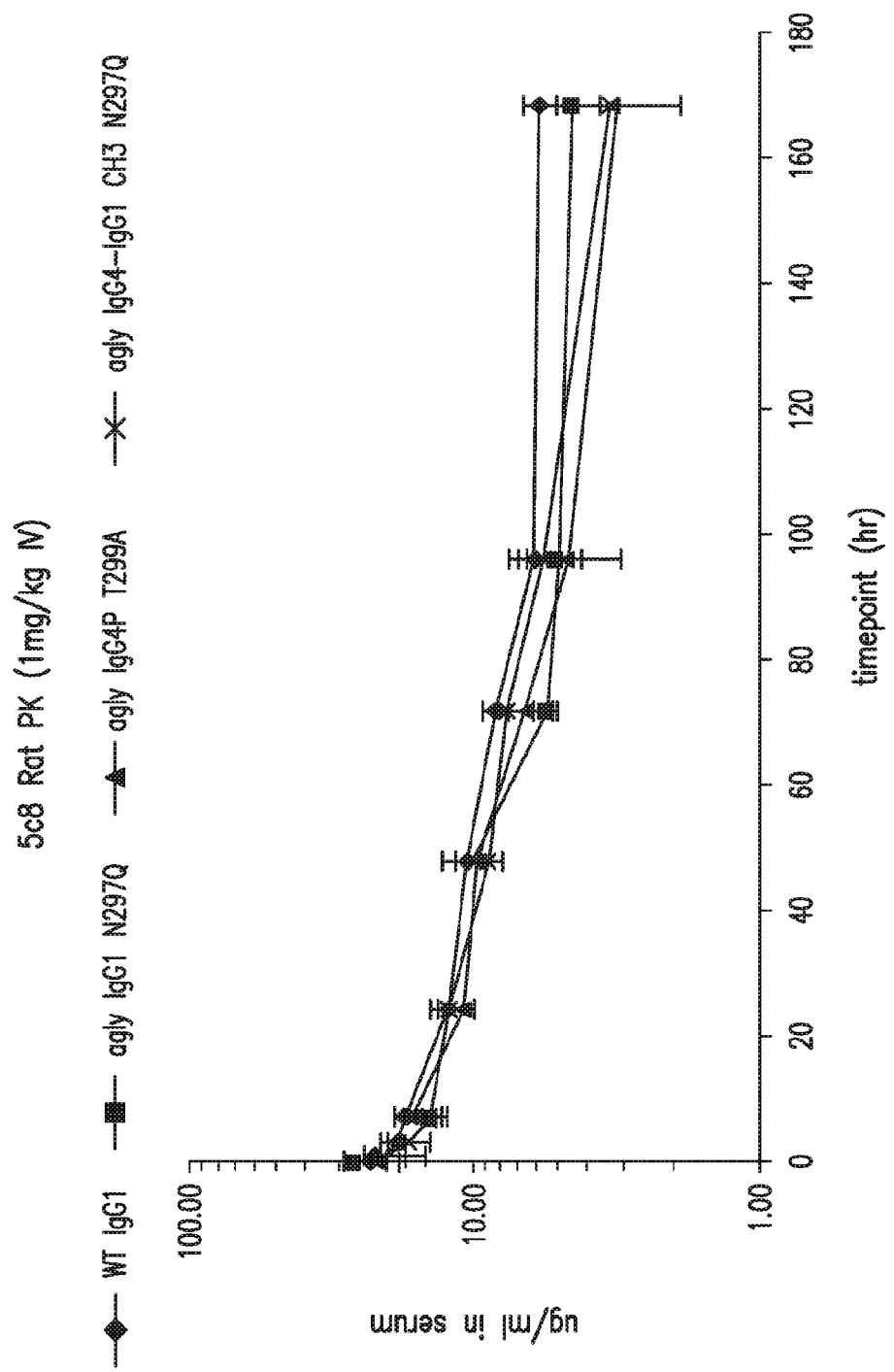

N297Q IgG4-CH2/IgG1-CH3 had the same half-life as the T299A IgG4 antibody which, as expected, was slightly shorter than the aglycolsylated IgG1 (Table 12.5). The data is plotted in FIG. 19C.

TABLE 12.1

Protein yield from IL culture and % Monomer as measured by Analytical Size-Exclusion Chromatography

| | Final AA Substitution | yield (mg) | % monomer |
|---|---|---|---|
| pEAG2296 | S228P/T299A/IgG1-CH3 | 7.24 | 98% |
| pEAG2287 | S228P/T299K/IgG1-CH3 | 14.2 | 100% |
| EAG2412 | S228P/N297Q/IgG1-CH3 | 13.75 | 99.30% |
| YC407 | S228P, T299A | 4.07 | 96.90% |
| CN579 | S228P, T299K | 11.55 | 90% |
| EAG2391 | N297Q | 7.8 | 100% |

TABLE 12.2

Melting Temperatures of IgG4-CH2/IgG1-CH3 constructs as measured

| | Final AA Substitution | pH 6.0 | | | pH 4.5 | | | Source |
|---|---|---|---|---|---|---|---|---|
| | | CH2 | CH3 | Fab | CH2 | CH3 | Fab | |
| EAG2296 | S228P/T299A/IgG1-CH3 | 54.6 | 85.2 | 76.4 | 35.1 | 77.5 | 68.1 | CHO |
| EAG2287 | S228P/T299K/IgG1-CH3 | 60 | 85.2 | 76.4 | 41.4 | 77.4 | 68.1 | CHO |
| EAG2412 | S228P/N297Q/IgG1-CH3 | 53 | 85 | 76 | 35 | 78 | 68 | CHO |

TABLE 12.3

Turbidity and % Monomer of Constructs at Time Points During Agitation

| | | Turbidity | | | | % Monomer | | | |
|---|---|---|---|---|---|---|---|---|---|
| | Time | 0 hr | 6 hr | 24 hr | 48 hr | 0 hr | 6 hr | 24 hr | 48 hr |
| EAG2296 | S228/T299A/IgG1-CH3 | 0 | 0.007 | 0.16 | 0.12 | 100 | 100 | 96.2 | 95.3 |
| EAG2287 | S228P/T299K/IgG1-CH3 | 0 | 0.005 | 0.077 | 0.045 | 100 | 100 | 100 | 95.7 |
| EAG2412 | S228P/N297Q/IgG1-CH3 | 0 | 0.006 | 0.18 | 0.14 | 100 | 100 | 97.3 | 95.2 |

TABLE 12.4

FcγR affinity characterization of IgG4/IgG1 variants (NB indicates no binding)

| | IC$_{50}$(uM) | | |
|---|---|---|---|
| | CD64 | CD32 | CD16 |
| EAG2296 | >5000 | >7000 | 1324 |
| EAG2287 | 4040 | >7000 | NB[a] |
| EAG2412 | >5000 | NB[a] | >5000 |

[a]No binding observed

TABLE 12.5

Pharmacokinetics of Stability engineered Constructs in Rats

Pharmacokinetics of Stability Engineered Constructs in Male Sprague-Dawley Rats after a Single IV Bolus Injection of 1 mg/kg

| Compound_ID | Animal Info | $C_{0, extrapolated}$ Mg/mL | $T_{1/2}$ Hr | AUC Hr*mg/L | CL mL/hr/kg | Vss mL/kg |
|---|---|---|---|---|---|---|
| IgG1 | Rat #1 | 26 | 149 | 2,900 | 0.34 | 73 |
| | Rat #2 | 18 | 143 | 2,425 | 0.41 | 84 |
| | Rat #3 | 25 | 83 | 1,918 | 0.52 | 63 |
| | N | 3 | 3 | 3 | 3 | 3 |
| | Mean | 23 | 125 | 2,414 | 0.43 | 73 |
| | SE | 2 | 21 | 284 | 0.05 | 6 |
| | CV % | 18 | 29 | 20 | 21 | 15 |
| N297Q IgG1 | Rat #4 | 24 | 134 | 1,919 | 0.52 | 86 |
| | Rat #5 | 22 | 128 | 2,360 | 0.42 | 76 |
| | Rat #6 | 30 | 66 | 1,557 | 0.64 | 60 |
| | N | 3 | 3 | 3 | 3 | 3 |
| | Mean | 25 | 109 | 1,945 | 0.53 | 74 |
| | SE | 2 | 22 | 232 | 0.06 | 7 |
| | CV % | 15 | 35 | 21 | 21 | 18 |
| T299A IgG4.P | Rat #7 | 26 | 78 | 1,709 | 0.59 | 64 |
| | Rat #8 | 20 | 49 | 1,046 | 0.96 | 66 |
| | Rat #9 | 26 | 98 | 1,964 | 0.51 | 69 |
| | N | 3 | 3 | 3 | 3 | 3 |
| | Mean | 24 | 75 | 1,573 | 0.68 | 66 |
| | SE | 2 | 14 | 273 | 0.14 | 1 |
| | CV % | 15 | 33 | 30 | 35 | 3 |
| N297Q IgG4.P CH2/IgG1-CH3 | Rat #10 | 21 | 87 | 1,802 | 0.55 | 70 |
| | Rat #11 | 25 | 75 | 1,574 | 0.64 | 67 |
| | Rat #12 | 29 | 70 | 1,552 | 0.64 | 65 |
| | N | 3 | 3 | 3 | 3 | 3 |
| | Mean | 25 | 78 | 1,643 | 0.61 | 67 |
| | SE | 2 | 5 | 80 | 0.03 | 1 |
| | CV % | 16 | 11 | 8 | 8 | 4 |

Example 10. T299 is a Determinant of Stability and Effector Function

The proteins described in this section are all derived from the 5c8 antibody and, unless indicated otherwise, comprise a CH1, CH2 and CH3 domain of an IgG1 antibody. Protein was produced and purified as described in Example 5. The effects of the mutations on the melting temperatures of the CH2 and CH3 domains were measured by DSC at pH 6.0 and pH 4.5 (detailed in Example 6). The effector function of the aglycosylated variant antibodies of the invention was characterized by their ability to bind Fc receptors or a complement molecule such as C1q. Binding to Fcγ receptors was analyzed using solution affinity surface plasmon resonance and binding to complement factor C1q was analyzed by ELISA (Example 8).

The IgG1 T299X and N297X/T299K aglycosylated constructs were expressed in CHO as detailed in Example 5, with yields ranging from 7 to 30 mg per 1 liter culture (Table 13.1). The addition of secondary mutations at position N297 in combination with T299K did decrease the thermal stability of the CH2 domain by 1.5 to 4.4° C. (Table 13.2). In addition, the T299X mutations showed the greatest gain in stability from the positively charged side chains of Arg (T299R) and Lys (T299K) (Table 13.2). The two polar side chains, Asn (T299N) and Gln (T299Q), both showed a greater stability compared to T299A but not as great as the positively charged side chains. Proline (T299P) showed a small decrease in stability compared to T299A and the larger hydrophobic side chain Phe (T299F) decreased the thermal stability of the CH2 domain by 2.4° C. Finally, the negatively charged side chain Glu (T299E) had very little effect on the CH2 thermal stability. These results demonstrate the novel properties of substituting a positively charged side chain at position T299 to increase thermal stability in the CH2 domain.

Figure 20A:
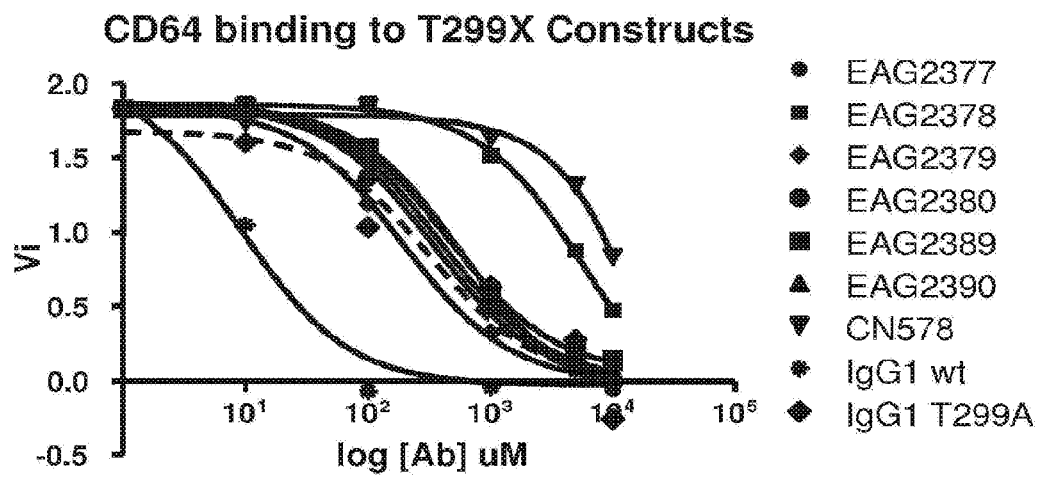
FIG. 20 panel A illustrates titration curves used to evaluate binding of T318X (Kabat numbering) (T299X, EU numbering) constructs to CD64 and that positively charged side chains T318R (Kabat numbering) (T299R, EU numbering) and T318KA (Kabat numbering) (T299K, EU numbering) impart low affinities for CD64. Panel B illustrates titration curves used to evaluate binding of CD64 to various alternative constructs. Panels C and D illustrate titration curves used to evaluate binding of constructs to CD32aR and panels E and F illustrate binding of constructs to CD16. Panels G and H illustrate the results of a C1q ELISA.
Figure 20B:
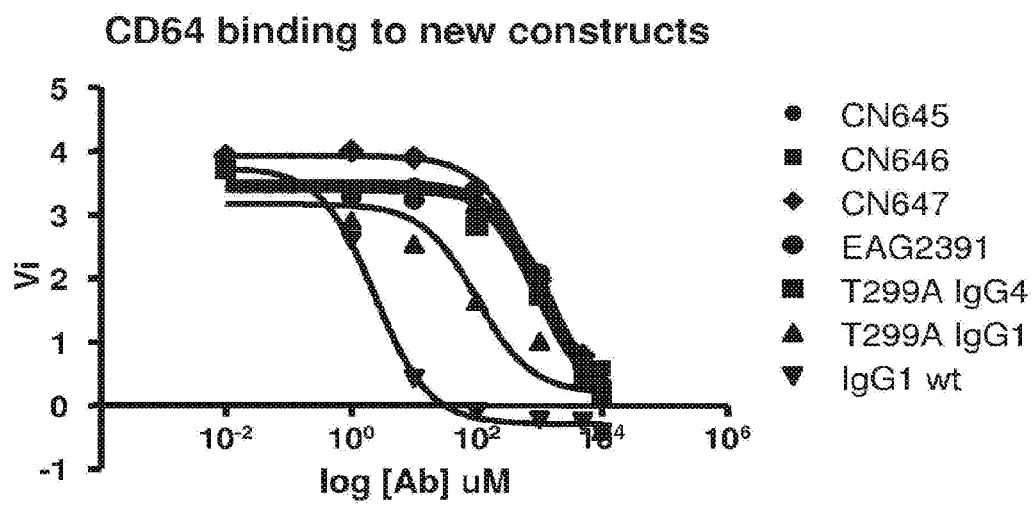
Figure 20C:
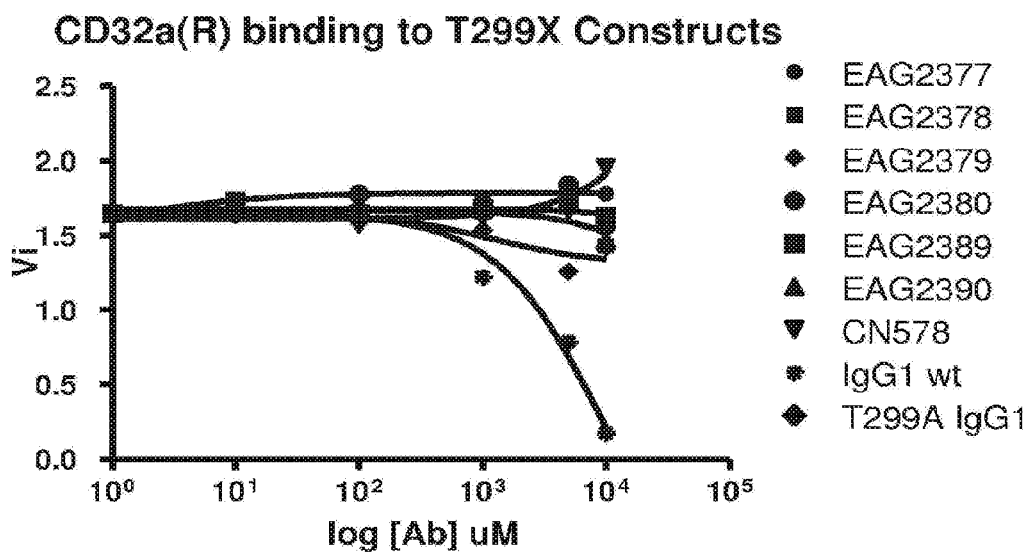
Figure 20D:
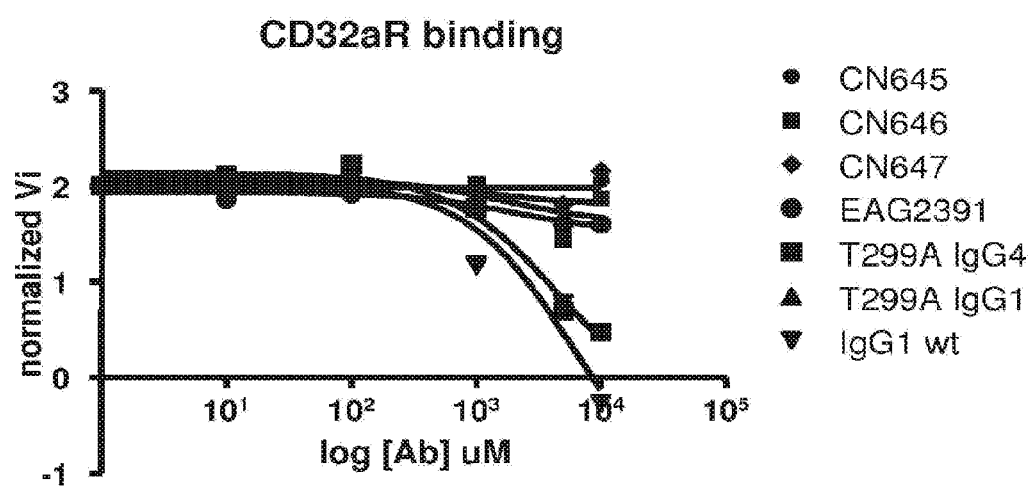
Figure 20E:
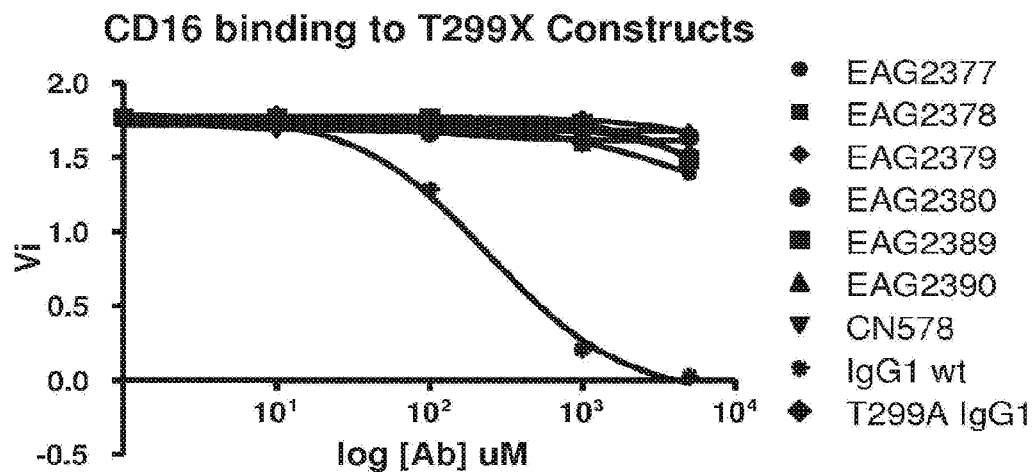
Figure 20F:
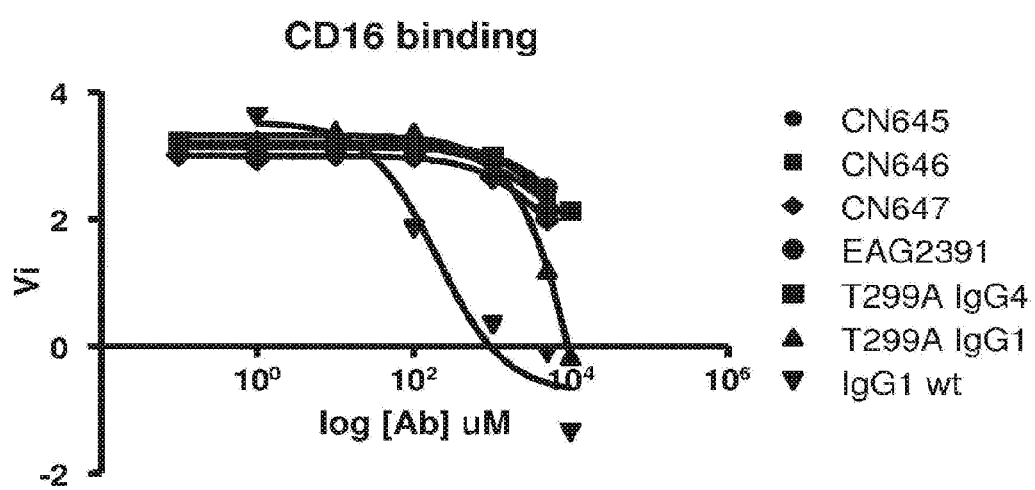
Figure 20G:
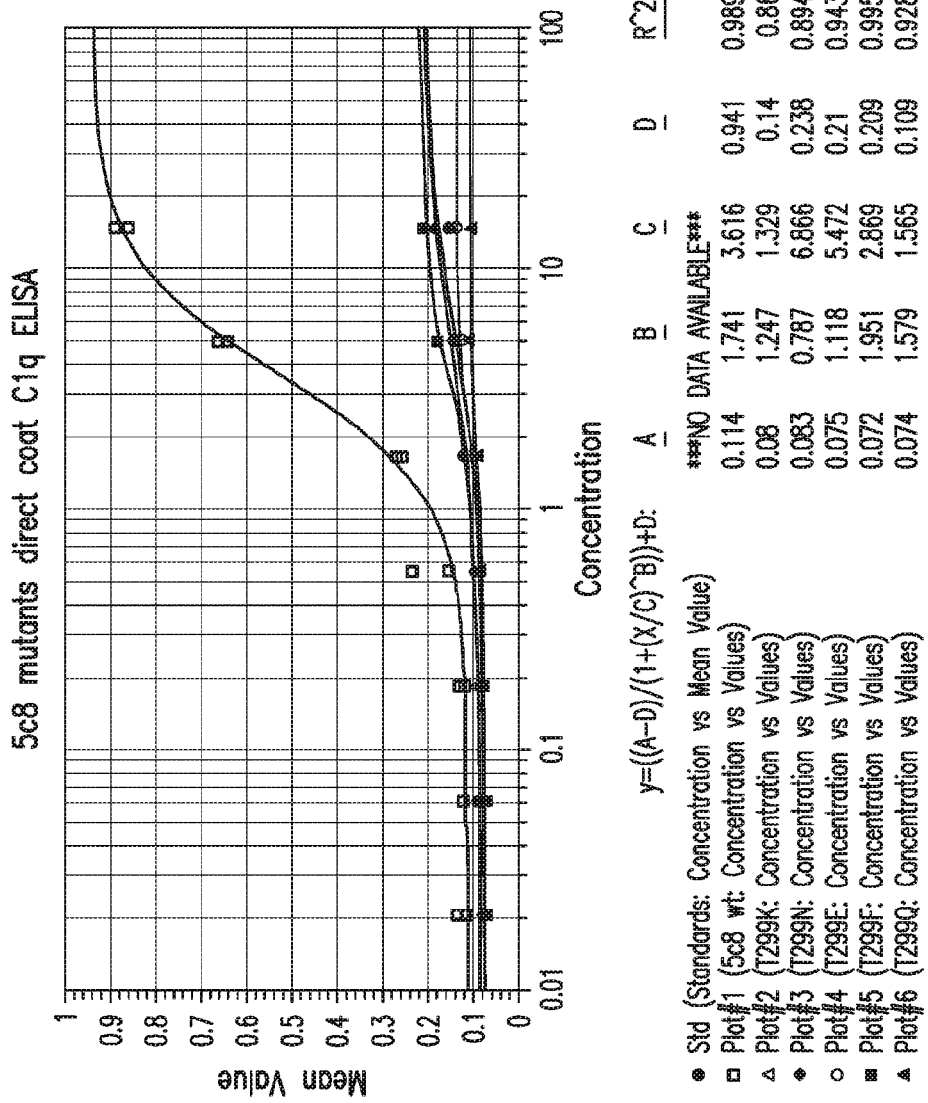
Figure 20G:
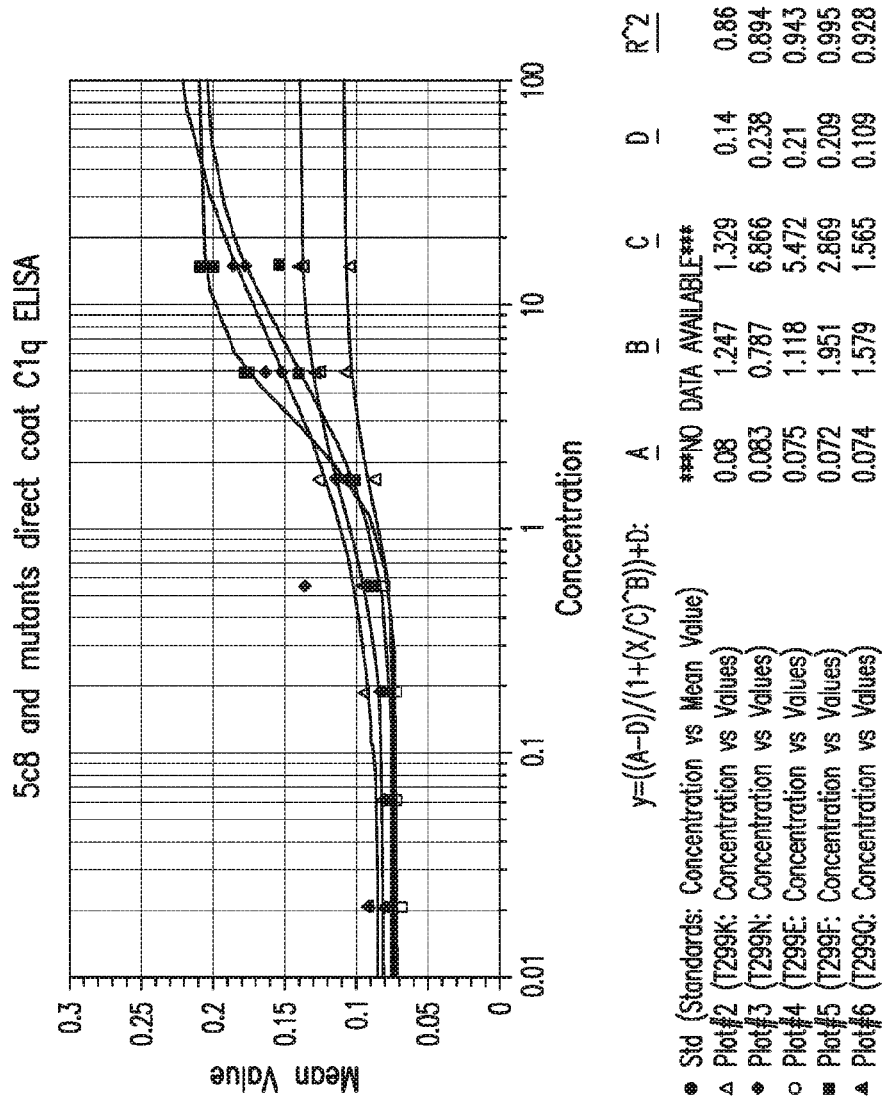
Figure 20H:
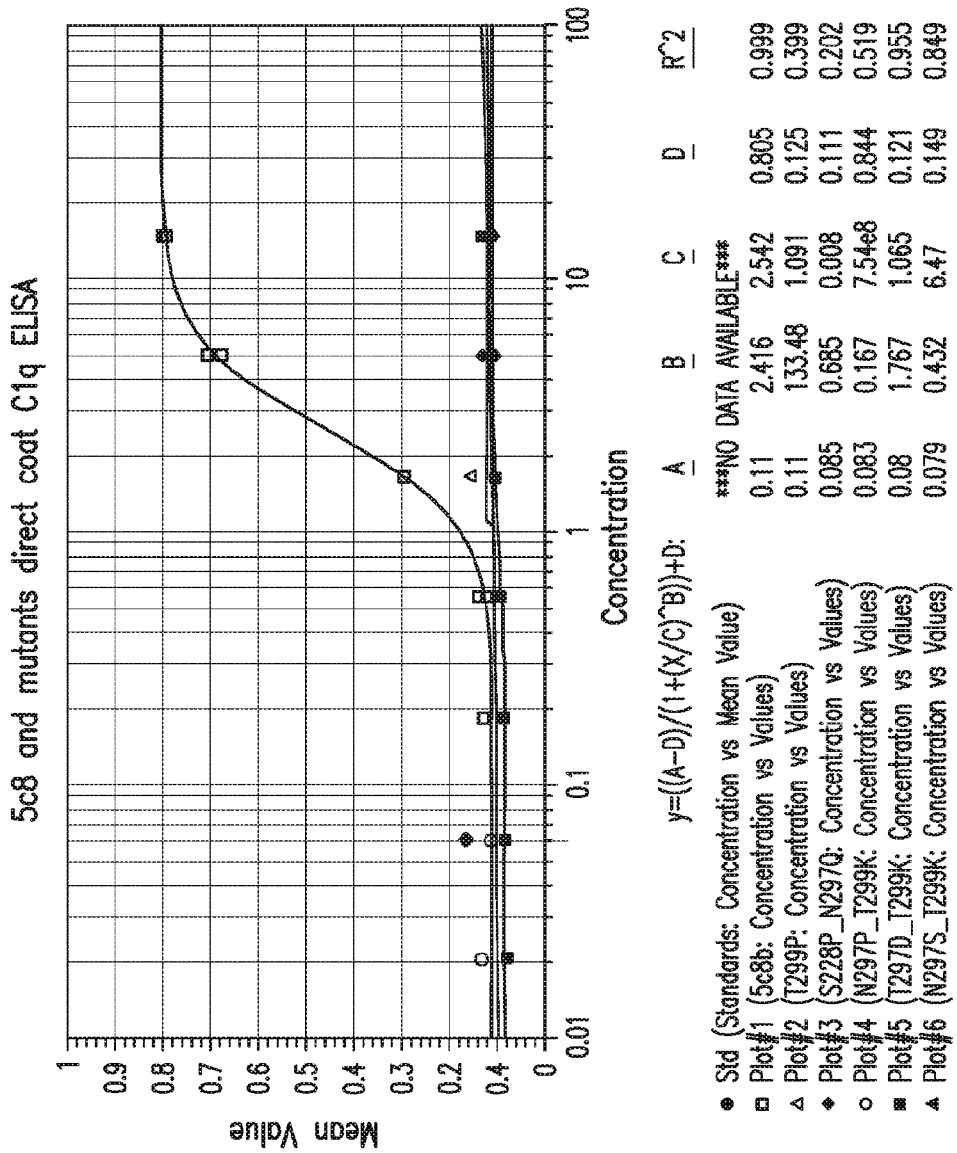
Figure 20H:
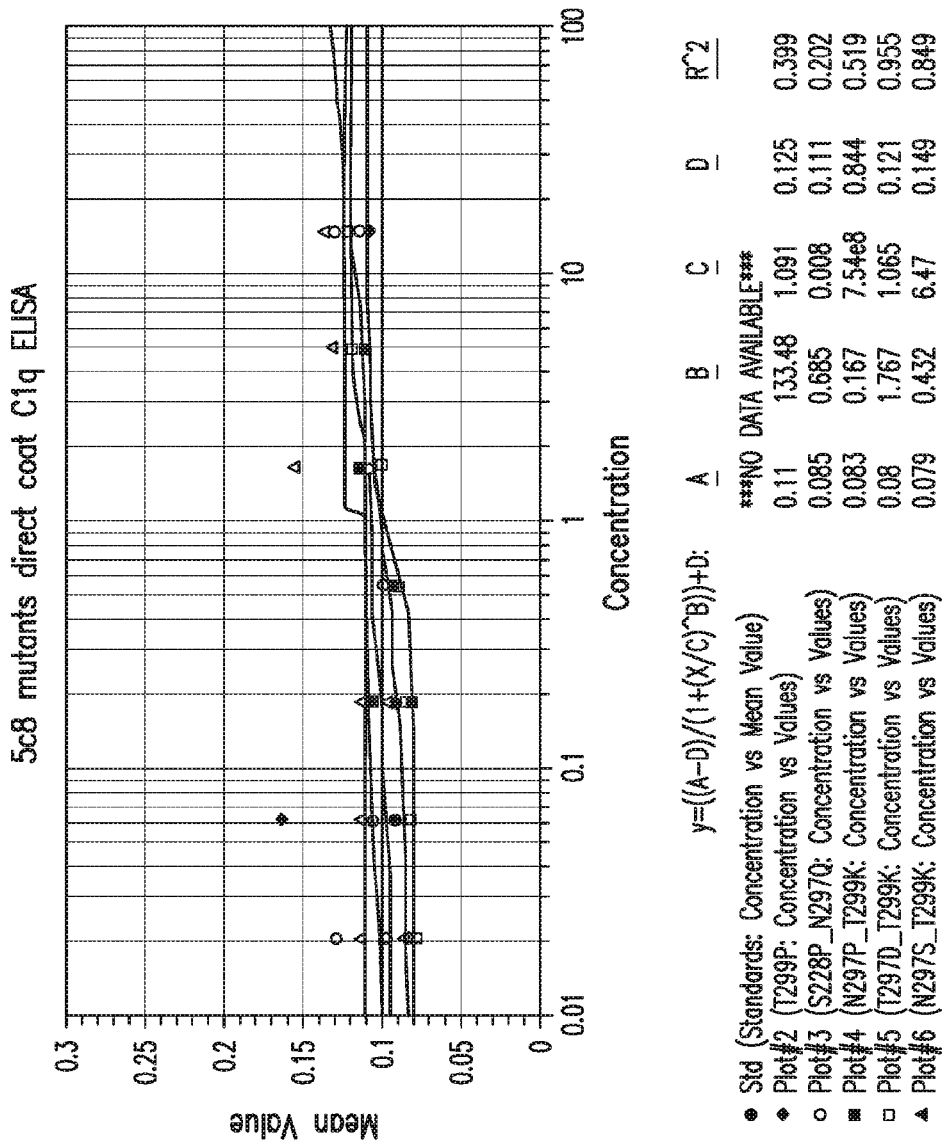

It is observed that the N297X, T299K mutations (CN645, CN646, and CN647) all slightly increased the affinity for CD64 while maintaining the very low affinity for CD32a and CD16 (FIGS. 20B, 20D and 20F). The T299X mutations showed a consistently low affinity to CD 16, however, the low affinity for CD32a was increased in the case of T299E (Table 13.3 and FIGS. 20C, 18E). It is also interesting to note, that only the positively charged side chains T299R and T299K impart low affinities for CD64 (Table 13.3 and FIG. 20A). Finally, T299K, T299P and T299Q are dead to trace C1q binding; T299N, T299E, T299F show slightly elevated but still very low binding to C1q (FIGS. 20G and 20H). N297P/T299K, N297D/T299K, and N297S/T299K show no binding to C1q (FIG. 20H).

TABLE 13.1

Protein yield from IL culture and % Monomer as measured by Analytical Size-Exclusion Chromatography

| | Final AA Substitution | yield (mg) | % monomer |
|---|---|---|---|
| CN647 | N297D, T299K | 7.4 | 100% |
| CN646 | N297S, T299K | 30.47 | 98.50% |
| CN645 | N297P, T299K | 9.3 | 100% |
| EAG2389 | T299Q | 12.6 | 100% |
| EAG2390 | T299P | 22.3 | 100% |
| EAG2377 | T299N | 8.7 | 100% |
| EAG2378 | T299R | 14.1 | 100.00% |
| EAG2379 | T299E | 10.1 | 100% |
| EAG2380 | T299F | 12.6 | 100% |

TABLE 13.2

Melting Temperatures of T299X constructs as measured by DSC

| | Final AA Substitution | pH 6.0 | | | pH 4.5 | | | Source |
|---|---|---|---|---|---|---|---|---|
| | | CH2 | CH3 | Fab | CH2 | CH3 | Fab | |
| | IgG1 agly (T299A) | 58.8 | 85.3 | 77.2 | 45.1 | 77 | 68.4 | CHO |
| | IgG1 wt | 71.5 | 84.9 | 77.48 | 60 | 75.5 | 69 | CHO |
| CN578 | T299K | 65.4 | 85.22 | 77.7 | 47.6 | 72.22 | 67.8 | CHO |
| CN647 | N297D, T299K | 63.9 | 85.2 | 77.5 | 49.3 | 74 | 69.5 | CHO |
| CN646 | N297S, T299K | 61 | 84.3 | 77.5 | 44.5 | 74.2 | 70.1 | CHO |
| CN645 | N297P, T299K | 62.1 | 85.3 | 77.6 | 45.6 | 73.5 | 70 | CHO |
| EAG2389 | T299Q | 61.4 | 85.1 | 76.8 | | | | CHO |
| EAG2390 | T299P | 58.2 | 85 | 76.9 | | | | CHO |
| EAG2377 | T299N | 61.9 | 85 | 76.7 | | | | CHO |
| EAG2378 | T299R | 64.9 | 85.3 | 77.7 | | | | CHO |
| EAG2379 | T299E | 59.4 | 85.1 | 76.8 | | | | CHO |
| EAG2380 | T299F | 56.4 | 85.1 | 77.5 | | | | CHO |

TABLE 13.3

FcγR affinity characterization of T299X variants (NB indicates no binding)

| | IC$_{50}$(uM) | | |
|---|---|---|---|
| | CD64 | CD32a | CD16 |
| CN578 | >6000 | >6000 | 1324 |
| CN645 | 4389 | >6000 | >1000 |
| CN646 | 3165 | >6000 | >1000 |
| CN647 | 4476 | >6000 | >1000 |
| EAG2389 | 455 | >6000 | >1000 |
| EAG2390 | 392 | >6000 | >1000 |
| EAG2377 | 586 | >6000 | >1000 |
| EAG2378 | 5966 | >6000 | >1000 |
| EAG2379 | 196 | 1279 | >1000 |
| EAG2380 | 345 | >6000 | >1000 |

Example 11. Stabilized Fc Constructs Show the Application of Stability Mutants are Independent of Fab The proteins described in this section comprise binding sites derived from the 5c8 antibody. The EAG2476 construct comprises Fc moieties from an IgG4 immunoglobulin molecule and EAG2478 comprises Fc moieties from an IgG1 molecule (EAG2476 and EAG2478 are the Fc versions (no Fab) of YC406 and CN578 constructs, respectively).

Figure 21A:
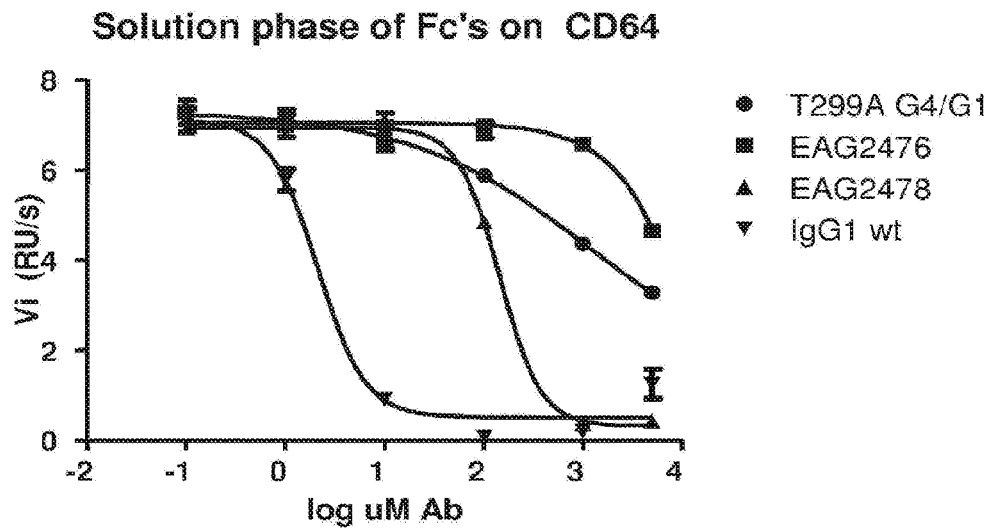
FIG. 21 panel A illustrates titration curves used to evaluate binding of constructs to CD64 and panel B illustrates titration curves used to evaluate the binding of constructs to CD16.
Figure 21B:
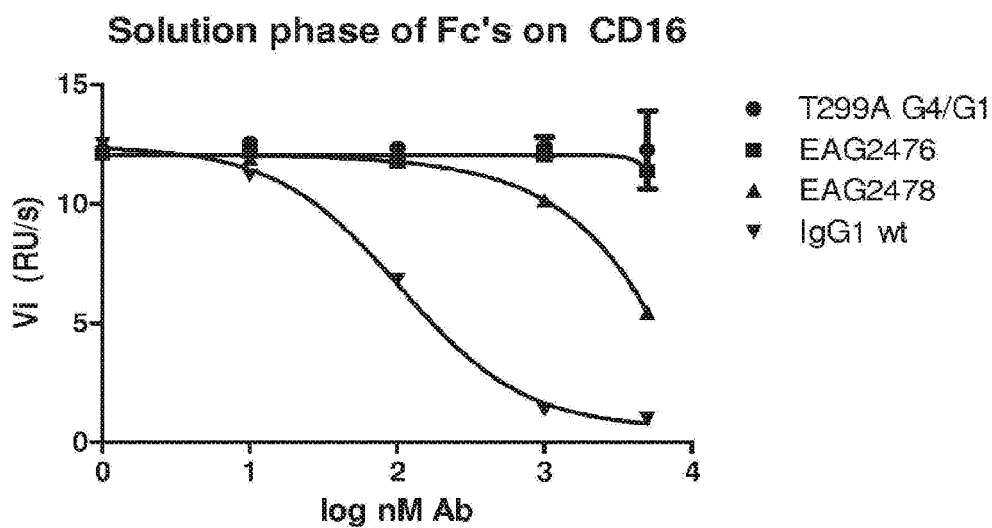

Protein was produced and purified as described in Example 5. The effects of the mutations on the melting temperatures of the CH2 and CH3 domains were measured by DSC at pH 6.0 (detailed in Example 6). The effector function of the aglycosylated variant antibodies of the invention are shown in FIG. 21. The antibodies were characterized by their ability to bind Fc receptors. Binding to Fcγ receptors was analyzed using solution affinity surface plasmon resonance (Example 8).

The stabilized Fc aglycosylated constructs were expressed in CHO as detailed in Example 5, with yields detailed in (Table 14.1). The mutations in the CH2 domain (T299K, T307P and L309K) showed the same thermal stability in the presence or absence of the Fab (Table 14.2) as well as having the same Fc γ receptor binding affinities (Table 14.3). Taken together, the stabilizing mutations detailed in this invention are Fab independent as expected and are applicable to stabilizing the Fc domain regardless of the Fab contribution.

TABLE 10.1

Protein yield from 4L culture and % Monomer as measured by Analytical Size-Exclusion Chromatography

|  | Final AA Substitution | yield (m) | % monomer |
|---|---|---|---|
| EAG2476 | YC406-Fc | 207.4 | 96.50% |
| EAG2478 | CN578-Fc | 184.8 | 96.30% |

TABLE 10.2

Melting Temperatures of Fc constructs as measured by DSC

|  |  | pH 6.0 | | |
|---|---|---|---|---|
|  | Final AA Substitution | CH2 | CH3 | Fab |
| EAG2476 | YC406-Fc | 65 | 67 |  |
| YC406 | S228P, T299K, T307P, D399S, L309 | 66.2 | 74.1 | 77.23 |
| EAG2478 | CN578-Fc | 66 | 84 |  |
| CN578 | T299LK (IgG1) | 65.4 | 85.22 | 77.7 |

TABLE 10.3

FcyR affinity characterization of T299X variants (NB indicates no binding)

|  | IC$_{50}$ (uM) | |
|---|---|---|
|  | CD64 | CD16 |
| EAG2476 | >5000 | 1324 |
| YC406 | >5000 | >1000 |
| EAG2478 | >5000 | −6000 |
| CN578 | >5000 | >5000 |

Example 12

To produce an antibody of the invention with desirable properties, including thermal stability, less precipitation upon purification, and improved titer of antibody production from antibody-secreting cells, numerous antibody constructs were generated with a light chain comprising the variable light chain sequence of SEQ ID NO: 11 attached to a human kappa light chain constant region and a heavy chain comprising the variable heavy chain sequence of SEQ ID NO: 4 attached to various heavy chain constant regions. Among the various heavy chain constant regions tested, the sequence changes resulted in surprisingly large results.

For example, coupling the variable heavy chain of SEQ ID NO: 4 to a Fc region comprising CH1, hinge with a S228P mutation (EU numbering), CH2, and CH3 region of a human IgG4, where the IgG4 had been aglycosylated by eliminating the N-linked glycosylation motif, NXS/T, with amino acid changes at asparagine residue 297 or at threonine residue 299 (EU numbering) resulted in an antibody with poor thermal stability and a propensity to precipitate upon exposure to low pH during Protein A elution. Surprisingly, when a chimeric Fc region comprising the CH1, hinge with a S228P mutation (EU numbering), and CH2 of human IgG4 and a N297Q mutation (EU numbering) in the CH2 domain coupled to the CH3 region of human IgG1 was used to make an antibody heavy chain comprising the variable heavy chain sequence of SEQ ID NO: 4 and a light chain comprising the variable light chain sequence of SEQ ID NO: 11 attached to a human kappa light chain constant region, the resulting antibody had increased thermal stability that correlated with less precipitation upon purification, and increased production of antibody from antibody-producing cells. In other words, an antibody containing the variable light chain comprising the sequence of SEQ ID NO: 11 attached to a human kappa light chain constant region and the variable heavy chain comprising the sequence of SEQ ID NO: 4 attached to a chimeric Fc region comprising the CH1, hinge with a S228P mutation (EU numbering), and CH2 with a N297Q mutation (EU numbering) of human IgG4 coupled to the CH3 region of human IgG1, had surprisingly higher thermal stability, lower precipitation upon purification of the antibody, and higher antibody yield from antibody-producing cells, particularly when compared to the aglycosylated human IgG4 with an S228P (EU index numbering).

Example 13. Protein Conformation, Dynamics and Structure of Stabilized Effectorless Antibodies as Determined by Hydrogen/Deuterium Exchange Mass Spectroscopy and X-Ray Crystallography Structure and dynamics contribute significantly to the function of proteins. Understanding the underlying structural mechanisms is critical to explaining observed functional effects. For this reason, we have examined the effects of the previously detailed gain-in-stability mutations on protein structure and dynamics by both hydrogen/deuterium exchange mass spectroscopy (HfDX MS) and x-ray crystallography.

A. Hydrogen/Deuterium Exchange Mass Spectroscopy

Detecting hydrogen/deuterium exchange by mass spectroscopy is an approach for characterizing protein dynamics and conformation. Protein dynamics/conformation affects the rate of exchange of deuterium for hydrogen in proteins, therefore measuring the deuteration of proteins over time can illuminate changes to conformation when a protein structure is modified (such as with mutations). Therefore, we examined the effects of the stabilizing mutations on the hydrogen/deuterium exchange of our aglycosylated antibody Fc backbone.

Antibody (in 50 mM sodium phosphate, 100 mM sodium chloride H2O, pH 6.0) was diluted 20-fold with 50 mM sodium phosphate, 100 mM sodium chloride, D20, pD 6.0 and incubated at room temperature for various amounts of time (10 s, 1, 10, 60, and 240 min). The exchange reaction was quenched by reducing the pH to 2.6 with a 1:1 dilution with 200 mM sodium phosphate, 0.5 M TCEP and 4 M guanidine HCl, H2O, pH 2.4. Quenched samples were digested, desalted and separated online using a Waters UPLC system based on a nanoACQUITY™ platform. Approximately 20 pmoles of exchanged and quenched antibody was injected into an immobilized pepsin column. The online digestion was performed over 2 min in water containing 0.05% formic acid at 15° C. at a flow rate of 0.1 nL/min. The resulting peptic peptides were trapped on an ACQUITY™ UPLC BEH C18 1.7 μm peptide trap (Waters, Milford, MA) maintained at 0° C. and desalted with water, 0.05% formic acid. Flow was diverted by a switching valve, and the trapped peptides eluted from the trap at 40 μl/min onto a Waters ACQUITY™ UPLC BEH Cl 8 1.7 μm, 1 mm×100 mm column held at 0° C. (average back-pressure was approximately 9000 psi). A 6 min linear acetonitrile gradient (8-40%) with 0.05% formic acid was used to separate the peptides. The eluate was directed into a Waters Synapt mass spectrometer with electrospray ionization and lock-mass correction (using Glu-fibrinogen peptide). Mass spectra were acquired over the m/z range 260-1800. Pepsin fragments were identified using a combination of exact mass and MS/MS, aided by Waters IdentityE software. Peptide deuterium levels were determined as described by Weis et al. using the Excel based program HX-Express.

H/DX-MS data for intact IgG4.P versus N297Q IgG4.P, N297Q IgG4.P versus N297Q IgG4.P-CH2/IgG1-CH3 and T299A IgG4.P versus YC406 (T299K, T207P, L309K, D399S) were collected as described above. Comparison of the intact (glycosylated) IgG4 and the aglycosylated N297Q IgG4 shows regions of sequence in which the aglycosylated form shows greater exchange. More H/D exchange is observed in peptides L235-F241, F241-D249, I253-V262, V263-F275, and H310-E318. Higher exchange in IgG4 peptides M358-L365, T41-V422 and A431-S442 compared to the same peptides in the N297Q IgG4.P-CH2/IgG1-CH3 construct shows the gain in stability generated from the IgG1-CH3 in combination with the N297Q IgG4-CH2. In this case, the CH3 domain from IgG4 shows greater exchange in 3 distinct region of the CH3 compared to the IgG1-CH3. Finally, peptides L235-F241, F241-M252, V263-F275, V266-F275, and V282-F296 show the gain in stability by the mutant construct YC406 compared to aglycosylated IgG4 (T299A) in the sequence regions specifically more prone to exchange because of deglycosylation. Interestingly, the D399S mutation in the CH3 domain, while generating a slight increase in thermal stability, imparts greater exchange than the wild type sequence. Overall, H/D exchange MS showed that changes in conformation as a result of deglycosylation were either partially or fully recovered by the stability mutations.

B. X-Ray Crystallography of Stability Enhanced Fc Constructs

The EAG2476 construct (agly IgG4-Fc T299K, T307P, L309K, D399S) was crystallized and data collected to 2.8A resolution (data completeness overall 92%; high resolution shell 66%). The structure was built into the electron density and refined to an R/Rfree of 27.7/33.9% respectively. The structure reveals the two Fc chains in the asymmetric unit (ASU) superimposable with very little deviation between the two chains. Loops V266-E272 and in particular β291-V302 are quite different than that observed in wild type IgG4 crystal structure (pdb IADQ). This may be a direct result of the mutation T299K.

The crystal structure of the EAG2478 construct (agly IgG1 Fc T299K) was solved to 2.5 Å resolution (data completeness overall 92%; high resolution shell 66%). The structure was built and refined to an R/Rfree of 27.4/35.8% respectively. Unlike the structure of EAG2476, the two Fc chains in ASU are not identical in the EAG2478 structure. Chain A is observed to be more similar to the structure of an enzymatically deglycosylated IgG1 Fc (pdb 3DNK). The CH2 domains in the EAG2478 structure are closer together than observed in the enzymatically deglycosylated IgG1 Fc (pdb 3DNK) and a murine aglycosylated IgG1 Fc (pdb 3HKF). The CH2 domains are more open in the EAG2476 structure than observed in the EAG2478 structure. The structures reveal that in both cases the T299K mutation is directed towards the Y129 side chain of a docked Fc gamma III receptor, which would explain the decreased affinity for the receptor observed for this mutation.

Example 14. Protein Purification

Proteins having a mature light chain of SEQ ID NO: 81 (Mature light chain of HP1/2 hG4P agly(N297Q) G1 H1L3 ND001) and a mature heavy chain of SEQ ID NO: 80 (Mature heavy chain of HP1/2 hG4P agly(N297Q) G1 H1L3 ND004/ND006) were stably expressed in Chinese Hamster Ovary (CHO) cells and purified. The resulting molecule is called HP1/2 H1L3 aglycosyl IgG4P/IgG1 chimera S228P N297Q (Kabat numbering) or HP1/2 hG4P agly(N297Q) G1 H1L3.

Figure 22A:
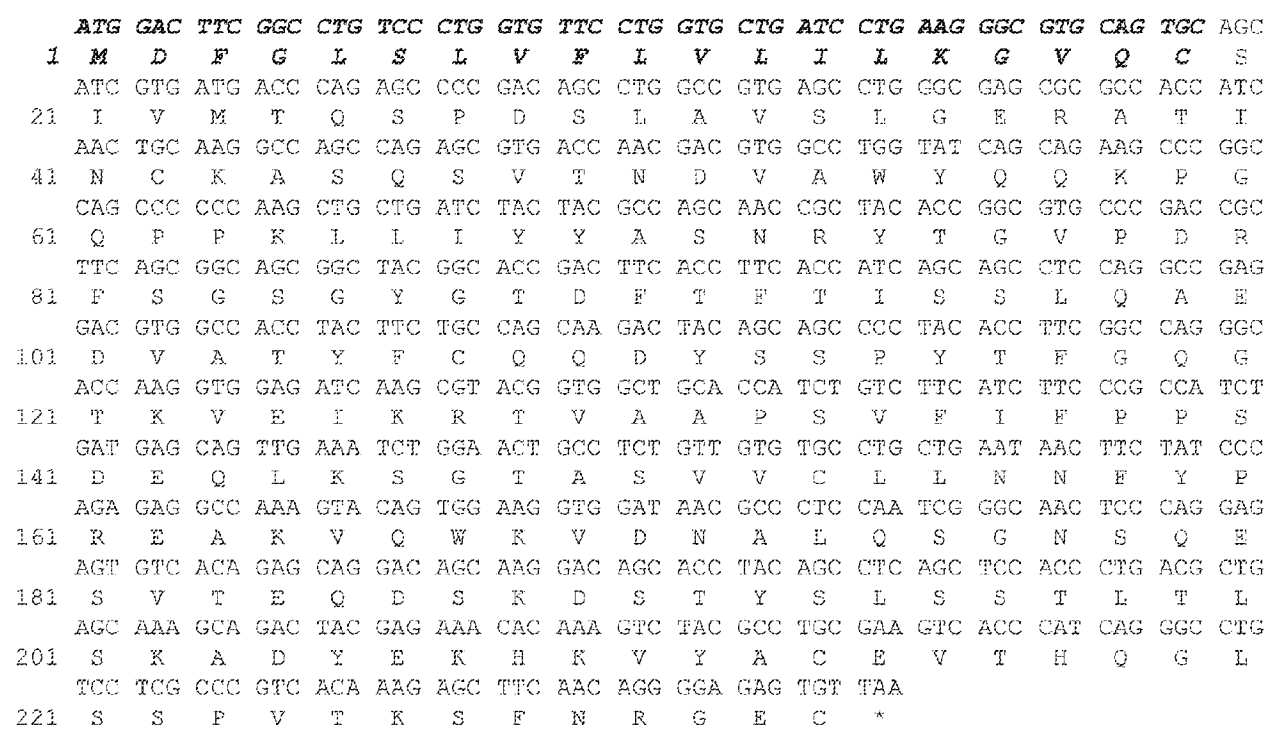

FIG. 22A shows the nucleotide sequence (SEQ ID NO: 91) and amino acid sequence (SEQ ID NO: 92) of the light chain of HP1/2 hG4P agly(N297Q, EU Numbering) G1, kappa light chain (H1L3), including the signal peptide sequence (signal peptide sequence and encoding DNA shown as bolded italics font in FIG. 22A).

FIG. 22B shows the nucleotide sequence (SEQ ID NO: 93) and amino acid sequence (SEQ ID NO: 94) of the light chain of HP1/2 hG4P agly(N297Q, EU Numbering) G1, heavy chain (H1L3), including the signal peptide sequence (signal peptide sequence and encoding DNA shown as bold italics font in FIG. 22B).

FIG. 23A includes the amino acid sequence of HP1/2 hG4P agly(N297Q) G1, kappa light chain (H1L3), including the signal sequences (underlined text) for both the light chain (top) and the heavy chain (bottom).

FIG. 23B includes the amino acid sequence of HP1/2 hG4P agly(N297Q) G1, kappa light chain (H1L3) having a mature light chain of SEQ ID NO: 81 and a mature heavy chain of SEQ ID NO: 80. In FIG. 23B, the complementarity determining regions (CDR) sequences in the light chain (amino acid residues 24-34, 50-56, and 89-97) and in the heavy chain (residues 28-35, 50-66, and 99-110) underlined.

Pyrogen-free containers and solutions were used throughout the purification process. The purification process was carried out at room temperature.

HP1/2 hG4P agly(N297Q) G1 H1L3 was stably expressed in Chinese Hamster ovary (CHO) cells and purified.

For purification, briefly, 7.5 L of the CHO media containing approximately 10 grams of HP1/2 hG4P agly (N297Q) G1 H1L3 (estimated titer by Octet®: 1310 mg/L) was loaded on a 400 mL rProtein A Sepharose™ Fast Flow column (GE 17-1279-04, i.d. 50 mm) at 40-120 mL/h in 25 mM Sodium Phosphate, pH 7.0, 0.1 M NaCl. The column was washed with 4×400 mL of the same buffer, then 3×400 mL of 25 mM Na2HPO4, pH 5.5, 0.1 M NaCl. The HP1/2 hG4P agly(N297Q) G1 H1L3 was eluted with 1000 mL of 25 mM Sodium Phosphate, pH 2.8, 0.1 M NaCl, pH was neutralized with 25 mM Sodium Phosphate, pH 8.6. The sample was 0.2μ filtered with a Thermo Scientific Nalgene filter and stored at 4° C. The protein content (calculated extinction coefficient for 1 mg/mL HP1/2 hG4P agly (N297Q) G1 H1L3=1.49) of the eluted samples was estimated from absorbance spectra using NanoDrop™ 2000 Spectrophotometer that reports the value at 280 nm.

The rProtein A eluted pool was loaded on a 150 mL TMAE column (EMD 1.16881.0500, i.d. 50 mm) in 10 mM Sodium Phosphate, pH 7.0, 0.1 M NaCl. The flow through was collected and checked by SDS-PAGE. The sample was concentrated, buffer exchanged into 25 mM Sodium Phosphate, pH 7.0, 25 mM NaCl using a Millipore Pellicon®-2 ultrafiltration unit and re-loaded onto the same TMAE column in 25 mM Sodium Phosphate, pH 7.0, 25 mM NaCl. The flow through was collected and adjusted to 140 mM NaCl by adding 15.24 mL of 4 M NaCl to the 514 mL sample, then 0.2μ filtered with a Thermo Scientific Nalgene filter, aliquoted and stored at −80° C. 9,384 mg of HP1/2 hG4P agly(N297Q) G1 H1L3 was produced representing 96% of the theoretical yield.

Example 15. Protein Characterization

The proteins described in Example 14 were characterized via several different methods as discussed below.

A. UV Spectrum

Figure 24:
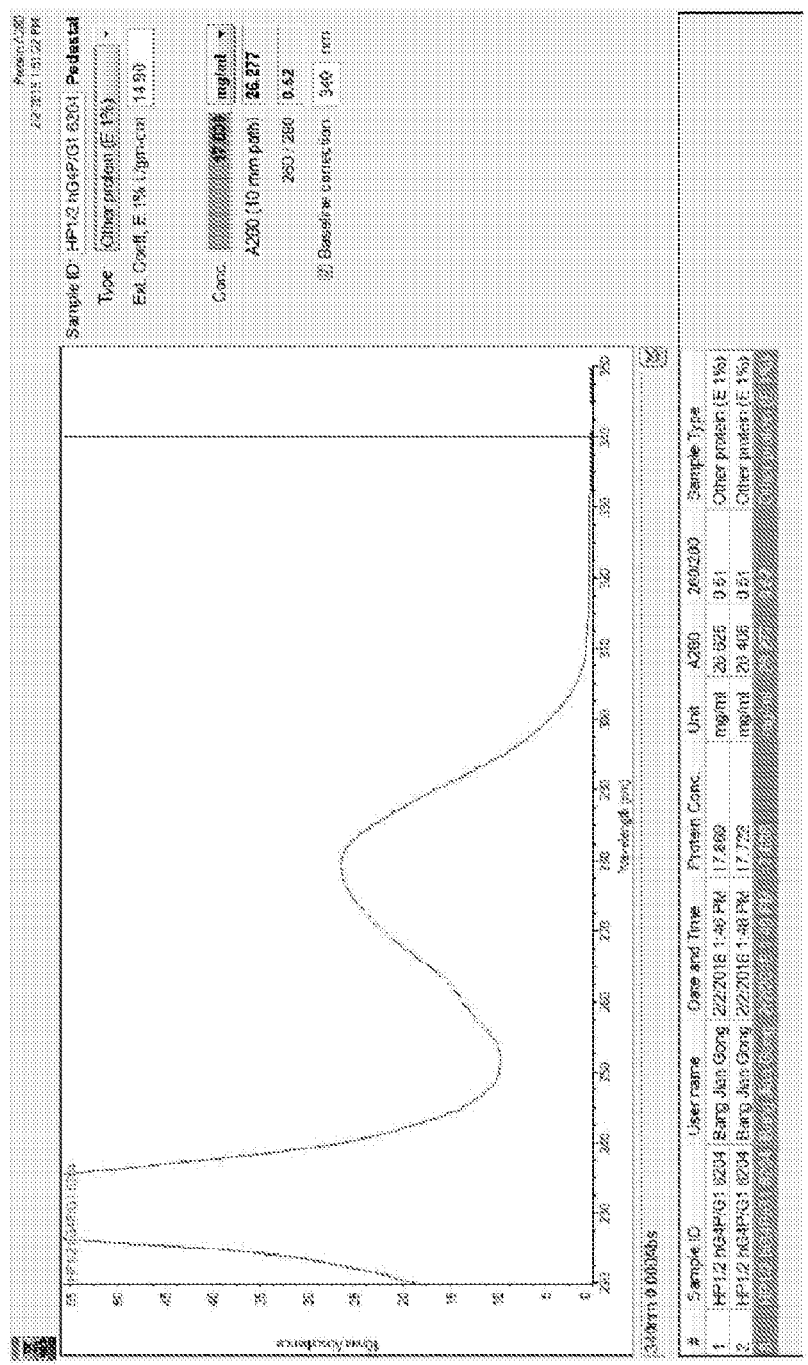
FIG. 24 provides a UV spectrum of a protein having a mature light chain of SEQ ID NO: 81 (Mature light chain of HP1/2 hG4P agly(N297Q, EU Numbering) G1 H1L3 ND001) and a mature heavy chain of SEQ ID NO: 80 (Mature heavy chain of HP1/2 hG4P agly(N297Q, EU Numbering) G1 H1L3 ND004/ND006).

FIG. 24 provides a UV spectrum of a protein having a mature light chain of SEQ ID NO: 81 (Mature light chain of HP1/2 hG4P agly(N297Q) G1 H1L3 ND001) and a mature heavy chain of SEQ ID NO: 80 (Mature heavy chain of HP1/2 hG4P agly(N297Q) G1 H1L3 ND004/ND006). The UV spectrum of HP1/2 hG4P agly(N297Q) G1 H1L3 (RS) was measured directly from the undiluted sample in 25 mM Sodium Phosphate, 140 mM NaCl pH 7.0 on a NanoDrop™ 2000 Spectrophotometer. The protein concentration of 17.74 mg/mL was determined using the calculated extinction coefficient of $\varepsilon_{280}^{0.1\%}=1.49$/cm.

B. Sodium Dodecyl Sulfate-Polyacrylamide Gel Electrophoresis (SDS-PAGE)

Figure 25:
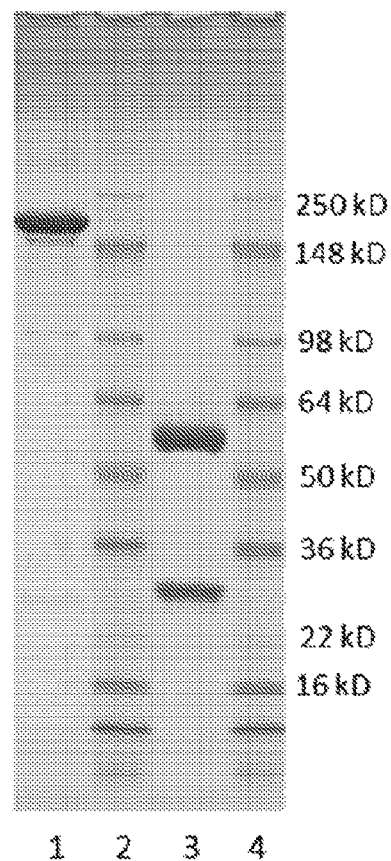
FIG. 25 illustrates the results of SDS-PAGE of a protein having a mature light chain of SEQ ID NO: 81 (Mature light chain of HP1/2 hG4P agly(N297Q, EU Numbering) G1 H1L3 ND001) and a mature heavy chain of SEQ ID NO: 80 (Mature heavy chain of HP1/2 hG4P agly(N297Q, EU Numbering) G1 H1L3 ND004/ND006). Non-reducing conditions are shown in the left two lanes (rows 1 and 2), and reducing conditions are shown in the right two lanes (rows 3 and 4). Lane 1 is HP1/2 hG4P agly(N297Q, EU Numbering) G1 H1L3 ND001) under non-reducing conditions; lane 2 is a molecular weight marker under non-reducing conditions; lane 3 is HP1/2 hG4P agly(N297Q, EU Numbering) G1 H1L3 ND001) under reducing conditions, and lane 4 is a molecular weight marker under reducing conditions.

FIG. 25 illustrates the results of SDS-PAGE of a protein having a mature light chain of SEQ ID NO: 81 (Mature light chain of HP1/2 hG4P agly(N297Q) G1 H1L3 ND001) and a mature heavy chain of SEQ ID NO: 80 (Mature heavy chain of HP1/2 hG4P agly(N297Q) G1 H1L3 ND004/ND006). Aliquots of HP1/2 hG4P agly(N297Q) G1 H1L3 were prepared in a sample buffer containing DTT for the reduced samples or a sample buffer without DTT for the non-reduced samples. SDS-PAGE was run on 4-20% polyacrylamide gradient gels from Invitrogen and the gel was stained with Simply Blue™ stain (Invitrogen) and de-stained with distilled water. FIG. 25 shows results from the analysis of the HP1/2 hG4P agly(N297Q) G1 H1L3 (RS). Under reducing conditions, the gel shows two bands representing the expected molecular weights of heavy and light chains of HP1/2 hG4P agly(N297Q) G1 H1L3, 50 and 25 kDa, respectively. Under non-reduced conditions, the major band has the expected molecular weight of 150 kDa for the $HC_2LC_2$ tetrameric structure of an antibody. The sample contains <0.5% of higher molecular-weight forms.

C. Isoelectric Focusing (IEF)

Figure 26:
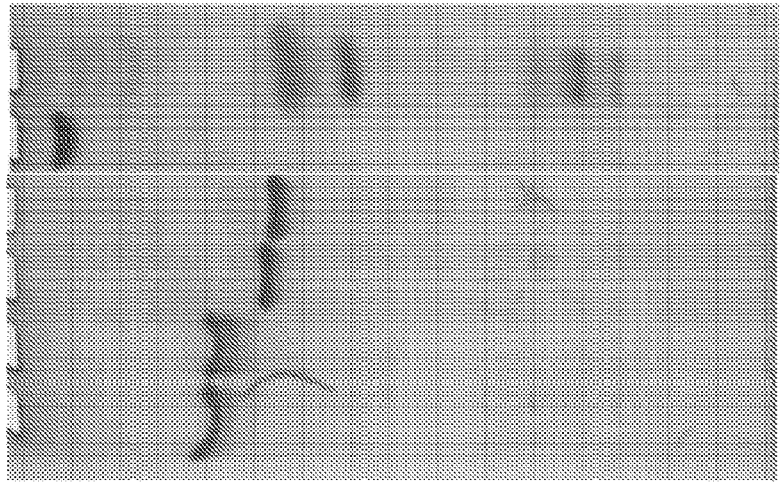
FIG. 26 illustrates the results of IEF of a protein having a mature light chain of SEQ ID NO: 81 (Mature light chain of HP1/2 hG4P agly(N297Q, EU Numbering) G1 H1L3 ND001) and a mature heavy chain of SEQ ID NO: 80 (Mature heavy chain of HP1/2 hG4P agly(N297Q, EU Numbering) G1 H1L3 ND004/ND006).

FIG. 26 illustrates the results of IEF of a protein having a mature light chain of SEQ ID NO: 81 (Mature light chain of HP1/2 hG4P agly(N297Q) G1 H1L3 ND001) and a mature heavy chain of SEQ ID NO: 80 (Mature heavy chain of HP1/2 hG4P agly(N297Q) G1 H1L3 ND004/ND006). Samples were prepared in IEF sample buffer 3-10 and were run on a Novex pH 3-10 IEF Gel (Thermo Fisher EC66552BOX) at 130V constant for 92 minutes. The gel was fixed with 12% TCA for 10 minutes, stained with Simply Blue™ stain (Invitrogen) and de-stained with distilled water. The HP1/2 hG4P agly(N297Q) G1 H1L3 RS runs as a single major band and several minor more acetic variants. The calculated pI is 6.22 for HP1/2 hG4P agly (N297Q) G1 H1L3. FIG. 26 also shows the same construct expressed in CHO DG44i cells, two other HP1/2 H1L3 constructs fused to wild type IgG4P Fc and IgG4PE Fc. The gel mobility of the molecules is consistent with the different pI values of the molecules. Noted in the lane designations are calculated pIs for all the samples.

D. Analytical Size Exclusion Chromatography

Figure 27:
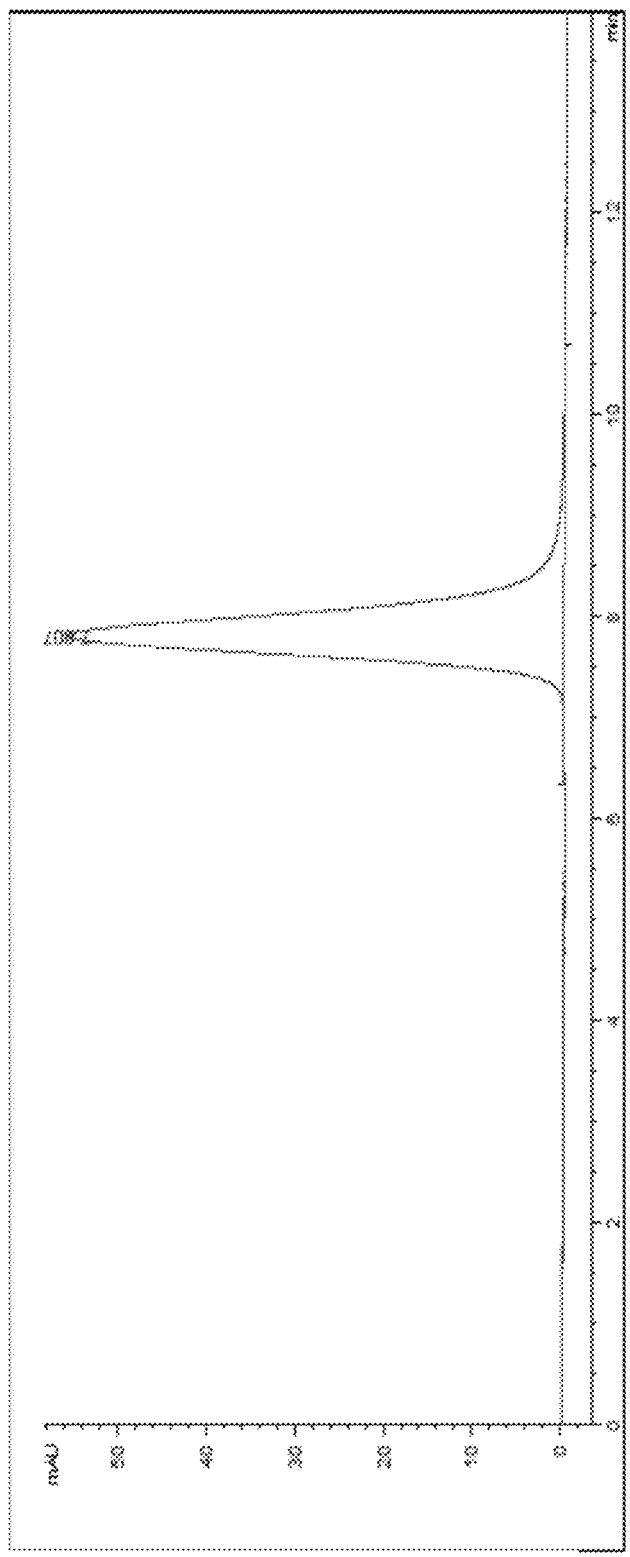
FIG. 27 illustrates the results of analytical size exclusion chromatography of a protein having a mature light chain of SEQ ID NO: 81 (Mature light chain of HP1/2 hG4P agly (N297Q, EU Numbering) G1 H1L3 ND001) and a mature heavy chain of SEQ ID NO: 80 (Mature heavy chain of HP1/2 hG4P agly(N297Q, EU Numbering) G1 H1L3 ND004/ND006).

FIG. 27 illustrates the results of analytical size exclusion chromatography of a protein having a mature light chain of SEQ ID NO: 81 (Mature light chain of HP1/2 hG4P agly (N297Q) G1 H1 L3 ND001) and a mature heavy chain of SEQ ID NO: 80 (Mature heavy chain of HP1/2 hG4P agly(N297Q) G1 H1L3 ND004/ND006). 20 µg of the research standard was run on a Superdex™ 200 Increase 5/150 GL column (GE 28-9909-45) using an Agilent 1200 Series HPLC system at a flow rate of 0.2 ml/minute in PBS (10 mM Sodium Phosphate, 0.15 M NaCl, pH 7.5) diluted from 20×PBS (Thermo Scientific 28348). The absorbance of the eluate was monitored at 280 nm and is shown in FIG. 27.

HP1/2 hG4P agly(N297Q) G1 H1L3 eluted at 7.8 minutes as a single peak with no detectable aggregates or low molecular weight components.

E. Endotoxin

Endotoxin was determined using Charles River Endosafe™ PTS20 cartridges (0.05-5 EU/ml) according to manufacturer's instructions. The endotoxin level found in the research standard was <0.06 EU/mg which was suitable for injection in NHP.

F. Differential Scanning Calorimetry (DSC)

Figure 28:
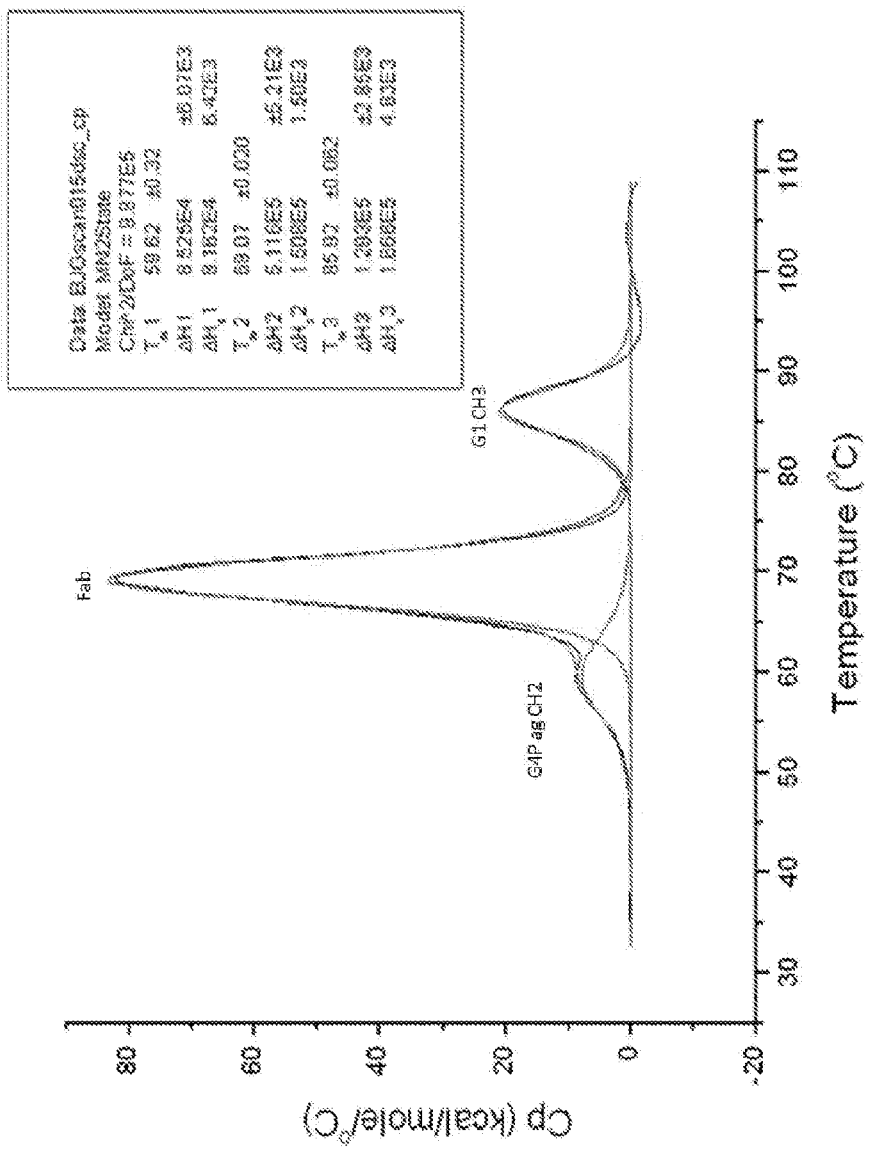
FIGS. 28-30 illustrate the results of DSC of a protein having a mature light chain of SEQ ID NO: 81 (Mature light chain of HP1/2 hG4P agly(N297Q, EU Numbering) G1 H1L3 ND001) and a mature heavy chain of SEQ ID NO: 80 (Mature heavy chain of HP1/2 hG4P agly(N297Q) G1 H1L3 ND004/ND006). The melting curves for HP1/2 hG4P agly (N297Q, EU Numbering) G1 H1L3 intact antibody, Fc and Fab2 fragment are shown in FIG. 28, FIG. 29, and FIG. 30, respectively.
Figure 29:
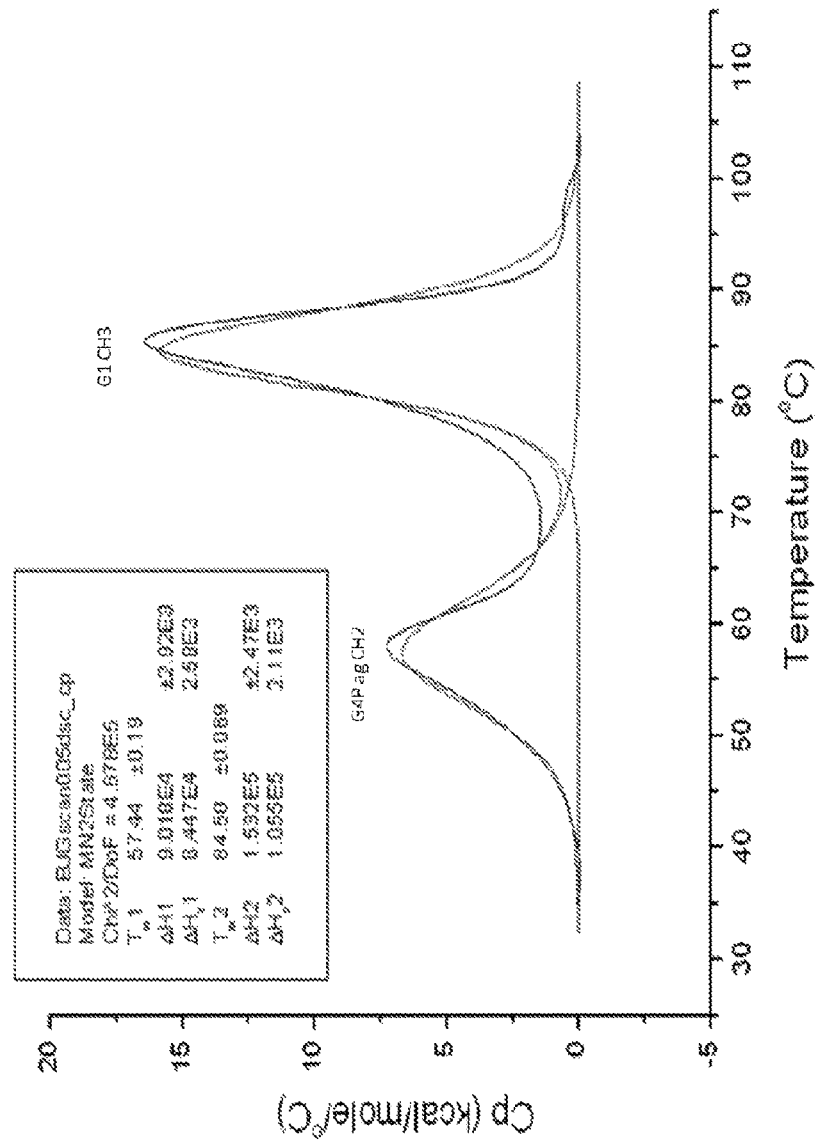
Figure 30:
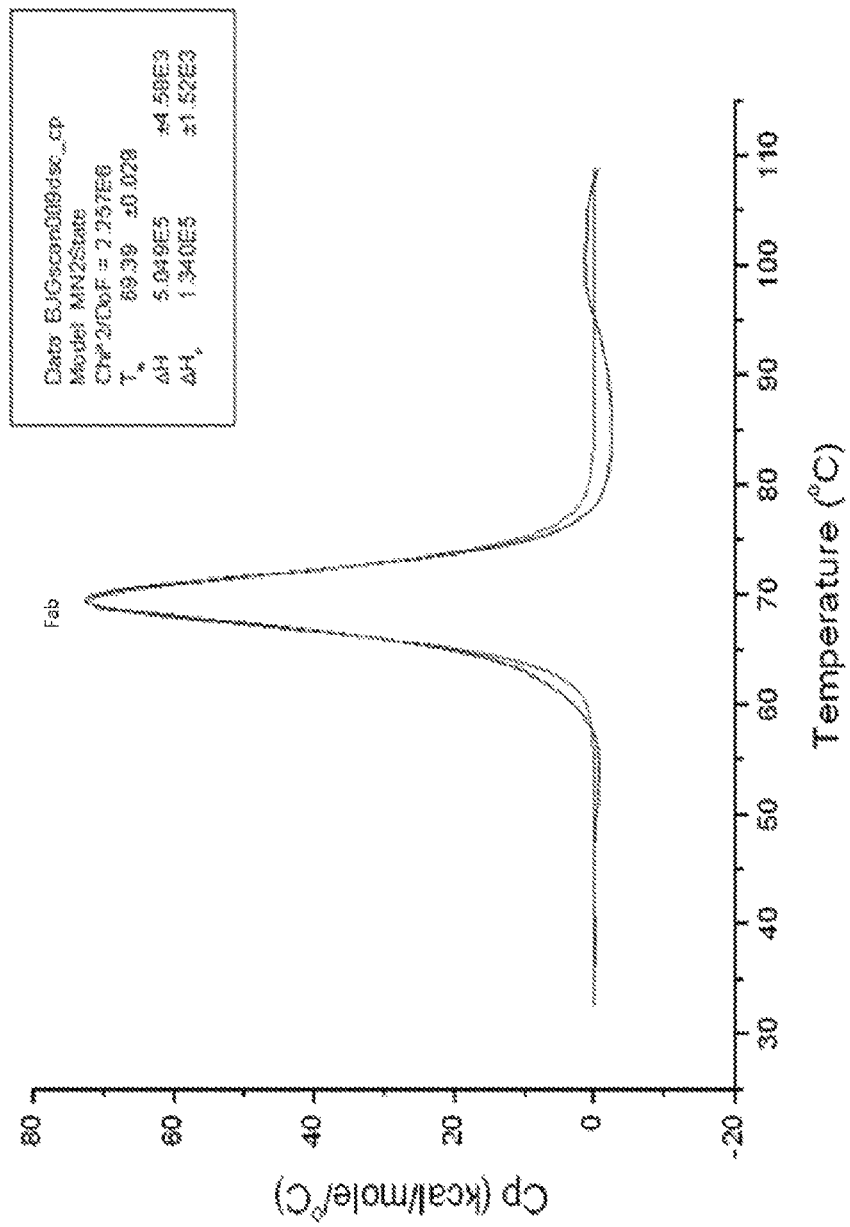

FIG. 28-30 illustrate the results of DSC of a protein having a mature light chain of SEQ ID NO: 81 (Mature light chain of HP1/2 hG4P agly(N297Q) G1 H1L3 ND001) and a mature heavy chain of SEQ ID NO: 80 (Mature heavy chain of HP1/2 hG4P agly(N297Q) G1 H1L3 ND004/ND006). HP1/2 hG4P agly(N297Q) G1 H1L3 research standard was diluted to ~1 mg/mL in PBS then dialyzed vs. PBS at 4° C. for ~20 hours. Approximately 400 µg (400 µL) per sample was added to a 96 well plate. Scans were performed from 20 to 120° C. at 2° C./min, using the medium feedback mode for enhanced peak resolution. Tm values (phase transition temperature at which 50% of the protein molecules are unfolded in a dynamic non-reversible two-state equilibrium) were measured for each domain using the MicroCal DSC instrument. Two buffer scans were performed to define the baseline for subtraction, and data were analyzed using the Origin software. For comparison, a sample of HP1/2 hG4P agly(N297Q) G1 H1L3 Fc fragment (Batch BJG2018-1-3-0088-E2) was also analyzed. As verification of the assignment for the Fab domain, a Fab2 fragment of the research standard was generated and analyzed. The melting curves for HP1/2 hG4P agly(N297Q) G1 H1L3 intact antibody, Fc and Fab2 fragment are shown in FIG. 28, FIG. 29, and FIG. 30, respectively, and the domain melting temperatures (Tm) are summarized in Table 11. Based on Tm values, the G4P CH2 domain of the antibody was the least stable with a phase transition temperature of 59.6° C., followed by the Fab domain at 69.1° C. and the G1 CH3 domain at 85.9° C. in the intact antibody. Tm values for the G4P CH2 domain of the antibody was at 57.4° C. and the G1 CH3 domain at 84.5° C. in the isolated Fc fragment. The Tm of Fab domain was at 69.4° C. for Fab2 fragment.

TABLE 11

Melting temperatures of the HP1/2 hG4P agly(N297Q) G1 H1L3 intact antibody, Fc domain and Fab2 fragment measured in FIGS. 28-30

| Sample | $T_m$ (° C.) G4P CH2 | $T_m$ (° C.) G1 CH3 | $T_m$ (° C.) Fab |
|---|---|---|---|
| HP1/2 hG4P agly/G1 | 59.6° C. | 85.9° C. | 69.1° C. |
| Fc Fragment | 57.4° C. | 84.5° C. | NA |
| Fab2 Fragment | NA | NA | 69.4° C. |

Example 16. Further Experimental Analysis of Proteins

The product attributes of two different HP1/2 proteins were explored. The first construct, Humanized HP1/2 H1/L3 huIgG4P agly(N297Q EU numbering)/IgG1 chimera or HP1/2 G4P agly/G1, comprises a mature light chain of SEQ ID NO: 81 and a mature heavy chain of SEQ ID NO: 80. The second construct, Humanized HP1/2 H1/L3 huIgG4P agly (T299A EU numbering) or HP1/2 G4P agly, comprises a mature light chain of SEQ ID NO: 81 and a mature heavy chain of SEQ ID NO: 89. The two engineered versions of HP1/2 were designed, expressed, purified, and characterized. The constructs were expressed as transients in CHO cells.

TABLE 12

Overview of Two Engineered Constructs

| 4DID Number | Construct | Cell Viability on Day 7 (%) | Antibody Concentration |
|---|---|---|---|
| 6146 | Humanized HP1/2 H1/L3 huIgG4P agly(N297Q)/IgG1 chimera ("HP1/2 G4P agly/G1") | 74.9 | 122 |
| 6147 | Humanized HP1/2 H1/L3 huIgG4P agly (T299A) ("HP1/2 G4P agly") | 68.5 | 102 |
| 6148 | Natalizumab huIgG4P agly (T299A) ("Natalizumab G4P agly") | 62 | 76 |
| 6149 | Natalizumab huIgG4P ("Natalizumab G4P") | 64.3 | 72 |

900 mL of the CHO media containing 72-122 mg/L of the constructs, as noted in the table above (estimated titer by Octet®), were loaded by gravity onto a 9 mL rProtein A Sepharose™ Fast Flow column (GE 17-1279-04). The columns were washed with 6×5 mL of 25 mM sodium phosphate, pH 7.0, 0.1 M NaCl, and then with 6×4 mL of 25 mM sodium phosphate, pH 5.5, 0.1 M NaCl. The mAbs were eluted with 7×5 mL of 25 mM sodium phosphate, pH 2.8, 0.1 M NaCl. The pH was neutralized by addition of sodium phosphate, pH 8.6 to a final concentration of 20 mM. Varying amounts of precipitate were observed. The samples were centrifuged at 3000 rpm for 5 min and the supernatant was filtered, aliquoted, and stored at −70° C. The protein content of the eluted samples was estimated from absorbance spectra using NanoDrop™ 2000 Spectrophotometer that reports the value at 280 nm prior to neutralization and after the neutralization-centrifugation-filtration steps.

When the four antibodies preparations following the ProA step were neutralized, there were large differences in the amounts of the proteins that were lost due to precipitation (see Table 13 below). The HP1/2 G4P agly G1 version was the better behaved of the constructs with only 3% of the product lost due to precipitation.

TABLE 13

Precipitation Percentage of the Four Engineered Constructs

| Construct | Precipitate (%) |
|---|---|
| Humanized HP1/2 H1/L3 huIgG4P agly(N297Q)/IgG1 chimera | 3 |
| Humanized HP1/2 H1/L3 huIgG4P agly(T299A) | 13 |
| Natalizumab huIgG4P agly (T299A) | 39 |
| Natalizumab huIgG4P | 20 |

As shown in the above Table 13, the most significant was the loss of 39% of the product seen when the natalizumab G4P agly sample was neutralized. By contrast, only a third of the amount (13%) of the corresponding HP1/2 construct (HP 1/2 G4P agly) was lost due to precipitation. The HP1/2 G4P agly G1 version was the best behaved of the constructs with only 3% of the product lost due to precipitation.

Figure 31:
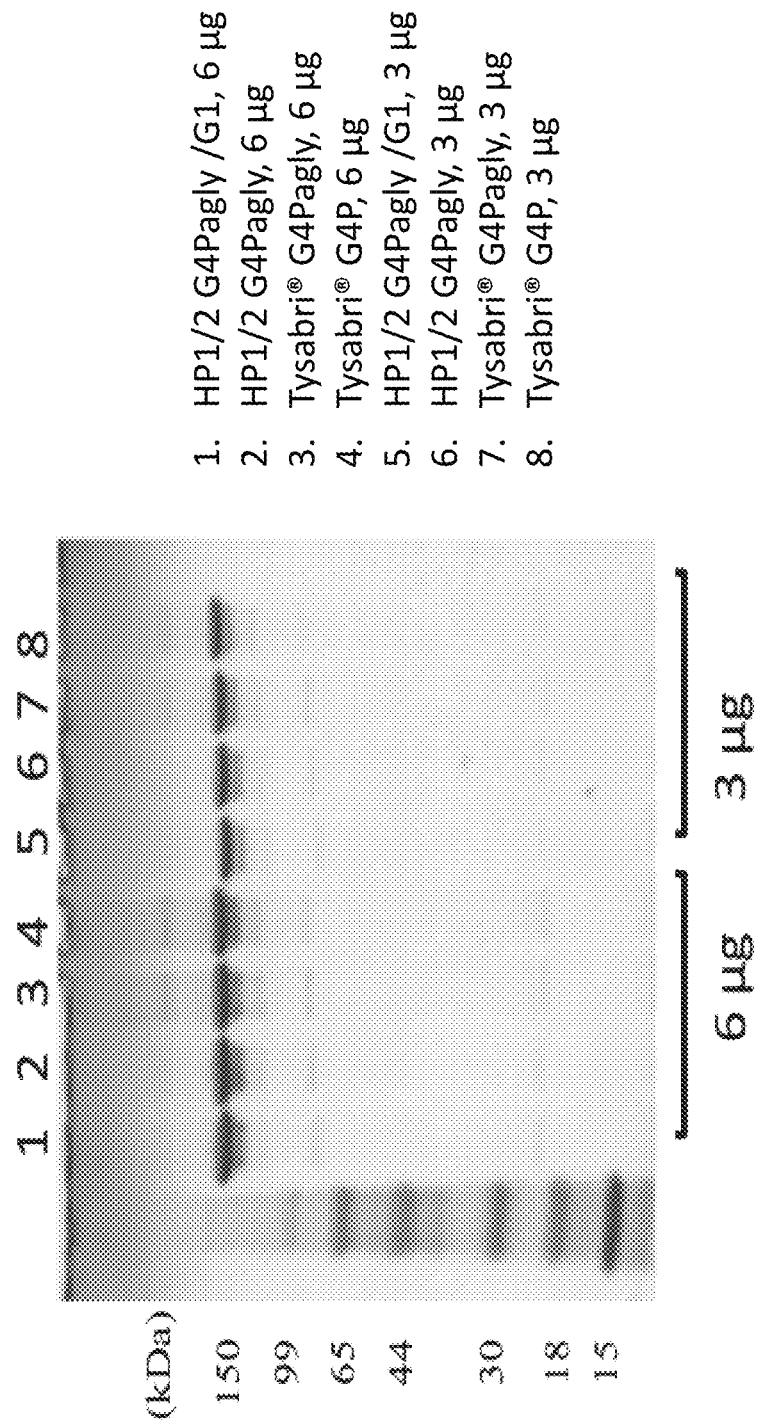
FIG. 31 illustrates the results of an SDS-PAGE analysis of HP1/2 samples under non-reducing conditions. Each sample was loaded at 6 and 3 μg/lane. Molecular weight markers are shown at the left of the panel. SDS-PAGE was run on 4-20% polyacrylamide gradient gels from Invitrogen and the gel was stained with Simply Blue™ stain (Invitrogen) and de-stained with distilled water. Lane 1 is HP1/2 hG4P agly(N297Q, EU Numbering) G1 H1L3 at 6 ug/lane; lane 2 is HP1/2 hG4P agly (T299A) at 6 ug/lane; lane 3 is natalizumab G4P agly at 6 ug/lane; lane 4 is natalizumab G4P at 6 ug/lane; lane 5 is HP1/2 hG4P agly(N297Q, EU Numbering) G1 H1L3 at 3 ug/lane; lane 6 is HP1/2 hG4P agly (T299A) at 3 ug/lane; lane 7 is natalizumab G4P agly at 3 ug/lane; lane 8 is natalizumab G4P at 3 ug/lane.

The soluble fraction of samples of the four constructs after centrifugation and filtration were characterized by SDS-PAGE and size exclusion chromatography (SEC). SDS-PAGE (FIG. 31) revealed a single prominent band of molecular mass of ~150 kDa for all four samples, consistent with the presence of the tetrameric 2-heavy chain, 2-light chain complex characteristic of IgG antibodies. A clear difference between the HP1/2 and natalizumab samples was the presence of a diffuse smear of higher molecular weight adducts in the natalizumab samples that ran from the prominent band to the top of the gel, indicating the present of soluble aggregates.

Figure 32A:
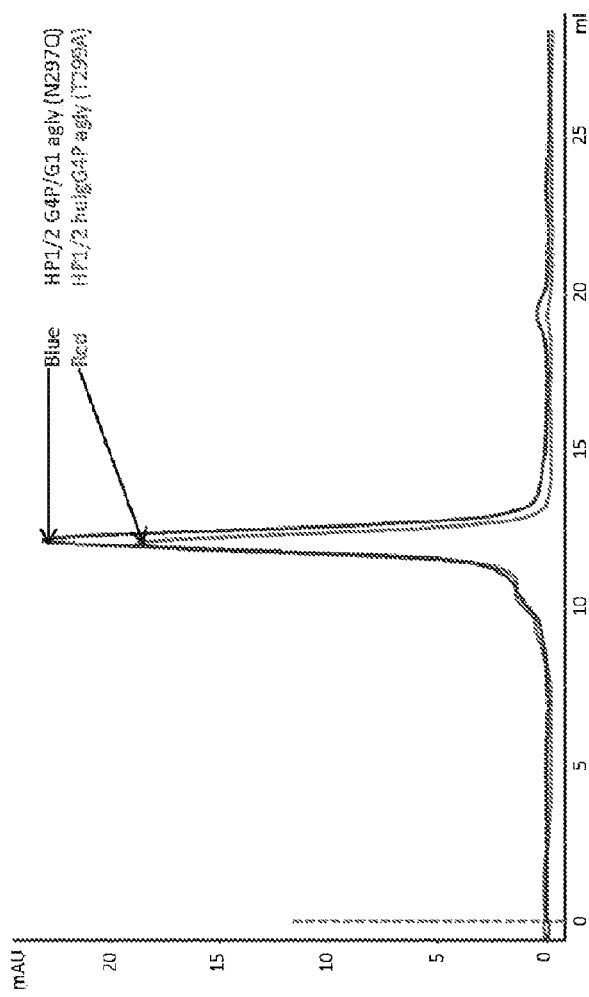
FIG. 32A illustrates the results of SEC analysis of HP1/2 samples. Samples were run on a Superdex™ Increase 5/150 GL column (GE 28-9909-45) at a flow rate of 0.2 ml/minute in PBS (10 mM sodium phosphate, 0.15 M NaCl, pH 7.5).
Figure 32B:
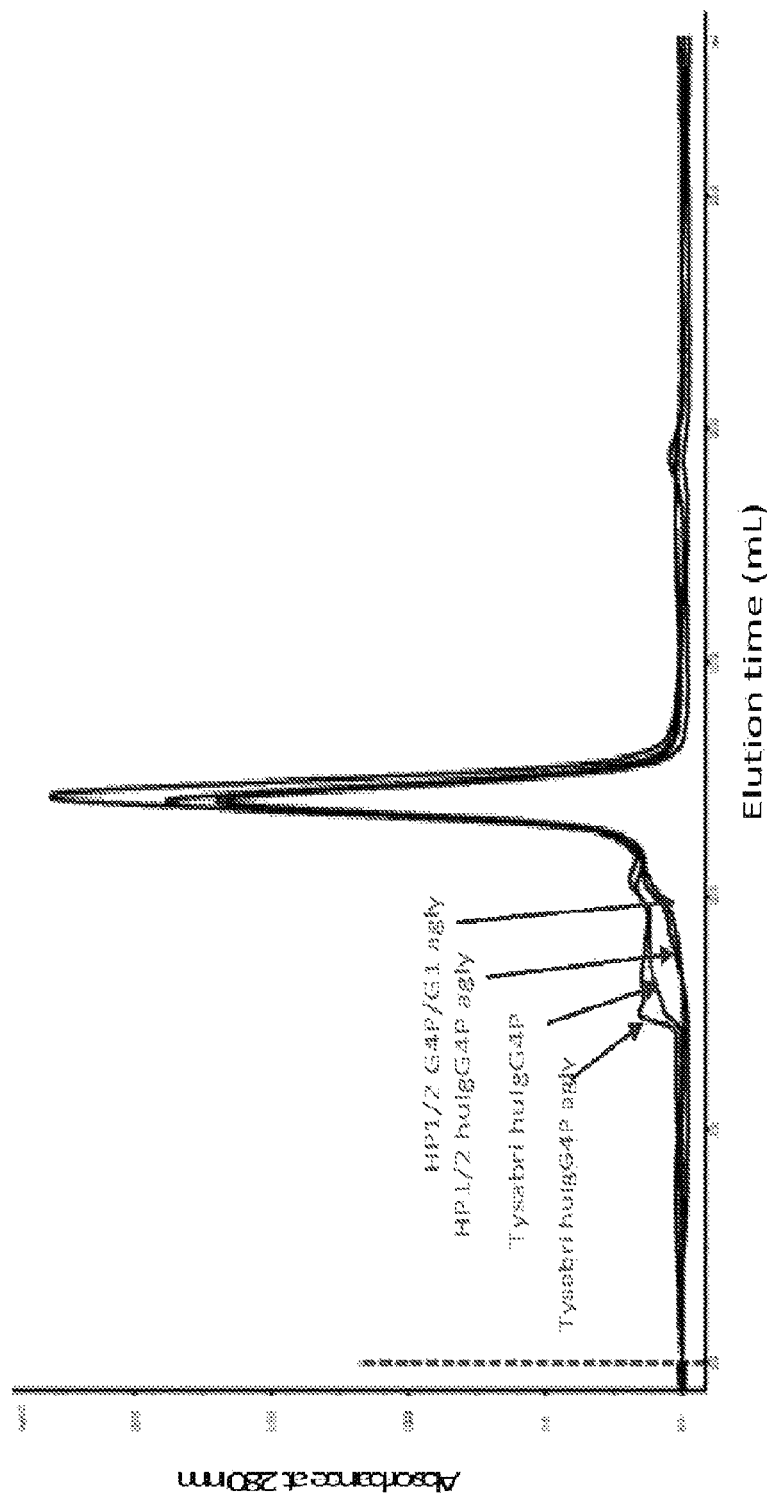
FIG. 32B illustrates the results of SEC analyses of HP1/2 hG4P agly(N297Q, EU Numbering) G1 H1L3, HP1/2 hG4P agly (T299A), natalizumab G4P agly, and natalizumab G4P. Samples were run on a Superdex™ 200 Increase 5/150 GL column (GE 28-9909-45) at a flow rate of 0.2 ml/minute in PBS (10 mM sodium phosphate, 0.15 M NaCl, pH 7.5).

FIG. 32A illustrates the results of SEC analysis of HP1/2 samples. FIG. 32B illustrates the results of SEC analysis of all four constructs. Samples were run on a Superdex™ Increase 5/150 GL column (GE 28-9909-45) at a flow rate of 0.2 ml/minute in PBS (10 mM sodium phosphate, 0.15 M NaCl, pH 7.5). SEC analysis of the four samples revealed a single major peak in all of the samples with an apparent molecular mass of ~150 kDa (FIGS. 32A and 32B).

Thus, consistent with the SDS-PAGE data, SEC analysis of the revealed higher molecular weight soluble aggregates in the natalizumab samples that elute before the main peak that were not detected or greatly reduced in the HP1/2 samples. Together these analyses revealed that the natalizumab samples contained soluble and insoluble aggregates that lead to poor yield and lower purity than was seen with the HP1/2 samples.

Figures 33A, 33B:
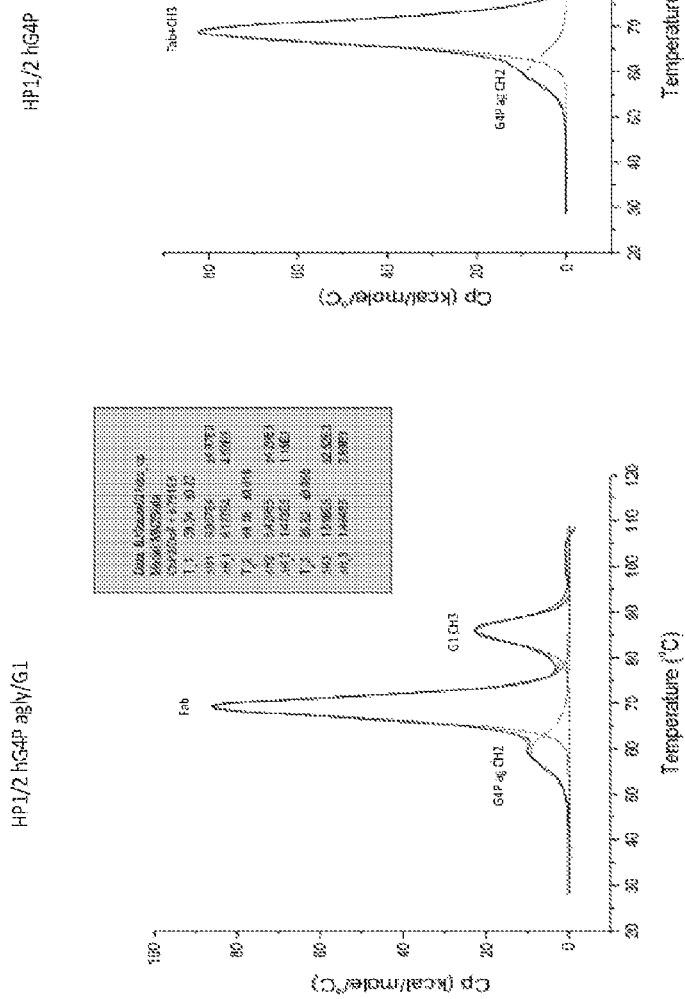
FIGS. 33a and 33b illustrate the results of DSC of Humanized HP1/2 H1/L3 huIgG4P agly (N297Q, EU Numbering)/IgG1 chimera (GP1/2 GrP agly/G1) and Humanized HP1/2 G1/L3 huIgG4P agly (T299A, EU Numbering) (HP1/2 hG4P), respectively.

The two HP1/2 samples were also characterized for stability by differential scanning calorimetry (DSC). FIGS. 33a and 33b illustrate the results of DSC of Humanized HP1/2 H1/L3 huIgG4P agly(N297Q)/IgG1 chimera (HP1/2 G4P agly G1, left) and Humanized HP1/2 G1/L3 huIgG4P agly (T299A) (HP1/2 G4Pagly, right). The two HP1/2 samples were characterized for stability by differential scanning calorimetry (DSC). Tm values were determined for each domain using a MicroCal DSC instrument. Scans were performed from 20 to 120° C. at 2° C./min. Tm values (phase transition temperature at which 50% of the protein molecules are unfolded in a dynamic non-reversible two-state equilibrium) were measured for each domain. As expected many of the thermal transitions are the same because the two constructs contain the same Fab region (69° C.), and aglycosyl CH2 domain (~60° C.).

The CH3 domain of HP1/2 G4P agly G1 version is very stable as was apparent from its Tm of ~85° C. whereas the CH3 domain of the HP1/2 G4Pagly version had a Tm of only ~69° C.

In other words, the HP1/2 G4P agly G1 (i.e., with a heavy chain having the amino acid sequence of SEQ ID NO: 80) had superior stability over the HP1/2 G4Pagly antibody.

Example 17: Clinical Pharmacokinetics and First-In-Human Dose Projection of HP1/2

Reverse translational integration of clinical inputs can be used to enhance confidence in predictions relating to clinical pharmacokinetics and pharmacodynamics. In this example, the technique was used to inform the clinical pharmacokinetic and pharmacodynamics of the recombinant, humanized anti-alpha-4 integrin antibody, HP1/2 H1/L3 huIgG4P agly(N297Q, EU Numbering)/IgG1 chimera (referred to in this example as "HP1/2" or "BIIB107"), which is from the same alpha 4 epitope subclass as natalizumab (NTZ). Holistic data integration was used to increase predictability and confidence in HP1/2 human pharmacokinetics (PKs) and efficacious dose projections.

Figure 34:
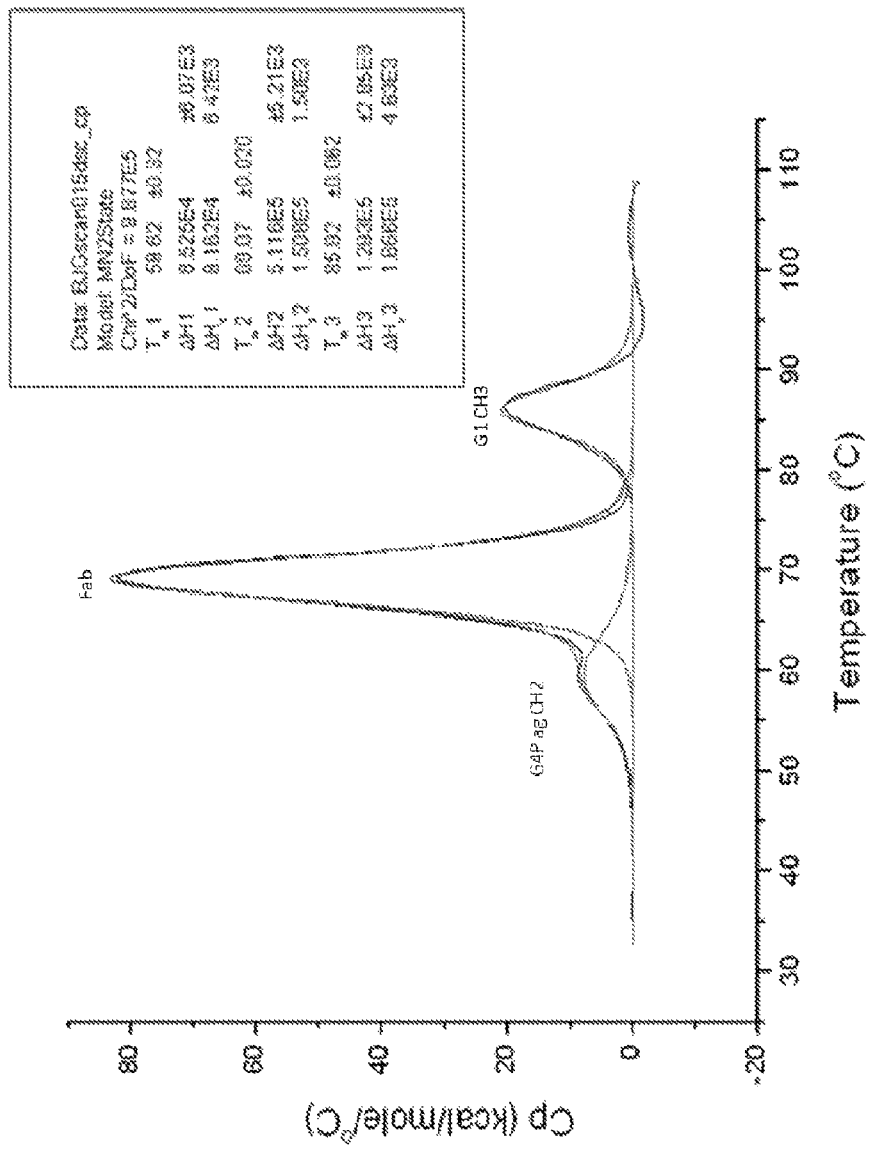
FIG. 34 is a line graph showing the pharmacokinetic time-course in cynomolgus monkeys following a single IV bolus administration of 3 mg/kg HP1/2 H1/L3 huIgG4P agly (N297Q, EU Numbering)/IgG1 chimera (GP1/2 GrP agly/G1) (referred to as HP12 in the figure; open circles), 30 mg/kg HP12 (closed circles), and 3 mg/kg natalizumab (Tysabri®, closed triangles).
Figure 35:
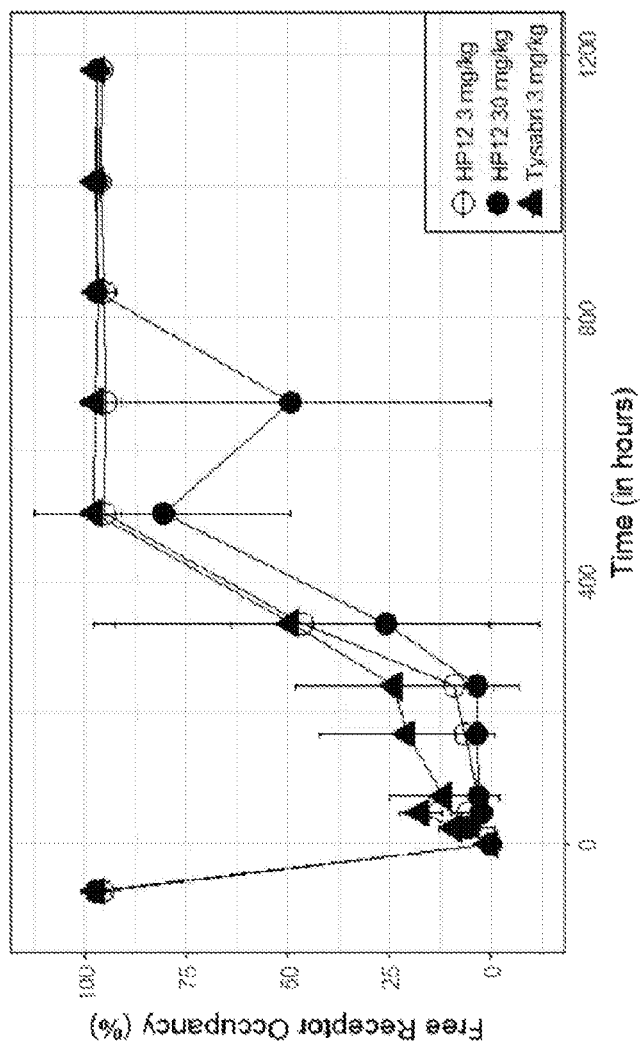
FIG. 35 is a line graph showing the free receptor time course in cynomolgus monkeys after a single IV bolus administration of 3 mg/kg HP1/2 H1/L3 huIgG4P agly (N297Q, EU Numbering)/IgG1 chimera (GP1/2 GrP agly/

Single IV doses of HP1/2 (3 and 30 mg/kg) and NTZ (3 mg/kg) were administered in cynomolgus monkeys (n=18). A total of 180 serum concentrations (60 NTZ, 120 HP1/2) and 252 PD (RO) measurements (84 NTZ, 168 HP1/2) from 18 cynomolgus monkeys were available for PKPD analyses. The observed PK mean time-course after a single IV bolus administration of 3-30 mg/kg HP1/2 and 3 mg/kg natalizumab (Tysabri®) in cynomolgus monkey is shown in FIG. 34. After the administration of the anti-VLA, free receptor was reduced to less than 10% of the baseline indicating greater than 90% receptor occupancy by both Tysabri® and BIIB107 in cynomolgus monkeys (see FIG. 35). The free VLA receptors gradually returned to the pre-dose level in about 500 h (21 days). HP1/2 appears to saturate VLA receptors (>=90%) for a longer duration (up to 300 hours) when compared with natalizumab (100 h) at the same dose (3 mg/kg), indicating greater potency of the HP1/2 relative to natalizumab. Of note, the higher HP 1/2 dose (30 mg/kg) resulted in approximately 2-fold longer receptor engagement, with levels returning to baseline after over 800 h.

The EC50 for the formation of drug-bound VLA (see Table 14) was relatively lower for HP1/2 (4.73 ug/mL) when compared to Tysabri® (6.40 ug/mL), indicating greater potency of HP1/2.

TABLE 14

Model-Estimate PKPD Parameters of Tysabri ® and BIIB107 in Monkey

| Parameters | Estimate (SE) | | Inter-animal variability (SE)[a] | |
|---|---|---|---|---|
| | HP1/2 | Natalizumab | HP1/2 | Natalizumab |
| Emax[b] (%) | 97.5 (3.86) | 95.97 (41.7) | 43.9 (3.85) | 71.2 (1.21) |
| $E_0$[b] (%) | 3.99 (2.19) | 2.87 (3.00) | | |
| $EC_{50}$ (ng/mL) | 4.73 (3.22) | 6.40 (5.70) | | |
| ε (additive) | 3.73 (2.0) | 6.42 (2.24) | | |

Inline table[a] Inter-animal variability expressed as coefficient of variation. The standard errors (SE) are expressed as relative standard errors in percentage.
[b]$E_0$ = 100 – $E_0$; Emax = 100 – Emax.

These data indicate that HP1/2 binds to cynomolgus monkey alpha-4 integrin with an affinity that is approximately 5-fold (intact HP1/2) and approximately 6-fold (Fab fragment) weaker than binding to the human receptor. Natalizumab intact binds approximately 2-fold weaker to cynomolgus alpha-4 integrin than human alpha-4 integrin, whereas Fab binding is the same between the two species. These data also indicate that HP1/2 binds to human alpha-4 integrin with a higher affinity than natalizumab. In other words, approximately 5-fold difference comparing intact; approximately 6-fold difference comparing Fab fragments; and over 19-fold difference between HP1/2 and natalizumab Fab fragment. This last comparison is important because natalizumab is a wildtype IgG4 which is known to undergo Fab arm exchange (scrambling) in vivo and it becomes functionally monovalent. In contrast, HP1/2 remains bivalent in vivo because it contains a point mutation (S228P EU numbering) that stabilizes the hinge and prevents scrambling. For the purpose of modeling the PD response it is thus appropriate to use the Kd of natalizumab Fab fragment and the Kd of HP1/2 intact in the equation set forth below.

As shown in FIG. 36, the expression of alpha-4 integrin on human and cynomolgus monkey lymphocytes was found to be within a 2-fold difference and needed no adjusted for human HP1/2 projections.

A two-compartment model with both linear and Michaelis-Menten eliminations and direct $E_{max}$ model was used to characterize the PKPD relationship between NTZ and HP1/2 serum concentrations and alpha-4 integrin saturation (receptor occupancy (RO)) in monkeys. HP1/2 human PKs were projected through allometric scaling on monkey PK parameters (k10, k12, k21 and V1). See Singh, A. P et al. The AAPS Journal, 17(2), 389-399. To ensure adequacy of the approach, a sensitivity analysis was performed using NTZ PK parameters obtained in monkeys and humans by taking the log of the ratio between human and monkey parameters relative to their respective body weight. The inherent monkey parameters were directly applied to human including Km, Vmax and the PD parameters ($E_{max}$, $EC_{50}$, $E_0$ and $V_1$). The $EC_{50}$ of HP1/2 in humans was projected based on data collected in the comparative PKPD study in monkeys, using the in vitro binding affinity ($K_d$) and NTZ $EC_{50}$ in humans. See Muralidharan, K. K. et al. Journal of Clinical Pharmacology, 57(8), 1017-1030. The data were integrated using an empirical scaling approach combining the $EC_{50}$ parameter values obtained in monkeys (m) and humans (h), after adjusting for potency ($K_d$) differences across species:

$$EC_{50,HP12,h} = EC_{50,NTZ,h} \times \left(\frac{EC_{50,HP12}}{EC_{50,NTZ}}\right)_m \times \left(\frac{K_{d,h}}{K_{d,m}}\right)_{HP12} \times \left(\frac{K_{d,m}}{K_{d,h}}\right)_{NTZ}$$

The PKPD parameters values from the final "humanized" model were propagated as distribution generated from the multivariate normal distribution with the mean vector set to the population parameters estimate and the covariance matrix of the estimates from the PKPD models. The dose producing a mean RO<=of 10% at Cmax was chosen to define the minimal anticipated biological effective level (MABEL) dose of HP1/2.

Receptor occupancy vs time profiles of HP1/2 and natalizumab were simulated following single IV administration (FIGS. 37A-37D). A single dose of 0.5 mg/kg administered every 4 weeks is expected to be efficacious, with subtherapeutic occupancy levels (<70%) starting to return to baseline after approximately 1 month post-dose. Both HP1/2 and NTZ exhibited a PK profile with target-mediated drug disposition and displayed dose-dependent, RO in monkeys. The $EC_{50}$ value for the formation of drug-bound alpha-4 is projected to be lower for HP1/2 (0.62 ug/mL) when compared to NTZ (2.51 ug/mL. See Muralidharan, K. K. et al. Journal of Clinical Pharmacology, 57(8), 1017-1030. There was overall good agreement between the predicted and observed NTZ human PK profiles, supporting the adequacy of the allometric scaling approach to project HP1/2 clinical PKs. The MABEL of HP1/2 in human is predicted to be 0.0004 mg/kg (as compared to ~0.003 mg/kg for NTZ, see FIG. 38).

In view of this Example 17, integration of available PKPD data across two humanized anti-alpha-4 integrin antibodies enabled the use of a reverse translational modeling approach for estimating receptor occupancy and human pharmacokinetics in order to identify a minimal anticipated biological effective level dose.

The embodiments of the invention described above are intended to be merely exemplary; numerous variations and modifications will be apparent to those skilled in the art. All such variations and modifications are intended to be within the scope of the present invention as defined in any appended claims.

We claim:

1. A recombinant anti-alpha 4 antibody or an anti-alpha 4 antibody fragment thereof comprising:
    (a) a variable light chain comprising the sequence of SEQ ID NO: 11;
    (b) a variable heavy chain comprising the sequence of SEQ ID NO: 4;
    (c) a human kappa light chain constant region comprising the sequence of SEQ ID NO: 82; and
    (d) a heavy chain constant region of human IgG1, said constant region comprising at least one mutation selected from the group consisting of S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme.

2. The recombinant anti-alpha 4 antibody or anti-alpha 4 antibody fragment of claim 1, wherein the heavy chain constant region of human IgG1 comprises at least two mutations selected from the group consisting of S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme.

3. The recombinant anti-alpha 4 antibody or anti-alpha 4 antibody fragment of claim 1, wherein the heavy chain constant region of human IgG1 comprises at least three, or at least four, or at least five, or at least six, or at least seven, or at least eight, or at least nine, or at least ten, or at least eleven, or at least twelve, or at least thirteen, or at least fourteen, or at least fifteen, or at least sixteen, or at least seventeen, or at least eighteen, or at least nineteen, or at least twenty, or at least twenty-one, or at least twenty-two, or at least twenty-three, or at least twenty-four, or at least twenty-five mutations selected from the group consisting of S127C, R129R, G135E, G136S, Q203R, I207T, N211D, R222R, P227S, S232Y, C233G, deletion of D234, deletion of R235, deletion of T236, H237P, T238P, L247F, H281Q, R287Q, Y313F, N314Q, A346G, A349S, P350S, and deletion of R478 according to Kabat numbering scheme.

4. The recombinant anti-alpha 4 antibody or anti-alpha 4 antibody fragment of claim 1, wherein the heavy chain constant region of human IgG1 comprises the following mutations: S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme.

5. A recombinant anti-alpha 4 antibody or an anti-alpha 4 antibody fragment thereof comprising:
    (a) a variable light chain comprising the sequence of SEQ ID NO: 11;
    (b) a variable heavy chain comprising the sequence of SEQ ID NO: 4;
    (c) a human kappa light chain constant region comprising the sequence of SEQ ID NO: 82; and
    (d) a chimeric Fc region comprising a hinge, a CH1 domain and a CH2 domain from an IgG antibody of the IgG4 isotype and a CH3 domain from an IgG antibody of the IgG1 isotype, said chimeric Fc region comprising at least one mutation selected from the group consisting of a substitution to a glutamine (Q) at position 297 EEG numbering or position 314 Kabat numbering in the CH2 region; a substitution to a proline (P) at amino acid position 228 EEG numbering or position 241 Kabat numbering in the hinge region; and a deletion of a lysine (K) at position 447 EEG numbering or position 478 Kabat numbering in the CH3 region.

6. The recombinant anti-alpha 4 antibody or anti-alpha 4 antibody fragment of claim 5, wherein said antibody or fragment has an increased thermal stability as compared to an antibody comprising (a) a variable light chain comprising the sequence of SEQ ID NO: 11; (b) a variable heavy chain comprising the sequence of SEQ ID NO: 4; (c) a human kappa light chain constant region comprising the sequence of SEQ ID NO: 82; and (d) an Fc region comprising a hinge, CH1 domain, CH2 domain, and CH3 domain of an IgG antibody of the IgG4 isotype, said Fc region comprising a substitution to a non-asparagine residue at position 297 EU numbering or position 314 Kabat numbering.

7. A recombinant anti-alpha 4 antibody or an anti-alpha 4 antibody fragment thereof comprising: (a) a variable light chain comprising the sequence of SEQ ID NO: 11; (b) a variable heavy chain comprising the sequence of SEQ ID NO: 4; (c) a human kappa light chain constant region comprising the sequence of SEQ ID NO: 82; and (d) a heavy chain constant region of human IgG4, said constant region comprising at least one mutation selected from the group consisting of S241P, N314Q, Q376R, E377D, M381L, R440K, E450Q, L476P, and deletion of K478 according to Kabat numbering scheme.

8. The recombinant anti-alpha 4 antibody or anti-alpha 4 antibody fragment of claim 7, wherein the heavy chain constant region of human IgG4 comprises at least two mutations selected from the group consisting of S241P, N314Q, Q376R, E377D, M381L, R440K, E450Q, L476P, and deletion of K478 according to Kabat numbering scheme.

9. The recombinant anti-alpha 4 antibody or anti-alpha 4 antibody fragment of claim 7, wherein the heavy chain constant region of human IgG4 comprises at least three, or at least four, or at least five, or at least six, or at least seven, or at least eight, or at least nine mutations selected from the group consisting of S241P, N314Q, Q376R, E377D, M381L, R440R, E450Q, L476P, and deletion of R478 according to Kabat numbering scheme.

10. The recombinant anti-alpha 4 antibody or anti-alpha 4 antibody fragment of claim 7, wherein the heavy chain constant region of human IgG4 comprises the following mutations: S241P, N314Q, Q376R, E377D, M381L, R440R, E450Q, L476P, and deletion of R478 according to Kabat numbering scheme.

11. A recombinant anti-alpha 4 antibody or an anti-alpha 4 antibody fragment thereof comprising:
(a) a heavy chain comprising the sequence of SEQ ID NO: 80; and
(b) a light chain comprising the sequence of SEQ ID NO: 81.

12. A polynucleotide encoding a protein comprising:
(a) a variable light chain comprising the sequence of SEQ ID NO: 11;
(b) a variable heavy chain comprising the sequence of SEQ ID NO: 4;
(c) a human kappa light chain constant region comprising the sequence of SEQ ID NO: 82; and
(d) a heavy chain constant region of human IgG1, said constant region comprising at least one mutation selected from the group consisting of S127C, R129R, G135E, G136S, Q203R, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme.

13. A method of alleviating a symptom of a patient suffering from multiple sclerosis, said method comprising:
administering to the patient a therapeutically effective amount of a recombinant anti-alpha 4 antibody comprising: (a) a variable light chain comprising the sequence of SEQ ID NO: 11; (b) a variable heavy chain comprising the sequence of SEQ ID NO: 4; (c) a human kappa light chain constant region comprising the sequence of SEQ ID NO: 82; and (d) a heavy chain constant region of human IgG1, said constant region comprising at least one mutation selected from the group consisting of S127C, R129R, G135E, G136S, Q203R, I207T, N211D, R222R, P227S, S232Y, C233G, deletion of D234, deletion of R235, deletion of T236, H237P, T238P, L247F, H281Q, R287Q, Y313F, N314Q, A346G, A349S, P350S, and deletion of K478 according to Kabat numbering scheme.

14. A host cell transfected with (a) a polynucleotide encoding an antibody heavy chain comprising a variable heavy chain comprising the sequence of SEQ ID NO: 4; and a heavy chain constant region of human IgG1, said constant region comprising at least one mutation selected from the group consisting of S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme; and
(b) a polynucleotide encoding an antibody light chain comprising a variable light chain comprising the sequence of SEQ ID NO: 11 and a human kappa light chain constant region comprising the sequence of SEQ ID NO: 82.

15. A method of making a recombinant anti-alpha 4 antibody, or an anti-alpha 4 antibody fragment thereof, by providing a host cell transfected with (a) a polynucleotide encoding an antibody heavy chain comprising the sequence of SEQ ID NO: 80, said polynucleotide positioned for expression in the cell; and
(b) a polynucleotide encoding an antibody light chain comprising the sequence of SEQ ID NO: 81, said polynucleotide positioned for expression in the cell; and
culturing the transfected host cell to produce the recombinant anti-alpha 4 antibody or anti-alpha 4 antibody fragment thereof.

16. The recombinant anti-alpha 4 antibody or the anti-alpha 4 antibody fragment of claim 1, further wherein said recombinant anti-alpha 4 antibody or anti-alpha 4 antibody fragment thereof has reduced susceptibility to scrambling relative to an antibody or fragment comprising a wild type IgG4 constant region.

17. A recombinant anti-alpha 4 antibody or an anti-alpha 4 antibody fragment of claim 5, further wherein said recombinant anti-alpha 4 antibody or anti-alpha 4-antibody fragment thereof has reduced susceptibility to scrambling relative to an antibody or fragment comprising a wild type IgG4 constant region.

18. The recombinant anti-alpha 4 antibody or anti-alpha 4 antibody fragment thereof of claim 7, further wherein said recombinant anti-alpha 4 antibody or anti-alpha 4 antibody fragment thereof has reduced susceptibility to scrambling relative to an antibody or fragment comprising a wild type IgG4 constant region.

19. The recombinant anti-alpha 4 antibody or anti-alpha 4 antibody fragment of claim 11, further wherein said recombinant anti-alpha 4 antibody or anti-alpha 4-antibody fragment thereof has reduced susceptibility to scrambling relative to an antibody or fragment comprising a wild type IgG4 constant region.

20. A method of reducing the susceptibility to scrambling of a recombinant anti-alpha 4 antibody or an anti-alpha 4 antibody fragment thereof relative to an antibody or fragment comprising a wild type IgG4 constant region, said method comprising: providing a host cell transfected with (a) a polynucleotide encoding an antibody light chain comprising a variable light chain comprising the sequence of SEQ ID NO: 11 and a human kappa light chain constant region comprising the sequence of SEQ ID NO: 82, said polynucleotide positioned for expression in the cell; and (b) a polynucleotide encoding an antibody heavy chain comprising a variable heavy chain comprising the sequence of SEQ ID NO: 4; and a heavy chain constant region of human IgG4, said polynucleotide positioned for expression in the cell; and introducing into said heavy chain constant region of human IgG4 at least one mutation selected from the group consisting of S241P, N314Q, Q376R, E377D, M381L, R440K, E450Q, L476P, and deletion of K478 according to Kabat numbering scheme.

21. A method of producing a recombinant anti-alpha 4 antibody or an anti-alpha 4 antibody fragment thereof having a reduced susceptibility to scrambling relative to an antibody or fragment comprising a wild type IgG4 constant region, said method comprising:

providing a host cell transfected with (a) a polynucleotide encoding an antibody heavy chain comprising the sequence of SEQ ID NO: 80, said polynucleotide positioned for expression in the cell; and (b) a polynucleotide encoding a light chain comprising the sequence of SEQ ID NO: 81, said polynucleotide positioned for expression in the cell; and culturing the transfected host cell to produce the recombinant anti-alpha 4 antibody molecule or alpha 4 binding fragment thereof.

22. The method of claim 21, wherein the host cell is a Chinese hamster ovary cell.

23. The method of claim 20, wherein the host cell is a Chinese hamster ovary cell.

24. The method of claim 14, wherein the host cell is a Chinese hamster ovary cell.

25. The method of claim 15, wherein the host cell is a Chinese hamster ovary cell.

26. A polynucleotide encoding a protein comprising:
(a) a variable light chain comprising the sequence of SEQ ID NO: 11;
(b) a variable heavy chain comprising the sequence of SEQ ID NO: 4;
(c) a human kappa light chain constant region comprising the sequence of SEQ ID NO: 82; and
(d) a chimeric Fc region comprising a hinge, a CH1 domain and a CH2 domain from an IgG antibody of the IgG4 isotype and a CH3 domain from an IgG antibody of the IgG1 isotype, said chimeric Fc region comprising at least one mutation selected from the group consisting of a substitution to a glutamine (Q) at position 297 EEG numbering or position 314 Kabat numbering in the CH2 region; a substitution to a proline (P) at amino acid position 228 EEG numbering or position 241 Kabat numbering in the hinge region; and a deletion of a lysine (K) at position 447 EEG numbering or position 478 Kabat numbering in the CH3 region.

27. The polynucleotide of claim 26, wherein the polynucleotide encodes a protein comprising: (a) a heavy chain comprising the sequence of SEQ ID NO: 80; and
(b) a light chain comprising the sequence of SEQ ID NO: 81.

28. A polynucleotide encoding a protein comprising:
(a) a variable light chain comprising the sequence of SEQ ID NO: 11;
(b) a variable heavy chain comprising the sequence of SEQ ID NO: 4;
(c) a human kappa light chain constant region comprising the sequence of SEQ ID NO: 82; and
(d) a heavy chain constant region of human IgG4, said constant region comprising at least one mutation selected from the group consisting of S241P, N314Q, Q376R, E377D, M381L, R440K, E450Q, L476P, and deletion of K478 according to Kabat numbering scheme.

29. A method of alleviating a symptom of a patient suffering from multiple sclerosis, said method comprising: administering to the patient a therapeutically effective amount of a recombinant anti-alpha 4 antibody comprising:
(a) a variable light chain comprising the sequence of SEQ ID NO: 11;
(b) a variable heavy chain comprising the sequence of SEQ ID NO: 4;
(c) a human kappa light chain constant region comprising the sequence of SEQ ID NO: 82; and
(d) a chimeric Fc region comprising a hinge, a CH1 domain and a CH2 domain from an IgG antibody of the IgG4 isotype and a CH3 domain from an IgG antibody of the IgG1 isotype, said chimeric Fc region comprising at least one mutation selected from the group consisting of a substitution to a glutamine (Q) at position 297 EEG numbering or position 314 Kabat numbering in the CH2 region; a substitution to a proline (P) at amino acid position 228 EEG numbering or position 241 Kabat numbering in the hinge region; and a deletion of a lysine (K) at position 447 EEG numbering or position 478 Kabat numbering in the CH3 region.

30. The method of claim 29, wherein the recombinant anti-alpha 4 antibody comprises: (a) a heavy chain comprising the sequence of SEQ ID NO: 80; and (b) a light chain comprising the sequence of SEQ ID NO: 81.

31. A method of alleviating a symptom of a patient suffering from multiple sclerosis, said method comprising: administering to the patient a therapeutically effective amount of a recombinant anti-alpha 4 antibody comprising:
(a) a variable light chain comprising the sequence of SEQ ID NO: 11;
(b) a variable heavy chain comprising the sequence of SEQ ID NO: 4;
(c) a human kappa light chain constant region comprising the sequence of SEQ ID NO: 82; and
(d) a heavy chain constant region of human IgG4, said constant region comprising at least one mutation selected from the group consisting of S241P, N314Q, Q376R, E377D, M381L, R440K, E450Q, L476P, and deletion of K478 according to Kabat numbering scheme.

32. A host cell transfected with (a) a polynucleotide encoding an antibody heavy chain comprising a variable heavy chain comprising the sequence of SEQ ID NO: 4, and a chimeric Fc region comprising a hinge, a CH1 domain and a CH2 domain from an IgG antibody of the IgG4 isotype and a CH3 domain from an IgG antibody of the IgG1 isotype, said chimeric Fc region comprising at least one mutation selected from the group consisting of a substitution to a glutamine (Q) at position 297 EEG numbering or position 314 Kabat numbering in the CH2 region; a substitution to a proline (P) at amino acid position 228 EEG numbering or position 241 Kabat numbering in the hinge region; and a deletion of a lysine (K) at position 447 EEG numbering or position 478 Kabat numbering in the CH3 region; and (b) a polynucleotide encoding an antibody light chain comprising a variable light chain comprising the sequence of SEQ ID NO: 11 and a human kappa light chain constant region comprising the sequence of SEQ ID NO: 82.

33. The host cell of claim 32, wherein the host cell is a Chinese hamster ovary cell.

34. The host cell of claim 32, wherein the host cell is transfected with (a) a polynucleotide encoding an antibody heavy chain comprising the sequence of SEQ ID NO: 80; and (b) a polynucleotide encoding an antibody light chain comprising the sequence of SEQ ID NO: 81.

35. A host cell transfected with (a) a polynucleotide encoding an antibody heavy chain comprising a variable heavy chain comprising the sequence of SEQ ID NO: 4, and a heavy chain constant region of human IgG4, said constant region comprising at least one mutation selected from the group consisting of S241P, N314Q, Q376R, E377D, M381L, R440K, E450Q, L476P, and deletion of K478 according to Kabat numbering scheme; and (b) a polynucleotide encoding an antibody light chain comprising a variable light chain comprising the sequence of SEQ ID NO: 11 and a human kappa light chain constant region comprising the sequence of SEQ ID NO: 82.

36. The host cell of claim 35, wherein the host cell is a Chinese hamster ovary cell.

37. A method of making a recombinant anti-alpha 4 antibody, or an anti-alpha 4-antibody fragment thereof, by providing a host cell transfected with (a) a polynucleotide encoding an antibody heavy chain comprising a variable heavy chain comprising the sequence of SEQ ID NO: 4, and a heavy chain constant region of human IgG1, said constant region comprising at least one mutation selected from the group consisting of S127C, K129R, G135E, G136S, Q203K, I207T, N211D, K222R, P227S, S232Y, C233G, deletion of D234, deletion of K235, deletion of T236, H237P, T238P, L247F, H281Q, K287Q, Y313F, N314Q, A346G, A349S, P350S, and deletion of K478 according to Kabat numbering scheme; and (b) a polynucleotide encoding an antibody light chain comprising a variable light chain comprising the sequence of SEQ ID NO: 11, and a human kappa light chain constant region comprising the sequence of SEQ ID NO: 82; and culturing the transfected host cell to produce the recombinant anti-alpha 4 antibody or anti-alpha 4 antibody fragment thereof.

38. The method of claim 37, wherein the host cell is a Chinese hamster ovary cell.

39. A method of making a recombinant anti-alpha 4 antibody, or an anti-alpha 4-antibody fragment thereof, by providing a host cell transfected with (a) a polynucleotide encoding an antibody heavy chain comprising a variable heavy chain comprising the sequence of SEQ ID NO: 4, and a chimeric Fc region comprising a hinge, a CH1 domain and a CH2 domain from an IgG antibody of the IgG4 isotype and a CH3 domain from an IgG antibody of the IgG1 isotype, said chimeric Fc region comprising at least one mutation selected from the group consisting of a substitution to a glutamine (Q) at position 297 EEG numbering or position 314 Kabat numbering in the CH2 region; a substitution to a proline (P) at amino acid position 228 EEG numbering or position 241 Kabat numbering in the hinge region; and a deletion of a lysine (K) at position 447 EEG numbering or position 478 Kabat numbering in the CH3 region; and (b) a polynucleotide encoding an antibody light chain comprising a variable light chain comprising the sequence of SEQ ID NO: 11, and a human kappa light chain constant region comprising the sequence of SEQ ID NO: 82; and culturing the transfected host cell to produce the recombinant anti-alpha 4 antibody or anti-alpha 4 antibody fragment thereof.

40. The method of claim 39, wherein the host cell is a Chinese hamster ovary cell.

41. A method of making a recombinant anti-alpha 4 antibody, or an anti-alpha 4-antibody fragment thereof, by providing a host cell transfected with (a) a polynucleotide encoding an antibody heavy chain comprising a variable heavy chain comprising the sequence of SEQ ID NO: 4, and a heavy chain constant region of human IgG4, said constant region comprising at least one mutation selected from the group consisting of S241P, N314Q, Q376R, E377D, M381L, R440K, E450Q, L476P, and deletion of K478 according to Kabat numbering scheme; and (b) a polynucleotide encoding an antibody light chain comprising a variable light chain comprising the sequence of SEQ ID NO: 11, and a human kappa light chain constant region comprising the sequence of SEQ ID NO: 82; and culturing the transfected host cell to produce the recombinant anti-alpha 4 antibody or anti-alpha 4 antibody fragment thereof.

42. The method of claim 41, wherein the host cell is a Chinese hamster ovary cell.

* * * * *

UNITED STATES PATENT AND TRADEMARK OFFICE
CERTIFICATE OF CORRECTION

PATENT NO. : 12,037,398 B2
APPLICATION NO. : 15/734915
DATED : July 16, 2024
INVENTOR(S) : Janine Lisa Ferrant-Orgettas et al.

It is certified that error appears in the above-identified patent and that said Letters Patent is hereby corrected as shown below:

In the Specification

Figure 18:
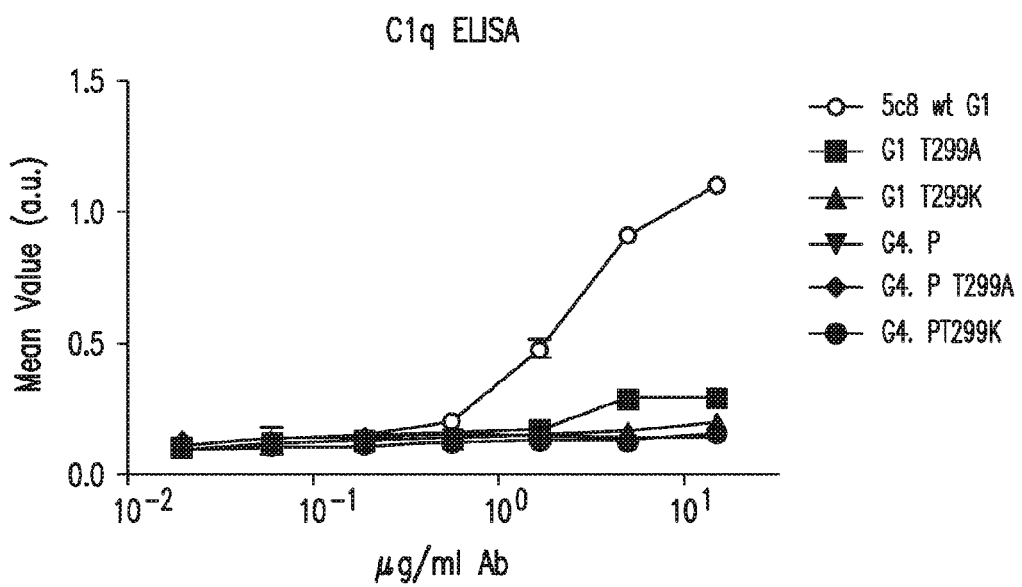
FIG. 18 depicts the titration curves used to evaluate binding of exemplary IgG1 and IgG4 Fc constructs of the invention to complement factor C1q.

At Column 125, Line 22, change "(Table 13.3 and FIGS. 20C, 18E). It is also interesting to" to -- (Table 13.3 and FIGS. 20C, 20E). It is also interesting to --.

Signed and Sealed this
Third Day of September, 2024

Katherine Kelly Vidal
Director of the United States Patent and Trademark Office